US007157418B1

(12) United States Patent
McDonald et al.

(10) Patent No.: US 7,157,418 B1
(45) Date of Patent: Jan. 2, 2007

(54) METHODS AND COMPOSITIONS FOR TREATING SECONDARY TISSUE DAMAGE AND OTHER INFLAMMATORY CONDITIONS AND DISORDERS

(75) Inventors: John R. McDonald, Calgary (CA); Philip J. Coggins, Calgary (CA)

(73) Assignee: Osprey Pharmaceuticals, Ltd. (CA)

( * ) Notice: Subject to any disclaimer, the term of this patent is extended or adjusted under 35 U.S.C. 154(b) by 0 days.

(21) Appl. No.: 09/360,242

(22) Filed: Jul. 22, 1999

Related U.S. Application Data

(63) Continuation-in-part of application No. PCT/CA99/00659, filed on Jul. 21, 1999.

(60) Provisional application No. 60/155,186, filed on Jul. 22, 1998.

(51) Int. Cl.
*A01N 37/18* (2006.01)
*C07K 1/00* (2006.01)
*C07K 14/00* (2006.01)
*C07K 16/00* (2006.01)
*A61K 45/00* (2006.01)

(52) U.S. Cl. .......................... 514/2; 424/85.1; 530/402

(58) Field of Classification Search ................ 530/300, 530/350, 351, 402; 424/851; 514/2
See application file for complete search history.

(56) References Cited

U.S. PATENT DOCUMENTS

| | | | | |
|---|---|---|---|---|
| 4,036,945 | A | 7/1977 | Haber | 424/1 |
| 4,215,051 | A | 7/1980 | Schroeder et al. | 260/346.7 |
| 4,331,647 | A | 5/1982 | Goldenberg | 424/1 |
| 4,569,789 | A | 2/1986 | Blattler et al. | 260/112 R |
| 4,575,013 | A | 3/1986 | Bartley | 241/275 |
| 4,719,179 | A | 1/1988 | Barany | 435/172.1 |
| 4,745,051 | A | 5/1988 | Smith et al. | 435/68 |
| 4,894,443 | A | 1/1990 | Greenfield et al. | 530/388 |
| 4,920,143 | A | 4/1990 | Levy et al. | 514/410 |
| 4,946,778 | A | 8/1990 | Ladner et al. | 435/69.6 |
| 4,952,394 | A | 8/1990 | Senter | 424/85.91 |
| 4,952,496 | A | 8/1990 | Studier et al. | 435/91 |
| 4,968,715 | A | 11/1990 | Dougherty et al. | 514/410 |
| 5,028,594 | A | 7/1991 | Carson | 514/23 |
| 5,041,292 | A | 8/1991 | Feijen | 424/484 |
| 5,053,423 | A | 10/1991 | Liu | 514/410 |
| 5,082,927 | A | 1/1992 | Pastan et al. | 530/351 |
| 5,084,556 | A | 1/1992 | Brown | 530/351 |
| 5,087,617 | A | 2/1992 | Smith | 514/44 |
| 5,087,636 | A | 2/1992 | Jamieson et al. | 514/410 |
| 5,093,246 | A | 3/1992 | Cech et al. | 435/91 |
| 5,093,349 | A | 3/1992 | Pandey et al. | 514/410 |
| 5,109,016 | A | 4/1992 | Dixon et al. | 514/410 |
| 5,109,124 | A | 4/1992 | Ramachandran et al. | 536/27 |
| 5,116,742 | A | 5/1992 | Cech et al. | 435/91 |
| 5,122,463 | A | 6/1992 | Varshavsky et al. | 435/172.3 |
| 5,135,917 | A | 8/1992 | Burch | 514/44 |
| 5,137,877 | A | 8/1992 | Kaneko et al. | 514/25 |
| 5,144,019 | A | 9/1992 | Rossi et al. | 536/27 |
| 5,149,708 | A | 9/1992 | Dolphin et al. | 514/410 |
| 5,152,980 | A | 10/1992 | Strom et al. | 424/85.2 |
| 5,168,053 | A | 12/1992 | Altman et al. | 435/91 |
| 5,169,784 | A | 12/1992 | Summers et al. | 435/320.1 |
| 5,171,749 | A | 12/1992 | Levy et al. | 514/410 |
| 5,173,403 | A | 12/1992 | Tang et al. | 435/6 |
| 5,175,269 | A | 12/1992 | Stavrianopoulos | 536/27 |
| 5,176,996 | A | 1/1993 | Hogan et al. | 435/6 |
| 5,180,818 | A | 1/1993 | Cech et al. | 536/23.1 |
| 5,187,153 | A | 2/1993 | Cordell et al. | 514/12 |
| 5,190,931 | A | 3/1993 | Inouye | 435/91 |
| 5,192,788 | A | 3/1993 | Dixon et al. | 514/410 |
| 5,202,317 | A | 4/1993 | Bruice | 514/185 |
| 5,204,254 | A | 4/1993 | Schmid et al. | 435/202 |
| 5,212,058 | A | 5/1993 | Baker et al. | 435/252.33 |
| 5,212,286 | A | 5/1993 | Lewicki et al. | 530/324 |
| 5,215,907 | A | 6/1993 | Tang et al. | 435/219 |
| 5,217,966 | A | 6/1993 | Bruice | 514/185 |
| 5,218,088 | A | 6/1993 | Gorenstein et al. | 536/25.34 |
| 5,220,013 | A | 6/1993 | Ponte et al. | 536/23.5 |
| 5,223,483 | A | 6/1993 | Thomas et al. | 514/12 |

(Continued)

FOREIGN PATENT DOCUMENTS

EP 0531434 7/1999

(Continued)

OTHER PUBLICATIONS

Rudinger J. et al. Characteristics of the amino acids as components of a peptide hormone sequence in Peptide Hormones. pp. 1-7. Edited by Parsons, JA Mill Hill, London, 1976).*

(Continued)

*Primary Examiner*—Robert S. Landsman
(74) *Attorney, Agent, or Firm*—Fish & Richardson P.C.; Stephanie Seidman

(57) ABSTRACT

Conjugates containing as a ligand a chemokine receptor targeting agents, such as chemokines, and a targeted agent, such as a toxin are provided. These conjugates are used to treat inflammatory responses associated with activation, proliferation and migration of immune effector cells, including leukocyte cell types, neutrophiles, macrophages, and eosinophils. The conjugates provided herein are used to lessen or inhibit these processes to prevent or at least lessen the resulting secondary effects. In particular, the conjugates are used to target toxins to receptors on secondary tissue damage-promoting cells. The ligand moiety can be selected to deliver the cell toxin to such secondary tissue damage-promoting cells as mononuclear phagocytes, leukocytes, natural killer cells, dendritic cells, and T and B lymphocytes, thereby suppressing the proliferation, migration, or physiological activity of such cells. Among preferred conjugates are fusion proteins having a chemokine, or a biologically active fragment thereof, as the ligand moiety linked to a cell toxin via a peptide linker of from 2 to about 60 amino acid residues.

56 Claims, 5 Drawing Sheets

U.S. PATENT DOCUMENTS

| | | | |
|---|---|---|---|
| 5,227,293 A | 7/1993 | Stengelin et al. | 435/69.7 |
| 5,227,469 A | 7/1993 | Lazarus et al. | 530/324 |
| 5,229,279 A | 7/1993 | Peoples et al. | 435/135 |
| 5,231,008 A | 7/1993 | Oeda et al. | 435/69.1 |
| 5,237,016 A | 8/1993 | Ghosh et al. | 252/329.4 |
| 5,238,940 A | 8/1993 | Liu et al. | 514/410 |
| 5,240,831 A | 8/1993 | Barnes | 435/69.1 |
| 5,242,687 A | 9/1993 | Tykocinski et al. | 424/93 |
| 5,243,041 A | 9/1993 | Fernandez-Pol | 536/23.5 |
| 5,244,805 A | 9/1993 | Miller | 435/320.1 |
| 5,252,720 A | 10/1993 | Sessler et al. | 534/11 |
| 5,257,970 A | 11/1993 | Dougherty | 604/20 |
| 5,262,309 A | 11/1993 | Nakamura et al. | 435/69.5 |
| 5,266,317 A | 11/1993 | Tomalski et al. | 424/93 |
| 5,270,458 A | 12/1993 | Lemischka | 536/23.5 |
| 5,272,262 A | 12/1993 | Rossi et al. | 536/23.2 |
| 5,278,050 A | 1/1994 | Summers | 435/69.1 |
| 5,281,525 A | 1/1994 | Mitsushima et al. | 435/197 |
| 5,326,559 A | 7/1994 | Miller | 424/85.2 |
| 5,346,686 A | 9/1994 | Lyle et al. | 424/1.41 |
| 5,349,066 A | 9/1994 | Kaneko et al. | 546/294 |
| 5,413,778 A | 5/1995 | Kunkel et al. | 424/1.41 |
| 5,563,048 A | 10/1996 | Honjo et al. | 435/69.1 |
| 5,576,288 A | 11/1996 | Lappi et al. | 514/2 |
| 5,585,254 A | 12/1996 | Maxwell et al. | 435/172.3 |
| 5,605,671 A | 2/1997 | Lyle et al. | 424/1.41 |
| 5,612,474 A | 3/1997 | Patel | 536/27.14 |
| 5,614,191 A | 3/1997 | Puri et al. | 424/178.1 |
| 5,618,528 A | 4/1997 | Cooper et al. | 424/78.3 |
| 5,622,958 A | 4/1997 | Danishefsky et al. | 514/280 |
| 5,631,018 A | 5/1997 | Zalipsky et al. | 424/450 |
| 5,633,149 A | 5/1997 | Guegler et al. | 435/69.5 |
| 5,635,599 A | 6/1997 | Pastan et al. | 530/351 |
| 5,645,835 A | 7/1997 | Fell, Jr. et al. | 424/134.1 |
| 5,648,334 A | 7/1997 | Davis et al. | 514/12 |
| 5,705,163 A | 1/1998 | Pastan et al. | 424/260.1 |
| 5,714,166 A | 2/1998 | Tomalia et al. | 424/486 |
| 5,714,578 A | 2/1998 | Yoshimura et al. | 560/324 |
| 5,723,147 A | 3/1998 | Kim et al. | 424/450 |
| 5,750,565 A | 5/1998 | Cai et al. | 514/473 |
| 5,766,627 A | 6/1998 | Sankaram et al. | 424/450 |
| 5,783,181 A | 7/1998 | Browne et al. | 424/85.2 |
| 5,910,431 A | 6/1999 | Ni et al. | 435/69.5 |
| 5,919,456 A | 7/1999 | Puri et al. | 424/181.1 |
| 6,001,649 A | 12/1999 | Caput et al. | 435/365.1 |
| 6,031,080 A | 2/2000 | Williams et al. | 530/351 |
| 6,051,697 A | 4/2000 | Bandman et al. | 536/23.1 |
| 6,100,387 A | 8/2000 | Hermann et al. | 536/23.4 |
| 6,730,296 B1 | 5/2004 | Herrmann et al. | |
| 6,852,508 B1 | 2/2005 | Herrmann et al. | |

FOREIGN PATENT DOCUMENTS

| | | |
|---|---|---|
| WO | 8805077 | 7/1988 |
| WO | 9012597 | 11/1990 |
| WO | 9111465 | 8/1991 |
| WO | 9118012 | 11/1991 |
| WO | 9209629 | 6/1992 |
| WO | 9301286 | 1/1993 |
| WO | 9302192 | 2/1993 |
| WO | 9303709 | 3/1993 |
| WO | 9310139 | 5/1993 |
| WO | 9323062 | 11/1993 |
| WO | 9324620 | 12/1993 |
| WO | 9325228 | 12/1993 |
| WO | 9407535 | 4/1994 |
| WO | 9407542 | 4/1994 |
| WO | 9512414 | 5/1995 |
| WO | 9606641 | 3/1996 |
| WO | 9623888 | 8/1996 |
| WO | 9700946 | 1/1997 |
| WO | 9727299 | 7/1997 |
| WO | 9811229 | 3/1998 |
| WO | 9813495 | 4/1998 |
| WO | 9833914 | 6/1998 |
| WO | 9838212 | 9/1998 |
| WO | 9846645 | 10/1998 |
| WO | 9846788 | 10/1998 |
| WO | 9920759 | 4/1999 |
| WO | 9925734 | 5/1999 |
| WO | 9928473 | 6/1999 |
| WO | 9932631 | 7/1999 |
| WO | 9933990 | 7/1999 |
| WO | 9954440 | 10/1999 |
| WO | 9958678 | 11/1999 |
| WO | 0004926 | 2/2000 |
| WO | 0006605 | 2/2000 |

OTHER PUBLICATIONS

Cunningham BC and Wells JA. High-resolution epitope mapping of hGH-receptor interactions by alanine-scanning mutagenesis. Science. vol. 244, pp. 1081-1085, 1989.*

George et al. Current methods in sequence comparison and analysis. In Macromolecular Sequencing and Synthesis—selected methods and applications. Ed Schlesinger, Alan R. Liss, Inc, NY. pp. 127-149, 1988.*

Volk H-D, et al. Mechanisms of dichotomous action of IL-2-Pseudomonas exotoxin 40 (IL-2-PE40) on cell-mediated and humoral immune response. J. Immunol., vol. 253, pp. 2497-2505, 1994.*

Ogata M, et al. Cytotoxic activity of a recombinant fusion protein between interleukin 4 and Pseudomonas endotoxin. Proc. Natl. Acad. Sci. USA vol. 86, pp. 4215-4219, 1989.*

Roby P, et al. Oncology Reports 3:175-179, 1996.*

Benjamini E. et al. In Immunology:A Short Course. 3$^{rd}$ ed. Wiley-Liss, Inc, 1996, p. 15.*

Rogers et al. Gene Transfer in Plants: Production of Transformed Plants Using Ti Plasmid Vectors. *Methods for Plant Molecular Biology*, Academic Press, San Diego, Section VIII, pp. 423-463, 1988.

Abu el Asrar et al., Monocyte chemotactic protein-1 in proliferative vitreoretinal disorders, *Am. J. Ophthalmol.*, 123:599-606, 1997.

Adamus et al., Similiar pattern of MCP-1 expression in spinal cords and eyes of lewis rats with experimental autoimmune encephalomyelitis associated anterior uveitis, *J. Neurosci. Res.*, 50: 531-8, 1997.

Agrawal et al., Oligodeoxynucleoside methylphosphonates: synthesis and enzymic degradation, *Tetrehedron Lett.* 28:3539-3542 (1987).

Aksünger et al., Role of interleukin 8 in the pathogenesis of proliferative vitreoretinopathy, *Ophthalmologica*, 211: 223-5, 1997.

Albini et al., HIB-1 tat protein mimicry of chemokines, *Proc. Natl. Acad. Sci, USA* 95:13153-13158 (1998).

Ali et al., Mechanisms of inflammation and leukocyte activation, *Adv. Rheumatol.*, 81:1-28, 1997.

An et al., Eary HIV-1 infection of the central nervous system, *Arch Anat Cytol Pathol* 45:94-105 (1997).

Armstrong et al., A phase I study of chemically synthesized verotoxin (Shiga-like toxin) Pk-trisaccaride receptors attached to chromosorb for preventing hemolytic-uremic syndrome, *J. Infect. Dis.* 171: 1042-5, 1995.

Badolato and Oppenhiem, Role of cytokines, acute-phase proteins, and chemokines in the progression of rheumatoid arthritis, *Semin. Arthritis Rheum*, 2: 526-38, 1996.

Baggiolini et al., Interleukin-8 and related chemotactic cytokines—CXC and CC chemokines, *Advances in Immunology* 55:97-179 (1994).

Balashov et al., CR5 + and CXCR3 + T cells are increased in multiple sclerosis and their ligands MIP-1α and IP-10 are expressed in demyelinating brain lesions, *Proc. Natl. Acad. Sci. USA* 96:6873-6878 (1999).

Banati et al., Cytotoxicity of microglia, *Glia* 7:111-8, 1993.
Barnes et al., Polyclonal antibody directed against human RANTES ameliorates disease in the lewis rat adjuvantinduced arthritis model, *J. Clin. Invest.* 101(12): 2910-2919 (1998).
Bartholdi and Schwab, Expression of Pro-inflammatory cytokine and chemokine mRNA upon experimental spinal cord injury in mouse: an in situ hybridization study, *Euro J of Neuroscience* 9: 1422-1438 (1997).
Batra et al., Insertion of constant region domains of human $IgG_1$ into CD4-PE40 increases its plasma half-life, *Molecular Immunol.* 30:379-386 (1993).
Bäumert et al., RNA-Protein neighbourhoods of the ribosome obtained by crosslinking, *Eur. J. Biochem.* 89:353-359 (1978).
Bazan et al., A new class of membrane-bound chemokine with $CX_3C$ motif, *Nature*, 385:640-4, 1997.
Beall et al., Site-directed mutagenesis of monocyte chemoattractant protein-1 identifies two regions of the polypeptide essential for biological activity, *Biochem J.* 313:633-40 (1996).
Behroozi et al., 1,2-dithiolan-3-one 1-oxides: a class of thiol-activated DNA-cleaving agents that are structurally related to the natural product leinamycin, *Biochemistry* 35:1568-74, 1996.
Beitz et al., Antitumor activity of basic fibroblast growth factor-saporin mitotoxin *in Vitro* and *in Vivo*, *Cancer Research* 52:227-230 (1992).
Bell et al., Upregulation of the macrophage scavenger receptor in response to different forms of injury in the CNS, *J. Neurocytol.*, 23 605-13, 1994.
Benhar et al., *Pseudomonas* exotoxin A mutants, *J. Biol. Chem.*, 269: 13398-404, 1994.
Bennett et al., Spasticity in rats with sacral spinal cord injury, *J. Neutrotrauma* 16(1):69-84 (1999).
Benveniste, E.N., Cytokine circuits in brain, Implications for AIDS dementia complex, *Res. Publ. Assoc. Res. Nerv. Ment. Dis.*, 72: 71-88, 1994.
Benveniste, E.N., Role of macrophages/microglia in multiple sclerosis and experimental allergic encephalomyelitis, *J. Mol. Med.*, 75: 165-73, 1997.
Berman et al., Localization of monocyte chemoattractant peptide-1 expression in the central nervous system in experimental autoimmune encephalmyelitis and trauma in the rat, *J. Immunol.*, 156:3017-23, 1996.
Bird et al., Single-chain antigen-binding proteins, *Science* 242:423-426, 1988.
Bitter et al., Expression and secretion vectors for yeast, *Methods Enzymol.* 153:516-544 (1987).
Bitter, Heterologous Gene Expression in Yeast, *Methods in Enzymol.*, 152: 673-684, 1987.
Bleul et al., A highly efficacious lymphocyte chemoattractant, stromal cell-derived factor 1 (SDF-1), *J. Exp. Med.*, 184: 1101-9, 1996.
Blight, A.R., Morphometric analysis of a model of spinal cord injury in guinea pigs, with behavioral evidence of delayed secondary pathology, *J. Neurol. Sci.* 103: 156-71, 1991.
Blight, et al., Increased levels of the excitotoxin quinolinic acid is spinal cord following contusion injury, *Brain Res.*, 632: 314-16, 1993.
Blight, Morphometric analysis of blood vessels in chronic experimental spinal cord injury: hypervascularity and recovery of function, *J of Neurolog Sciences* 106:158-174 (1991).
Bogden et al., Chemotherapy responsiveness of human tumors as first transplant generation xenografts in the normal mouse, *Cancer(Philadelphia)* 48:10-20 (1981).
Brinkmann and Pastan, Immunotoxins against cancer, *Biochim. et Biophys. Acta* 1198:27-45, 1994.
Brisson et al., Expression of a bacterial gene in plants by using a viral vector, *Nature* 310:511-514, 1984.
Broglie et al., Light regulated expression of a pea ribulose-1, 5-bisphosphate carboxylase small subunit gene in transformed plant cells, *Science* 224:838-843, 1984.
Brosius et al., Regulation of ribosomal RNA promoters witha synthetic lac operator, *Proc. Natl. Acad. Sci.* 81:6929 (1984).
Brumeanu et al., Derivatization with monomethoxypolyethylene glycol of Igs expressing viral epitopes obviates adjuvant requirements, *J Immunol.*, 154: 3088-95, 1995.
Buchner et al., A method for increasing the yield of properly folded recombinant fusion proteins: single-chain immunotoxins from renaturation of bacterial inclusion bodies, *Anal. Biochem.* 205:263-270 (1992).
Campbell et al., Temporal role of chemokines ina murine model of cockroach allergen-induced airway hyperractivity and eosinophilia, *J. of Immunology* 7047-7053 (1998).
Carlson et al., Acute inflammatory response in spinal cord following impact injury, *Experimental Neurology* 151:77-88 (1998).
Carlsson et al., Protein thiolation and reversible protein-protein conjugation, *Biochem. J.* 173:723-737 (1978).
Carr et al., Monocyte chemoattractant protein 1 acts as a T-lymphocyte chemoattractant, *Proc. Natl. Acad. Sci. U.S.A.* 91:3652-3656 (1994).
Carter et al., Humanization of an anti-p185$^{HER2}$ antibody for human cancer therapy, *Proc. Nat'l Acad. Sci. USA* 89:4285-9, 1992.
Caruthers et al., Chemical synthesis of deoxyoligonucleotides by phosphoramidite method, *Method in Enzymology* 154:287-313 (1987).
Chabot et al., Microglial production of TNF-α is induced by activated T lymphocytes, *J. Clin. Invest.* 100:604-12 (1997).
Chandler et al., Targeting tumor cells via EGF receptors: selective toxicity of an HBEGF-toxin fusion protein, *Int J. Cancer* 78:106-11 (1998).
Chao et al., Modulation of human microglial cell superoxide production by cytokines, *J. Leukoc. Biol.* 58: 65-70, 1995.
Charteris et al., Inflammatory cells in proliferative vitreoretinopathy subretinal membranes *Ophthalmology*,100: 43-46, 1993.
Cheng et al., A versatile method for the coupling of protein to DNA: synthesis of α-macroglobulin-DNA conjugates, *Nucleic Acids Res.* 11: 659-669 (1983).
Christie et al., Expression of the macrophage scavenger receptor, a multifucntional lipoprotein, in microglia associated with senile plaques in alzheimer's disease, *Am. J. Pathol.*, 148: 399-403, 1996.
Chu et al., Synthesis of an amplifiable reporter RNA for bioassays, *Nucl. Acids Res.* 14:5591-5603 (1986).
Chu et al., Ligation of oligonucleotides to nucleic acids or proteins via disulfide bonds, *Nucleic Acids Res* 16(9):3671-3691 (1988).
Chu et al., Derivatization of unprotected polynucleotides, *Nucleic Acids Res.* 11:6513-6529 (1983).
Clark-Lewis et al., Structure-activity relatinships of chemokines, *J. Leukoc Biol.* 57:703-11 (1995).
Clusel et al., *Ex vivo* regulation of specific gene expression by nanomolar concentration of double-stranded dumbbell oligonucleotides, *Nucl. Acids Res.* 3405-3411 (1993).
Cohen et al., Nonchromosomal antibiotic resistance in bacteria: genetic transformation of *Escherichia coli* by R-factor DNA, *Proc. Natl. Acad. Sci. USA* 69:2110-2114 (1972).
Colbére-Garapin et al., A new dominant hybrid selective marker for higher eukaryotic cells, *J. Mol. Biol.*, 150:1-14, 1981.
Combadiere et al., Monocyte chemoattractant protein-3 is a functional ligand for CC chemokine receptors 1 and 2B, *J. Mol. Chem.*, 270: 29671-5, 1995.
Cone and Mulligan, High-efficiency gene transfer into mammalian cells: generation of helper-free recombinant retrovirus with broad mammalian host range, *Proc. Natl. Acad. Sci. USA*, 81:6349-6353, 1984.
Coruzzi et al., Tissue-specific and light-regulated expression of a pea nuclear gene encoding the small subunit of ribulose-1, 5-bisphosphate carboxylase, *EMBO J.* 3:1671-1680, 1984.
Cumber et al., Structural features of the antibody-A chain linkage that influence the activity and stability of ricin A chain immunotoxins, *Bioconj. Chem.* 3:397-401, 1992.
Current Protocols in Molecular Biology, Ausubel et al., eds., Chapter 13, Current Protocols, 1987-1994, John Wiley and Sons, Inc. 1994-1999.
Dang et al., Nuclear and nucleolar targeting sequences of c-erb-An, c-myb, N-myc, p. 53, HSP70, and HIV tat proteins, *J. Biol. Chem.* 264: 18019-18023 (1989).

Dang et al., Identification of the human c-myc protein nuclear translocation signal, *Mol. Cell. Biol.* 8:4048-4058 (1988).

Daugherty et al., Cloning, expression, and characterization of the human eosinophil eotaxin receptor, *J. Exp. Med.* 183: 2349-54, 1996.

De Boer et al., The tac promoter: a functional hybrid derived from the *trp* and *lac* promoters, *Proc. Natl. Acad. Sci. USA* 80:21 (1983).

De Benedetti et al., Cytokines in juvenile rheumatoid arthritis, *Curr. Opin. Rheumatol.*, 9: 428-33, 1997.

Debinski et al, Interleukin-4 receptors expressed on tumor cells may serve as a target for anticancer therapy using chimeric *pseudomonas* exotoxin, *Int. J. Cancer* 58: 744-748 (1994).

Desbaillets et al., Upregulation of interleukin 8 by oxygen-deprived cells in glioblastoma suggests a role in leukocyte activation, chemotaxis, and angiogenesis, *J. Exp. Med.* 186 (8): 1201-1212 (1997).

Dickson et al., Microglia and cytokines in neurological disease, with special reference to AIDS and alzheimer's disease, *Glia* 7: 75-83, 1993.

Driscoll et al., Cytokines and particle-induced inflammatory cell recruitment, *Environ. Health Perspect.*, 105: Suppl 5: 64: 1159-64, 1997.

Duffaud et al. Expression and secretion of foreign proteins in *Escherichia coli, Meth. Enz.* 153:492-507 (1987).

Dusart et al., Secondary cell death and the inflammatory reaction after dorsal hemisection of the rat spinal cord, *Eur. J. Neurosci.* 6: 712-14, 1994.

Eckstein et al., Phosphorothioates in molecular biology, *Trends Biol. Sci.* 14:97-100 (1989).

Eckstein, Nucleoside phosphorothioates, *Annu. Rev. Biochem.* 54:367-402 (1985).

El Khoury et al., Scavenger receptor-mediated adhesion of microglia to β-amyloid fibrils, *Nature* 382: 716-19, 1996.

Eukaryotic Viral Vectors, Cold Spring Harbor Laboratory, Gluzman ed., 1982.

Faden et al., Pharmacological strategies in CNS trauma, *TIPS Revs.*, 13: 29-35, 1992.

Faden et al., The role of excitatory amino acids and NMDA receptors in traumatic brain injury, *Science* 244: 798-800, 1989.

Fahey et al., Macrophage inflammatory protein 1 modulates macrophage function, *J. Immunol.*, 148: 2764-9, 1992.

Fattom et al., Comparative immunogenicity of conjugates composed of the *Staphylococcus aureus* type 8 capsular polysaccharide bound to carrier proteins by adipic acid dihydrazide or N-succinimidyle-3-(2-pyridyldithiol) propionate, *Infection & Immun.* 60:584-589 (1992).

Felix et al., Pegylated peptides IV, Enhanced biological activity of site-directed pegylated GRF analogs, *Int. J. Peptide Res.*, 46:253-64, 1995.

Fiser et al., Photoaffinity reaction between polyuridylic acid and protein S1 on the *Escherichia coli* ribosome, *FEBS Lett.* 52:281-283 (1975).

Fletcher, et al., Antinociceptive effect of bupivacaine encapsulated in poly(D,L)-lactide-co-glycolide microspheres in the acute inflammatory pain model of carrageenin-injected rates, *Anesth. Analg.* 84:90-94, 1997.

Folkman and Klagsbrun, Angiogenic factors, *Science* 235:442-447 (1987).

Forbes et al., Inhibition of neutrophil adhesion does not prevent ischemic spinal cord injury, *Ann. Thorac Surg* 58:1064-8 (1994).

Forssman et al., Eotaxin-2, a novel C chemokine that is selective for the chemokine receptor CCR3, and acts like eotaxin on human eosinophil and basophil leukocytes, *J. Exp. Med.*, 185:2171-6, 1997.

Franci et al., Monocyte chemoattractant protein-3, but not monocyte chemoattractant protein-2 receptor, is a functional ligand of the human monocyte chemoattractant protein-1, *J. Immunol.*, 154:6511-7, 1995.

Fuentes et al., Controlled recruitment of monocytes and macrophages to specific organs through transgenic expression of monocyte chemoattractant protein-1, *J. Immunol.*, 155:5769-76, 1995.

Furie and Randolph, Chemokines and tissue injury, *Am. J. Pathol.*, 146: 1287-301, 1995.

Galasso et al., Excitotoxic brain injury stimulates expression of the chemokine receptor CCR5 in neonatal rats, *Am. J. Pathol.* 153:1631-40 (1998).

Gebicke-Haerter et al., Rat microglial intrleukin-3, *J. Neuroimmunol.* 50: 203-14, 1994.

Gehrmann et al., Microglia: intrinsic immuneffector cell of the brain, *Brain Res. Rev.*, 20:269-87, 1995.

Ghrnikar et al., Chemokine expression in rat stab wound brian injury, *J. of Neuroscience Res.* 46:727-733 (1996).

Gieni et al., Comparison of [$^3$H]thymidine incorporation with MTT—and MTS-based bioassays for human and murine IL-2 and IL-4 analysis, *J. Immunol Methods* 18785-93 (1995).

Giulian et al., Inhibition of mononuclear phagocytes reduces ischemic injury in the spinal cord, *Ann. Neurol.*, 27: 33-42, 1990.

Giulian et al., Interleukin-1 injected into mammalian brain stimulates astrogliosis and neovasculariation, *J. Neurosci.*, 8:2485-90, 1988.

Giulian et al., Brain glia release factors with opposing actions upon neuronal survival, *J. Neurosci.*, 13: 29-37, 1993.

Giulian, D., Ameboid microglia as effectors of inflammation in the central nervous system, *J. Neurol. Res.*, 18: 155-171, 1987.

Giulian et al., Interleukin-1 is an astroglial growth factor in the developing brain, *J. Neurosci.*, 8: 709-14, 1988.

Giulian et al., Reactive mononuclear phagocytes release neurotoxins after ischemic and traumatic injury to the central nervous system, *J. Neurosci. Res.*, 36: 681-93, 1993b.

Giulian et al., Cell surface morphology identifies mciroglia as a distinct class of mononuclear phagocyte, *J. Neurosci.*, 15: 7712-26, 1995b.

Giulian et al., Study of receptor-mediated neurotoxins released by HIV-1-infected mononuclear phagocytes found in human brain, J. Neurosci., 16: 3193-53, 1996.

Giulian et al., The impact of microglia-derived cytokines upon gliosis in the CNS, *Dev. Neurosci.*, 16: 128-36, 1994.

Giulian et al., Senile plaques stimulate microglia to release a neurotoxin found in alzheimer brain, *Neurochem, Int.*, 27: 119-37, 1995a.

Giulian et al., Colony-stimulating factors as promoters of ameboid microglia, *J. Neurosci.*, 8: 4707-17, 1988c.

Giulian et al., The role of mononuclear phagocytes in wound healing after traumatic injury to adult mammalian brain, *J. Neurosci.*, 9: 4416-29, 1989.

Glabinski et al., Regulation and functionof central nervous system chemokines, *Int. J. Dev. Neurosci.*, 13: 153-65, 1995.

Glabinski et al., Chemokine monocyte chemoattractant protein-1 is expressed by astrocytes after mechanical injury to the brain, *J. Immunol.*, 156: 4363-8, 1996.

Goldmacher et al., Photoactivation of toxin conjugates, *Bioconj. Chem.* 3:104-107 (1992).

Gong et al., RANTES and MCP-3 antagonists bind multiple chemokine receptors, *J. Biol. Chem.*, 271: 10521-27, 1996.

Gonzalez-Deniselle et al., The 21-aminosteroid U-74389F increases the number of glial fibrillary acidic protein-expressing astrocytes in the spinal cord of control and wobbler mice, *Cell Mol. Neurobiol.*, 16: 61-72, 1996.

Goodchild, In: *Perspectives in Bioconjugate Chemistry*, Mears, ed., American Chemical Society, Washington, D.C. pp. 77-99 (1993).

*Goodman And Gilman's: The Pharmacological Bases of Therapeutics*, 8th ed., Pergamon Press, 1990.

Gordon et al., Topographical localization of the C-terminal region of the voltage-dependent sodium channel from *Electrophorus electricus* using antibodies raised against a synthetic peptide, *Proc. Natl. Acad Sci.* 84:308-312 (1987).

Gourmala et al., Differential and time-dependent expression of monocyte chemoattractant protein-1 mRNA by astrocytes and macrophages in rat brain: effects of ischemia and peripheral lipopolysaccharide administration, *J. Neuroimmunol.*, 74: 35-44, 1997.

Goya et al., Identification of CCR8 as the specific for the human β-Chemokine 1-309: cloning and molecular characterization of murine CCR8 as the receptor for TCA-3, *J. Immunol.* 160:1975-81, 1998.

Graves et al., Chemokines, a family chemotactic cytokines, *Crit. Rev. Oral Biol. Med.*, 6: 109-18, 1995.

Griffiths-Johnson et al., Animal models of asthma: role of chemokines, *Methods in Enzymology* 288:241-266 (1997).

Grimaldi et al., Depeltion of eosinophils in mice through the use of antibodies specific for C-C chemokine receptor 3 (CCR3), *J of Leukocyte Biology* 65: 846-853 (1999).

Gurley, et al., Upstream sequences required for efficient expression of a soybean heat shock gene, *Mol. Cell. Biol.* 6:559-565, 1986.

Haelens et al., Leukocyte migration and activation by murine chemokines, *Immunobiol.*, 195: 499-521, 1996.

Hamada et al., Isolation and characterization of a novel secretory protein, stromal cell-derived factor-2 (SDF-2) using the signal sequence trap method, *Gene*, 176: 211-4, 1996.

Harlow and Lane, *Antibodies: A Laboratory Manual*, Cold Spring Harbor Laboratory, New York, 1988.

Hartman and Mulligan, Two dominant-acting selectable markets for gene transfer studies in mammalian cells, *Proc. Natl. Acad. Sci. USA*, 85:8047-51, 1988.

Hartung et al., Inflammatory mediators in demyelinating disorders of the CNS and PNS, *J. Neuroimmunol.*, 40: 197-210, 1992.

Hauss-Wegrzyniak et al., Chronic neuroinflammation in rats reproduces components of the neurobiology of Alzheimer's disease, *Brain Research* 780-294-303 (1998).

Hayashi et al., Production and fucntion of monocyte chemoattractant protein-1 and other β-chemokines in murine glial cells, *J. Neurommunol.* 60: 143-50, 1995.

Hazum et al., A photocleavable protecting group for the thiol function of cysteine, in *Pept., Proc. Eur. Pept. Symp.*, 16th, Brunfeldt, K (Ed), pp. 105-110 (1981).

He et al., CCR3 and CCR5 are co-receptors for HIV-1 infection of microglia, *Nature*, 385: 645-49, 1997.

Helissey et al., DNA minor groove cleaving agents: synthesis, binding and strand cleaving properites of anthraquinone-oligopyrrolecarboxamide hybrids, *Anticancer Drug Res.* 11:527-51, 1996.

Hoogenhout et al., Growth pattern of tumor xenografts in wistar rats after treatment with cyclophosphamide, total lymphoid irradiation and/or cyclosporin A, *Int. J. Radiat. Oncol., Biol. Phys.* 9:871-879 (1983).

Hosaka et al., Expression of the chemokine superfamily in rheumatoid arthritis, *Clin. Exp. Immunol.*, 97:451-7, 1994.

Houghton et al., Chemotherapy of childhood rhabdomysarcomas growing as xenografts in immune-deprived mice, *Cancer Res.* 42:535-539 (1982).

Howard et al., Chemokines: progress toward identifying molecular targets for therapeutic agents, *Trends Biotechnol.*, 14: 46-51, 1996.

Hromas et al., Isolation of ALP, a novel divergent murine C chemokine with a unique carboxy terminal extension, *Biochem and Biophys Res Comm.* 258:737-740 (1999).

Hromas et al., Cloning of BRAK, a novel divergent CXC chemokine preferentially expressed in normal versus malignant cells, *Biochemical and Biophysical Res. Comm.* 255:703-706 (1999).

Hurwitz et al., Tumor necrosis factor α and transforming growth factor β upregulate astrocyte expression of monocyte chemoattractant protein-1, *J Neuroimmunol.*, 57: 193-8, 1995.

Husain et al., Complete regression of establishe human glioblastoma tumor xenograft by interleukin-4 toxin therapy, *Cancer Research* 58:3649-3653 (1998).

Huston et al., Protein engineering of antibody binding sites: recovery of specific activity in an anti-digoxin single-chain Fv analogue produced in *Escherichia coli*, *PNAS* 85:5879-5883, 1988.

Imai et al., Identification and molecular characterization of Fractalkine receptor $CX_3CR1$, which mediates both leukocyte migration and adhesion, *Cell*, 91:521-30, 1997.

Inbar et al., Localization of antibody-combing sites within the variable portions of heavy and light chains, *Proc. Nat'l Acad. Sci. USA* 69:2659-62, 1972.

Islam et al., Structure-activity studies of antitumor agents based on Pyrrolo(1,2-abenzimidazoles: new reductive alkylating DNA cleaving agents, *J. Med. Chem.* 34 2954-61, 1991.

Jager et al., Oligonucleotide N-Alkylphosphoramidates: synthesis and binding to polynucleotides, *Biochemistry* 27:7237-7246 (1988).

Janabi et al., Establishment of human microglial cell lines after transfection of primary cultures of embryonic miroglial cells with the SV40 large T antigen, *Neurosci Lett* 195: 105-8 (1995).

Jones et al., Replacing the complementarity-determining regions in a human antibody with those from a mouse, *Nature* 321:522-5, 1986.

Jose et al., Eotaxin: cloning of an eosinophil chemoattractant cytokine and increased mRNA expression in allergen-challenged guinea-pig lungs, *Biochem. Biophys. Res. Commun.*, 205: 788-94, 1994b.

Jose et al., Eotaxin: a potent eosinophil chemoattractant cytokine detected in a guinea pig model of allergic airways inflammation, *J. Exp. Med.*, 179-881-7, 1994a.

Kasama et al., Interleukin-10 expression and chemokine regulation during the evolution of murine type II collagen-induced arthritis, *J Clin. Invest.* 95:2868-2876 (1995).

Keffer et al., Transgenic mice expression human tumour necrosis factor: a predictive genetic model arthritis, *The EMBO J.* 10(13):4025-4031 (1991).

Kernova et al., Levels of some cytokines in subretinal fluid in proliferative vitreoretinopathy and rhegmatogenous retinal detachment, *Euro J of Ophthal.* 7(1):64-67 (1997).

Kim et al., Cloning and sequence analysis of another shiga-like toxin lle varient gene (*Slt-llera*) from an *Escherichia coli* R107 strain isolated from rabbit, *Microbiol. Immunol.* 41:805-8, 1997.

Kim et al., Expression of monocyte chemoattractant protein-1 and macrophage inflammatory protein-1 after cerebral ischemia in the rat, *J. Neuroimmunol.*, 56:127-34, 1995.

Kim et al., Chemokines: signal lamps for trafficking of T and B cells for development and effector function, *J of Leukocyte Biology* 65:6-15 (1999).

Koch et al., Interleukin-8 as macrophage-derived mediator of angiogenesis, *Science* 258:1798-1801 (1992).

Köhler and Milstein, Continuous cultures of fused cells secreting antibody of predefined specificity, *Nature* 256:495-7, 1975.

Kreitman and Pastan, Accumulation of a recombinant immunotoxin in a tumor *in Vivo*: fewer than 1000 molecules per cell are sufficient for complete responses, *Cancerl Research* 58:968-975 (1998).

Krucker et al., Transgenic mice with cerebral expression of human immunodeficiency virus type-1 coat protein GP120 show divergent changes is short-and long-term potentiation in CA1 hippocampus, *Neuroscience* 83(3):691-700 (1998).

Kumagai et al., Inhibition of matrix metalloproteinases prevents allergen-induced airway inflammation in a murine model of asthma, *J. of Immunology* 4212-4219 (1999).

Kunkel et al., The role chemokines in inflammatory joint disease, *J. Leukoc. Biol.*, 59: 6-12, 1996.

Ladurner et al., Glutamine, alanine or glycine repeats inserted into the loop of a protein have minimal effects on stability and folding rates, *J. Mol. Biol.* 273:330-337, 1997.

Larrick and Fry, PCR amplification of antibody genes, *Methods*, 2: 106-10, 1991.

Larsen et al., The neutrophil-activating protein (NAP-1) is also chemotactic for T lymphocytes, *Science* 243:1464-1466 (1989).

Lee et al., GM-CSF promotes proliferation of human fetal and adult microglia in primary cultures, *Glia* 12: 309-18, 1994.

Lee et al., A novel DNA cleaving agent, 2,2'-BIX(2-Aminoethyl)-4, 4'-Bithiazole, induces thymocyte apoptosis, *Biochem. Mol. Biol. Int.* 40:151-7, 1996.

Leek et al., Cytokine networks in solid human tumors: regulation of angiogenesis, *J. Leukoc. Biol.*, 56: 423-35, 1994.

Leibovich et al., Macrophage-induced angiogenesis is mediated by tumour necrosis factor-α, *Nature* 329:630-632 (1987).

Leonard et al., Human monocyte chemoattractant protein-1 (MCP-1), *Immunol. Today*, 11: 97-103, 1990.

Letsinger et al., Some developments in the phosphite-triester method for synthesis of oligonucleotides, *Tetrahedron* 40:137-143 (1984).

Lewis et al., Cytokine regulation of angiogenesis in breast cancer: the role of tumor-associated macrophages, *J. Leukoc. Biol.* 57:747-51, 1995.

Liu et al., TNF is a potent anti-inflammatory cytokine in autoimmune-mediated demyelination, *Nature Medicine* 4(1): 78-82 (1998).

Liu et al., Neuronal and glial apoptosis after traumatic spinal cord injury, *J. of Neuroscience* 17(14):5395-5406 (1997).

Logan and Shenk, Adenovirus tripartite leader sequence enhances translation of mRNAs later after infection, *Proc. Natl. Acad. Sci. USA*, 81: 3655-3659, 1984.

Losman et al., Baboon anti-idiotype antibodies mimic a carcinoembryonic antigen epitope, *Int. J. Cancer*, 46:310-314, 1990.

Lowy et al., Isolation of transforming DNA: cloning the hamster aprt gene, *Cell*, 22:817-31, 1980.

Lu and Felix, Pegylated peptides I: solid-phase synthesis of $N^a$-pegylated peptides using Fmoc strategy, *Peptide Res.*, 6: 142-6, 1993.

Lu and Felix, Pegylated peptides II, Soldi-phase synthesis of amino-,carboxy- and side-chain pegylated peptides, *Int. J. Peptide Protein Res.*, 43: 127-138, 1994.

Luckow et al., Trends in the development of baculovirus expression vectors, *Bio/technology* 6:47-55 (1988).

MacDonald et al., Spliced mRNA encoding the murine cytomegalovirus chemokine homolog predicts a β chemokine of novel structure, *J of Virology* 73(5):3682-3691 (1999).

Mackay, Chemokines: What chemokine is that? *Curr. Biol.* 7: R384-6, 1997.

Mackett et al., Vaccinia virus: a selectable eukaryotic cloning and expression vector, *Proc. Natl. Acad. Sci. USA*, 79: 7415-7419, 1982.

Mackett et al., General method for production and selection of infectious vaccinia virus recombinants expressing foreign genes, *J. Virol.*, 49: 857-864, 1984.

Mahan et al., Phase change enzyme immunoassay, *Anal. Biochem.* 162:163-170 (1987).

Maniatis et al., *Molecular Cloning: A Laboratory Manual*, Cold Spring Harbor Laboratory press, Cold Spring Harbor, NY (1982).

Maniatis et al., Labeling the 5' ends of DNA with T4 polynucleotide kinase, *Molecular Cloning: A Laboratory Manual*, Cold Spring Harbor Laboratory, New York, p. 122 (1982).

Mantyh et al., Inhibition of hyperagesia by ablation of Lamina I spinal neurons expressing the substance P receptor, *Science*, 278: 275-79, 1997.

McConlogue et al., Ornithine decarboxylase in difluoromethylornithine-resistant mouse lymphoma cells, *J of Biological Chem.* 258:(13):8384-8388 (1983).

McDonald et al., Large-scale purification and characterization of recombinant fibroblast growth factor saporin mitotoxin, *Protein Expr. and Pharm.* 9:97-108 (1996).

McIntosh, T.K., Novel pharmacologic therapies in the treatment of experimental traumatic brain injury: a review, *J. Neurotrauma*, 10: 215-61, 1993.

Mesri et al., *J. Biol. Chem.* 268:4852-62, 1993.

Miller et al., Syntheses and properties of adenine and thymine nucleoside alkyl phosphotriesters, the neutral analogs of dinucleoside monophosphates, *J. Am. Chem. Soc.* 93:6657-6665 (1971).

Millon et al., Synthesis of a new reagant, ethyl 4-azidobenzoylaminoacetimidate, and its use for RNA-protein cross-linking within *Escherichia coli* ribosomal 30-S subunits, *Eur. J. Biochem.*110:485-454.

Moody et al., *Nucl. Acids Res.* 12:4769-4782 (1989).

Mosmann, T., Rapid colorimetric assay for cellular growth and survival: application to proliferation and cytotoxicity assays, *J Immunol Methods* 65:55-63 (1983).

Mott, et al., Maximizing gene expression from plasmid vectors containing the y $P_L$ promoer: strategies for overproducing transcription termination factor p, *Proc. Natl. Acad. Sci. U.S.a.* 82:88-92 (1985).

Mühleisen et al., Reactive microglia in Creutzfeldt-Jakob disease, *Neuropathol. App. Neurobiol.*, 21:505-517, 1995.

Mulligan and Berg, Selection for animal cells that express the *Escherichia coli* gene coding for xanthine-guanine phosphoribosyltransferase, *Proc. Natl. Acad. Sci. USA*, 78: 2072-6, 1981.

Murakami et al., Structural and functional analysis of the promoter region of the human MCP-3 gene: transactivation of expression by novel recognition sequences adjacent to the transcription initiation site, *DNA Cell Biol.* 16:173-83.

Muruve et al., Adenoviral gene therapy leads to rapid induction of multiple chemokines and acute neutrophil-dependent hepatic injury in vivo, *Human Gene Therapy* 10:965-976 (1999).

Newton et al., Angiogenin single-chain immunofusions: influence of peptide linkers and spacers between fusion protein domains, *Biochemistry* 35:545-553, 1996.

Noble et al., Astrocytes and catalase prevent the toxicity of catecholamines to oligodendrocytes, *Brain Res.* 633:83-90 (1994).

Nogrady, *Medicinal Chemistry, A Biochemical Approach*, Oxford University Press, New York, pp. 375-393 (1985).

O'Hare et al., Transformation of mouse fibroblasts to methotrexate resistance by a recombinant plasmid expressing a prokaryotic dihydrofolate reductase, *Proc. Natl. Acad. Sci. USA*, 78: 1527-31, 1981.

Ogawa et al., A cytotoxic ribonuclease targeting specific transfer RNA anticodons, *Science* 283:2097-2100 (1999).

Oh et al., Astrocytes promote process outgrowth by adult human oligodendrocytes in vitro through interaction between bFGF and astrocyte extracellular matrix, *Glia* 17:237-53 (1996).

Oh et al., The promoting effects of bFGF and astrocyte extracellular matrix on process outgrowth by adult human oligodendrocytes are mediated by protein kinase, *Brain Res.* 757:236-44 (1997).

Oppenheimer-Marks et al., Interleukin 15 is produced by endothelial cells and increases the transendothelial migration of T cells in vitro and in the SCID mouse-human rheumatoid arthritis model in vivo, *J. Clin. Invest.* 101(6):1261-1272 (1998).

Orlandi et al., Cloning immunoglobulin variable domains for expression by the polymerase chain reaction, *Proc. Nat'l Acad. Sci. USA* 86:3833-7, 1989.

Oste et al., The use of *sym*-triazine trichloride in RNA-protein cross-linking studies with *Escherichia coli* ribosomal subunits, *Mol. Gen. Genet.* 168:81-86 (1979).

Pack et al., Improved bivalent miniantibodies, with identical avidity as whole antibodies, produced by high cell density fermentation of *Escherichia coli*, *Bio/Technology* 11:1271-77, 1993.

Panicali et al., Construction of poxviruses as cloning vectors: insertion of the thymidine kinase gene from herpes simplex virus into the DNA of infectious vaccinia virus, *Proc. Natl. Acad. Sci. USA*, 79: 4927-4931, 1982.

Panter et al., Alteration extracellular amino acids after traumatic spinal cord injury, *Annu. Neurol.*, 27:96-99, 1990.

Pastan et al., Recombinant toxins as novel therapeutic agents, *Annu. Rev. Biochem.* 61:331-54, 1992.

Pease et al., Microbial corruption of the chemokine system: an expanding paradigm, *Seminar in Immunol.* 10:169-178 (1998).

Peterson et al., Differential production of and migratory response to β chemokines by human microglia and astrocytes, *J. Infect. Dis.*, 175: 478-81, 1997.

Phillips et al., Transforming growth factor-α*Pseudomonas* exotoxin fusion protein (TGF-α-PE38) treatment of subcutaneous and intracranial human glioma and medulloblastoma xenografts in athymic mice, *Cancer Research* 54:1008-1015 (1994).

Pierce Chemicals "Solutions, Cross-linking of Proteins: Basic Concepts and Strategies," Seminar #12, Rockford, IL.

Pierce Catalog, Immuno Technology Catalog & Handbook, 1992-1993.

Piguet et al., Tumor necrosis factor/cachectin plays a key role in bleomycin-induced pneumopathy and fibrosis, *J. Exp. Med.* 170:655-663 (1989).

*Plant Molecular Biology*, 2d ed., Covey, S.N., Ed., Ch. 7-9, Blackie, London (1988).

Ponath et al., Cloning of the human eosinophil chemoattractant, eotaxin, *J. Clin. Invest.*, 97: 604-12, 1996.

Popovich et al., Elevation of the neurotoxin quinolinic acid occurs following spinal cord trauma, *Brain Res.*, 633: 348-52, 1994.

Porter, R.R., The hydrolysis of rabbit γ-Globulin and antibodies with crystalline papain, *Biochem. J.*, 73: 119-126, 1959.

Power et al., Neurovirulence in feline immunodeficiency virus-infected neonatal cats is viral strain specific and dependent on systemic immune suppression, *J. of Virology* 72(11):9109-9115 (1998).

Powers, J.M., 1994 AANP Presidential Symposium Presentation, Presidential Address: The pathology of peroxisomal disorders with pathogenetic considerations, *J. Neuropathol. Exp. Neurol.*, 54: 710-9, 1995.

Prendergast et al., Massive steroids do not reduce the zone of injury after penetrating spinal cord injury, *J. Trauma*, 37: 576-9, 1994.

Probert et al., Spontaneous inflammatory demyelinating disease in transgenic mice showing centralnervous system-specific expression of tumor necrosis factor α, *Proc. Natl. Acad. Sci. USA*, 92: 11294-8, 1995.

Probert et al., Dissection of the pathologies induced by transmembrane and wild-type tumor necrosis factor in transgenic mice, *J. Leukoc. Biol.*, 59: 518-25, 1996.

Proost et al., Human monocyte chemotactic proteins-2 and -3: structural and functional comparison with MCP-1, *J. Leukoc. Biol.*, 59: 67-74, 1996.

Proudfoot et al., Chemokine receptors—future therapeutic targets for HIV? *Biochem Pharmacology* 57:451-463 (1999).

Raine, C.S., Multiple sclerosis: immune system molecule expression in the central nervous system, *J. Neuropathol. Exp. Neurol.*, 53: 328-37, 1994.

Raivich et al., Increase of macrophase colony-stimulating factor and granulocyte-macrophage colony-stimulating factor receptors in the regenerating rat facial nucleus, *J. Neurosci. Res.* 30: 682-6, 1991.

Rathanaswami et al., Expression of the cytokine RANTES in human rheumatoid synovial fibroblasts, *J. Biol. Chem.* 268: 5834-9, 1993.

Redford et al., Vascular changes and demyelination induced by the intraneural injection of tumour necrosis factor, *Brain*, 118: 869-78, 1995.

Reiter et al., Recombinant Fv immunotoxins and Fv fragments as novel agents for cancer therapy and diagnosis, *Trends Biotechnol* 16(12):513-20 (1998).

Reiter et al., Antibody engineering of recombinant Fv immunotoxins for improved targeting of cancer: disulfide-stabilizing Fv immunotoxins, *Clin Can Res*. 2:245-252 (1996).

*Remington's Pharmaceutical Sciences*, 17th ed., Mack Publishing Co., Easton, Pa., 1990.

Renno et al., TNF-α expression by resident microglia and infiltrating leukocytes in the central nervous system of mice with experimental allergic encephalomyelitis, *J. Immunol.*, 154: 944-53, 1995.

Reichmann et al., Reshaping human antibodies for therapy, *Nature* 332:323-7. 1988.

Riley et al., The ecological role of bacteriocins in bacterial competition, *Trends in Microbiology* 7(3):129-133 (1999).

Rinke et al., The use of azidoarylimidoesters in RNA-protein cross-linking studies with *Escherichia coli* ribosomes, *J. Mol. Biol.* 137:301-314 (1980).

Riordan et al., Identification of the cystic fibrosis gene: cloning and characterization of complementary DNA, *Science* 245:1066-1073 (1989).

Romanic et al., Extracellular matrix-degrading proteinases in the nervous system, *Brain Pathol.*, 4: 145-46, 1994.

Rossi et al., Lungkine, a novel CXC chemokine, specifically expressed by lung bronchoepithelial cells, *J of Immunology* 5490-5497 (1999).

Rothstein, In *DNA Cloning, vol. II, A Practical Approach*, Ed. DM Glover, IRL Press, Wash., D.C., Cloning in Yeast, Chp. 3 (1986).

Routier et al., Synthesis, DNA binding, and cleaving properties of an ellipticine--salen.copper conjugate, *Bioconjug. Chem.*, 8: 789-92, 1997.

Sakai et al., Potential withdrawal of rheumatoid synovium by the induction of apoptosis using a novel in vivo model of rheumatoid arthritis, *Arthritis & Rheumatism* 41(7):1251-1257 (1998).

Sambrook et al., *Molecular Cloning, A Laboratory Manual*, Cold Spring Harbor Laboratory Press, vol. 3, p. B. 13-15 (1989).

Sambrook et al., *Molecular Cloning, A Laboratory Manual*, Cold Spring Harbor Laboratory Press, Cold Spring Harbor, NY (1989).

Sandvig and Van Deurs, Endocytosis, intracellular transport, and cytotoxic action of shigs toxin and ricin, *Physiol.* Rev. 76:949-66, 1996.

Santerre et al., Expression of prokaryotic genes for hygromycin B and G418 resistance as dominant-selection markers in mouse L cells, *Gene*, 30: 147-56, 1984.

Sarver, et al., Bovine papilloma virus deoxyribonucleic acid : a novel eucaryotic cloning vector, *Mol. Cell. Biol.* 1: 486-96, 1981.

Schall et al., Chemokines. leukocyte trafficking, and inflammation, *Current Biol.*, 6: 865-73, 1994.

Schaniel et al., Activated murine B lymphocytes and dendritic cells produce a novel CC chemokine which acts selectively on activated T cells, *J. Exp. Med.* 188(3):451-463 (1998).

Schrier et al., Role of chemokines and cytokines in a reactivation model of arthritis in rats induced by injection with streptococcal cell walls, *J . of Leukocyte Biology* 63:359-363 (1998).

Schrier et al., the effects of the nude (*nu/nu*) mutation on bleomycin-induced pulmonary fibrosis, *Am Rev Respir Dis* 12:614-617 (1983).

Seetharam et al., Increased cytotoxic activity of *Pseudomonoas* exotoxin and two chimeric toxins ending in KDEL, *J. Biol. Chem.* 266:17376-17381 (1991).

Selmaj et al., Prevention of chronic relapsing experimental autoimmune encephalomyelitis by soluable tumor necrosis factor receptor I, *J. Neuroimmunol.*, 56: 135-41, 1995.

Senter et al., Novel photocleavable protein crosslinking reagents nd their use in the preparation of antibody-toxin conjugates, *Photochem. Photobiol.* 42:231-237 (1985).

Shirozu et al., Structure and chromosomal localization of the human stromal cell-derived factor 1 (SDF1) gene, *Genomics*, 28: 495-500, 1995.

Shirozu et al., Characterization of novel secreted and membrane proteins isolated by the signal sequence trap method, *Genomics*, 37: 273-80, 1996.

Singer et al., Optimal humanization of 1B4, an anti-CD18 murine monoclonal antibody, is achieved by correct choice of human V-region framework sequences, *J. Immunol.* 150:2844-67, 1993.

Sippy et al., Increased expression of tumor necrosis factor-α receptors in the brains of patients with AIDS, *J. Acquir. Defic. Syndr. Hum. Retrovirol.*, 10: 511-21, 1995.

Skibo et al., Structure-activity studies of benzimidazole-based DNA-cleaving agents. Comparison of benzimidazole, pyrrolobenzimidazole, and tetrahydropyridobenzimidazole analogues, *J. Med. Chem.* 37:78-92, 1994.

Skinner et al., Inhibition of prokaryotic translation by the Shiga toxin enzymatic subunit, *Microb. Pathog.* 24:117-22, 1998.

Skinner et al., Investigation of ribosome binding by the shiga toxin A1 subunit, using competition and site-directed mutagenesis, *J. of Bacteriology* 179(4):1368-1374 (1997).

Smarda et al., Colicins -- exocellular lethal proteins, *Folia Microbiol (Praha)* 43:563-82 (1998).

Smith et al., Diacerhein treatment reduces the severity of osteoarthritis in the canine cruciate-deficiency model of osteoarthritis, *Arthritis Rheum* 42:545-54 (1999).

Smith, M. E., Phagocytosis of myelin by microglia in vitro, *J. Neurosci. Res.*, 35: 480-587, 1993.

Sobel, R.A., The pathology of multiple sclerosis, *Neurol. Clin.*, 13: 1-21, 1995.

Soliven and Szuchet, Signal transduction pathways in oligodendrocytes: role of tumor necrosis factor-α, *Int. J. Dev. Neurosci.*, 13: 351-67, 1995.

Sorensen et al., Expression of specific chemokines and chemokine receptors in the central nervous system of multiple sclerosis patients, *J. of Clin Investg.* 103(6):807-815 (1999).

Sozzani et al., Receptor expression and responsiveness of human dendritic cells to a defined set of CC and CXC chemokine, *J. Immunol.*, 159: 1993-2000, 1997.

Sperling et al., Photochemical cross-linking of histones to DNA in nucleosomes, *Nucleic Acids Res.* 5:2755-2773 (1978).

Stastny et al., The use of daunomycin-antibody immunoconjugates in managing soft tissue sarcomas: nude mouse xenograft model, *Cancer Res.* 53:5740-5744 (1993).

Stec et al., Synthesis and absolute configuration of P-chiral O-isopropyl oligonucleotide triesters, *Tetrehedron Letts.* 26:2191-2194 (1985).

Stein, In: *Phosphorothioate Oligodeoxynucleotide Analogues*, Chapter 5, Cohen, Ed., Macmillan Press, London, pp. 97-117 (1989).

Steinhauser et al., IL-10 is a major mediator of sepsis-induced impairment in lung antibacterial host defense, *J. of Immunology* 392-399 (1999).

Steitz et al., Mapping of MCP-1 functional domains by peptide analysis and site-directed mutagenesis, *FEBS Lett.* 430:158-64 (1998).

Stirpe et al., Ribosome-inactivating proteins from plants: present status and future prospects, *Bio/Technology* 10:405-12, 1992.

Strieter et al., The good, the bad, and the ugly, The role of chemokines in models of human disease, *J. Immunol.*, 156:3583-86, 1997.

Stuve et al., Interferon β-1b decreases the migration of T lymphocytes in vitro: effects onmatrix metalloproteinase-9, *Ann Neurol.* 40:853-63 (1996).

Stuve et al., Chemokine-enhanced migration of human peripheral blood mononuclear cells is antagonized by interferon β-1b through an effect on matrix metalloproteinase-9, *J. Neuroimmunol* 80:38-46 (1997).

Sullenger et al., Tethering ribozymes to a retroviral packaging signal for destruction of viral RNA, *Science* 262:1566-1569 (1994).

Sun et al. Expression of chemokine genes in rat glial cells: the effect of myelin basic protein-reactive encephalitogenic T cells, *J. Neurosci. Res.*, 48: 192-200, 1997.

Sunderkötter et al., Macrophages and angiogenesis, *J. Leukoc. Biol.*, 55: 410-22, 1994.

Suzumura et al., Interleukin-4 induces proliferation and activation of microglia but suppresses their induction of class II major histocompatibility complex antigen expression, *J. Neuroimmunol.*, 53: 209-18, 1994.

Szybalska and Szybalski, Genetics of human cell lines, IV, DNA-mediated heritable transformation of a biochemical trait, *Proc. Natl. Sci. USA*, 48:2026-30, 1962.

Takamatsu et al., Expression of bacterial chloramphenicol acetyltransferase gene in tobacco plants mediate dby TMV-RNA, *EMBO J.* 6:307-311, 1987.

Takami et al., Induction of macrophage inflammatory protein MIP-1 α mRNA on glial cells after focal cerebrial ischemia in the rat, *Neurosci. Lett.*, 227: 173-6, 1997.

Tanabe et al., Functional expression of the CXC-chemokine receptor-4/fusin on mouse microglial cells and astrocytes, *J. Immunol.* 159:905-11, 1997.

Tanaka et al., Proteoglycans on endothelial cells present adhesion-inducing cytokines to leukocytes, *Immunology Today*, 14: 111-15, 1993.

Taoka et al., Spinal cord injury in the rat, *Progress in Neurobiology* 56:341-358 (1998).

Tashiro et al., Signal sequence trap: a cloning strategy for secreted proteins and Type I membrane proteins, *Science* 261:600-603 (1993).

Taub et al., Chemokines, inflammation and immune system, *Ther. Immunol.*, 1: 229-46, 1994.

The Molecular Biology of the Yeast Saccharomyces, Eds, Strathern et al., Cold Spring Harbor Press, vol. I and II, 1982.

Thorpe et al., New coupling agents for the synthesis of immunoctoxins containing a hindered disulfide bond with improved stability *in Vitro*, *Cancer Res.* 47:5924-5931 (1987).

Toggas et al., Central nervous system damage produced by expression of the HIV-1 coat protein gp120 in transgenic mice, *Letters to Nature* 188-192 (1993).

Tyor et al., A model of human immunodeficiency virus encephalitis in *scid* mice, *Proc. Natl. Acad. Sci. USA* 90:8658-8662 (1993).

Ueda et al., Chemically synthesized SDF-1 α analogue, N33A, is a potent chemotactic agent for CXCR4/Fusion/LESTR-expressing humanleukocytes, *J. Biol. Chem.*, 272: 24966-70, 1997.

Unno et al., Synthesis and biological evaluation of novel cyclic enediyne compounds related to dynemicin A as antitumor agents, *Chem. Pharm. Bull.* 45: 125-33, 1997.

Unno et al., Structure-activity relationships of cyclic enediynes related to dynemicin A-I, Synthesis and antitumor activity of 9-acetoxy enediynes equipped with aryl carbamate moieties, *Bioorg. Med. Chem.*, 5: 883-901, 1997.

Unno et al., Structure-activity relationships of cyclic enediynes related to dynemicin A--II, Synthesis and antitumor activity 0f 9- and 12-substituted enediynes equipped with aryl carbamate moieties, *Bioorg. Med. Chem.*, 5: 903-19, 1997.

Van Meir, Cytokines and tumors of the central nervous system, *Glia*, 15:264-88, 1995.

Vanin et al., p-Azidophenylglyoxal: a heterobifunctional photosensitive reagent, *FEBS Lett.* 124:89-92 (1981).

Vannucci et al., Rat model of perinatal hypoxic-ischemic brain damage, *J. of Neuroscience Res.* 55: 158-163 (1999).

Verhoeyen et al. Reshaping human antibodies: grafting an antilysozyme activity, *Science* 239: 1534-6, 1988.

Vialard et al., Synthesis of the membrane fusion and hemagglutinin proteins of measles virus, using a novel baculovirus vector containing the β-galactosidase gene, *J. Virol.* 64:37-50 (1990).

Vieira et al., The pUC plasmids, an M13mp7-derived system for insertion mutagenesis and sequencing with synthetic universal primers, *Gene* 19:259-268 (1982).

Viliger et al., Production of monocyte chemoattractant protein-1 by inflamed synovial tissue and cultured synoviocytes, *J. Immunol.*, 149: 722-27, 1992.

von Luettichau et al., Rantes chemokines expression in diseased and normal human tissues, *Cytokines*, 8:89-98.

Walden et al., Major histocompatibility complex-restricted and unrestricted activation of helper T cell lines by liposome-bound antigens, *J. Mol. Cell Immunol.* 2 :191-197 (1986).

Walz et al., Purification and amino acid sequencing of NAF, a novel neutrophil-activating factor produced by monocytes, *Biochem. Biophys. Res. Commun.* 149:755 (1987).

Wang et al., Produced expression of interferon-inducible protein-10 in ischemic cortex after permanent occlusion of the middle cerebral artery in rat, *J. of Neurochemistry* 71(3):1194-1204 (1998).

Watson et al., *Molecular Biology of the Gene*, 4th Edition, The Benjamin/Cummings Pub. Co., p. 224 (1987).

Wawrzynczak et al., Molecular and biological properties of an abrin A chain immunotoxin designed for therapy of human small cell lung cancer, *Br. J. Cancer* 66:361-366 (1992).

Weber et al., Monocyte chemotactic protein MCP-2 activates human basophil and eosinophil leukocytes similar to MCP-3', *J. Immunol.*, 154: 4166-72, 1995.

Weinberg, Antibodies to OX-40 (CD134) can identify and eliminate autoreactive T cells: implications for human autoimmune disease, *Molecular Medicine Today* 76-83 (1998).

Weller et al., Retinal microglia: a new cell in idiopathic proliferative vitreoretinopathy?, *Exp. Eye Res.*, 53: 275-81, 1991

Wellhoner et al., Uptake and concentration of bioactive macromolecules by K562 cells via the transferrin cycle utilizing an acid-labile transferrin conjugate, *J. Biol. Chem.* 266:4309-4314 (1991).

Westmoreland et al., Chemokine receptor expression on resident and inflammatory cells in the brain of macaques with simian immunodeficiency virus encephalitis, *American J. of Pathology* 152:659-665 (1998).

Whitlow, M. et al., An improved linker for single-chain Fv with reduced aggregation and enhanced proteolytic stability, *Protein Engineering* 6:989-995, 1993.

Whitlow and Filpula, Single-chain FV proteins and their fusion proteins, *Methods*, 2:97-105, 1991.

Wigler et al., Transfer of purified herpes virus thymidine kinase gene to cultured mouse cells, *Cell*, 11: 223,32, 1977.

Wigler et al., DNA-mediated transfer of the adenine phosphoribosyltransferase locus into mammalian cells, *Proc. Natl. Acad. Sci. USA* 76:1373-1376 (1979).

Wigler et al., Transformation of mammalian cells with an amplifiable dominant-acting gene, *Proc. Natl. Acad. Sci. USA*, 77: 3567-70, 1980.

Wool et al., Ribotoxin recognition of ribosomal RNA and a proposal for the mechanism of translocation, *TIBS* 17:266-269 (1992).

Wykrzykowska et al., Early regeneration of thymic progenitors in *Rhesus macaques* infected with simina immunodeficiency virus, *J. Exp. Med.* 187(11):1767-1778 (1999).

Xu et al., Human recombinant monocyte chemotactic protein and other c-c chemokines bind and induce directional migration of dendritic cells in vitro, *J. Leukoc. Biol.*, 60:365-71, 1996.

Xu et al., DNA damage produced by enediynes in the human phosphoglycerate kinase gene in vivo: esperamicin A1 as a nucleosome footprinting agent, *Biochemistry* 37:1890-7, 1998.

Yeager et al., Neutron diffraction analysis of the structure of rod photoreceptor membranes in intact retinas, *J. Mol. Biol.* 137:315-318 (1980).

Yen et al., Synthesis of water-soluble copolymers containing photocleavable bonds, *Makromol. Chem.* 190:69-82 (1989).

Yi et al., CXCR-4 is expressed by primary macrophages and supports CCR5-independent infection by dual-tropic but not T-tropic isolates of human immunodeficiency virus Type 1, *J. Virol.*, 72: 772-7, 1998.

Yong et al., In *Protocols for Neural Cell Culture*(A. Richardson and S. Fedoroff, eds.), Humana Press, St. Louis, Chapter 11, 157-172 (1997).

Zajicek et al., Interactions between oligodenrocytes and microglia, *Brain* 115: 1611-31, 1992.

Zollman et al., Purification of recombinant shiga-like toxin Type I A, fragment from *Escherichia coli*, *Protein Expr. Purif* 5:291-5 (1994).

Abstract No. XP000881561, P. Roby, et al., Melanoma-specific cytotoxicity of a human MGSA/GROalpha C-terminal peptide conjugated to daunorubicin, *Oncology Reports*, 3:1777-178 discussion (1996).

Abstract No. XP000881538, Ray, E., et al., Receptor mediated endocytosis of IL-B: a fluorescent microscopic evidence and implication of the process in ligand induced biological response in human neutrophils, *Cytokine*, 9(8):587-569 (1997).

al-Jaufy, A.Y., et al., Purification and characterization of a Shiga toxin A subunit-CD4 fusion protein cytotoxic to human immunodeficiency virus-infected cells, *Infect. Immun.*, 63:3073-8 (1995).

al-Jaufy, A.Y., et al., Cytotoxicity of a shiga toxin A subunit-CD4 fusion protein to human immunodeficiency virus-infected cells, *Infect. Immun.*, 62:956-60 (1994).

Albini et al., HIV-1 tat protein mimicry of chemokines, *Proc. Natl. Acad. Sci. USA* 95:13153-13158 (1998).

Baldwin, G.C., et al., *Blood*, 11:3279-82 (1993).

Barbieri, L., et al., Polynucleotideadenosine glycosidase activity of ribosome-inactivating proteins: effect on DNA, RNA and poly(A), *Nucleic Acids Res.*, 25:518-22 (1997).

Barthelemy, I., et al., The expression of saporin, a ribosome-inactivating protein from the plant *Saponaria officinalis*, in *Escherichia coli*, *J. Biol. Chem.*, 268:6541-8 (1993).

Battelli, M.G., et al., Toxicity of ribosome-inactivating proteins-containing immunotoxins to a human bladder carcinoma cell line, *Int. J. Cancer*,65:485-90 (1996).

Beall, C.J., et al., Site-directed mutagenesis of monocyte chemoattractant protein-I identifies two regions of the polypeptide essential for biological activity, *Biochem. J.*,313:633-40 (1996).

Benveniste, E.N., Cytokine circuits in brain. Implications for AIDS dementia complex, *Res. Publ. Assoc. Res. Nerv. Ment. Dis.*, 72:71-89 (1994).

Bergamaschi, G., et al., Saporin, a ribosome-inactivating protein used to prepare immunotoxins, induces cell death via apoptosis, *Br. J. Haematol.*, 93:789-94 (1996).

Bolognesi, A., et al., New ribosome-inactivating proteins with polynucleotideadenosine glycosidase and antiviral activities from *Basella rubra* L. and *Bougainvillea spectabillis*, *Willd. Planta*, 203:422-9 (1997).

Bolognesi, A., et al., Induction of apoptosis by ribosome-inactivating proteins and related immunotoxins, *Int. J. Cancer*,68:349-55.

Bonini, J.A., et al., Cloning, expression, and chromosomal mapping of a novel human CC-chemokine receptor (CCR10) that displays high-affinity binding for MCP-1 and MCP-3, *DNA Cell Biol.*,16:1249-56 (1997).

Book, A.A., et al., 192 IgG-saporin: 2. Neuropathology in the rat brain, *Acta Neuropathol.*,89:519-26 (1995).

Book, A.A., et al., 192 IgG-saporin: I. specific lethality for cholinergic neurons in the basal forebrain of the rat, *J. Neuropathol. Exp. Neurol.*, 53: 95-102 (1994).

Boulay, J.L., et al., The interleukin-4 family of lymphokines, *Curr. Opin. Immunol.*, 4:294-8 (1992).

Brigotti, M., et al., The RNA-N-glycosidase activity of Shiga-like toxin I:kinetic parameters of the native and activated toxin, *Toxicin.*,35:1431-7 (1997).

Brinkman, U., et al., Immunotoxins against cancer, *Biochim. Biophys. Acta*,1198:27-45 (1994).

Challita-Eid, P.M., et al., A RANTES-antibody fusion protein retains antigen specificity and chemokine function, *J. Immunol.*,161:3729-36 (1998).

Chandler, J.C., et al., Genetic engineering of immunotoxins, *Semin. Pediatr. Surg.*,5:206-11 (1996).

Chandler, L.A., et al., Targeting tumor cells via EGF receptors: selective toxicity of an HBEGF-toxin fusion protein, *Int. J. Cancer*,78:106-11 (1998).

Christie, R.H., *J. Neuropthol. Exp. Neurol.*,55:491-8 (1996).

Christophers, E., et al., Psoriasis: mechanisms and entry points for possible therapeutic inverventions, *Australas J. Dermatol.*, 37 Suppl. 1:S4-6 (1996).

Clark-Lewis, I., et al., Structure-activity relationships of chemokines, *J. Leukoc. Biol.*, 57:703-11 (1995).

Crowe, S.M., GM-CSF and its effects on replication of HIV-1 in cells of macrophage lineage, *J. Leukoc. Biol.*, 62:41-8 (1997).

Debinski, W., et al., An immunotoxin with increased activity and homogeneity produced by reducing the number of lysine residues in recombinant Pseudomonas exotoxin, *Bioconjug. Chem.*, 5:40-6 (1994).

Essand, M., et al., Anti-prostate immunotoxins:cytotoxicity of E4 antibody-Pseudomonas exotoxin constructs, *Int. J. Cancer*, 77:123-7 (1998).

Gebicke-Haerter, P.J., et al., Rat microglial interleukin-3, *J. Neuroimmunol.*, 50:203-14 (1994).

Ghetie, V., et al., *Pharmac. Ther.*, 63:209-34 (1994).

Giulian, D., et al., The role of mononuclear phagocytes in wound healing after traumatic injury to adult mammalian brain, *J. Neurosci.*,9 :4416-29 (1989).

Glabinski, A.R., et al., Central nervous system chemokine mRNA accumulation follows initial leukocyte entry at the onset of acute murine experimental autoimmune encephalomyelitis, *Brain Behav. Immun.*, 9:315-30 (1995).

Gonzalo et al., Eosinophil recruitment to the lung in a murine model of allergic inflammation, *J. Clin. Invest.* 98(10):2332-2345 (1996).

Gottlieb, S.L., et al., Response to psoriasis to a lymphocyte-selective toxin (DAB389IL-2) suggests a primary immune, but not keratinocyte, pathogenic basis, *Nat. Med. 1*:442-7 (1995).

Hoang, T., et al., *J. Biol. Chem.*, 268:11881-7 (1993).

Husain, S.R., et al., Complete regression of establilshed human glioblastoma tumor xenograft by interleukin-4 toxin therapy, *Cancer Res.*,58:3649-53 (1998).

Jose, P.J., et al., Eotaxin: cloning of an eosinophil chemoattractant cytokine and increased mRNA expression in allergen-challenged guinea-pig lungs, *Biochem. Biophys. Res. Commun.*, 205:788-94 (1994).

Keppler-Hafkemeyer, et al., Role of caspases in immunotoxin-induced apoptosis of cancer cells, *Biochemistry*, 37:16934-42 (1998).

King, C.R., et al., The performance of e23(Fv)PEs, recombinant toxins targeting the erbB-2 protein, *Semin. Cancer Biol.*, 7:79-86 (1996)

Kloss, C.U., et al., Proliferation of ramified microglia on as astrocyte monolayer: characterization of stimulatory and inhibitory cytokines, *J. Neurosci Res.*, 49:248-54 (1997).

Kreitman, R.J., et al., Recombinant toxins containing human granulocyte-macrophage colony-stimulating factor and either pseudomonas exotoxin or diphtheria toxin kill gastrointestinal cancer and leukemia cells, *Blood*, 90:252-9 (1997).

Lappi, D.A., et al., Expression and activities of a recombinant basis fibroblast growth factor-saporin fusion protein, *J. Biol. Chem.*, 269:12552-8 (1994).

Lappi, D.A., et al., Characterization of a saporin mitotoxin specifically cytotoxic to cells bearing the granulocyte-macrophage colony-stimulating factor-receptor, *Growth Factors*,9:31-9 (1993).

Lappi, D.A., et al., Mitotoxin: growth factor-targeted cytotoxic molecules, *Prog. Growth Factor Res.*,2:223-36 (1990).

Lee, S.C., et al., Cytokine production by human fetal microglia and astrocytes. Differential induction by lipopolysaccharide and IL-I beta *J. Immunol.*, 150:2659-67 (1993).

MacDonald et al., Spliced mRNA encoding the murine cytomegalovirus chemokine homolog predicts a β chemokine of novel structure, *J. of Virology* 73(5):3682-3691 (1999).

Mantyh, P.W., et al., Inhibition of hyperalgesia by ablation of lamina spinal neurons expressing the substance P receptor, *Science*, 278:275-9 (1977).

Matsumoto et al., Pivotal role of interleukin-8 in the acute respiratory distress syndrome and cerebral reperfusion injury, *J. of Leukocyte Biology* 62:582 (1997).

Mayne, M., et al., HIV-I tat molecular diversity ad induction of TNF-alpha : implications for HIV-induced neurological disease, *Neuroimmunomodulation*, 5:184-92 (1988).

McDonald, J.R., et al., Large-scare purification and characterization of recombinant fibroblast growth factor-saporin mitotoxin, *Protein Expr. Purif.*,8:97-108 (1996).

Mock and Pugsley, The BtuB group Col plasmids and homology between the colicins they encode, *J. of Bacteriology* 150(3):1069-1076 (1982).

Novella, A., et al., Expression of adhesion molecules and functional stimulation in human neutrophils: modulation by GM-CSF and role of the Bcr gene, *Br. J. Haematol.*, 98:621-6 (1997).

P. Roby, et al., Melanoma-specific cytotoxicity of a human MGSA/GROalpha C-terminal peptide conjugated to daunorubicin, *Oncology Reports*,3:175-179 (1996).

Panchagnula, R., et al., Monoclonal antibodies in drug targeting, *J. Clin. Pharm. Ther.*,22:7-19 (1997).

Puri, R.K., et al., Preclinical development of a recombinant toxin contaiing circularly permuted interleukin 4 and truncated Pseudomonas exotoxin for therapy of malignant astrocytoma, *Cancer Res.*,56:5631-7 (1996).

Puri, R.K., et al., Targeting of interleukin-13 receptor on human renal cell carcinoma cells by a recombinant chimeric protein composed of interleukin-13 and a truncated form of Pseudomonas exotoxin A (PE38QQR), *Blood*,87:4333-9 (1996).

Ransohoff, R.M., et al., Chemokines and chemokine receptors in model neurological pathologies:molecular and immunocytochemical approaches, *Methods Enzymol.*,287:319-48 (1997).

Ray, E., et al., Receptor mediated endocytosis of IL-8: a fluorescent microscopic evidence and implication of the process in ligand induced biological response in human neutrophils, *Cytokine*,9(8):587-569 (1997).

Reiter, Y., et al., Peptide-specific killing of antigen-presenting cells by a recombinant antibody-toxin fusion protein targeted to major histocompatibility complex/peptide class I complexes with T cell receptor-like specificity, *Proc. Natl. Acad. Sci.*, 94:4631-6 (1997).

Roncuzzi, L., et al., DNA-nuclease activity of the single-chain ribosome-inactivating proteins dianthin 30, saporin 6 and gelonin, *FEBS Lett.*,392:16-20 (1996).

Rosemuller, H., et al., Treatment of acute myelocytic leukemia with interleukin-6 Pseudomonas exotoxin fusion protein in a rat leukemia model, *Leukemia*,10:1796-803 (1996).

Rossner, S., et al., Cholinergic immunolesions by 192IgG-saporin--useful tool to simulate pathogenic aspects of Alzheimer's disease, *Int. J. Dev. Neurosci.*,18:835-50 (1997).

Rozemuller, H., et al., Sensitivity of human acute myeloid leukaemia to diphtheria toxin-GM-CSF fusion protein, *Br. J. Haematol.*, 98:952-9 (1997).

Rucker et al., Utilization of chemokine receptors, orphan receptors, and herpesvirus-encoded receptors by diverse human and simian immunodeficiency viruses, *J. of Virology* 71(12):8999-9007 (1997).

Satyamurthy, P., et al., *Proteins: structure, function and genetics*,19:340-2 (1994).

Schall, T.J., et al., Chemokines, leukocyte trafficking, and inflammation, *Curr. Opin. Immunol.*,6:865-73 (1994).

Sibille and Reynolds, Macrophages and polymorphonuclear neutrophils in lung defense and injury, *Am. Rev. Respir. Dis.* 141:471-501 (1990).

Siegall, C.B., et al., Targeted toxins as anticancer agents, *Cancer*, 74:1006-12 (1994).

Silbert, D.I., Glycosaminoglycans of bovine aorta endothelial cells: Identification and localization by use of a platelet factor 4-fluorescein probe, *Journal of Histochemistry and Cytochemistry*, 38(4):589-593 (1990).

Skinner, L.M., et al., Investigation of ribosome binding by the Shiga toxin A1 subunit, using competition and site-directed mutagenesis, *J. Bacteriol.*, 179:1368-74 (1997).

Skinner, L.M., et al., Inhibition of prokaryotic translation by the Shiga toxin enzymatic subunit, *Microb. Pathog.* 24 :117-22 (1998).

Steitz, S.A., et al., Mapping of MCP-1 functional domains by peptide analysis and site-directed mutagenesis, *FEBS Lett.*, 430:158-64 (1998).

Stirpe, F., et al., Ribosome-inactivating proteins from plant:present status and future prospects, *Biotechnology*(NY), 10:405-12 (1992).

Strieter and Kunkel, Acute lung injury the role of cytokines in the elicitation of neutrophils, *J. of Investigative Medicine* 42(40:640 (1994).

Suh, J.K., et al., Shiga toxin attacks bacterial ribosomes as effectively as eucaryotic ribosomes, *Biochemistry*,37:9394-8 (1998).

Suzumura, A., et al., Interleukin-4 induces proliferation and activation of microglia but suppresses their induction of class II major histocompatibility complex antigen expression, *J. Neuroimmunol.*, 53:209-18 (1994).

Tesh, V.L., et al., Purified Shiga-like toxins induce expression of proinflammatory cytokines from murein peritoneal macrophages, *Infect. Immun.*, 62:5085-94 (1994).

Van Damme, E.J., et al., Type I ribosome-inactivating proteins are the most abundant proteins in iris (*Iris hollandica* var. Professor Blaauw) bulbs: characterization and molecular cloning, *Biochem. J.*, 324:963-70 (1997).

Van Oijen, M.G., et al., Rationale for the use of immunotoxins in the treatment of HIV-infected humans, *J. Drug Target*, 5:75-91 (1998).

Ward, S.G., et al., Chemokines: understanding their role in T-lymphocyte biology, *Biochem J.*, 333:457-70 (1998).

Waurzyniak, B., et al., In vivo toxicity, pharmacokinetics, and antileukemic activity of TXU (Anti-CD7)-pokeweed antiviral protein immunotoxin, *Clin. Cancer Res.*,3:881-90 (1997).

Welbourn and Young, Endotoxin, septic shock and acute lung injury: neutrophils, macrophages and inflammatory mediators, *Br. J. Surg.* 79:998-1003 (1992).

Wiley, R.G. et al., Destruction of neurokinin-I receptor expressing cells in vitro and in vivo using substance P-saporin in rats, *Neurosci. Lett.*, 230:97-100 (1997).

Wiley, R.G., et al., Targeting toxins to neural antigens and receptors, *Semin. Cancer Biol.*, 7:71-7 (1996).

Windsor et al., Role of the neutrophil in adult respiratory distress syndrome, *Br. J. Surg.* 80:10-17 (1993).

Wu, M., et al., Are immunoconjugates useful for therapy with autoimmune diseases?, *Int. J. Immunopharmacol.*, 19:83-93 (1997).

Yang, D., et al., Recombinant heregulin-Pseudomonas exotoxin fusion proteins:interactions with the heregulin receptors and anti-tumor activity in vivio, *Clin. Cancer Res.*, 4:993-1004 (1998).

Ying et al., Enhanced expression of eotaxin and CCR3 mRNA and protein in atopic asthma. Association with airway hyperresponsiveness and predominant co-localization of eotaxin mRNA to bronchial epithelial and endothelial cells, *Eur. J. Immunol.* 27:3507-3516 (1997).

Yoshie, O., et al., Novel lymphocyte-specific CC chemokines and their receptors, *J. Leukoc. Biol.*, 62:634-44 (1997).

Youle, R.J., et al., Immunotoxins for central nervous system malignancy, *Semin. Cancer Biol.*, 7:65-70 (1996).

Zurawski, G., et al., Interleukin 13 elicits a subset of the activities of its close relative interleukin 4, *Stem Cells*(*Dayt*), 12:169-74 (1994).

Database STN Abstract Caesar accession no. 1900, citing Shemyakin et al., "Construction and expression in *Escherichia coli* cells of the fusion protein diphtheria toxin human interleukin 2", *Mol. Biol.* 26:1088-1098 (1992).

Meneghetti and LeMaistre, "Initial clinical experiences with an interleukin-2 fusion toxin", *Targeted Diagn. Ther.* 7(*Genet. Eng. Toxins*):395-401 (1992).

Nagpal and Chandraratna, "New dermatological agents for the treatment of psoriasis", *Annu. Rep. Med. Chem.* 32:201-210 (1997)

Ralph, P., "Clinical and preclinical studies presented at the Keystone Symposium on arthritis, related diseases, and cytokines", *Lympokine and Cytokine Research* 12:261-263 (1993).

Ray and Samanta, "Receptor mediated endocytosis of IL-8: A fluorescent microscopic evidence and implication of the process in ligand-induced biological response in human neurophils", *Cytokine* 9 :587-596 (1997).

Roberge et al., "Selective immunosuppression of activated T cells with the chimeric toxin IL-2-PE40", *J. Immunol.* 143:3498-3502 (1989).

Roby and Page, "Melanoma-specific cytotoxicity of a human MGSA/Groα C-terminal peptide conjugated to daunorubicin" *Oncology Reports* 3:175-179 (1996).

Strom et al., "Interleukin-2 receptor-directed therapies: Antibody- or cytokine-based targeting molecules", *Annu. Rev. Med.* 44: 343-353 (1993).

Callard, R. and A. Gearing. *The Cytokine Facts Book* San Diego: Academic Press. 1994. p. 3.

Coles et al., "Monoclonal Antibody Treatments Exposes Three Mechanisms Underlying the Clinical Course of Multiple Sclerosis," *Ann. Neurol.* 46:296-304 (1999).

Gong et al., "RANTES and MCP-3 Antagonists Bind Multiple Chemokine," *The Journal to Biological Chemistry* 271: 10521-10527 (1996).

Huitinga et al. "Supression of Experimental Allergic Encephalomyelitis in Lewis Rats After Elimination of Macrophages," *J. Exp. Med.* 172: 1025-1033 (1990).

McDonald et al., "The therapeutic potential of chemokine-toxin fusion proteins," *IDrugs* 4(4): 427-442 (2001).

Ofulue, A.F. and M. Ko. "Effects of depletion of neuriphils or macrophages on development of cigarette smoked-induced emphysema," *Am. J. Physiol.* 277(Lung Cell. Mol. Physiol. 21):L97-L105 (1999).

Paolillo et al., "Quantitative MRI in patients with secondary progressive MS treated with monoclonal antibosy Campath 1H," *Neurology* 53: 751-757 (1999).

Popovich et al. "Depletion of Hematogenous Macrophages Promotes Partial Hindlimb Recovery and Neuroanatomical Repair after Experimental Spinal Cord Injury," *Experimental Neurology* 158: 351-365 (1999).

Pouvreau et al. "Effect of macrophage depletion by liposomes containing dichloromethylene-diphosphonate on endotoxin-induced uveitis," *J. Neuroimmunol.* 86(2): 171-181 (1998).

Sandhu, Protein engineering of antibodies, *Crit. Rev. Biotech.* 12:437-62, 1992.

Roby et al. "Cell-binding and growth-stimulating activities of the C-terminal part of human MGSA/Groalpha", Biochem. Biophys. Res. Comm. 206:792-798; (1995).

Agostini et al., "Immune effector cells in idiopathic pulmonary fibrosis", *Curr Opin Pulm Med*, 3:348-355 (1997).

Anderson et al., "Neutrophil elastase inhibitors as treatments of emphysema and chronic bronchitis", *Curr Opin Antiinflamm Immunomod Invest Drugs*, 1:29-38 (1999).

Arimilli et al., "Chemokines in autoimmune diseases", *Immunological Rev*, 177:43-51 (2000).

Barnes, P.J., "Chronic obstructive pulmonary disease: new opportunities for drug development", *Trends Pharmacol Sci*, 19:415-423 (1998).

Barone et al., "Inflammatory mediators and stroke: new opportunities for novel therapeutics", *J Cereb Blood Flow Metab*, 19:819-834 (1999).

Barrera et al., "Synovial Macrophage Depletion with Clodronate-containing Liposomes in Rheumatoid Arthritis", *Arthritis Rheum*, 43:1951-1959 (2000).

Bellanti, J.A., "Cytokines and allergic disease: clinical aspects", *Allergy Asthma Proc*, 19:337-41 (1998).

Bellingan, G., "Inflammatory cell activation in sepsis", *Br Med Bull*, 55:12-29 (1999).

Belperio et al., "CXC chemokines in angiogenesis", *J Leukoc Biol*, 68:1-8 (2000).

Benveniste, E.N., "Role of macrophages/microglia in multiple sclerosis and experimental allergic encephalomyelitis", *J Mol Med*, 75:165-173 (1997).

Blair et al., "HIV-1 entry-an expanding portal for drug discovery", *Drug Discov Today*, 5:183-194 (2000).

Boismenu et al., "Insights from mouse models of colitis", *J Leukoc Biol*, 67:267-278 (2000).

Bonifati et al., "Cytokines in psoriasis", *Int J Dermatol*, 38:241-51 (1999).

Brühl et al., "Depletion of CCR5-Expressing Cells with Bispecific Antibodies and Chemokine Toxins: A New Strategy in the Treatment of Chronic Inflammatory Diseases and HIV", *J Immunol*, 166:2420-2426 (2001).

Buechler et al., "Synthesis and characterization of a homogeneous chemical conjugate between basic fibroblast growth factor and saporin", *Eur J Biochem*, 234:706-713 (1995).

Camp et al., "In situ cytokine production by breast cancer tumor-infiltrating lymphocytes", *Ann Surg Oncol*, 3:176-184 (1996).

Capeans et al., "C—C chemokines in the vitreous of patients with proliferative vitreoretinopathy and proliferative diabetic retinopathy", *Retina*, 18:546-550 (1998).

Carlson et al., "Acute inflammatory response in spinal cord following impact injury", *Exp Neurol*, 151:77-88 (1998).

Carteron, N.L., "Cytokines in rheumatoid arthritis: trials and tribulations", *Mol Med Today*, 6:315-323 (2000).

Czaplewski et al., "Identification of Amino Acid Residues Critical for Aggregation of Human CC Chemokines Macrophage Inflammatory Protein (MIP)-1α, MIP-β, and RANTES", *J Biol Chem*, 274:16077-16084 (1999).

DeGraba, T.J., "The role of inflammation after acute stroke: utility of pursuing anti- adhesion molecule therapy", *Neurology*, 51:S62-S68 (1998).

DiSepio et al., "Novel approaches for the treatment of psoriasis", *Drug Discov Today*, 4:222-231 (1999).

Downey et al., "Mechanisms of acute lung injury", *Curr Opin Pulm Med*, 3:234-241 (1997).

Edwards et al., "Sustained improvement in rheumatoid arthritis following a protocol designed to deplete B lymphocytes", *Rheumatology*, 40:205-211 (2000).

El Khoury et al., "Microglia, scavenger receptors, and the pathogenesis of Alzheimer's disease", *Neurobiol Aging*, 19:S81-S84 (1998).

El Khoury et al., "Scavenger receptor-mediated adhesion of microglia to beta-amyloid fibrils", *Nature*, 382:716-719 (1996).

Emilie et al., "Cytokines and chemokines in HIV infection: implications for therapy", *Int Rev Immunol*, 16:705-726 (1998).

Esser et al., "Intercellular adhesion molecule-1 levels in plasma and vitreous from patients with vitreoritinal disorders", *Ger J Ophthalmol*,4:269-274 (1995).

Esser et al., "Macrophages in proliferative vitreoretinopathy and proliferative diabetic retinopathy: differentiation of subpopulations", *Br J Ophthalmol*, 731-733 (1993).

Faunce et al., "Neutrophil chemokine production in the skin following scald injury", *Burns*, 25:403-410 (1999).

Ferrara et al., "Pathophysiologic mechanisms of acute graft-vs.-host disease", *Biol Blood Marrow Transplant*, 5:347-356 (1999).

Feuerstein et al., "The role of cytokines in the neuropathology of stroke and neurotrauma", *Neuroimmunomodulation*, 5:143-159 (1998).

Fox et al., "Innate immunity and graft rejection", *Immunol Rev*, 173:141-147 (2000).

Frankel et al., "Targeted Toxins", *Clin Cancer Res*, 6:326-334 (2000).

Fry, D.E., "Sepsis syndrome", *Am Surg.*, 66:126-132 (2000).

Gasparini, G., "The rationale and future potential of angiogenesis inhibitors in neoplasia", *Drugs*, 58:17-38 (1999).

Gerard et al., "Chemokines and disease", *Nature Immunol*, 2:108-115 (2001).

Gerli et al., CD30+ T cells in rheumatoid synovitis: mechanisms of recruitment and functional role, *J Immunol*, 164:4399-4407 (2000).

Gerszten et al., "Chemokines, leukocytes, and atherosclerosis", *J Lab Clin Med*, 13:687-692 (2000).

Ghirnikar et al., "Chemokine antagonist infusion attenuates cellular infiltration following spinal cord contusion injury in rat", *J Neurosci Res*, 59:63-73 (2000).

Ghirnikar et al., "Chemokine expression in rat stab wound brain injury", *J Neurosci Res*, 46:727-733 (1996).

Ghirnikar et al., "Inflammation in traumatic brain injury: role of cytokines and chemokines", *Neurochem Res*, 23:329-340 (1998).

Gipson et al., "Regulatory effects of endogenous protease inhibitors in acute lung inflammatory injury", *J Immunol*, 162:3653-3662 (1999).

Glabinskiet al., "Chemokine monocyte chemoattractant protein-1 is expressed by astrocytes after mechanical injury to the brain", *J Immunol*, 156:4363-4368 (1996).

Gordon et al., "Rat Xenograft Survival in Mice Treated with Donor-specific Transfusion and Anti-CD 154 Antibody is Enhanced by Elimination of Host CD4+Cells", *Transplantation*, 71:319-327 (2001).

Griffioen et al., "Angiogenesis: potentials for pharmacologic intervention in the treatment of cancer, cardiovascular diseases, and chronic inflammation", *Pharmacol Rev*, 52:237-268 (2000).

Gutierrez-Ramos et al., "Non-redundant functional groups of chemokines operate in a coordinate manner during the inflammatory response in the lung", *Immunolog Rev*, 177:31-42 (2000).

Hillet al., "The role of cytokines in acute graft-versus-host disease", *Cytokines Cell Mol Ther*, 3:257-266 (1997).

Hintzen et al., "Analysis of effector CD4 (OX-40+) and CD8 (CD45RA+CD27) T lymphocytes in active multiple sclerosis", *Acta Neurol Scand*, 101:57-60 (2000).

Honget al., "Coexpression of cyclooxygenase-2 and matrix metalloproteinases in human aortic atherosclerotic lesions", *Yonsei Med J*, 41:82-88 (2000).

Huang et al., "Chemokines and chemokine receptors in inflammation of the nervous system: manifold roles and exquisite regulation", *Immunol Rev*, 177:52-67 (2000).

Hunter et al., "BB-10010: An Active Variant of Human Macrophage Inflammatory Protein-1α With Improved Pharmaceutical Properties", *Blood* 86:4400-4408 (1995).

Inoue et al., "Interleukin 8 expression regulates tumorigenicity and metastases in androgen-independent prostate cancer", *Clin Cancer Res*, 6:2104-2119 (2000).

Isaksson et al., "Expression of ICAM-1 and CD11b after experimental spinal cord injury in rats", *J Neurotrauma*, 16:165-173 (1999).

Janabi et al., "Establishment of human microglial cell lines after transfection of primary cultures of embryonic microglial cells with the SV40 large T antigen", *Neurosci Lett*, 195:105-108 (1995).

Kaneko et al., "Circulating levels of beta-chemokines in systemic lupus erythematosus", *J Rheumatol*, 26:568-573 (1999).

Karasek, M.A., "Progress in our understanding of the biology of psoriasis", *Cutis*, 64:319-322 (1999).

Karima et al., "The molecular pathogenesis of endotoxic shock and organ failure", *Mol Med Today*, 5:123-132 (1999).

Kelley et al., "Cytokines in pathogenesis of systemic lupus erythematosus", *Semin Nephrol*, 19:57-66 (1999).

Kelley et al., "The molecular role of mast cells in atherosclerotic cardiovascular disease", *Mol Med Today*, 6:304-308 (2000).

Kolioset al., "Mediators of inflammation: production and implication in inflammatory bowel disease", *Hepatogastroenterology*, 45:1601-1609 (1998).

Konig et al., "Mig, GROalpha and RANTES messenger RNA expression in lining layer, infiltrates and different leucocyte populations of synovial tissue from patients with rheumatoid arthritis, psoriatic arthritis and osteoarthritis", *Virchows Arch*, 436:449-458 (2000).

Kreitman, R.J., "Immunotoxins in cancer therapy", *Curr Opin Immunol*, 11:570-578 (1999).

Krietman et al., "A circularly permuted recombinant interleukin 4 toxin with increased activity", *Proc Natl Acad Sci U.S.A.*, 91:6889-6893 (1994).

Kunkel et al., "The role of chemokines in the immunopathology of pulmonary disease", *Forum(Genoval)*, 9:339-355 (1999).

Lin et al., "Inflammatory cytokines and cell response in surgery", *Surgery*, 127:117-126 (2000).

Loetscher et al., "Chemokines and their receptors in lymphocyte traffic and HIV infection", *Adv Immunol*, 74:127-180 (2000).

MacDermott et al., "The central role of chemokines (chemotactic cytokines) in the immunopathogenesis of ulcerative colitis and Crohn's disease", *Inflamm Bowel Dis*, 54-67 (1998).

Mahida, Y.R., "The key role of macrophages in the immunopathogenesis of inflammatory bowel disease", *Inflamm Bowel Dis*, 6:21-33 (2000).

Martinez et al., "Cytokines in human lung fibrosis", *Arch Toxicol Suppl*, 18:127-139 (1996).

McGeer et al., "The importance of inflammatory mechanisms in Alzheimer disease", *Exp Gerontol*, 33:371-378 (1998).

Meda et al., "Beta-amyloid (25-35) peptide and IFN-gamma synergistically induce the production of the chemotactic cytokine MCP-1/JE in monocytes and microglial cells", *J Immunol*, 157:1213-1218 (1996).

Menzies-Gow et al., "Eosiophil chemokines and their receptors: an attractive target in asthma?", *Lancet*, 355:1741-1743 (2000).

Miller et al., "Inhibition by leukocyte depletion of neointima formation after balloon angioplasty in a rabbit model of restenosis", *Cardiovascular Res*, 49:838-850 (2001).

Mohammed et al., "Clinical aspects and treatment of chronic obstructive pulmonary disease", *Curr Opin Antiinflamm Immunomod Invest Drugs*, 1:21-28 (1999).

Moreland et al., "Interleukin-2 Diphtheria Fusion Protein ($DAB_{486}IL$-2) In Refractory Rheumatoid Arthritis", *Arthritis Rheum*, 38:1177-1186 (1995).

Murphy et al., "New strategies for preventing graft-versus-host disease", *Curr Opin Immunol*, 11:509-515 (1999).

Muruve et al., "Adenoviral gene therapy leads to rapid induction of multiple chemokines and acute neutrophil-dependent hepatic injury in vivo", *Hum Gene Ther*, 10:965-976 (1999).

Nelson et al., "Chemokines, Chemokine Receptors, and Allograft Rejection", *Immunity*, 14:377-386 (2001).

Pantoni et al., "Cytokines and cell adhesion molecules in *Cerebral ischemia*: experimental bases and therapeutic perspectives", *Arterioscler Thromb Vasc Biol*, 18:503-513 (1998).

Pouvreau et al., "Effect of macrophage depletion by liposomes containing dichloromethylene-diphosphonate on endotoxin-induced uveitis", *J Neuroimmunol*, 86:171-181 (1998).

Proudfoot et al., "The strategy of blocking the chemokine system to combat disease", *Immunology Rev*, 177:246-256 (2000).

Puri et al., "Preclinical Development of a Recombinant Toxin Containing Circularly Permuted Interleukin 4 and Truncated *Pseudomonas* Exotoxin for Therapy of Malignant Astrocytoma", *Cancer Res*, 56:5631-5637 (1996).

Rajan et al., "Experimental Autoimmune Encephalomyelitis on the SJL Mouse: Effect of γδ T Cell Depletion on Chemokine and Chemokine Receptor Expression in the Central Nervous System", *J Immunol*, 164:2120-2130 (2000).

Rankin et al., "Eotaxin and eosinophil recruitment: implications for human disease", *Mol Med Today*, 6:20-27 (2000).

Ransohoff, R.M., "Mechanisms of inflammation in MS tissue: adhesion molecules and chemokines", *J Neuroimmunol*, 98:57-68 (1999).

Rudick et al., "Selecting relapsing remitting multiple sclerosis patients for treatment: the case for early treatment", *J Neuroimmunol*, 98:22-28 (1999).

Sakaguchi et al., "Cytokine production by T cells infiltrating in the eye of uveitis patients", *Jpn J Ophthalmol*, 42:262-268 (1998).

Salcedo et al., "Human endothelial cells express CCR2 and respond to MCP-1: direct of MCP-1 in angiogenesis and tumor progression", *Blood* 96:34-40 (2000).

Sampson, A.P., "The role of eosinophils and neutrophils in inflammation", *Clin Exp Allergy*, 30 Suppl 1:22-27 (2000).

Schrohenloher et al., "Suppression of *in vitro* IgM Rheumatoid Factor Production by Diphtheria Toxin Interleukin 2 Recombinant Fusion Protein ($DAB_{486}$IL-2) in Patients with Refractory Rheumatoid Arthritis", *J Rheumatol*, 23:1845-1848 (1996).

Sedlacek et al., "Matrix metalloproteinase MMP-19 (RASI-1) is expressed on the surface of activated peripheral blood mononuclear cells and is detected as an autoantigen in rheumatoid arthritis", *Immunobiol*, 198:408-423 (1998).

Segerer et al., "Chemokines, Chemokine Receptors, and Renal Disease: From Basic Science To Pathophysiologic and Therapeutic Studies", *J Am Soc Nephrol*, 11:152-176 (2000).

Shapiro, S.D., "The macrophage in chronic obstructive pulmonary disease", *Am J Respir Crit Care Med*, 160:S29-S32 (1999).

Sheridan et al., "Death in the burn unit: sterile multiple organ failure", *Burns*, 24:307-311 (1998).

Strieter et al., "Chemokines in ling injury: Thomas A. Neff Lecture", *Chest*, 116:103S-110S (1999).

Struyf, et al., "Cutting Edge: Enhanced Anti-HIV-1 Activity and Altered Chemotactic Potency of $NH_2$-Terminally Processed Macrophage-Derived Chemokine (MDC) Imply an Additional MDC Receptor", *J Immunol*, 161:2672-2675 (1998).

Sullivan et al., "The role of inflammation in vascular diseases", *J Leukoc Biol*, 6:591-602 (2000).

Szekanecz et al., "Angiogenesis in rheumatoid arthritis: pathogenic and clinical significance", *J Investig Med*, 46:27-41 (1998).

Szekanecz et al., "Temporal expression of inflammatory cytokines and chemokines in rat adjuvant-induced arthritis", *Arthritis Rheum*, 43:1266-1277 (2000).

Takahashi et al., "The Participation of IL-8 in the Synovial Lesions at an Early Stage of Rheumatoid Arthritis", *Tohoku J Exp Med*, 188:75-87 (1999).

Taoka et al., "Role of neutrophils in spinal cord injury in the rat", *Neuroscience*, 79:1177-1182 (1997).

Teran, L.M., "CCL chemokines and asthma", *Immunol Today*, 21:235-242 (2000).

Terui et al., "Role of neutrophils in induction of acute inflammation in T-cell mediated immune dermatosis, psoriasis: a neutrophil-associated inflammation-boosting loop", *Exp Dermatol*, 9:1-10 (2000).

Tesar et al., "Cytokines and adhesion molecules in renal vasculitis and lupus nephritis", *Nephrol Dial Transplant*, 13:1662-1667 (1998).

Trapp et al., "Pathogenesis of tissue injury in MS lesions", *J Neuroimmunol*, 98:49-56 (1999).

Uckun et al., "Pharmacokinetic Features, Immunogenicity, and Toxicity of B43(anti-CD19)-Pokeweed Antiviral Protein Immunotoxin in Cynomolgus Monkeys", *Clin Cancer Res*, 3:325-337 (1997).

Verma et al., "Chemokines in acute anterior uveitis", *Curr Eye Res*, 16:1202-1208 (1997).

Wang et al., "Chemokines and their role in tumor growth and metastasis", *J Immunol Methods*, 220:1-17 (1998).

Wang et al., "Identification and molecular characterization of rat CXCR3: receptor expression and interferon-inducible protein-10 binding are increased in focal stroke", *Mol Pharmacol*, 57:1190-1198 (2000).

Watanabe et al., "Atherosclerosis and inflammtion mononuclear cell recruitment and adhesion molecules with reference to the implication of ICAM-1/LFA-1 pathway in atherogenesis", *Int J Cardiol*, 66 Suppl 1 :S45-S53 (1998).

Weber et al., "Deletion of the $NH_2$-Terminal Residue Converts Monocyte Chemotactic Protein 1 from an Activator of Basophil Mediator Release to Eosinophil Chemoattractant", *J Exp Med*, 183:681-685 (1996).

Weidemann et al., "Proteolytic processing of the Alzheimer's disease amyloid precursor protein within its cytoplasmic domain by caspase-like proteases", *J Biol Chem*, 274:5823-5829 (1999).

Weinberg et al., "Blocking OX-40/OX-40 Ligand Interaction In Vitro and In Vivo Leads to Decreased T Cell Function and Amelioration of Experimental Allergic Encephalomyelitis", *J Immunol*, 162:1818-1826 (1999).

Whalen et al., "Reduced brain edema after traumatic brain injury in mice deficient in P- selection and intercellular adhesion molecule-1", *J Leukoc Biol*, 67:160-168 (2000).

Williams et al., "Structure/Function Analysis of Interleukin-2-Toxin ($DAB_{486}$-IL -2)", *J Biol Chem*, 265:11885-11889 (1990).

Williams et al., "Immunocytochemical appearance of cytokines, prostaglandin $E_2$ and lipocortin-1 in the CNS during the incubation period of murine scrapie correlates with progressive PrP accumulations", *Brain Res*, 754:171-180 (1997).

Williams et al., "Biology of Adult Human Microglia in Culture: Comparisons with Peripheral Blood Monocytes and Astrocytes", *J Neuropathol Exp Neurol*, 51(5):538-549 (1992).

Williams et al., "Chemokine regulation of neutrophil function in surgical inflammation", *Arch Surg*, 134:1360-1366 (1999).

Wu et al., "Mechanisms of leukocyte trafficking into the CNS", *J Neuroviral*, 6 Suppl 1:S82-S85 (2000).

Wuyts, et al., "Isolation of the CXC chemokines ENA-78, GROα and GROγ from tumor cell and leukocytes reveals $NH_2$-terminal heterogeneity", *Eur J Biochem*, 260:421-429 (1999).

Wuyts, et al., "$NH_2$ - and COOH-Terminal Truncations of Murine Granulocyte Chemotactic Protein-2 Augment in In Vitro and In Vivo Neutrophil Chemotactic Potency", *J Immunol*, 163:6155-6163 (1999).

Xia et al., "Chemokines/chemokine receptors in the central nervous system and Alzheimer's disease", *J Neuroviral*, 5:32-41 (1999).

Xia et al., "Immunohistochemical study of the beta-chemokine receptors CCR3 and CCR5 and their ligands in normal and Alzheimer's disease brains", *Am J Pathol*, 153:31-37 (1998).

Yang et al., "Macrophages and MHC class II positive cells in the choroid during endotoxin induced uveitis", *Br J Ophthalmol*, 81:396-401 (1997).

Yong et al., "Interferon beta in the treatment of multiple sclerosis: mechanisms of action", *Neurol*, 51:682-689 (1998).

Yu et al., "Anti-CD3ε F(ab')$_2$ Prevents Graft-Versus-Host Disease by Selectively Depleting Donor T Cells Activated by Recipient Alloantigens", *J Immunol*, 166:5835-5839 (2001).

Zheng et al., "Intracelluar CXCR4 signaling, neuronal apoptosis and neuropathogenic mechanisms of HIV-1-associated dementia", *J Neuroimmunol*, 98:185-200 (1999).

Zhang-Hoover et al., "A critical role for alveolar macrophages in elicitation of pulmonary immune fibrosis", *Immunol*, 101:501-511 (2000).

Zito et al., "Depletion of systemic macrophages by liposome-encapsulated clodronate attenuates striatal macrophage invasion and neurodegeneration following local endotoxin infusion in gerbils", *Brain Res*, 892:13-26 (2001).

EMBL database ID HS1301003, Accession No. AA505654 for chemokine (Lingkine), Jul. 4, 1997.

Holzer et al., "A fusion protein of IL-8 and a Fab antibody fragment binds to IL-8 receptors and induces neutrophil activation", *Cytokine* 8:214-221 (1996).

Ippoliti et al., "A chimeric saporin-transferrin conjugate compared to ricin toxin: role of the carrier in intracellular transport and toxicity", *FASEB J.* 9: 1220-1225 (1995).

Peeters et al. "Comparison of four bifunctional reagents for coupling peptides to proteins and the effect of the three moieties on the immunogenicity of the conjugates", *Journal of Immunological Methods 120*: 133-143 (1989).

Chandler LA, Sosnowski BA, McDonald JR, Price JE, Aukerman SL, Baird A, Pierce GF, Houston LL, "Targeting tumor cells via EGF receptors: selective toxicity of an HBEGF-toxin fusion protein", *Int J Cancer*. Sep. 25, 1998; 78(1) :106-11.

Adamus et al., "Similar pattern of MCP-1 expression in spinal cords and eyes of Lewis rats with experimental autoimmune encephalomyelitis associated anterior uveitis," Journal of Neuroscience Research 50: 531-538 (1997).

Amerio et al., "Eotaxins and CCR3 receptor in inflammatory and allergic skin diseases: therapeutical implications," Current Drug Targets—Inflammation & Allergy 2(1): 81-94 (2003).

Badolato et al., "Interleukin-15 (IL-15) induces IL-8 and monocyte chemotactic protein 1 production in human monocytes," Blood 90(7): 2804-2809 (1997).

Baggiolini, M., "Chemokines in pathology and medicine," Journal of Internal Medicine 250: 91-104 (2001).

Barnes et al., "Polyclonal antibody directed against human RANTES ameliorates disease in the Lewis rat adjuvant-induced arthritis model," J. Clin. Invest. 101(12): 2910-2919 (1998).

Batra, "Anti-Tac(Fv)-PE40, a single chain antibody Pseudomonas fusion protein directed at interleukin 2 receptor bearing cells," Journal Of Biological Chemistry 265(25): 15198-15202 (1990).

Boring et al., "Molecular cloning and functional expression of murine JE (monocyte chemoattractant protein 1) and murine macrophage inflammatory protein 1 alpha receptors: evidence for two closely linked C—C chemokine receptors on chromosome 9," The Journal of Biological Chemistry 271(13): 7551-7558 (1996).

Boring et al., "Impaired monocyte migration and reduced type I (Th1) cytokine responses in C—C chemokine receptor 2 knockout mice," J Clin Invest 100: 2552-2561 (1997).

Braman, S.S. and F.J. Martinez, "COPD: Awareness, early diagnosis, and intervention CME/CE," Live Web Conference, Nov. 17, 2005, www.medscape.com, 31 pages.

Chan et al., "Reactivity of murine cytokine fusion toxin, diphteria toxin$_{390}$-murine interleukin-3 (DT$_{390}$-mIL-3), with bone marrow progenitor cells," Blood 88: 1445-1456 (1996).

Charo, I.F. and M.B. Taubman, "Chemokines in the pathogenesis of vascular disease," Circulation Research 95: 858-866 (2004).

Chiang et al., "Macrophage/microglial-mediated primary demyelination and motor disease induced by the central nervous system production of interleukin-3 in transgenic mice," J. Clin. Invest. 97(6): 1512-1524 (1996).

Couser et al., "Sensitized cells come of age: a new era in renal immunology with important therapeutic implications," J. Am Soc. Nephrol. 10: 664-665 (1999).

De Klerck et al., "Pro-inflammatory properties of stromal cell-derived factor-1 (CXCL12) in collagen-induced arthritis," Arthritis Research & Therapy 7: R1208-R1220 (2005).

Debinski et al., "Human glioma cells overexpress receptors for interleukin 13 and are extremely sensitive to a novel chimeric protein composed of interleukin 13 and pseudomonas exotoxin," Clinical Cancer Research 1: 1253-1258 (1995).

Frankel et al., "Characterization of a ricin fusion toxin targeted to the interleukin-2 receptor," Protein Engineering 9(10):913-919 (1996).

Fryer et al., "Neuronal eotaxin and the effects of CCR3 antagonist on airway hyperactivity and M2 receptor dysfunction," The Journal of Clinical Investigation 116(1): 228-236 (2006).

Fujinaka et al., "Suppression of anti-glomerular basement membrane nephritis by administration of anti-monocyte chemoattractant protein-1 antibody in WKY rats,", J Am Soc Nephrol 8: 1174-1178 (1997).

Hu et al., "Depletion of T lymphocytes with immunotoxin retards the progress of experimental allergic encephalomyelitis in rhesus monkeys," Cellular Immunology 177: 26-34 (1997).

Hur et al., "Macrophage Activation Syndrome in a Child with Systemic Juvenile Rheumatoid Arthritis," J Korean Med Sci 20: 695-8 (2005).

Hvas et al., "Perivascular T cells express the pro-inflammatory chemokine RANTES mRNA in multiple sclerosis lesions," Scand. J. Immunol. 46: 195-203 (1997).

Johnson et al., "Chemokine inhibition—why, when, where, which, and how?" Biochemical Society Transactions 32(2): 366-377 (2004).

Kaartinen et al., "Extracellular mass cell granules carry apolipoprotein B-100-containing lipoproteins into phagocytes in human arterial intima. Functional coupling of exocytosis and phagodytosis in neighboring cells," Arteriosclerosis, thrombosis, and vascular biology 15: 2047-2054 (1995).

Kaartinen et al., "Mast cells in rupture-prone areas of human coronary atheromas produce and store TNF-α," Circulation 94: 2787-2792 (1996).

Kaikita et al., "Targeted deletion of CC chemokine receptor 2 attenuates left ventricular remodeling after experimental myocardial infarction," American Journal of Pathology 165(2): 439-447 (2004).

Kreitman, R.J. and I. Pastan, "Recombinant toxins containing human granulocyte-macrophage colony-stimulating factor and either pseudomonas exotoxin or diphtheria toxin kill gastrointestinal cancer and leukemia cells," Blood 90(1):252-259 (1997).

Lavaud et al., "Early influx of glomerular macrophages precedes glomerulosclerois in the obese Zucker rat model," J Am Soc Nephrol 7(12): 2604-2615 (1996).

Leek et al., "Association of macrophage infiltration with angiogenesis and prognosis in invasive breast carcinoma," Cancer Research 56: 4625-4629 (1996).

Linton et al., "Proatherogenic Role for NK Cells Revealed," Arterioscler Thromb Vasc Biol 24: 992-994 (2003).

Makita et al., "Effect of anti-macrophage migration inhibitory factor antibody on lipopolysaccharide-induced pulmonary neutrophil accumulation," Am J Respir Crit Care Med 158: 573-579 (1998).

Mansfield et al., "Recombinant RFB4 immunotoxins exhibit potent cytotoxic activity for CD22-bearing cells and tumors," Blood 90(5): 2020-2026 (1997).

Matsumoto et al., "Common T cell receptor clonotype in lacrimal glands and labial salivary glands from patients with Sjögren's syndrome," J Clin Invest 97(8): 1969-1977 (1996).

Matsumura et al., "Neutral endopeptidase 24.11 in neutrophils modulates protective effects of natriuretic peptides neutrophils-induced endothelial cytotoxity," J Clin Invest 97(10): 2192-2203 (1996).

Metcalfe et al., Mast Cells, Physiological Reviews 77(4): 1033-1079 (1997).

Middleton et al., "Leukocyte extravasation: chemokine transport and presentation by the endothelium," Blood 100(12): 3853-3860 (2002).

Mörner et al., "Primary human immunodeficiency virus type 2 (HIV-2) isolates, like HIV-1 isolates, frequently use CCR5 but show promiscuity in coreceptor usage," Journal of Virology 73(3): 2343-2349 (1999).

Moser, B. and P. Loetscher, "Lymphocyte traffic control by chemokines," Nature Immunology 2(2): 123-128 (2001).

Murdoch et al., "Mechanisms regulating the recruitment of macrophages into hypoxic areas of tumors and other ischemic tissues," Blood 104(8): 2224-2234 (2004).

Ofulue et al., "Time course of neutrophil and macrophage elastinolytic activities in cigarette smoke-induced emphysema," Am J Physiol 275(6 Pt 1):L1134-44 (1998).

Ogata et al., "The role of monocyte chemoattractant protein-1 (MCP-1) in the pathogenesis of collagen-induced arthritis in rats," Journal of Pathology 182: 106-114 (1997).

Pawluczyk, I.Z. and K.P.G. Harris, "Macrophages promote prosclerotic responses in cultured rat mesangial cells: a mechanism for initiation of glomerulosclerosis," J Am Soc Nephrol 8: 1525-1536 (1997).

Qin et al., "The chemokine receptors CXCR3 and CCR5 mark subsets of T cells associated with certain inflammatory reactions," J Clin Invest 101: 746-754 (1998).

Rastaldi et al., "Adhesion molecules expression in noncrescentic acute post-streptococcal glomerulonephritis," J Am Soc Nephrol 7: 2419-2427 (1996).

Rep et al., "Treatment with depleting CD4 monoclonal antibody results in a preferential loss of circulating naive T cells but does not affect IFN-gamma secreting TH1 cells in humans," J Clin Invest 99(9):2225-31 (1997).

Sakane et al., "Etiopathology of Behcet's Disease Immunological Aspects," Yonsei Medical Journal 38(6): 350-358 (1997).

Sallusto et al., "Selective expression of eotaxin receptor CCR3 by human T helper 2 cells," Science 277: 2005-2007 (1997).

Sansores et al., "Effect of exposure of guinea pigs to cigarette smoke on elastolytic activity of pulmonary macrophages," CHEST 112: 214-219 (1997).

Schuh et al., "Intrapulmonary targeting of RANTES/CCL5-responsive cells prevents chronic fungal asthma," Eur J Immunol 33: 3080-3090 (2003).

Shapiro, S.D., "The Macrophage in Chronic Obstructive Pulmonary Disease," Am J Respir Crit Care Med 160: S29-S32 (1999).

Speyer et al., "Novel chemokine responsiveness and mobilization of neutrophils during sepsis," American Journal of Pathology 165(6): 2187-2196 (2004).

Stout, R.D. and J. Suttles, "T Cell Signaling of Macrophage Function in Inflammatory Disease," Frontiers in Bioscience 2: d197-206 (May 1, 1997).

Takada et al., "Increased serum levels of interferon-gamma-inducible protein 10 and monokine induced by gamma interferon in patients with haemophagocytic lymphohistiocytosis," Clin Exp Immunol 133: 448-453 (2003).

Tangirala et al., "Regulation of expression of the human monocyte chemotactic protein-1 receptor (hCCR2) by cytokines," Journal of Biological Chemistry 272(12): 8050-8056 (1997).

Teixeira et al., "Chemokine-induced eosinophil recruitment. Evidence of a role for endogenous eotaxin in an vivo allergy model in mouse skin," J Clin Invest 100: 1657-1666 (1997).

Tetley, T.D., "Macrophages and the Pathogenesis of COPD," CHEST 121: 156S-159S (2002).

Tran et al., "Immune invasion of the central nervous system parenchyma and experimental allergic encephalomyelitis, but not leukocyte extravasation from blood, are prevented in macrophage-depleted mice," Journal of Immunology 161: 3767-3775 (1998).

Vallera et al., "Anti-graft-versus-host disease effect of $DT_{390}$-anti-CD3sFv, a single-chain Fv fusion immunotoxin specifically targeting the CD3 epsilon moiety of the T-cell receptor," Blood 88(6): 2342-2353 (1996).

Vallera et al., "Renal dysfunction accounts for the dose limiting toxicity of $DT_{390}$anti-CD3sFv, a potential new recombinant anti-GVHD immunotoxin," Protein Engineering 10(9): 1071-1076 (1997).

Wada et al., "Intervention of crescentic glomerulonephritis by antibodies to monocyte chemotactic and activating factor (MCAF/MCP-1)," FASEB J 10: 1418-1425 (1996).

Weisberg et al., "CCR2 modulates inflammatory and metabolic effects of high-fat feeding," The Journal of Clinical Investigation 116(1): 115-124 (2006).

Xu et al., "Chronic inflammation in fat plays a crucial role in the development of obesity-related insulin resistance," J Clin Invest 112: 1821-1830 (2003).

Youngs et al., "Chemokines induce migrational responses in human breast carcinoma cell lines," Int J Cancer 71: 257-266 (1997).

Zoja et al., "Renal expression of monocyte chemoattractant protein-1 in lupus autoimmune mice," J Am Soc Nephrol 8: 720-729 (1997).

Zwacka et al., "$CD4^+$ T-lymphocytes mediate ischemia/reperfusion-induced inflammatory responses in mouse liver," J Clin Invest 100(2): 279-289 (1997).

Hatakeyama,M., "Helicobacter pylori CagA—a bacterial intruder conspiring gastric carcinogenesis," International Journal of Cancer, published online Mar. 23, 2006 (e-pub).

Hesselgesser et al., "Identification and Characterization on the CXCR4 Chernokine Receptor in Human T Cell Lines: Ligand Binding, Biological Activity, and HIV-1 Infectivity," J. Immunol. 160: 877-883 (1998).

Richmond et al., "How do chernokine/chernokine receptor activations affect tumorigenesis?" Novartis Found Symp. 256: 74-89, discussion 89-91, 106-11, 266-9 (2004) [PubMed Abstract only].

Sehgal et al., "Molecular Characterization of CXCR-4: A Potential Brain Tumor-Associated Gene," Journal of Surgical Oncology 69: 239-248 (1998).

Signoret et al., "Phorbol Ester and SDF-1 Induce Rapid Endocytosis and Down Modulation of the Chernokine Receptor CXCR4," The Journal of Cell Biology 139(3): 651-664 (1997).

\* cited by examiner

```
Amino                                              Carboxy
Terminus                                           Terminus
┌─────────────┬─────────────┬─────────────┐
│   LIGAND    │   LINKER    │    TOXIN    │
└─────────────┴─────────────┴─────────────┘
```

With One Of The Amino Acid Sequences Of The Type Listed In Table 3

With The Amino Acid Sequence of Saporin-6, or Another Toxin Sequence Of The Type Listed In Table 4

FIG. 1A

```
┌─────────────┬─────────────┬─────────────┐
│    TOXIN    │   LINKER    │   LIGAND    │
└─────────────┴─────────────┴─────────────┘
```

FIG. 1B

```
┌────────┬────────┬────────┬────────┬────────┐
│ LIGAND │ LINKER │ TOXIN  │ LINKER │ LIGAND │
└────────┴────────┴────────┴────────┴────────┘
```

FIG. 1C

SEQUENCE LISTING

```
<160> NUMBER OF SEQ ID NOS: 93

<210> SEQ ID NO 1
<211> LENGTH: 5
<212> TYPE: PRT
<213> ORGANISM: Artificial Sequence
<220> FEATURE:
<223> OTHER INFORMATION: homo sapien - peptide linker for use in
      conjugates

<400> SEQUENCE: 1

Gly Gly Gly Gly Ser
1               5

<210> SEQ ID NO 2
<211> LENGTH: 5
<212> TYPE: PRT
<213> ORGANISM: Artificial Sequence
<220> FEATURE:
<221> NAME/KEY: REPEAT
<222> LOCATION: (1)...(5)
<223> OTHER INFORMATION: homo sapien - peptide linker for use in
      conjugates

<400> SEQUENCE: 2

Gly Gly Gly Gly Ser
 1               5

<210> SEQ ID NO 3
<211> LENGTH: 12
<212> TYPE: PRT
<213> ORGANISM: Artificial Sequence
<220> FEATURE:
<223> OTHER INFORMATION: homo sapien - peptide linker for use in
      conjugates
```

```
<400> SEQUENCE: 3

Gly Lys Ser Ser Gly Ser Gly Ser Glu Ser Lys Ser
 1               5                  10

<210> SEQ ID NO 4
<211> LENGTH: 14
<212> TYPE: PRT
<213> ORGANISM: Artificial Sequence
<220> FEATURE:
<223> OTHER INFORMATION: homo sapien - peptide linker for use in
      conjugates

<400> SEQUENCE: 4

Gly Ser Thr Ser Gly Ser Gly Lys Ser Ser Glu Gly Lys Gly
 1               5                  10

<210> SEQ ID NO 5
<211> LENGTH: 18
<212> TYPE: PRT
<213> ORGANISM: Artificial Sequence
<220> FEATURE:
<223> OTHER INFORMATION: homo sapien - peptide linker for use in
      conjugates

<400> SEQUENCE: 5

Gly Ser Thr Ser Gly Ser Gly Lys Ser Ser Glu Gly Ser Gly Ser Thr
 1               5                  10                  15

Lys Gly

<210> SEQ ID NO 6
<211> LENGTH: 14
<212> TYPE: PRT
<213> ORGANISM: Artificial Sequence
<220> FEATURE:
<223> OTHER INFORMATION: homo sapien - peptide linker for use in
      conjugates

<400> SEQUENCE: 6

Gly Ser Thr Ser Gly Ser Gly Lys Ser Ser Glu Gly Lys Gly
 1               5                  10

<210> SEQ ID NO 7
<211> LENGTH: 18
<212> TYPE: PRT
<213> ORGANISM: Artificial Sequence
<220> FEATURE:
<223> OTHER INFORMATION: homo sapien - peptide linker for use in
      conjugates

<400> SEQUENCE: 7

Gly Ser Thr Ser Gly Ser Gly Lys Pro Gly Ser Gly Glu Gly Ser Thr
 1               5                  10                  15

Lys Gly

<210> SEQ ID NO 8
<211> LENGTH: 14
<212> TYPE: PRT
<213> ORGANISM: Artificial Sequence
<220> FEATURE:
<223> OTHER INFORMATION: homo sapien - peptide linker for use in
      conjugates

<400> SEQUENCE: 8

Glu Gly Lys Ser Ser Gly Ser Gly Ser Glu Ser Lys Glu Phe
 1               5                  10
```

```
<210> SEQ ID NO 9
<211> LENGTH: 5
<212> TYPE: PRT
<213> ORGANISM: Artificial Sequence
<220> FEATURE:
<223> OTHER INFORMATION: homo sapien - peptide linker for use in
      conjugates

<400> SEQUENCE: 9

Ser Arg Ser Ser Gly
 1               5

<210> SEQ ID NO 10
<211> LENGTH: 5
<212> TYPE: PRT
<213> ORGANISM: Artificial Sequence
<220> FEATURE:
<223> OTHER INFORMATION: homo sapien - peptide linker for use in
      conjugates

<400> SEQUENCE: 10

Ser Gly Ser Ser Cys
 1               5

<210> SEQ ID NO 11
<211> LENGTH: 28
<212> TYPE: PRT
<213> ORGANISM: diphtheria toxin trypsin sensitive linker

<400> SEQUENCE: 11

Ala Met Gly Arg Ser Gly Gly Cys Ala Gly Asn Arg Val Gly Ser
 1               5                  10                  15

Ser Leu Ser Cys Gly Gly Leu Asn Leu Gln Ala Met
            20                  25

<210> SEQ ID NO 12
<211> LENGTH: 6
<212> TYPE: PRT
<213> ORGANISM: homo sapien
<220> FEATURE:
<221> NAME/KEY: REPEAT
<222> LOCATION: (3)...(3)
<223> OTHER INFORMATION: repeat unit 2-4 times
<220> FEATURE:
<221> NAME/KEY: REPEAT
<222> LOCATION: (3)...(4)
<223> OTHER INFORMATION: repeat family 1-11 times

<400> SEQUENCE: 12

Ala Met Gly Ser Ala Met
 1               5

<210> SEQ ID NO 13
<211> LENGTH: 74
<212> TYPE: PRT
<213> ORGANISM: homo sapien
<220> FEATURE:
<223> OTHER INFORMATION: Human Chemokine Polypeptide: Eotaxin

<400> SEQUENCE: 13

Gly Pro Ala Ser Val Pro Thr Thr Cys Cys Phe Asn Leu Ala Asn Arg
 1               5                  10                  15

Lys Ile Pro Leu Gln Arg Leu Glu Ser Tyr Arg Arg Ile Thr Ser Gly
            20                  25                  30

Lys Cys Pro Gln Lys Ala Val Ile Phe Lys Thr Lys Leu Ala Lys Asp
```

```
                35                  40                  45
Ile Cys Ala Asp Pro Lys Lys Trp Val Gln Asp Ser Met Lys Tyr
    50                  55                  60

Leu Asp Gln Lys Ser Pro Thr Pro Lys Pro
65                  70
```

<210> SEQ ID NO 14
<211> LENGTH: 77
<212> TYPE: PRT
<213> ORGANISM: homo sapien
<220> FEATURE:
<223> OTHER INFORMATION: Human Chemokine Polypeptide: GCP-2

<400> SEQUENCE: 14

```
Gly Pro Val Ser Ala Val Leu Thr Glu Leu Arg Cys Thr Cys Leu Arg
1               5                   10                  15

Val Thr Leu Arg Val Asn Pro Lys Thr Ile Gly Lys Leu Gln Val Phe
                20                  25                  30

Pro Ala Gly Pro Gln Cys Ser Lys Val Glu Val Val Ala Ser Leu Lys
            35                  40                  45

Asn Gly Lys Gln Val Cys Leu Asp Pro Glu Ala Pro Phe Leu Lys Lys
        50                  55                  60

Val Ile Gln Lys Ile Leu Asp Ser Gly Asn Lys Lys Asn
65                  70                  75
```

<210> SEQ ID NO 15
<211> LENGTH: 127
<212> TYPE: PRT
<213> ORGANISM: homo sapien
<220> FEATURE:
<223> OTHER INFORMATION: Human Chemokine Polypeptide: GM-CSF

<400> SEQUENCE: 15

```
Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
                20                  25                  30

Ala Ala Glu Met Asn Glu Thr Val Glu Val Ile Ser Glu Met Phe Asp
            35                  40                  45

Leu Gln Glu Pro Thr Cys Leu Gln Thr Arg Leu Glu Leu Tyr Lys Gln
        50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Glu Ser Phe Lys Glu Asn Leu Lys Asp
            100                 105                 110

Phe Leu Leu Val Ile Pro Phe Asp Cys Trp Glu Pro Val Gln Glu
        115                 120                 125
```

<210> SEQ ID NO 16
<211> LENGTH: 73
<212> TYPE: PRT
<213> ORGANISM: homo sapien
<220> FEATURE:
<223> OTHER INFORMATION: Human Chemokine Polypeptide: MGSA/GRO-Alpha

<400> SEQUENCE: 16

```
Ala Ser Val Ala Thr Glu Leu Arg Cys Gln Cys Leu Gln Thr Leu Gln
1               5                   10                  15
```

```
Gly Ile His Pro Lys Asn Ile Gln Ser Val Asn Val Lys Ser Pro Gly
            20                  25                  30

Pro His Cys Ala Gln Thr Glu Val Ile Ala Thr Leu Lys Asn Gly Arg
            35                  40                  45

Lys Ala Cys Leu Asn Pro Ala Ser Pro Ile Val Lys Lys Ile Ile Glu
 50                  55                  60

Lys Met Leu Asn Ser Asp Lys Ser Asn
 65                  70

<210> SEQ ID NO 17
<211> LENGTH: 73
<212> TYPE: PRT
<213> ORGANISM: homo sapien
<220> FEATURE:
<223> OTHER INFORMATION: Human Chemokine Polypeptide: I309

<400> SEQUENCE: 17

Lys Ser Met Gln Val Pro Phe Ser Arg Cys Cys Phe Ser Phe Ala Glu
 1               5                  10                  15

Gln Glu Ile Pro Leu Arg Ala Ile Leu Cys Tyr Arg Asn Thr Ser Ser
            20                  25                  30

Ile Cys Ser Asn Glu Gly Leu Ile Phe Lys Leu Lys Arg Gly Lys Glu
            35                  40                  45

Ala Cys Ala Leu Asp Thr Val Gly Trp Val Gln Arg His Arg Lys Met
 50                  55                  60

Leu Arg His Cys Pro Ser Lys Arg Lys
 65                  70

<210> SEQ ID NO 18
<211> LENGTH: 133
<212> TYPE: PRT
<213> ORGANISM: homo sapien
<220> FEATURE:
<223> OTHER INFORMATION: Human Chemokine Polypeptide: Interleukin-3
      (IL-3)

<400> SEQUENCE: 18

Ala Pro Met Thr Gln Thr Thr Pro Leu Lys Thr Ser Trp Val Asn Cys
 1               5                  10                  15

Ser Asn Met Ile Asp Glu Ile Ile Thr His Leu Lys Gln Pro Pro Leu
            20                  25                  30

Pro Leu Leu Asp Phe Asn Asn Leu Asn Gly Glu Asp Gln Asp Ile Leu
            35                  40                  45

Met Glu Asn Asn Leu Arg Arg Pro Asn Leu Glu Ala Phe Asn Arg Ala
 50                  55                  60

Val Lys Ser Leu Gln Asn Ala Ser Ala Ile Glu Ser Ile Leu Lys Asn
 65                  70                  75                  80

Leu Leu Pro Cys Leu Pro Leu Ala Thr Ala Ala Pro Thr Arg His Pro
                 85                  90                  95

Ile His Ile Lys Asp Gly Asp Trp Asn Glu Phe Arg Arg Lys Leu Thr
            100                 105                 110

Phe Tyr Leu Lys Thr Leu Glu Asn Ala Gln Ala Gln Gln Thr Thr Leu
            115                 120                 125

Ser Leu Ala Ile Phe
    130

<210> SEQ ID NO 19
<211> LENGTH: 77
```

```
<212> TYPE: PRT
<213> ORGANISM: homo sapien
<220> FEATURE:
<223> OTHER INFORMATION: Human Chemokine Polypeptide: Interleukin-8
      (IL-8)

<400> SEQUENCE: 19

Ala Val Leu Pro Arg Ser Ala Lys Glu Leu Arg Cys Gln Cys Ile Lys
 1               5                  10                  15

Thr Tyr Ser Lys Pro Phe His Pro Lys Phe Ile Lys Glu Leu Arg Val
                20                  25                  30

Ile Glu Ser Gly Pro His Cys Ala Asn Thr Glu Ile Ile Val Lys Leu
            35                  40                  45

Ser Asp Gly Arg Glu Leu Cys Leu Asp Pro Lys Glu Asn Trp Val Gln
        50                  55                  60

Arg Val Val Glu Lys Phe Leu Lys Arg Ala Glu Asn Ser
65                  70                  75

<210> SEQ ID NO 20
<211> LENGTH: 76
<212> TYPE: PRT
<213> ORGANISM: homo sapien
<220> FEATURE:
<223> OTHER INFORMATION: Human Chemokine Polypeptide: MCP-1

<400> SEQUENCE: 20

Gln Pro Asp Ala Ile Asn Ala Pro Val Thr Cys Cys Tyr Asn Phe Thr
 1               5                  10                  15

Asn Arg Lys Ile Ser Val Gln Arg Leu Ala Ser Tyr Arg Arg Ile Thr
                20                  25                  30

Ser Ser Lys Cys Pro Lys Glu Ala Val Ile Phe Lys Thr Ile Val Ala
            35                  40                  45

Lys Glu Ile Cys Ala Asp Pro Lys Gln Lys Trp Val Gln Asp Ser Met
        50                  55                  60

Asp His Leu Asp Lys Gln Thr Gln Thr Pro Lys Thr
65                  70                  75

<210> SEQ ID NO 21
<211> LENGTH: 76
<212> TYPE: PRT
<213> ORGANISM: homo sapien
<220> FEATURE:
<223> OTHER INFORMATION: Human Chemokine Polypeptide: MCP-2

<400> SEQUENCE: 21

Gln Pro Asp Ser Val Ser Ile Pro Ile Thr Cys Cys Phe Asn Val Ile
 1               5                  10                  15

Asn Arg Lys Ile Pro Ile Gln Arg Leu Glu Ser Tyr Thr Arg Ile Thr
                20                  25                  30

Asn Ile Gln Cys Pro Lys Glu Ala Val Ile Phe Lys Thr Lys Arg Gly
            35                  40                  45

Lys Glu Val Cys Ala Asp Pro Lys Glu Arg Trp Val Arg Asp Ser Met
        50                  55                  60

Lys His Leu Asp Gln Ile Phe Gln Asn Leu Lys Pro
65                  70                  75

<210> SEQ ID NO 22
<211> LENGTH: 76
<212> TYPE: PRT
<213> ORGANISM: homo sapien
<220> FEATURE:
```

<223> OTHER INFORMATION: Human Chemokine Polypeptide: MCP-3

<400> SEQUENCE: 22

```
Gln Pro Val Gly Ile Asn Thr Ser Thr Thr Cys Cys Tyr Arg Phe Ile
 1               5                  10                  15

Asn Lys Lys Ile Pro Lys Gln Arg Leu Glu Ser Tyr Arg Arg Thr Thr
            20                  25                  30

Ser Ser His Cys Pro Arg Glu Ala Val Ile Phe Lys Thr Lys Leu Asp
        35                  40                  45

Lys Glu Ile Cys Ala Asp Pro Thr Gln Lys Trp Val Gln Asp Phe Met
    50                  55                  60

Lys His Leu Asp Lys Lys Thr Gln Thr Pro Lys Leu
65                  70                  75
```

<210> SEQ ID NO 23
<211> LENGTH: 75
<212> TYPE: PRT
<213> ORGANISM: homo sapien
<220> FEATURE:
<223> OTHER INFORMATION: Human Chemokine Polypeptide: MCP-4

<400> SEQUENCE: 23

```
Gln Pro Asp Ala Leu Asn Val Pro Ser Thr Cys Cys Phe Thr Phe Ser
 1               5                  10                  15

Ser Lys Lys Ile Ser Leu Gln Arg Leu Lys Ser Tyr Val Ile Thr Thr
            20                  25                  30

Ser Arg Cys Pro Gln Lys Ala Val Ile Phe Arg Thr Lys Leu Gly Lys
        35                  40                  45

Glu Ile Cys Ala Asp Pro Lys Glu Lys Trp Val Gln Asn Tyr Met Lys
    50                  55                  60

His Leu Gly Arg Lys Ala His Thr Leu Lys Thr
65                  70                  75
```

<210> SEQ ID NO 24
<211> LENGTH: 70
<212> TYPE: PRT
<213> ORGANISM: homo sapien
<220> FEATURE:
<223> OTHER INFORMATION: Human Chemokine Polypeptide: MIP-1-Alpha

<400> SEQUENCE: 24

```
Ala Ser Leu Ala Ala Asp Thr Pro Thr Ala Cys Cys Phe Ser Tyr Thr
 1               5                  10                  15

Ser Arg Gln Ile Pro Gln Asn Phe Ile Ala Asp Tyr Phe Glu Thr Ser
            20                  25                  30

Ser Gln Cys Ser Lys Pro Gly Val Ile Phe Leu Thr Lys Arg Ser Arg
        35                  40                  45

Gln Val Cys Ala Asp Pro Ser Glu Glu Trp Val Gln Lys Tyr Val Ser
    50                  55                  60

Asp Leu Glu Leu Ser Ala
65                  70
```

<210> SEQ ID NO 25
<211> LENGTH: 129
<212> TYPE: PRT
<213> ORGANISM: homo sapien
<220> FEATURE:
<223> OTHER INFORMATION: Human Chemokine Polypeptide: Interleukin-4
      (IL-4)

<400> SEQUENCE: 25

```
His Lys Cys Asp Ile Thr Leu Gln Glu Ile Ile Lys Thr Leu Asn Ser
  1               5                  10                  15
Leu Thr Glu Gln Lys Thr Leu Cys Thr Glu Leu Thr Val Thr Asp Ile
             20                  25                  30
Phe Ala Ala Ser Lys Asn Thr Thr Glu Lys Glu Thr Phe Cys Arg Ala
         35                  40                  45
Ala Thr Val Leu Arg Gln Phe Tyr Ser His His Glu Lys Asp Thr Arg
     50                  55                  60
Cys Leu Gly Ala Thr Ala Gln Gln Phe His Arg His Lys Gln Leu Ile
 65                  70                  75                  80
Arg Phe Leu Lys Arg Leu Asp Arg Asn Leu Trp Gly Leu Ala Gly Leu
                 85                  90                  95
Asn Ser Cys Pro Val Lys Glu Ala Asn Gln Ser Thr Leu Glu Asn Phe
            100                 105                 110
Leu Glu Arg Leu Lys Thr Ile Met Arg Glu Lys Tyr Ser Lys Cys Ser
            115                 120                 125
Ser
```

```
<210> SEQ ID NO 26
<211> LENGTH: 73
<212> TYPE: PRT
<213> ORGANISM: homo sapien
<220> FEATURE:
<223> OTHER INFORMATION: Human Chemokine Poypeptide: MGSA/GRO-Beta

<400> SEQUENCE: 26

Ala Pro Leu Ala Thr Glu Leu Arg Cys Gln Cys Leu Gln Thr Leu Gln
  1               5                  10                  15
Gly Ile His Leu Lys Asn Ile Gln Ser Val Lys Val Lys Ser Pro Gly
             20                  25                  30
Pro His Cys Ala Gln Thr Glu Val Ile Ala Thr Leu Lys Asn Gly Gln
         35                  40                  45
Lys Ala Cys Leu Asn Pro Ala Ser Pro Met Val Lys Lys Ile Ile Glu
     50                  55                  60
Lys Met Leu Lys Asn Gly Lys Ser Asn
 65                  70
```

```
<210> SEQ ID NO 27
<211> LENGTH: 73
<212> TYPE: PRT
<213> ORGANISM: homo sapien
<220> FEATURE:
<223> OTHER INFORMATION: Human Chemokine Polypeptide: MGSA/GRO-gamma

<400> SEQUENCE: 27

Ala Ser Val Val Thr Glu Leu Arg Cys Gln Cys Leu Gln Thr Leu Gln
  1               5                  10                  15
Gly Ile His Leu Lys Asn Ile Gln Ser Val Asn Val Arg Ser Pro Gly
             20                  25                  30
Pro His Cys Ala Gln Thr Glu Val Ile Ala Thr Leu Lys Asn Gly Lys
         35                  40                  45
Lys Ala Cys Leu Asn Pro Ala Ser Pro Met Val Gln Lys Ile Ile Glu
     50                  55                  60
Lys Ile Leu Asn Lys Gly Ser Thr Asn
 65                  70
```

```
<210> SEQ ID NO 28
```

```
<211> LENGTH: 69
<212> TYPE: PRT
<213> ORGANISM: homo sapien
<220> FEATURE:
<223> OTHER INFORMATION: Human Chemokine Polypeptide: PARC (MIP-4)

<400> SEQUENCE: 28

Ala Gln Val Gly Thr Asn Lys Glu Leu Cys Cys Leu Val Tyr Thr Ser
 1               5                  10                  15

Trp Gln Ile Pro Gln Lys Phe Ile Val Asp Tyr Ser Glu Thr Ser Pro
            20                  25                  30

Gln Cys Pro Lys Pro Gly Val Ile Leu Leu Thr Lys Arg Gly Arg Gln
        35                  40                  45

Ile Cys Ala Asp Pro Asn Lys Lys Trp Val Gln Lys Tyr Ile Ser Asp
    50                  55                  60

Leu Lys Leu Asn Ala
65

<210> SEQ ID NO 29
<211> LENGTH: 68
<212> TYPE: PRT
<213> ORGANISM: homo sapien
<220> FEATURE:
<223> OTHER INFORMATION: Human Chemokine Polypeptide: RANTES

<400> SEQUENCE: 29

Ser Pro Tyr Ser Ser Asp Thr Thr Pro Cys Cys Phe Ala Tyr Ile Ala
 1               5                  10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
    50                  55                  60

Leu Glu Met Ser
65

<210> SEQ ID NO 30
<211> LENGTH: 69
<212> TYPE: PRT
<213> ORGANISM: homo sapien
<220> FEATURE:
<223> OTHER INFORMATION: Human Chemokine Polypeptide: MIP-1-Beta

<400> SEQUENCE: 30

Ala Pro Met Gly Ser Asp Pro Pro Thr Ala Cys Cys Phe Ser Tyr Thr
 1               5                  10                  15

Ala Arg Lys Leu Pro Arg Asn Phe Val Val Asp Tyr Tyr Glu Thr Ser
            20                  25                  30

Ser Leu Cys Ser Gln Pro Ala Val Val Phe Gln Thr Lys Arg Ser Lys
        35                  40                  45

Gln Val Cys Ala Asp Pro Ser Glu Ser Trp Val Gln Glu Tyr Val Tyr
    50                  55                  60

Asp Leu Glu Leu Asn
65

<210> SEQ ID NO 31
<211> LENGTH: 323
<212> TYPE: PRT
<213> ORGANISM: homo sapien
<220> FEATURE:
```

<223> OTHER INFORMATION: Human Chemokine Polypeptide: RAP

<400> SEQUENCE: 31

```
Tyr Ser Arg Glu Lys Asn Gln Pro Lys Pro Ser Pro Lys Arg Glu Ser
  1               5                  10                  15
Gly Glu Glu Phe Arg Met Glu Lys Leu Asn Gln Leu Trp Glu Lys Ala
             20                  25                  30
Gln Arg Leu His Leu Pro Pro Val Arg Leu Ala Glu Leu His Ala Asp
         35                  40                  45
Leu Lys Ile Gln Glu Arg Asp Glu Leu Ala Trp Lys Lys Leu Lys Leu
 50                  55                  60
Asp Gly Leu Asp Glu Asp Gly Glu Lys Glu Ala Arg Leu Ile Arg Asn
 65                  70                  75                  80
Leu Asn Val Ile Leu Ala Lys Tyr Gly Leu Asp Gly Lys Lys Asp Ala
                 85                  90                  95
Arg Gln Val Thr Ser Asn Ser Leu Ser Gly Thr Gln Glu Asp Gly Leu
            100                 105                 110
Asp Asp Pro Arg Leu Glu Lys Leu Trp His Lys Ala Lys Thr Ser Gly
        115                 120                 125
Lys Phe Ser Gly Glu Glu Leu Asp Lys Leu Trp Arg Glu Phe Leu His
130                 135                 140
His Lys Glu Lys Val His Glu Tyr Asn Val Leu Leu Glu Thr Leu Ser
145                 150                 155                 160
Arg Thr Glu Glu Ile His Glu Asn Val Ile Ser Pro Ser Asp Leu Ser
                165                 170                 175
Asp Ile Lys Gly Ser Val Leu His Ser Arg His Thr Glu Leu Lys Glu
            180                 185                 190
Lys Leu Arg Ser Ile Asn Gln Gly Leu Asp Arg Leu Arg Arg Val Ser
        195                 200                 205
His Gln Gly Tyr Ser Thr Glu Ala Glu Phe Glu Glu Pro Arg Val Ile
    210                 215                 220
Asp Leu Trp Asp Leu Ala Gln Ser Ala Asn Leu Thr Asp Lys Glu Leu
225                 230                 235                 240
Glu Ala Phe Arg Glu Glu Leu Lys His Phe Glu Ala Lys Ile Glu Lys
                245                 250                 255
His Asn His Tyr Gln Lys Gln Leu Glu Ile Ala His Glu Lys Leu Arg
            260                 265                 270
His Ala Glu Ser Val Gly Asp Gly Glu Arg Val Ser Arg Ser Arg Glu
        275                 280                 285
Lys His Ala Leu Leu Glu Gly Arg Thr Lys Glu Leu Gly Tyr Thr Val
    290                 295                 300
Lys Lys His Leu Gln Asp Leu Ser Gly Arg Ile Ser Arg Ala Arg His
305                 310                 315                 320
Asn Glu Leu
```

<210> SEQ ID NO 32
<211> LENGTH: 89
<212> TYPE: PRT
<213> ORGANISM: Homo sapiens
<220> FEATURE:
<223> OTHER INFORMATION: Human Chemokine Polypeptide: Stromal cell-derived Factor-1-Aplha (SDF-1-Alpha)
<300> PUBLICATION INFORMATION:
<303> JOURNAL: Genomics
<304> VOLUME: 28
<306> PAGES: 495-500
<307> DATE: 1995

```
<400> SEQUENCE: 32

Met Asn Ala Lys Val Val Val Leu Val Leu Val Leu Thr Ala Leu
  1               5                  10                  15

Cys Leu Ser Asp Gly Lys Pro Val Ser Leu Ser Tyr Arg Cys Pro Cys
             20                  25                  30

Arg Phe Phe Glu Ser His Val Ala Arg Ala Asn Val Lys His Leu Lys
         35                  40                  45

Ile Leu Asn Thr Pro Asn Cys Ala Leu Gln Ile Val Ala Arg Leu Lys
     50                  55                  60

Asn Asn Asn Arg Gln Val Cys Ile Asp Pro Lys Leu Lys Trp Ile Gln
 65                  70                  75                  80

Glu Tyr Leu Glu Lys Ala Leu Asn Lys
                 85

<210> SEQ ID NO 33
<211> LENGTH: 71
<212> TYPE: PRT
<213> ORGANISM: homo sapien
<220> FEATURE:
<223> OTHER INFORMATION: Human Chemokine Polypeptide: TARC

<400> SEQUENCE: 33

Ala Arg Gly Thr Asn Val Gly Arg Glu Cys Cys Leu Glu Tyr Phe Lys
  1               5                  10                  15

Gly Ala Ile Pro Leu Arg Lys Leu Lys Thr Trp Tyr Gln Thr Ser Glu
             20                  25                  30

Asp Cys Ser Arg Asp Ala Ile Val Phe Val Thr Val Gln Gly Arg Ala
         35                  40                  45

Ile Cys Ser Asp Pro Asn Asn Lys Arg Val Lys Asn Ala Val Lys Tyr
     50                  55                  60

Leu Gln Ser Leu Glu Arg Ser
 65                  70

<210> SEQ ID NO 34
<211> LENGTH: 247
<212> TYPE: PRT
<213> ORGANISM: Bryonia dioica

<400> SEQUENCE: 34

Asp Val Ser Phe Arg Leu Ser Gly Ala Thr Thr Ser Tyr Gly Val
  1               5                  10                  15

Phe Ile Lys Asn Leu Arg Glu Ala Leu Pro Tyr Glu Arg Lys Val Tyr
             20                  25                  30

Asn Ile Pro Leu Leu Arg Ser Ser Ile Ser Gly Ser Gly Arg Tyr Thr
         35                  40                  45

Leu Leu His Leu Thr Asn Tyr Ala Asp Glu Thr Ile Ser Val Ala Val
     50                  55                  60

Asp Val Thr Asn Val Tyr Ile Met Gly Tyr Leu Ala Gly Asp Val Ser
 65                  70                  75                  80

Tyr Phe Phe Asn Glu Ala Ser Ala Thr Glu Ala Ala Lys Phe Val Phe
                 85                  90                  95

Lys Asp Ala Lys Lys Val Thr Leu Pro Tyr Ser Gly Asn Tyr Glu
            100                 105                 110

Arg Leu Gln Thr Ala Ala Gly Lys Ile Arg Glu Asn Ile Pro Leu Gly
            115                 120                 125

Leu Pro Ala Leu Asp Ser Ala Ile Thr Thr Leu Tyr Tyr Tyr Thr Ala
```

```
                130                 135                 140
Ser Ser Ala Ala Ser Ala Leu Leu Val Leu Ile Gln Ser Thr Ala Glu
145                 150                 155                 160

Ser Ala Arg Tyr Lys Phe Ile Glu Gln Gln Ile Gly Lys Arg Val Asp
                165                 170                 175

Lys Thr Phe Leu Pro Ser Leu Ala Thr Ile Ser Leu Glu Asn Asn Trp
                180                 185                 190

Ser Ala Leu Ser Lys Gln Ile Gln Ile Ala Ser Thr Asn Asn Gly Gln
            195                 200                 205

Phe Glu Ser Pro Val Val Leu Ile Asp Gly Asn Asn Gln Arg Val Ser
210                 215                 220

Ile Thr Asn Ala Ser Ala Arg Val Val Thr Ser Asn Ile Ala Leu Leu
225                 230                 235                 240

Leu Asn Arg Asn Asn Ile Ala
                245

<210> SEQ ID NO 35
<211> LENGTH: 275
<212> TYPE: PRT
<213> ORGANISM: Saponaria officinalis

<400> SEQUENCE: 35

Val Thr Ser Ile Thr Leu Asp Leu Val Asn Pro Thr Ala Gly Gln Tyr
1               5                   10                  15

Ser Ser Phe Val Asp Lys Ile Arg Asn Asn Val Lys Asp Pro Asn Leu
                20                  25                  30

Lys Tyr Gly Gly Thr Asp Ile Ala Val Ile Gly Pro Pro Ser Lys Glu
            35                  40                  45

Lys Phe Leu Arg Ile Asn Phe Gln Ser Ser Arg Gly Thr Val Ser Leu
        50                  55                  60

Gly Leu Lys Arg Asp Asn Leu Tyr Val Val Ala Tyr Leu Ala Met Asp
65                  70                  75                  80

Asn Thr Asn Val Asn Arg Ala Tyr Tyr Phe Arg Ser Glu Ile Thr Ser
                85                  90                  95

Ala Glu Ser Thr Ala Leu Phe Pro Glu Ala Thr Thr Ala Asn Gln Lys
                100                 105                 110

Ala Leu Glu Tyr Thr Glu Asp Tyr Gln Ser Ile Glu Lys Asn Ala Gln
            115                 120                 125

Ile Thr Gln Gly Asp Gln Ser Arg Lys Glu Leu Gly Leu Gly Ile Asp
        130                 135                 140

Leu Leu Ser Thr Ser Met Glu Ala Val Asn Lys Lys Ala Arg Val Val
145                 150                 155                 160

Lys Asp Glu Ala Arg Phe Leu Leu Ile Ala Ile Gln Met Thr Ala Glu
                165                 170                 175

Ala Ala Arg Phe Arg Tyr Ile Gln Asn Leu Val Ile Lys Asn Phe Pro
                180                 185                 190

Asn Lys Phe Asn Ser Glu Asn Lys Val Ile Gln Phe Glu Val Asn Trp
            195                 200                 205

Lys Lys Ile Ser Thr Ala Ile Tyr Gly Asp Ala Lys Asn Gly Val Phe
        210                 215                 220

Asn Lys Asp Tyr Asp Phe Gly Phe Gly Lys Val Arg Gln Val Lys Asp
225                 230                 235                 240

Leu Gln Met Gly Leu Leu Met Tyr Leu Gly Lys Pro Lys Ser Ser Asn
                245                 250                 255
```

-continued

```
Glu Ala Asn Ser Thr Val Arg His Tyr Gly Pro Leu Lys Pro Thr Leu
            260                 265                 270

Leu Ile Thr
        275
```

```
<210> SEQ ID NO 36
<211> LENGTH: 250
<212> TYPE: PRT
<213> ORGANISM: Momordica charantia

<400> SEQUENCE: 36

Ala Pro Thr Leu Glu Thr Ile Ala Ser Leu Asp Leu Asn Asn Pro Thr
 1               5                  10                  15

Thr Tyr Leu Ser Phe Ile Thr Asn Ile Arg Thr Lys Val Ala Asp Lys
            20                  25                  30

Thr Glu Gln Cys Thr Ile Gln Lys Ile Ser Lys Thr Phe Thr Gln Arg
        35                  40                  45

Tyr Ser Tyr Ile Asp Leu Ile Val Ser Ser Thr Gln Lys Ile Thr Leu
    50                  55                  60

Ala Ile Asp Met Ala Asp Leu Tyr Val Leu Gly Tyr Ser Asp Ile Ala
65                  70                  75                  80

Asn Asn Lys Gly Arg Ala Phe Phe Phe Lys Asp Val Thr Glu Ala Val
                85                  90                  95

Ala Asn Asn Phe Phe Pro Gly Ala Thr Gly Thr Asn Arg Ile Lys Leu
            100                 105                 110

Thr Phe Thr Gly Ser Tyr Gly Asp Leu Glu Lys Asn Gly Gly Leu Arg
        115                 120                 125

Lys Asp Asn Pro Leu Gly Ile Phe Arg Leu Glu Asn Ser Ile Val Asn
    130                 135                 140

Ile Tyr Gly Lys Ala Gly Asp Val Lys Lys Gln Ala Lys Phe Phe Leu
145                 150                 155                 160

Leu Ala Ile Gln Met Val Ser Glu Ala Ala Arg Phe Lys Tyr Ile Ser
                165                 170                 175

Asp Lys Ile Pro Ser Glu Lys Tyr Glu Glu Val Thr Val Asp Glu Tyr
            180                 185                 190

Met Thr Ala Leu Glu Asn Asn Trp Ala Lys Leu Ser Thr Ala Val Tyr
        195                 200                 205

Asn Ser Lys Pro Ser Thr Thr Thr Ala Thr Lys Cys Gln Leu Ala Thr
    210                 215                 220

Ser Pro Val Thr Ile Ser Pro Trp Ile Phe Lys Thr Val Glu Glu Ile
225                 230                 235                 240

Lys Leu Val Met Gly Leu Leu Lys Ser Ser
                245                 250
```

```
<210> SEQ ID NO 37
<211> LENGTH: 293
<212> TYPE: PRT
<213> ORGANISM: Shigella dysenteriae

<400> SEQUENCE: 37

Lys Glu Phe Thr Leu Asp Phe Ser Thr Ala Lys Thr Tyr Val Asp Ser
 1               5                  10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Thr Gly Asp Asn
        35                  40                  45

```
Leu Phe Ala Val Asp Val Arg Gly Ile Asp Pro Glu Gly Arg Phe
     50                  55                  60

Asn Asn Leu Arg Leu Ile Val Glu Arg Asn Asn Leu Tyr Val Thr Gly
 65                  70                  75                  80

Phe Val Asn Arg Thr Asn Asn Val Phe Tyr Arg Phe Ala Asp Phe Ser
                 85                  90                  95

His Val Thr Phe Pro Gly Thr Thr Ala Val Thr Leu Ser Gly Asp Ser
                100                 105                 110

Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Asp Leu Met Ser
        130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg Met Ala Ser Asp Glu
                245                 250                 255

Phe Pro Ser Met Cys Pro Ala Asp Gly Arg Val Arg Gly Ile Thr His
                260                 265                 270

Asn Lys Ile Leu Trp Asp Ser Ser Thr Leu Gly Ala Ile Leu Met Arg
            275                 280                 285

Arg Thr Ile Ser Ser
        290

<210> SEQ ID NO 38
<211> LENGTH: 319
<212> TYPE: PRT
<213> ORGANISM: Escherichia coli

<400> SEQUENCE: 38

Met Lys Cys Ile Leu Phe Lys Trp Val Leu Cys Leu Leu Leu Gly Phe
  1               5                  10                  15

Ser Ser Val Ser Tyr Ser Arg Glu Phe Thr Ile Asp Phe Ser Thr Gln
                 20                  25                  30

Gln Ser Tyr Val Ser Ser Leu Asn Ser Ile Arg Thr Glu Ile Ser Thr
             35                  40                  45

Pro Leu Glu His Ile Ser Gln Gly Thr Thr Ser Val Ser Val Ile Asn
     50                  55                  60

His Thr Pro Pro Gly Ser Tyr Phe Ala Val Asp Ile Arg Gly Leu Asp
 65                  70                  75                  80

Val Tyr Gln Ala Arg Phe Asp His Leu Arg Leu Ile Ile Glu Gln Asn
                 85                  90                  95

Asn Leu Tyr Val Ala Gly Phe Val Asn Thr Ala Thr Asn Thr Phe Tyr
                100                 105                 110

Arg Phe Ser Asp Phe Thr His Ile Ser Val Pro Gly Val Thr Thr Val
            115                 120                 125
```

-continued

```
Ser Met Thr Thr Asp Ser Ser Tyr Thr Thr Leu Gln Arg Val Ala Ala
        130                 135                 140

Leu Glu Arg Ser Gly Met Gln Ile Ser Arg His Ser Leu Val Ser Ser
145                 150                 155                 160

Tyr Leu Ala Leu Met Glu Phe Ser Gly Asn Thr Met Thr Arg Asp Ala
                165                 170                 175

Ser Arg Ala Val Leu Arg Phe Val Thr Val Thr Ala Glu Ala Leu Arg
            180                 185                 190

Phe Arg Gln Ile Gln Arg Glu Phe Arg Gln Ala Leu Ser Glu Thr Ala
        195                 200                 205

Pro Val Tyr Thr Met Thr Pro Gly Asp Val Asp Leu Thr Leu Asn Trp
    210                 215                 220

Gly Arg Ile Ser Asn Val Leu Pro Glu Tyr Arg Gly Glu Asp Gly Val
225                 230                 235                 240

Arg Val Gly Arg Ile Ser Phe Asn Asn Ile Ser Ala Ile Leu Gly Thr
                245                 250                 255

Val Ala Val Ile Leu Asn Cys His His Gln Gly Ala Arg Ser Val Arg
            260                 265                 270

Ala Val Asn Glu Glu Ser Gln Pro Glu Cys Gln Ile Thr Gly Asp Arg
        275                 280                 285

Pro Val Ile Lys Ile Asn Asn Thr Leu Trp Glu Ser Asn Thr Ala Ala
    290                 295                 300

Ala Phe Leu Asn Arg Lys Ser Gln Phe Leu Tyr Thr Thr Gly Lys
305                 310                 315
```

<210> SEQ ID NO 39
<211> LENGTH: 247
<212> TYPE: PRT
<213> ORGANISM: Trichosanthews kirilowii

<400> SEQUENCE: 39

```
Asp Val Ser Phe Arg Leu Ser Gly Ala Thr Ser Ser Ser Tyr Gly Val
1               5                   10                  15

Phe Ile Ser Asn Leu Arg Lys Ala Leu Pro Asn Glu Arg Lys Leu Tyr
                20                  25                  30

Asp Ile Pro Leu Leu Arg Ser Ser Leu Pro Gly Ser Gln Arg Tyr Ala
            35                  40                  45

Leu Ile His Leu Thr Asn Tyr Ala Asp Glu Thr Ile Ser Val Ala Ile
        50                  55                  60

Asp Val Thr Asn Val Tyr Ile Met Gly Tyr Arg Ala Gly Asp Thr Ser
65                  70                  75                  80

Tyr Phe Phe Asn Glu Ala Ser Ala Thr Glu Ala Ala Lys Tyr Val Phe
                85                  90                  95

Lys Asp Ala Met Arg Lys Val Thr Leu Pro Tyr Ser Gly Asn Tyr Glu
            100                 105                 110

Arg Leu Gln Thr Ala Ala Gly Lys Ile Arg Glu Asn Ile Pro Leu Gly
        115                 120                 125

Leu Pro Ala Leu Asp Ser Ala Ile Thr Thr Leu Phe Tyr Tyr Asn Ala
    130                 135                 140

Asn Ser Ala Ala Ser Ala Leu Met Val Leu Ile Gln Ser Thr Ser Glu
145                 150                 155                 160

Ala Ala Arg Tyr Lys Phe Ile Glu Gln Gln Ile Gly Lys Arg Val Asp
                165                 170                 175

Lys Thr Phe Leu Pro Ser Leu Ala Ile Ile Ser Leu Glu Asn Ser Trp
```

```
              180                 185                 190
Ser Ala Leu Ser Lys Gln Ile Gln Ile Ala Ser Thr Asn Asn Gly Gln
        195                 200                 205

Phe Glu Ser Pro Val Val Leu Ile Asn Ala Gln Asn Gln Arg Val Thr
        210                 215                 220

Ile Thr Asn Val Asp Ala Gly Val Val Thr Ser Asn Ile Ala Leu Leu
225                 230                 235                 240

Leu Asn Arg Asn Asn Met Ala
                245
```

<210> SEQ ID NO 40
<211> LENGTH: 88
<212> TYPE: DNA
<213> ORGANISM: Artificial Sequence
<220> FEATURE:
<223> OTHER INFORMATION: Homo sapien His-Tag leader sequence

<400> SEQUENCE: 40

```
aaggagatatacc atg ggc agc agc cat cat cat cat cat cac agc agc        49
              Met Gly Ser Ser His His His His His His Ser Ser
                1               5                  10 ggc ctg gtg ccg cgc ggc agc cat atg ctc gag gat ccg                  88
Gly Leu Val Pro Arg Gly Ser His Met Leu Glu Asp Pro
         15                  20                  25
```

<210> SEQ ID NO 41
<211> LENGTH: 37
<212> TYPE: DNA
<213> ORGANISM: Artificial Sequence
<220> FEATURE:
<223> OTHER INFORMATION: Homo sapien forward primer (Eotaxin)

<400> SEQUENCE: 41
gggtaatagc atatggggcc agcttctgtc ccaacca                             37

<210> SEQ ID NO 42
<211> LENGTH: 44
<212> TYPE: DNA
<213> ORGANISM: Artificial Sequence
<220> FEATURE:
<223> OTHER INFORMATION: Homo sapien reverse primer (Eotaxin)

<400> SEQUENCE: 42
cccgaattct ttcatcgctg gctttggagt tggagatttt tggt                     44

<210> SEQ ID NO 43
<211> LENGTH: 39
<212> TYPE: DNA
<213> ORGANISM: Artificial Sequence
<220> FEATURE:
<223> OTHER INFORMATION: Homo sapien forward primer (MCP-1)

<400> SEQUENCE: 43
gggtaatagc atatgcagcc agatgcaatc aatgcccca                           39

<210> SEQ ID NO 44
<211> LENGTH: 41
<212> TYPE: DNA
<213> ORGANISM: Artificial Sequence
<220> FEATURE:
<223> OTHER INFORMATION: Homo sapien reverse primer (MCP-1)

<400> SEQUENCE: 44
cccgaattct ttcatcgcag tcttcggagt ttgggtttct t                        41

<210> SEQ ID NO 45
<211> LENGTH: 27
<212> TYPE: DNA
<213> ORGANISM: Artificial Sequence
<220> FEATURE:
<223> OTHER INFORMATION: Homo sapien forward primer (MCP-3)

<400> SEQUENCE: 45
catatgcaac cggtaggcat caacacg                                27

<210> SEQ ID NO 46
<211> LENGTH: 33
<212> TYPE: DNA
<213> ORGANISM: Artificial Sequence
<220> FEATURE:
<223> OTHER INFORMATION: Homo sapien reverse primer (MCP-3)

<400> SEQUENCE: 46
cactagtaac catcgcaagc ttcggggtct gag                         33

<210> SEQ ID NO 47
<211> LENGTH: 38
<212> TYPE: DNA
<213> ORGANISM: Artificial Sequence
<220> FEATURE:
<223> OTHER INFORMATION: Homo sapien forward primer (SDF-1-Beta)

<400> SEQUENCE: 47
gggtaatagc atatgaagcc cgtcagcctg agctacag                    38

<210> SEQ ID NO 48
<211> LENGTH: 46
<212> TYPE: DNA
<213> ORGANISM: Artificial Sequence
<220> FEATURE:
<223> OTHER INFORMATION: Homo sapien reverse primer (SDF-1-Beta)

<400> SEQUENCE: 48
cccgaattct ttcatcgcca tcttgaacct cttgtttaaa gctttc           46

<210> SEQ ID NO 49
<211> LENGTH: 39
<212> TYPE: DNA
<213> ORGANISM: Artificial Sequence
<220> FEATURE:
<223> OTHER INFORMATION: Shigella dysenteriae forward primer (Shiga)

<400> SEQUENCE: 49
gggtaatagc atatgaaaga attcaccctg gacttttcc                   39

<210> SEQ ID NO 50
<211> LENGTH: 28
<212> TYPE: DNA
<213> ORGANISM: Artificial Sequence
<220> FEATURE:
<223> OTHER INFORMATION: Shigella dysenteriae reverse primer (Shiga)

<400> SEQUENCE: 50
cccggatcca ctagtattaa gcgtggtg                               28

<210> SEQ ID NO 51
<211> LENGTH: 45
<212> TYPE: DNA
<213> ORGANISM: Artificial Sequence
<220> FEATURE:

-continued

<223> OTHER INFORMATION: Shigella dysenteriae reverse primer
      (Shiga-His6)

<400> SEQUENCE: 51
cccggatcca ctagtttaat gatgatggtg gtggtggcaa ttgag        45

<210> SEQ ID NO 52
<211> LENGTH: 978
<212> TYPE: DNA
<213> ORGANISM: Artificial Sequence
<220> FEATURE:
<221> NAME/KEY: CDS
<222> LOCATION: (1)..(978)
<220> FEATURE:
<223> OTHER INFORMATION: Description of Artificial Sequence: Construct
      encoding chemokine-toxin fusion protein MCP1-AM-truncated Shiga-A1
      Subunit

<400> SEQUENCE: 52

```
atg cag cca gat gca atc aat gcc cca gtc acc tgc tgt tat aac ttc      48
Met Gln Pro Asp Ala Ile Asn Ala Pro Val Thr Cys Cys Tyr Asn Phe
 1               5                  10                  15 acc aat agg aag atc tca gtg cag agg ctc gcg agc tat aga aga atc      96
Thr Asn Arg Lys Ile Ser Val Gln Arg Leu Ala Ser Tyr Arg Arg Ile
             20                  25                  30 acc agc agc aag tgt ccc aaa gaa gct gtg atc ttc aag acc att gtg     144
Thr Ser Ser Lys Cys Pro Lys Glu Ala Val Ile Phe Lys Thr Ile Val
         35                  40                  45 gcc aag gag atc tgt gct gac ccc aag cag aag tgg gtt cag gat tcc     192
Ala Lys Glu Ile Cys Ala Asp Pro Lys Gln Lys Trp Val Gln Asp Ser
     50                  55                  60 atg gac cac ctg gac aag caa acc caa act ccg aag act gcg atg aaa     240
Met Asp His Leu Asp Lys Gln Thr Gln Thr Pro Lys Thr Ala Met Lys
 65                  70                  75                  80 gaa ttc acc ctg gac ttt tcc act gca aaa act tac gtc gat agc ctg     288
Glu Phe Thr Leu Asp Phe Ser Thr Ala Lys Thr Tyr Val Asp Ser Leu
                 85                  90                  95 aat gtg att cgt tcc gcg atc ggt acg ccg ctg caa acg att tcc agc     336
Asn Val Ile Arg Ser Ala Ile Gly Thr Pro Leu Gln Thr Ile Ser Ser
            100                 105                 110 ggt ggt act tcc ctc ctg atg att gat tcc ggt acg ggt gat aac ttg     384
Gly Gly Thr Ser Leu Leu Met Ile Asp Ser Gly Thr Gly Asp Asn Leu
        115                 120                 125 ttt gct gtt gat gtg cgc ggc att gac ccg gaa gaa ggc cgt ttt aat     432
Phe Ala Val Asp Val Arg Gly Ile Asp Pro Glu Glu Gly Arg Phe Asn
    130                 135                 140 aat ctg cgt ctg atc gtc gaa cgc aac aac ctg tat gtg acg ggt ttt     480
Asn Leu Arg Leu Ile Val Glu Arg Asn Asn Leu Tyr Val Thr Gly Phe
145                 150                 155                 160 gtg aac cgt acg aac aac gtc ttc tat cgt ttc gct gat ttc tcc cac     528
Val Asn Arg Thr Asn Asn Val Phe Tyr Arg Phe Ala Asp Phe Ser His
                165                 170                 175 gta acg ttt ccg ggc acc act gct gtt act ctg agc ggc gat tct tct     576
Val Thr Phe Pro Gly Thr Thr Ala Val Thr Leu Ser Gly Asp Ser Ser
            180                 185                 190 tat act acg tta cag cgt gtg gct ggt atc agc cgc act ggt atg caa     624
Tyr Thr Thr Leu Gln Arg Val Ala Gly Ile Ser Arg Thr Gly Met Gln
        195                 200                 205 atc aat cgc cat tct ctg acg acc agc tat ctg gac tta atg agc cat     672
Ile Asn Arg His Ser Leu Thr Thr Ser Tyr Leu Asp Leu Met Ser His
    210                 215                 220 tct ggc acc agc ctg acc cag tct gtt gcc cgt gcg atg ctg cgc ttc     720
```

| | |
|---|---|
| Ser Gly Thr Ser Leu Thr Gln Ser Val Ala Arg Ala Met Leu Arg Phe<br>225     230     235     240 | |
| gtg acg gtc acc gcc gaa gcc ctg cgt ttc cgt caa atc caa cgc ggc<br>Val Thr Val Thr Ala Glu Ala Leu Arg Phe Arg Gln Ile Gln Arg Gly<br>     245     250     255 | 768 |
| ttc cgc acc act tta gac gat ctg tct ggc cgc agc tat gtg atg act<br>Phe Arg Thr Thr Leu Asp Asp Leu Ser Gly Arg Ser Tyr Val Met Thr<br>    260     265     270 | 816 |
| gcc gaa gat gtc gat ctg acc ctg aac tgg ggt cgc ttg tct tcc gtt<br>Ala Glu Asp Val Asp Leu Thr Leu Asn Trp Gly Arg Leu Ser Ser Val<br>   275     280     285 | 864 |
| ctg ccg gat tat cac ggt cag gat tct gtc cgt gtt ggc cgt atc agc<br>Leu Pro Asp Tyr His Gly Gln Asp Ser Val Arg Val Gly Arg Ile Ser<br>290     295     300 | 912 |
| ttt ggc tct att aat gcc atc cta ggc tcc gtc gca ctg att ctc aat<br>Phe Gly Ser Ile Asn Ala Ile Leu Gly Ser Val Ala Leu Ile Leu Asn<br>305     310     315     320 | 960 |
| tgc cac cac cac gct taa<br>Cys His His His Ala<br>     325 | 978 |

<210> SEQ ID NO 53
<211> LENGTH: 984
<212> TYPE: DNA
<213> ORGANISM: Artificial Sequence
<220> FEATURE:
<221> NAME/KEY: CDS
<222> LOCATION: (1)..(984)
<220> FEATURE:
<223> OTHER INFORMATION: Description of Artificial Sequence: Construct
  encoding chemokine-toxin fusion protein MCP1-AM-truncated Shiga-A1
  Subunit HIS6

<400> SEQUENCE: 53

```
Asn Leu Arg Leu Ile Val Glu Arg Asn Asn Leu Tyr Val Thr Gly Phe
145                 150                 155                 160 gtg aac cgt acg aac aac gtc ttc tat cgt ttc gct gat ttc tcc cac      528
Val Asn Arg Thr Asn Asn Val Phe Tyr Arg Phe Ala Asp Phe Ser His
                165                 170                 175 gta acg ttt ccg ggc acc act gct gtt act ctg agc ggc gat tct tct      576
Val Thr Phe Pro Gly Thr Thr Ala Val Thr Leu Ser Gly Asp Ser Ser
            180                 185                 190 tat act acg tta cag cgt gtg gct ggt atc agc cgc act ggt atg caa      624
Tyr Thr Thr Leu Gln Arg Val Ala Gly Ile Ser Arg Thr Gly Met Gln
        195                 200                 205 atc aat cgc cat tct ctg acg acc agc tat ctg gac tta atg agc cat      672
Ile Asn Arg His Ser Leu Thr Thr Ser Tyr Leu Asp Leu Met Ser His
    210                 215                 220 tct ggc acc agc ctg acc cag tct gtt gcc cgt gcg atg ctg cgc ttc      720
Ser Gly Thr Ser Leu Thr Gln Ser Val Ala Arg Ala Met Leu Arg Phe
225                 230                 235                 240 gtg acg gtc acc gcc gaa gcc ctg cgt ttc cgt caa atc caa cgc ggc      768
Val Thr Val Thr Ala Glu Ala Leu Arg Phe Arg Gln Ile Gln Arg Gly
                245                 250                 255 ttc cgc acc act tta gac gat ctg tct ggc cgc agc tat gtg atg act      816
Phe Arg Thr Thr Leu Asp Asp Leu Ser Gly Arg Ser Tyr Val Met Thr
            260                 265                 270 gcc gaa gat gtc gat ctg acc ctg aac tgg ggt cgc ttg tct tcc gtt      864
Ala Glu Asp Val Asp Leu Thr Leu Asn Trp Gly Arg Leu Ser Ser Val
        275                 280                 285 ctg ccg gat tat cac ggt cag gat tct gtc cgt gtt ggc cgt atc agc      912
Leu Pro Asp Tyr His Gly Gln Asp Ser Val Arg Val Gly Arg Ile Ser
    290                 295                 300 ttt ggc tct att aat gcc atc cta ggc tcc gtc gca ctg att ctc aat      960
Phe Gly Ser Ile Asn Ala Ile Leu Gly Ser Val Ala Leu Ile Leu Asn
305                 310                 315                 320 tgc cac cac cac cat cat cat taa                                      984
Cys His His His His His His
                325

<210> SEQ ID NO 54
<211> LENGTH: 999
<212> TYPE: DNA
<213> ORGANISM: Artificial Sequence
<220> FEATURE:
<221> NAME/KEY: CDS
<222> LOCATION: (1)..(999)
<220> FEATURE:
<223> OTHER INFORMATION: Description of Artificial Sequence: Construct
      encoding chemokine-toxin fussion protein MCP1-AM-SAPORIN

<400> SEQUENCE: 54 atg cag cca gat gca atc aat gcc cca gtc acc tgc tgt tat aac ttc       48
Met Gln Pro Asp Ala Ile Asn Ala Pro Val Thr Cys Cys Tyr Asn Phe
1

|  |  |  |  |  |  |  |  |  |  |  |  |  |  |  |  |
|---|---|---|---|---|---|---|---|---|---|---|---|---|---|---|---|
| | | 65 | | | | 70 | | | | 75 | | | | 80 | |
| act | agt | att | acc | ctg | gac | ctg | gtc | aat | ccg | acc | gcc | ggc | caa | tat | agc | 288
| Thr | Ser | Ile | Thr | Leu | Asp | Leu | Val | Asn | Pro | Thr | Ala | Gly | Gln | Tyr | Ser |
| | | | | | 85 | | | | 90 | | | | | 95 | |
| agc | ttc | gtg | gat | aag | att | cgt | aac | aac | gta | aaa | gat | ccg | aat | ctg | aaa | 336
| Ser | Phe | Val | Asp | Lys | Ile | Arg | Asn | Asn | Val | Lys | Asp | Pro | Asn | Leu | Lys |
| | | | | 100 | | | | | 105 | | | | | 110 | |
| tac | ggt | ggt | act | gat | att | gcg | gtc | atc | ggt | ccg | ccg | agc | aaa | gaa | aag | 384
| Tyr | Gly | Gly | Thr | Asp | Ile | Ala | Val | Ile | Gly | Pro | Pro | Ser | Lys | Glu | Lys |
| | | | 115 | | | | | 120 | | | | | 125 | | |
| ttc | ctg | cgc | att | aac | ttt | caa | agc | tcc | cgt | ggc | act | gtt | tct | ctg | ggc | 432
| Phe | Leu | Arg | Ile | Asn | Phe | Gln | Ser | Ser | Arg | Gly | Thr | Val | Ser | Leu | Gly |
| | | 130 | | | | | 135 | | | | | 140 | | | |
| ctg | aag | cgc | gat | aac | ctg | tat | gtt | gtt | gcc | tat | ctg | gcg | atg | gat | aat | 480
| Leu | Lys | Arg | Asp | Asn | Leu | Tyr | Val | Val | Ala | Tyr | Leu | Ala | Met | Asp | Asn |
| 145 | | | | | 150 | | | | | 155 | | | | | 160 |
| acg | aac | gtg | aac | cgc | gcc | tac | tac | ttt | cgt | agc | gag | att | acg | agc | gcg | 528
| Thr | Asn | Val | Asn | Arg | Ala | Tyr | Tyr | Phe | Arg | Ser | Glu | Ile | Thr | Ser | Ala |
| | | | | 165 | | | | | 170 | | | | | 175 | |
| gaa | tcc | act | gct | ctg | ttc | ccg | gag | gcg | acc | act | gca | aac | caa | aaa | gca | 576
| Glu | Ser | Thr | Ala | Leu | Phe | Pro | Glu | Ala | Thr | Thr | Ala | Asn | Gln | Lys | Ala |
| | | | 180 | | | | | 185 | | | | | 190 | | |
| ctg | gaa | tat | acg | gaa | gat | tac | cag | tcc | atc | gag | aag | aac | gcg | cag | atc | 624
| Leu | Glu | Tyr | Thr | Glu | Asp | Tyr | Gln | Ser | Ile | Glu | Lys | Asn | Ala | Gln | Ile |
| | | 195 | | | | | 200 | | | | | 205 | | | |
| acc | cag | ggc | gat | caa | tcc | cgc | aaa | gaa | ctg | ggt | ctg | ggt | att | gat | ctg | 672
| Thr | Gln | Gly | Asp | Gln | Ser | Arg | Lys | Glu | Leu | Gly | Leu | Gly | Ile | Asp | Leu |
| | 210 | | | | | 215 | | | | | 220 | | | | |
| ctg | agc | acg | agc | atg | gaa | gcg | gtc | aac | aaa | aaa | gct | cgc | gtg | gtt | aaa | 720
| Leu | Ser | Thr | Ser | Met | Glu | Ala | Val | Asn | Lys | Lys | Ala | Arg | Val | Val | Lys |
| 225 | | | | 230 | | | | | 235 | | | | | 240 | |
| gac | gaa | gcc | cgc | ttc | ctg | ctg | atc | gcc | att | cag | atg | acg | gca | gaa | gcc | 768
| Asp | Glu | Ala | Arg | Phe | Leu | Leu | Ile | Ala | Ile | Gln | Met | Thr | Ala | Glu | Ala |
| | | | 245 | | | | | 250 | | | | | 255 | | |
| gcc | cgt | ttc | cgc | tac | att | cag | aac | ctg | gtc | atc | aaa | aac | ttc | ccg | aac | 816
| Ala | Arg | Phe | Arg | Tyr | Ile | Gln | Asn | Leu | Val | Ile | Lys | Asn | Phe | Pro | Asn |
| | | 260 | | | | | 265 | | | | | 270 | | | |
| aag | ttc | aat | tcc | gag | aat | aaa | gtc | att | cag | ttc | gag | gtt | aat | tgg | aaa | 864
| Lys | Phe | Asn | Ser | Glu | Asn | Lys | Val | Ile | Gln | Phe | Glu | Val | Asn | Trp | Lys |
| | 275 | | | | | 280 | | | | | 285 | | | | |
| aaa | att | tcc | acc | gcc | att | tat | ggt | gac | gcg | aag | aac | ggt | gtt | ttc | aat | 912
| Lys | Ile | Ser | Thr | Ala | Ile | Tyr | Gly | Asp | Ala | Lys | Asn | Gly | Val | Phe | Asn |
| 290 | | | | 295 | | | | | 300 | | | | | | |
| aaa | gat | tat | gat | ttt | ggt | ttc | ggt | aag | gta | cgt | cag | gtg | aaa | gac | ctg | 960
| Lys | Asp | Tyr | Asp | Phe | Gly | Phe | Gly | Lys | Val | Arg | Gln | Val | Lys | Asp | Leu |
| 305 | | | | 310 | | | | | 315 | | | | | 320 | |
| caa | atg | ggt | ctg | ctg | atg | tac | cta | gga | aaa | ccg | aag | taa | | | | 999
| Gln | Met | Gly | Leu | Leu | Met | Tyr | Leu | Gly | Lys | Pro | Lys | | | | |
| | | | | 325 | | | | | 330 | | | | | | |

<210> SEQ ID NO 55
<211> LENGTH: 978
<212> TYPE: DNA
<213> ORGANISM: Artificial Sequence
<220> FEATURE:
<221> NAME/KEY: CDS
<222> LOCATION: (1)..(978)
<220> FEATURE:
<223> OTHER INFORMATION: Description of Artificial Sequence: Construct
      encoding chemokine-toxin fusion protein MCP3-AM-truncated Shiga-A1
      Subunit

<400> SEQUENCE: 55

```
atg caa ccg gta ggc atc aac acg tcg acc acg tgc tgt tat cgc ttt      48
Met Gln Pro Val Gly Ile Asn Thr Ser Thr Thr Cys Cys Tyr Arg Phe
 1               5                  10                  15 atc aac aag aaa atc ccg aaa caa cgc ctg gaa tcc tat cgt cgc acc      96
Ile Asn Lys Lys Ile Pro Lys Gln Arg Leu Glu Ser Tyr Arg Arg Thr
             20                  25                  30 act agc agc cac tgt ccg cgc gaa gca gtc atc ttc aaa acc aag ctc     144
Thr Ser Ser His Cys Pro Arg Glu Ala Val Ile Phe Lys Thr Lys Leu
         35                  40                  45 gat aag gaa atc tgt gca gac ccg act cag aaa tgg gtg caa gat ttt     192
Asp Lys Glu Ile Cys Ala Asp Pro Thr Gln Lys Trp Val Gln Asp Phe
 50                  55                  60 atg aaa cat ctg gat aag aaa act cag acc ccg aag ctt gcg atg aaa     240
Met Lys His Leu Asp Lys Lys Thr Gln Thr Pro Lys Leu Ala Met Lys
 65                  70                  75                  80 gaa ttc acc ctg gac ttt tcc act gca aaa act tac gtc gat agc ctg     288
Glu Phe Thr Leu Asp Phe Ser Thr Ala Lys Thr Tyr Val Asp Ser Leu
                 85                  90                  95 aat gtg att cgt tcc gcg atc ggt acg ccg ctg caa acg att tcc agc     336
Asn Val Ile Arg Ser Ala Ile Gly Thr Pro Leu Gln Thr Ile Ser Ser
            100                 105                 110 ggt ggt act tcc ctc ctg atg att gat tcc ggt acg ggt gat aac ttg     384
Gly Gly Thr Ser Leu Leu Met Ile Asp Ser Gly Thr Gly Asp Asn Leu
        115                 120                 125 ttt gct gtt gat gtg cgc ggc att gac ccg gaa gaa ggc cgt ttt aat     432
Phe Ala Val Asp Val Arg Gly Ile Asp Pro Glu Glu Gly Arg Phe Asn
    130                 135                 140 aat ctg cgt ctg atc gtc gaa cgc aac aac ctg tat gtg acg ggt ttt     480
Asn Leu Arg Leu Ile Val Glu Arg Asn Asn Leu Tyr Val Thr Gly Phe
145                 150                 155                 160 gtg aac cgt acg aac aac gtc ttc tat cgt ttc gct gat ttc tcc cac     528
Val Asn Arg Thr Asn Asn Val Phe Tyr Arg Phe Ala Asp Phe Ser His
                165                 170                 175 gta acg ttt ccg ggc acc act gct gtt act ctg agc ggc gat tct tct     576
Val Thr Phe Pro Gly Thr Thr Ala Val Thr Leu Ser Gly Asp Ser Ser
            180                 185                 190 tat act acg tta cag cgt gtg gct ggt atc agc cgc act ggt atg caa     624
Tyr Thr Thr Leu Gln Arg Val Ala Gly Ile Ser Arg Thr Gly Met Gln
        195                 200                 205 atc aat cgc cat tct ctg acg acc agc tat ctg gac tta atg agc cat     672
Ile Asn Arg His Ser Leu Thr Thr Ser Tyr Leu Asp Leu Met Ser His
    210                 215                 220 tct ggc acc agc ctg acc cag tct gtt gcc cgt gcg atg ctg cgc ttc     720
Ser Gly Thr Ser Leu Thr Gln Ser Val Ala Arg Ala Met Leu Arg Phe
225                 230                 235                 240 gtg acg gtc acc gcc gaa gcc ctg cgt ttc cgt caa atc caa cgc ggc     768
Val Thr Val Thr Ala Glu Ala Leu Arg Phe Arg Gln Ile Gln Arg Gly
                245                 250                 255 ttc cgc acc act tta gac gat ctg tct ggc cgc agc tat gtg atg act     816
Phe Arg Thr Thr Leu Asp Asp Leu Ser Gly Arg Ser Tyr Val Met Thr
            260                 265                 270 gcc gaa gat gtc gat ctg acc ctg aac tgg ggt cgc ttg tct tcc gtt     864
Ala Glu Asp Val Asp Leu Thr Leu Asn Trp Gly Arg Leu Ser Ser Val
        275                 280                 285 ctg ccg gat tat cac ggt cag gat tct gtc cgt gtt ggc cgt atc agc     912
Leu Pro Asp Tyr His Gly Gln Asp Ser Val Arg Val Gly Arg Ile Ser
    290                 295                 300 ttt ggc tct att aat gcc atc cta ggc tcc gtc gca ctg att ctc aat     960
```

```
Phe Gly Ser Ile Asn Ala Ile Leu Gly Ser Val Ala Leu Ile Leu Asn
305                 310                 315                 320 tgc cac cac cac gct taa                                              978
Cys His His His Ala
            325

<210> SEQ ID NO 56
<211> LENGTH: 984
<212> TYPE: DNA
<213> ORGANISM: Artificial Sequence
<220> FEATURE:
<221> NAME/KEY: CDS
<222> LOCATION: (1)..(984)
<220> FEATURE:
<223> OTHER INFORMATION: Description of Artificial Sequence: Construct
      encoding chemokine-toxin fusion protein MCP3-AM-truncated Shiga-A1
      subunit HIS6

<400> SEQUENCE: 56 atg caa ccg gta ggc atc aac acg tcg acc acg tgc tgt tat cgc ttt     48
Met Gln Pro Val Gly Ile Asn Thr Ser Thr Thr Cys Cys Tyr Arg Phe
1               5                   10                  15 atc aac aag aaa atc ccg aaa caa cgc ctg gaa tcc tat cgt cgc acc     96
Ile Asn Lys Lys Ile Pro Lys Gln Arg Leu Glu Ser Tyr Arg Arg Thr
                20                  25                  30 act agc agc cac tgt ccg cgc gaa gca gtc atc ttc aaa acc aag ctc    144
Thr Ser Ser His Cys Pro Arg Glu Ala Val Ile Phe Lys Thr Lys Leu
            35                  40                  45 gat aag gaa atc tgt gca gac ccg act cag aaa tgg gtg caa gat ttt    192
Asp Lys Glu Ile Cys Ala Asp Pro Thr Gln Lys Trp Val Gln Asp Phe
    50                  55                  60 atg aaa cat ctg gat aag aaa act cag acc ccg aag ctt gcg atg aaa    240
Met Lys His Leu Asp Lys Lys Thr Gln Thr Pro Lys Leu Ala Met Lys
65                  70                  75                  80 gaa ttc acc ctg gac ttt tcc act gca aaa act tac gtc gat agc ctg    288
Glu Phe Thr Leu Asp Phe Ser Thr Ala Lys Thr Tyr Val Asp Ser Leu
                85                  90                  95 aat gtg att cgt tcc gcg atc ggt acg ccg ctg caa acg att tcc agc    336
Asn Val Ile Arg Ser Ala Ile Gly Thr Pro Leu Gln Thr Ile Ser Ser
                100                 105                 110 ggt ggt act tcc ctc ctg atg att gat tcc ggt acg ggt gat aac ttg    384
Gly Gly Thr Ser Leu Leu Met Ile Asp Ser Gly Thr Gly Asp Asn Leu
            115                 120                 125 ttt gct gtt gat gtg cgc ggc att gac ccg gaa gaa ggc cgt ttt aat    432
Phe Ala Val Asp Val Arg Gly Ile Asp Pro Glu Glu Gly Arg Phe Asn
    130                 135                 140 aat ctg cgt ctg atc gtc gaa cgc aac aac ctg tat gtg acg ggt ttt    480
Asn Leu Arg Leu Ile Val Glu Arg Asn Asn Leu Tyr Val Thr Gly Phe
145                 150                 155                 160 gtg aac cgt acg aac aac gtc ttc tat cgt ttc gct gat ttc tcc cac    528
Val Asn Arg Thr Asn Asn Val Phe Tyr Arg Phe Ala Asp Phe Ser His
                165                 170                 175 gta acg ttt ccg ggc acc act gct gtt act ctg agc ggc gat tct tct    576
Val Thr Phe Pro Gly Thr Thr Ala Val Thr Leu Ser Gly Asp Ser Ser
                180                 185                 190 tat act acg tta cag cgt gtg gct ggt atc agc cgc act ggt atg caa    624
Tyr Thr Thr Leu Gln Arg Val Ala Gly Ile Ser Arg Thr Gly Met Gln
            195                 200                 205 atc aat cgc cat tct ctg acg acc agc tat ctg gac tta atg agc cat    672
Ile Asn Arg His Ser Leu Thr Thr Ser Tyr Leu Asp Leu Met Ser His
    210                 215                 220 tct ggc acc agc ctg acc cag tct gtt gcc cgt gcg atg ctg cgc ttc    720
```

| | | |
|---|---|---|
| Ser Gly Thr Ser Leu Thr Gln Ser Val Ala Arg Ala Met Leu Arg Phe<br>225                          230                      235                      240 | | |
| gtg acg gtc acc gcc gaa gcc ctg cgt ttc cgt caa atc caa cgc ggc<br>Val Thr Val Thr Ala Glu Ala Leu Arg Phe Arg Gln Ile Gln Arg Gly<br>                            245                      250                      255 | 768 | |
| ttc cgc act act tta gac gat ctg tct ggc cgc agc tat gtg atg act<br>Phe Arg Thr Thr Leu Asp Asp Leu Ser Gly Arg Ser Tyr Val Met Thr<br>                  260                      265                      270 | 816 | |
| gcc gaa gat gtc gat ctg acc ctg aac tgg ggt cgc ttg tct tcc gtt<br>Ala Glu Asp Val Asp Leu Thr Leu Asn Trp Gly Arg Leu Ser Ser Val<br>        275                      280                      285 | 864 | |
| ctg ccg gat tat cac ggt cag gat tct gtc cgt gtt ggc cgt atc agc<br>Leu Pro Asp Tyr His Gly Gln Asp Ser Val Arg Val Gly Arg Ile Ser<br>      290                      295                      300 | 912 | |
| ttt ggc tct att aat gcc atc cta ggc tcc gtc gca ctg att ctc aat<br>Phe Gly Ser Ile Asn Ala Ile Leu Gly Ser Val Ala Leu Ile Leu Asn<br>305                        310                      315                      320 | 960 | |
| tgc cac cac cac cat cat cat taa<br>Cys His His His His His His<br>                  325 | 984 | |

```
<210> SEQ ID NO 57
<211> LENGTH: 999
<212> TYPE: DNA
<213> ORGANISM: Artificial Sequence
<220> FEATURE:
<221> NAME/KEY: CDS
<222> LOCATION: (1)..(999)
<220> FEATURE:
<223> OTHER INFORMATION: Description of Artificial Sequence: Construct
      encoding chemokine-toxin Fusion Protein MCP3-AM-SAPORIN

<400> SEQUENCE: 57
```

| | | |
|---|---|---|
| atg caa ccg gta ggc atc aac acg tcc acc acg tgc tgt tat cgc ttt<br>Met Gln Pro Val Gly Ile Asn Thr Ser Thr Thr Cys Cys Tyr Arg Phe<br>1  -continued

```
                145                 150                 155                 160
acg aac gtg aac cgc gcc tac tac ttt cgt agc gag att acg agc gcg        528
Thr Asn Val Asn Arg Ala Tyr Tyr Phe Arg Ser Glu Ile Thr Ser Ala
                    165                 170                 175 gaa tcc act gct ctg ttc ccg gag gcg acc act gca aac caa aaa gca        576
Glu Ser Thr Ala Leu Phe Pro Glu Ala Thr Thr Ala Asn Gln Lys Ala
        180                 185                 190 ctg gaa tat acg gaa gat tac cag tcc atc gag aag aac gcg cag atc        624
Leu Glu Tyr Thr Glu Asp Tyr Gln Ser Ile Glu Lys Asn Ala Gln Ile
    195                 200                 205 acc cag ggc gat caa tcc cgc aaa gaa ctg ggt ctg ggt att gat ctg        672
Thr Gln Gly Asp Gln Ser Arg Lys Glu Leu Gly Leu Gly Ile Asp Leu
210                 215                 220 ctg agc acg agc atg gaa gcg gtc aac aaa aaa gct cgc gtg gtt aaa        720
Leu Ser Thr Ser Met Glu Ala Val Asn Lys Lys Ala Arg Val Val Lys
225                 230                 235                 240 gac gaa gcc cgc ttc ctg ctg atc gcc att cag atg acg gca gaa gcc        768
Asp Glu Ala Arg Phe Leu Leu Ile Ala Ile Gln Met Thr Ala Glu Ala
                    245                 250                 255 gcc cgt ttc cgc tac att cag aac ctg gtc atc aaa aac ttc ccg aac        816
Ala Arg Phe Arg Tyr Ile Gln Asn Leu Val Ile Lys Asn Phe Pro Asn
                260                 265                 270 aag ttc aat tcc gag aat aaa gtc att cag ttc gag gtt aat tgg aaa        864
Lys Phe Asn Ser Glu Asn Lys Val Ile Gln Phe Glu Val Asn Trp Lys
            275                 280                 285 aaa att tcc acc gcc att tat ggt gac gcg aag aac ggt gtt ttc aat        912
Lys Ile Ser Thr Ala Ile Tyr Gly Asp Ala Lys Asn Gly Val Phe Asn
        290                 295                 300 aaa gat tat gat ttt ggt ttc ggt aag gta cgt cag gtg aaa gac ctg        960
Lys Asp Tyr Asp Phe Gly Phe Gly Lys Val Arg Gln Val Lys Asp Leu
305                 310                 315                 320 caa atg ggt ctg ctg atg tac cta gga aaa ccg aag taa                    999
Gln Met Gly Leu Leu Met Tyr Leu Gly Lys Pro Lys
                    325                 330
```

<210> SEQ ID NO 58
<211> LENGTH: 963
<212> TYPE: DNA
<213> ORGANISM: Artificial Sequence
<220> FEATURE:
<223> OTHER INFORMATION: Description of Artificial Sequence: Construct
    encoding chemokine-toxin fusion protein SDF-1-Beta-AM-truncated
    Shiga-A1 Subunit
<220> FEATURE:
<221> NAME/KEY: CDS
<222> LOCATION: (1)..(963)

<400> SEQUENCE: 58

```
aag ccc gtc agc ctg agc tac aga tgc cca tgc cga ttc ttc gaa agc         48
Lys Pro Val Ser Leu Ser Tyr Arg Cys Pro Cys Arg Phe Phe Glu Ser
 1               5                  10                  15 cat gtt gcc aga gcc aac gtc aag cat ctc aaa att ctc aac act cca         96
His Val Ala Arg Ala Asn Val Lys His Leu Lys Ile Leu Asn Thr Pro
                20                  25                  30 aac tgt gcc ctt cag att gta gcc cgg ctg aag aac aac aac aga caa        144
Asn Cys Ala Leu Gln Ile Val Ala Arg Leu Lys Asn Asn Asn Arg Gln
            35                  40                  45 gtg tgc att gac ccg aag cta aag tgg att cag gag tac ctg gag aaa        192
Val Cys Ile Asp Pro Lys Leu Lys Trp Ile Gln Glu Tyr Leu Glu Lys
        50                  55                  60 gct tta aac aag agg ttc aag atg gcg atg aaa gaa ttc acc ctg gac        240
Ala Leu Asn Lys Arg Phe Lys Met Ala Met Lys Glu Phe Thr Leu Asp
```

```
                        65                  70                  75                  80
ttt tcc act gca aaa act tac gtc gat agc ctg aat gtg att cgt tcc         288
Phe Ser Thr Ala Lys Thr Tyr Val Asp Ser Leu Asn Val Ile Arg Ser
                    85                  90                  95 gcg atc ggt acg ccg ctg caa acg att tcc agc ggt ggt act tcc ctc         336
Ala Ile Gly Thr Pro Leu Gln Thr Ile Ser Ser Gly Gly Thr Ser Leu
                100                 105                 110 ctg atg att gat tcc ggt acg ggt gat aac ttg ttt gct gtt gat gtg         384
Leu Met Ile Asp Ser Gly Thr Gly Asp Asn Leu Phe Ala Val Asp Val
            115                 120                 125 cgc ggc att gac ccg gaa gaa ggc cgt ttt aat aat ctg cgt ctg atc         432
Arg Gly Ile Asp Pro Glu Glu Gly Arg Phe Asn Asn Leu Arg Leu Ile
        130                 135                 140 gtc gaa cgc aac aac ctg tat gtg acg ggt ttt gtg aac cgt acg aac         480
Val Glu Arg Asn Asn Leu Tyr Val Thr Gly Phe Val Asn Arg Thr Asn
145                 150                 155                 160 aac gtc ttc tat cgt ttc gct gat ttc tcc cac gta acg ttt ccg ggc         528
Asn Val Phe Tyr Arg Phe Ala Asp Phe Ser His Val Thr Phe Pro Gly
                165                 170                 175 acc act gct gtt act ctg agc ggc gat tct tct tat act acg tta cag         576
Thr Thr Ala Val Thr Leu Ser Gly Asp Ser Ser Tyr Thr Thr Leu Gln
                180                 185                 190 cgt gtg gct ggt atc agc cgc act ggt atg caa atc aat cgc cat tct         624
Arg Val Ala Gly Ile Ser Arg Thr Gly Met Gln Ile Asn Arg His Ser
            195                 200                 205 ctg acg acc agc tat ctg gac tta atg agc cat tct ggc acc agc ctg         672
Leu Thr Thr Ser Tyr Leu Asp Leu Met Ser His Ser Gly Thr Ser Leu
        210                 215                 220 acc cag tct gtt gcc cgt gcg atg ctg cgc ttc gtg acg gtc acc gcc         720
Thr Gln Ser Val Ala Arg Ala Met Leu Arg Phe Val Thr Val Thr Ala
225                 230                 235                 240 gaa gcc ctg cgt ttc cgt caa atc caa cgc ggc ttc cgc acc act tta         768
Glu Ala Leu Arg Phe Arg Gln Ile Gln Arg Gly Phe Arg Thr Thr Leu
                245                 250                 255 gac gat ctg tct ggc cgc agc tat gtg atg act gcc gaa gat gtc gat         816
Asp Asp Leu Ser Gly Arg Ser Tyr Val Met Thr Ala Glu Asp Val Asp
                260                 265                 270 ctg acc ctg aac tgg ggt cgc ttg tct tcc gtt ctg ccg gat tat cac         864
Leu Thr Leu Asn Trp Gly Arg Leu Ser Ser Val Leu Pro Asp Tyr His
            275                 280                 285 ggt cag gat tct gtc cgt gtt ggc cgt atc agc ttt ggc tct att aat         912
Gly Gln Asp Ser Val Arg Val Gly Arg Ile Ser Phe Gly Ser Ile Asn
        290                 295                 300 gcc atc cta ggc tcc gtc gca ctg att ctc aat tgc cac cac cac gct         960
Ala Ile Leu Gly Ser Val Ala Leu Ile Leu Asn Cys His His His Ala
305                 310                 315                 320 taa                                                                     963

<210> SEQ ID NO 59
<211> LENGTH: 969
<212> TYPE: DNA
<213> ORGANISM: Artificial Sequence
<220> FEATURE:
<223> OTHER INFORMATION: Description of Artificial Sequence: Construct
      encoding chemokine-toxin fusion protein SDF-1-Beta-AM-truncated
      Shiga-A1 Subunit HIS6
<220> FEATURE:
<221> NAME/KEY: CDS
<222> LOCATION: (1)..(969)

<400> SEQUENCE: 59
```

```
aag ccc gtc agc ctg agc tac aga tgc cca tgc cga ttc ttc gaa agc     48
Lys Pro Val Ser Leu Ser Tyr Arg Cys Pro Cys Arg Phe Phe Glu Ser
 1               5                  10                  15 cat gtt gcc aga gcc aac gtc aag cat ctc aaa att ctc aac act cca     96
His Val Ala Arg Ala Asn Val Lys His Leu Lys Ile Leu Asn Thr Pro
             20                  25                  30 aac tgt gcc ctt cag att gta gcc cgg ctg aag aac aac aac aga caa    144
Asn Cys Ala Leu Gln Ile Val Ala Arg Leu Lys Asn Asn Asn Arg Gln
         35                  40                  45 gtg tgc att gac ccg aag cta aag tgg att cag gag tac ctg gag aaa    192
Val Cys Ile Asp Pro Lys Leu Lys Trp Ile Gln Glu Tyr Leu Glu Lys
 50                  55                  60 gct tta aac aag agg ttc aag atg gcg atg aaa gaa ttc acc ctg gac    240
Ala Leu Asn Lys Arg Phe Lys Met Ala Met Lys Glu Phe Thr Leu Asp
 65                  70                  75                  80 ttt tcc act gca aaa act tac gtc gat agc ctg aat gtg att cgt tcc    288
Phe Ser Thr Ala Lys Thr Tyr Val Asp Ser Leu Asn Val Ile Arg Ser
                 85                  90                  95 gcg atc ggt acg ccg ctg caa acg att tcc agc ggt ggt act tcc ctc    336
Ala Ile Gly Thr Pro Leu Gln Thr Ile Ser Ser Gly Gly Thr Ser Leu
            100                 105                 110 ctg atg att gat tcc ggt acg ggt gat aac ttg ttt gct gtt gat gtg    384
Leu Met Ile Asp Ser Gly Thr Gly Asp Asn Leu Phe Ala Val Asp Val
        115                 120                 125 cgc ggc att gac ccg gaa gaa ggc cgt ttt aat aat ctg cgt ctg atc    432
Arg Gly Ile Asp Pro Glu Glu Gly Arg Phe Asn Asn Leu Arg Leu Ile
130                 135                 140 gtc gaa cgc aac aac ctg tat gtg acg ggt ttt gtg aac cgt acg aac    480
Val Glu Arg Asn Asn Leu Tyr Val Thr Gly Phe Val Asn Arg Thr Asn
145                 150                 155                 160 aac gtc ttc tat cgt ttc gct gat ttc tcc cac gta acg ttt ccg ggc    528
Asn Val Phe Tyr Arg Phe Ala Asp Phe Ser His Val Thr Phe Pro Gly
                165                 170                 175 acc act gct gtt act ctg agc ggc gat tct tct tat act acg tta cag    576
Thr Thr Ala Val Thr Leu Ser Gly Asp Ser Ser Tyr Thr Thr Leu Gln
            180                 185                 190 cgt gtg gct ggt atc agc cgc act ggt atg caa atc aat cgc cat tct    624
Arg Val Ala Gly Ile Ser Arg Thr Gly Met Gln Ile Asn Arg His Ser
        195                 200                 205 ctg acg acc agc tat ctg gac tta atg agc cat tct ggc acc agc ctg    672
Leu Thr Thr Ser Tyr Leu Asp Leu Met Ser His Ser Gly Thr Ser Leu
    210                 215                 220 acc cag tct gtt gcc cgt gcg atg ctg cgc ttc gtg acg gtc acc gcc    720
Thr Gln Ser Val Ala Arg Ala Met Leu Arg Phe Val Thr Val Thr Ala
225                 230                 235                 240 gaa gcc ctg cgt ttc cgt caa atc caa cgc ggc ttc cgc acc act tta    768
Glu Ala Leu Arg Phe Arg Gln Ile Gln Arg Gly Phe Arg Thr Thr Leu
                245                 250                 255 gac gat ctg tct ggc cgc agc tat gtg atg act gcc gaa gat gtc gat    816
Asp Asp Leu Ser Gly Arg Ser Tyr Val Met Thr Ala Glu Asp Val Asp
            260                 265                 270 ctg acc ctg aac tgg ggt cgc ttg tct tcc gtt ctg ccg gat tat cac    864
Leu Thr Leu Asn Trp Gly Arg Leu Ser Ser Val Leu Pro Asp Tyr His
        275                 280                 285 ggt cag gat tct gtc cgt gtt ggc cgt atc agc ttt ggc tct att aat    912
Gly Gln Asp Ser Val Arg Val Gly Arg Ile Ser Phe Gly Ser Ile Asn
    290                 295                 300 gcc atc cta ggc tcc gtc gca ctg att ctc aat tgc cac cac cac cat    960
Ala Ile Leu Gly Ser Val Ala Leu Ile Leu Asn Cys His His His His
305                 310                 315                 320
```

```
cat cat taa                                                           969
His His
```

<210> SEQ ID NO 60
<211> LENGTH: 984
<212> TYPE: DNA
<213> ORGANISM: Artificial Sequence
<220> FEATURE:
<223> OTHER INFORMATION: Description of Artificial Sequence: Construct
      encoding chemokine-toxin fusion protein SDF-1-Beta-AM-SAPORIN
<220> FEATURE:
<221> NAME/KEY: CDS
<222> LOCATION: (1)..(984)

<400> SEQUENCE: 60

```
aag ccc gtc agc ctg agc tac aga tgc cca tgc cga ttc ttc gaa agc    48
Lys Pro Val Ser Leu Ser Tyr Arg Cys Pro Cys Arg Phe Phe Glu Ser
 1               5                  10                  15 cat gtt gcc aga gcc aac gtc aag cat ctc aaa att ctc aac act cca    96
His Val Ala Arg Ala Asn Val Lys His Leu Lys Ile Leu Asn Thr Pro
                 20                  25                  30 aac tgt gcc ctt cag att gta gcc cgg ctg aag aac aac aac aga caa   144
Asn Cys Ala Leu Gln Ile Val Ala Arg Leu Lys Asn Asn Asn Arg Gln
             35                  40                  45 gtg tgc att gac ccg aag cta aag tgg att cag gag tac ctg gag aaa   192
Val Cys Ile Asp Pro Lys Leu Lys Trp Ile Gln Glu Tyr Leu Glu Lys
         50                  55                  60 gct tta aac aag agg ttc aag atg gcg atg gtt act agt att acc ctg   240
Ala Leu Asn Lys Arg Phe Lys Met Ala Met Val Thr Ser Ile Thr Leu
 65                  70                  75                  80 gac ctg gtc aat ccg acc gcc ggc caa tat agc agc ttc gtg gat aag   288
Asp Leu Val Asn Pro Thr Ala Gly Gln Tyr Ser Ser Phe Val Asp Lys
                 85                  90                  95 att cgt aac aac gta aaa gat ccg aat ctg aaa tac ggt ggt act gat   336
Ile Arg Asn Asn Val Lys Asp Pro Asn Leu Lys Tyr Gly Gly Thr Asp
                100                 105                 110 att gcg gtc atc ggt ccg ccg agc aaa gaa aag ttc ctg cgc att aac   384
Ile Ala Val Ile Gly Pro Pro Ser Lys Glu Lys Phe Leu Arg Ile Asn
            115                 120                 125 ttt caa agc tcc cgt ggc act gtt tct ctg ggc ctg aag cgc gat aac   432
Phe Gln Ser Ser Arg Gly Thr Val Ser Leu Gly Leu Lys Arg Asp Asn
        130                 135                 140 ctg tat gtt gtt gcc tat ctg gcg atg gat aat acg aac gtg aac cgc   480
Leu Tyr Val Val Ala Tyr Leu Ala Met Asp Asn Thr Asn Val Asn Arg
145                 150                 155                 160 gcc tac tac ttt cgt agc gag att acg agc gcg gaa tcc act gct ctg   528
Ala Tyr Tyr Phe Arg Ser Glu Ile Thr Ser Ala Glu Ser Thr Ala Leu
                165                 170                 175 ttc ccg gag gcg acc act gca aac caa aaa gca ctg gaa tat acg gaa   576
Phe Pro Glu Ala Thr Thr Ala Asn Gln Lys Ala Leu Glu Tyr Thr Glu
            180                 185                 190 gat tac cag tcc atc gag aag aac gcg cag atc acc cag ggc gat caa   624
Asp Tyr Gln Ser Ile Glu Lys Asn Ala Gln Ile Thr Gln Gly Asp Gln
        195                 200                 205 tcc cgc aaa gaa ctg ggt ctg ggt att gat ctg ctg agc acg agc atg   672
Ser Arg Lys Glu Leu Gly Leu Gly Ile Asp Leu Leu Ser Thr Ser Met
    210                 215                 220 gaa gcg gtc aac aaa aaa gct cgc gtg gtt aaa gac gaa gcc cgc ttc   720
Glu Ala Val Asn Lys Lys Ala Arg Val Val Lys Asp Glu Ala Arg Phe
225                 230                 235                 240 ctg ctg atc gcc att cag atg acg gca gaa gcc gcc cgt ttc cgc tac   768
Leu Leu Ile Ala Ile Gln Met Thr Ala Glu Ala Ala Arg Phe Arg Tyr
```

-continued

```
                Leu Leu Ile Ala Ile Gln Met Thr Ala Glu Ala Ala Arg Phe Arg Tyr
                                245                 250                 255 att cag aac ctg gtc atc aaa aac ttc ccg aac aag ttc aat tcc gag          816
Ile Gln Asn Leu Val Ile Lys Asn Phe Pro Asn Lys Phe Asn Ser Glu
            260                 265                 270 aat aaa gtc att cag ttc gag gtt aat tgg aaa aaa att tcc acc gcc          864
Asn Lys Val Ile Gln Phe Glu Val Asn Trp Lys Lys Ile Ser Thr Ala
            275                 280                 285 att tat ggt gac gcg aag aac ggt gtt ttc aat aaa gat tat gat ttt          912
Ile Tyr Gly Asp Ala Lys Asn Gly Val Phe Asn Lys Asp Tyr Asp Phe
            290                 295                 300 ggt ttc ggt aag gta cgt cag gtg aaa gac ctg caa atg ggt ctg ctg          960
Gly Phe Gly Lys Val Arg Gln Val Lys Asp Leu Gln Met Gly Leu Leu
305                 310                 315                 320 atg tac cta gga aaa ccg aag taa                                          984
Met Tyr Leu Gly Lys Pro Lys
                325

<210> SEQ ID NO 61
<211> LENGTH: 972
<212> TYPE: DNA
<213> ORGANISM: Artificial Sequence
<220> FEATURE:
<221> NAME/KEY: CDS
<222> LOCATION: (1)..(972)
<220> FEATURE:
<223> OTHER INFORMATION: Description of Artificial Sequence: Construct
      encoding chemokine-toxin fusion protein EOTAXIN-AM-truncated
      Shiga-A1 Subunit

<400> SEQUENCE: 61 atg ggg cca gct tct gtc cca acc acc tgc tgc ttt aac ctg gcc aat           48
Met Gly Pro Ala Ser Val Pro Thr Thr Cys Cys Phe Asn Leu Ala Asn
1               5                   10                  15 agg aag ata ccc ctt cag cga cta gag agc tac agg aga atc acc agt           96
Arg Lys Ile Pro Leu Gln Arg Leu Glu Ser Tyr Arg Arg Ile Thr Ser
            20                  25                  30 ggc aaa tgt ccc cag aaa gct gtg atc ttc aag acc aaa ctg gcc aag          144
Gly Lys Cys Pro Gln Lys Ala Val Ile Phe Lys Thr Lys Leu Ala Lys
        35                  40                  45 gat atc tgt gcc gac ccc aag aag aag tgg gtg cag gat tcc atg aag          192
Asp Ile Cys Ala Asp Pro Lys Lys Lys Trp Val Gln Asp Ser Met Lys
    50                  55                  60 tat ctg gac caa aaa tct cca act cca aag cca gcg atg aaa gaa ttc          240
Tyr Leu Asp Gln Lys Ser Pro Thr Pro Lys Pro Ala Met Lys Glu Phe
65                  70                  75                  80 acc ctg gac ttt tcc act gca aaa act tac gtc gat agc ctg aat gtg          288
Thr Leu Asp Phe Ser Thr Ala Lys Thr Tyr Val Asp Ser Leu Asn Val
                85                  90                  95 att cgt tcc gcg atc ggt acg ccg ctg caa acg att tcc agc ggt ggt          336
Ile Arg Ser Ala Ile Gly Thr Pro Leu Gln Thr Ile Ser Ser Gly Gly
            100                 105                 110 act tcc ctc ctg atg att gat tcc ggt acg ggt gat aac ttg ttt gct          384
Thr Ser Leu Leu Met Ile Asp Ser Gly Thr Gly Asp Asn Leu Phe Ala
        115                 120                 125 gtt gat gtg cgc ggc att gac ccg gaa gaa ggc cgt ttt aat aat ctg          432
Val Asp Val Arg Gly Ile Asp Pro Glu Glu Gly Arg Phe Asn Asn Leu
    130                 135                 140 cgt ctg atc gtc gaa cgc aac aac ctg tat gtg acg ggt ttt gtg aac          480
Arg Leu Ile Val Glu Arg Asn Asn Leu Tyr Val Thr Gly Phe Val Asn
145                 150                 155                 160 cgt acg aac aac gtc ttc tat cgt ttc gct gat ttc tcc cac gta acg          528
```

-continued

| | | |
|---|---|---|
| Arg Thr Asn Asn Val Phe Tyr Arg Phe Ala Asp Phe Ser His Val Thr<br>165                    170                    175 | | |
| ttt ccg ggc acc act gct gtt act ctg agc ggc gat tct tct tat act<br>Phe Pro Gly Thr Thr Ala Val Thr Leu Ser Gly Asp Ser Ser Tyr Thr<br>               180                  185                  190 | 576 | |
| acg tta cag cgt gtg gct ggt atc agc cgc act ggt atg caa atc aat<br>Thr Leu Gln Arg Val Ala Gly Ile Ser Arg Thr Gly Met Gln Ile Asn<br>        195                  200                  205 | 624 | |
| cgc cat tct ctg acg acc agc tat ctg gac tta atg agc cat tct ggc<br>Arg His Ser Leu Thr Thr Ser Tyr Leu Asp Leu Met Ser His Ser Gly<br>210                    215                    220 | 672 | |
| acc agc ctg acc cag tct gtt gcc cgt gcg atg ctg cgc ttc gtg acg<br>Thr Ser Leu Thr Gln Ser Val Ala Arg Ala Met Leu Arg Phe Val Thr<br>225                    230                    235                  240 | 720 | |
| gtc acc gcc gaa gcc ctg cgt ttc cgt caa atc caa cgc ggc ttc cgc<br>Val Thr Ala Glu Ala Leu Arg Phe Arg Gln Ile Gln Arg Gly Phe Arg<br>               245                  250                  255 | 768 | |
| acc act tta gac gat ctg tct ggc cgc agc tat gtg atg act gcc gaa<br>Thr Thr Leu Asp Asp Leu Ser Gly Arg Ser Tyr Val Met Thr Ala Glu<br>        260                  265                  270 | 816 | |
| gat gtc gat ctg acc ctg aac tgg ggt cgc ttg tct tcc gtt ctg ccg<br>Asp Val Asp Leu Thr Leu Asn Trp Gly Arg Leu Ser Ser Val Leu Pro<br>275                    280                    285 | 864 | |
| gat tat cac ggt cag gat tct gtc cgt gtt ggc cgt atc agc ttt ggc<br>Asp Tyr His Gly Gln Asp Ser Val Arg Val Gly Arg Ile Ser Phe Gly<br>        290                  295                  300 | 912 | |
| tct att aat gcc atc cta ggc tcc gtc gca ctg att ctc aat tgc cac<br>Ser Ile Asn Ala Ile Leu Gly Ser Val Ala Leu Ile Leu Asn Cys His<br>305                    310                    315                  320 | 960 | |
| cac cac gct taa<br>His His Ala | 972 | |

<210> SEQ ID NO 62
<211> LENGTH: 978
<212> TYPE: DNA
<213> ORGANISM: Artificial Sequence
<220> FEATURE:
<221> NAME/KEY: CDS
<222> LOCATION: (1)..(978)
<220> FEATURE:
<223> OTHER INFORMATION: Description of Artificial Sequence: Construct
     encoding chemokine-toxin fusion protein EOTAXIN-AM-truncated
     Shiga-A1 Subunit HIS6

<400> SEQUENCE: 62

| | | |
|---|---|---|
| atg ggg cca gct tct gtc cca acc acc tgc tgc ttt aac ctg gcc aat<br>Met Gly Pro Ala Ser Val Pro Thr Thr Cys Cys Phe Asn Leu Ala Asn<br>1               5                   10                   15 | 48 | |
| agg aag ata ccc ctt cag cga cta gag agc tac agg aga atc acc agt<br>Arg Lys Ile Pro Leu Gln Arg Leu Glu Ser Tyr Arg Arg Ile Thr Ser<br>                20                  25                  30 | 96 | |
| ggc aaa tgt ccc cag aaa gct gtg atc ttc aag acc aaa ctg gcc aag<br>Gly Lys Cys Pro Gln Lys Ala Val Ile Phe Lys Thr Lys Leu Ala Lys<br>        35                  40                  45 | 144 | |
| gat atc tgt gcc gac ccc aag aag aag tgg gtg cag gat tcc atg aag<br>Asp Ile Cys Ala Asp Pro Lys Lys Lys Trp Val Gln Asp Ser Met Lys<br>50                    55                    60 | 192 | |
| tat ctg gac caa aaa tct cca act cca aag cca gcg atg aaa gaa ttc<br>Tyr Leu Asp Gln Lys Ser Pro Thr Pro Lys Pro Ala Met Lys Glu Phe<br>65                    70                    75                  80 | 240 | |
| acc ctg gac ttt tcc act gca aaa act tac gtc gat agc ctg aat gtg<br>Thr Leu Asp Phe Ser Thr Ala Lys Thr Tyr Val Asp Ser Leu Asn Val | 288 | |

|   |   |
|---|---|
| att cgt tcc gcg atc ggt acg ccg ctg caa acg att tcc agc ggt ggt<br>Ile Arg Ser Ala Ile Gly Thr Pro Leu Gln Thr Ile Ser Ser Gly Gly<br>                        100                        105                     110 | 336 |
| act tcc ctc ctg atg att gat tcc ggt acg ggt gat aac ttg ttt gct<br>Thr Ser Leu Leu Met Ile Asp Ser Gly Thr Gly Asp Asn Leu Phe Ala<br>                 115                    120                   125 | 384 |
| gtt gat gtg cgc ggc att gac ccg gaa gaa ggc cgt ttt aat aat ctg<br>Val Asp Val Arg Gly Ile Asp Pro Glu Glu Gly Arg Phe Asn Asn Leu<br>130                    135                    140 | 432 |
| cgt ctg atc gtc gaa cgc aac aac ctg tat gtg acg ggt ttt gtg aac<br>Arg Leu Ile Val Glu Arg Asn Asn Leu Tyr Val Thr Gly Phe Val Asn<br>145                   150                    155                 160 | 480 |
| cgt acg aac aac gtc ttc tat cgt ttc gct gat ttc tcc cac gta acg<br>Arg Thr Asn Asn Val Phe Tyr Arg Phe Ala Asp Phe Ser His Val Thr<br>                        165                   170                 175 | 528 |
| ttt ccg ggc acc act gct gtt act ctg agc ggc gat tct tct tat act<br>Phe Pro Gly Thr Thr Ala Val Thr Leu Ser Gly Asp Ser Ser Tyr Thr<br>                 180                    185                   190 | 576 |
| acg tta cag cgt gtg gct ggt atc agc cgc act ggt atg caa atc aat<br>Thr Leu Gln Arg Val Ala Gly Ile Ser Arg Thr Gly Met Gln Ile Asn<br>                   195                    200                   205 | 624 |
| cgc cat tct ctg acg acc agc tat ctg gac tta atg agc cat tct ggc<br>Arg His Ser Leu Thr Thr Ser Tyr Leu Asp Leu Met Ser His Ser Gly<br>210                    215                    220 | 672 |
| acc agc ctg acc cag tct gtt gcc cgt gcg atg ctg cgc ttc gtg acg<br>Thr Ser Leu Thr Gln Ser Val Ala Arg Ala Met Leu Arg Phe Val Thr<br>225                   230                    235                 240 | 720 |
| gtc acc gcc gaa gcc ctg cgt ttc cgt caa atc caa cgc ggc ttc cgc<br>Val Thr Ala Glu Ala Leu Arg Phe Arg Gln Ile Gln Arg Gly Phe Arg<br>                        245                   250                 255 | 768 |
| acc act tta gac gat ctg tct ggc cgc agc tat gtg atg act gcc gaa<br>Thr Thr Leu Asp Asp Leu Ser Gly Arg Ser Tyr Val Met Thr Ala Glu<br>                 260                    265                   270 | 816 |
| gat gtc gat ctg acc ctg aac tgg ggt cgc ttg tct tcc gtt ctg ccg<br>Asp Val Asp Leu Thr Leu Asn Trp Gly Arg Leu Ser Ser Val Leu Pro<br>               275                    280                   285 | 864 |
| gat tat cac ggt cag gat tct gtc cgt gtt ggc cgt atc agc ttt ggc<br>Asp Tyr His Gly Gln Asp Ser Val Arg Val Gly Arg Ile Ser Phe Gly<br>       290                    295                    300 | 912 |
| tct att aat gcc atc cta ggc tcc gtc gca ctg att ctc aat tgc cac<br>Ser Ile Asn Ala Ile Leu Gly Ser Val Ala Leu Ile Leu Asn Cys His<br>305                    310                    315                 320 | 960 |
| cac cac cat cat cat taa<br>His His His His His<br>               325 | 978 |

<210> SEQ ID NO 63
<211> LENGTH: 993
<212> TYPE: DNA
<213> ORGANISM: Artificial Sequence
<220> FEATURE:
<221> NAME/KEY: CDS
<222> LOCATION: (1)..(993)
<220> FEATURE:
<223> OTHER INFORMATION: Description of Artificial Sequence: Construct
      encoding chemokine-toxin fusion protein EOTAXIN-AM-SAPORIN

<400> SEQUENCE: 63

|   |   |
|---|---|
| atg ggg cca gct tct gtc cca acc acc tgc tgc ttt aac ctg gcc aat<br>Met Gly Pro Ala Ser Val Pro Thr Thr Cys Cys Phe Asn Leu Ala Asn<br>1                   5                        10                     15 | 48 |

```
agg aag ata ccc ctt cag cga cta gag agc tac agg aga atc acc agt        96
Arg Lys Ile Pro Leu Gln Arg Leu Glu Ser Tyr Arg Arg Ile Thr Ser
            20                  25                  30 ggc aaa tgt ccc cag aaa gct gtg atc ttc aag acc aaa ctg gcc aag       144
Gly Lys Cys Pro Gln Lys Ala Val Ile Phe Lys Thr Lys Leu Ala Lys
        35                  40                  45 gat atc tgt gcc gac ccc aag aag aag tgg gtg cag gat tcc atg aag       192
Asp Ile Cys Ala Asp Pro Lys Lys Lys Trp Val Gln Asp Ser Met Lys
 50                  55                  60 tat ctg gac caa aaa tct cca act cca aag cca gcg atg gtt act agt       240
Tyr Leu Asp Gln Lys Ser Pro Thr Pro Lys Pro Ala Met Val Thr Ser
 65                  70                  75                  80 att acc ctg gac ctg gtc aat ccg acc gcc ggc caa tat agc agc ttc       288
Ile Thr Leu Asp Leu Val Asn Pro Thr Ala Gly Gln Tyr Ser Ser Phe
                85                  90                  95 gtg gat aag att cgt aac aac gta aaa gat ccg aat ctg aaa tac ggt       336
Val Asp Lys Ile Arg Asn Asn Val Lys Asp Pro Asn Leu Lys Tyr Gly
            100                 105                 110 ggt act gat att gcg gtc atc ggt ccg ccg agc aaa gaa aag ttc ctg       384
Gly Thr Asp Ile Ala Val Ile Gly Pro Pro Ser Lys Glu Lys Phe Leu
        115                 120                 125 cgc att aac ttt caa agc tcc cgt ggc act gtt tct ctg ggc ctg aag       432
Arg Ile Asn Phe Gln Ser Ser Arg Gly Thr Val Ser Leu Gly Leu Lys
130                 135                 140 cgc gat aac ctg tat gtt gtt gcc tat ctg gcg atg gat aat acg aac       480
Arg Asp Asn Leu Tyr Val Val Ala Tyr Leu Ala Met Asp Asn Thr Asn
145                 150                 155                 160 gtg aac cgc gcc tac tac ttt cgt agc gag att acg agc gcg gaa tcc       528
Val Asn Arg Ala Tyr Tyr Phe Arg Ser Glu Ile Thr Ser Ala Glu Ser
                165                 170                 175 act gct ctg ttc ccg gag gcg acc act gca aac caa aaa gca ctg gaa       576
Thr Ala Leu Phe Pro Glu Ala Thr Thr Ala Asn Gln Lys Ala Leu Glu
            180                 185                 190 tat acg gaa gat tac cag tcc atc gag aag aac gcg cag atc acc cag       624
Tyr Thr Glu Asp Tyr Gln Ser Ile Glu Lys Asn Ala Gln Ile Thr Gln
        195                 200                 205 ggc gat caa tcc cgc aaa gaa ctg ggt ctg ggt att gat ctg ctg agc       672
Gly Asp Gln Ser Arg Lys Glu Leu Gly Leu Gly Ile Asp Leu Leu Ser
210                 215                 220 acg agc atg gaa gcg gtc aac aaa aaa gct cgc gtg gtt aaa gac gaa       720
Thr Ser Met Glu Ala Val Asn Lys Lys Ala Arg Val Val Lys Asp Glu
225                 230                 235                 240 gcc cgc ttc ctg ctg atc gcc att cag atg acg gca gaa gcc gcc cgt       768
Ala Arg Phe Leu Leu Ile Ala Ile Gln Met Thr Ala Glu Ala Ala Arg
                245                 250                 255 ttc cgc tac att cag aac ctg gtc atc aaa aac ttc ccg aac aag ttc       816
Phe Arg Tyr Ile Gln Asn Leu Val Ile Lys Asn Phe Pro Asn Lys Phe
            260                 265                 270 aat tcc gag aat aaa gtc att cag ttc gag gtt aat tgg aaa aaa att       864
Asn Ser Glu Asn Lys Val Ile Gln Phe Glu Val Asn Trp Lys Lys Ile
        275                 280                 285 tcc acc gcc att tat ggt gac gcg aag aac ggt gtt ttc aat aaa gat       912
Ser Thr Ala Ile Tyr Gly Asp Ala Lys Asn Gly Val Phe Asn Lys Asp
290                 295                 300 tat gat ttt ggt ttc ggt aag gta cgt cag gtg aaa gac ctg caa atg       960
Tyr Asp Phe Gly Phe Gly Lys Val Arg Gln Val Lys Asp Leu Gln Met
305                 310                 315                 320 ggt ctg ctg atg tac cta gga aaa ccg aag taa                           993
Gly Leu Leu Met Tyr Leu Gly Lys Pro Lys
```

<210> SEQ ID NO 64
<211> LENGTH: 744
<212> TYPE: DNA
<213> ORGANISM: Artificial Sequence
<220> FEATURE:
<223> OTHER INFORMATION: Description of Artificial Sequence: Construct encoding Methionine-truncated Shiga-A1 Subunit fusion protien
<220> FEATURE:
<221> NAME/KEY: CDS
<222> LOCATION: (1)..(744)

<400> SEQUENCE: 64

```
atg aaa gaa ttc acc ctg gac ttt tcc act gca aaa act tac gtc gat        48
Met Lys Glu Phe Thr Leu Asp Phe Ser Thr Ala Lys Thr Tyr Val Asp
 1               5                  10                  15 agc ctg aat gtg att cgt tcc gcg atc ggt acg ccg ctg caa acg att        96
Ser Leu Asn Val Ile Arg Ser Ala Ile Gly Thr Pro Leu Gln Thr Ile
                20                  25                  30 tcc agc ggt ggt act tcc ctc ctg atg att gat tcc ggt acg ggt gat       144
Ser Ser Gly Gly Thr Ser Leu Leu Met Ile Asp Ser Gly Thr Gly Asp
            35                  40                  45 aac ttg ttt gct gtt gat gtg cgc ggc att gac ccg gaa gaa ggc cgt       192
Asn Leu Phe Ala Val Asp Val Arg Gly Ile Asp Pro Glu Glu Gly Arg
        50                  55                  60 ttt aat aat ctg cgt ctg atc gtc gaa cgc aac aac ctg tat gtg acg       240
Phe Asn Asn Leu Arg Leu Ile Val Glu Arg Asn Asn Leu Tyr Val Thr
 65                  70                  75                  80 ggt ttt gtg aac cgt acg aac aac gtc ttc tat cgt ttc gct gat ttc       288
Gly Phe Val Asn Arg Thr Asn Asn Val Phe Tyr Arg Phe Ala Asp Phe
                85                  90                  95 tcc cac gta acg ttt ccg ggc acc act gct gtt act ctg agc ggc gat       336
Ser His Val Thr Phe Pro Gly Thr Thr Ala Val Thr Leu Ser Gly Asp
                100                 105                 110 tct tct tat act acg tta cag cgt gtg gct ggt atc agc cgc act ggt       384
Ser Ser Tyr Thr Thr Leu Gln Arg Val Ala Gly Ile Ser Arg Thr Gly
            115                 120                 125 atg caa atc aat cgc cat tct ctg acg acc agc tat ctg gac tta atg       432
Met Gln Ile Asn Arg His Ser Leu Thr Thr Ser Tyr Leu Asp Leu Met
        130                 135                 140 agc cat tct ggc acc agc ctg acc cag tct gtt gcc cgt gcg atg ctg       480
Ser His Ser Gly Thr Ser Leu Thr Gln Ser Val Ala Arg Ala Met Leu
145                 150                 155                 160 cgc ttc gtg acg gtc acc gcc gaa gcc ctg cgt ttc cgt caa atc caa       528
Arg Phe Val Thr Val Thr Ala Glu Ala Leu Arg Phe Arg Gln Ile Gln
                165                 170                 175 cgc ggc ttc cgc acc act tta gac gat ctg tct ggc cgc agc tat gtg       576
Arg Gly Phe Arg Thr Thr Leu Asp Asp Leu Ser Gly Arg Ser Tyr Val
                180                 185                 190 atg act gcc gaa gat gtc gat ctg acc ctg aac tgg ggt cgc ttg tct       624
Met Thr Ala Glu Asp Val Asp Leu Thr Leu Asn Trp Gly Arg Leu Ser
            195                 200                 205 tcc gtt ctg ccg gat tat cac ggt cag gat tct gtc cgt gtt ggc cgt       672
Ser Val Leu Pro Asp Tyr His Gly Gln Asp Ser Val Arg Val Gly Arg
        210                 215                 220 atc agc ttt ggc tct att aat gcc atc cta ggc tcc gtc gca ctg att       720
Ile Ser Phe Gly Ser Ile Asn Ala Ile Leu Gly Ser Val Ala Leu Ile
225                 230                 235                 240 ctc aat tgc cac cac cac gct taa                                       744
Leu Asn Cys His His His Ala
                245
```

<210> SEQ ID NO 65
<211> LENGTH: 750
<212> TYPE: DNA
<213> ORGANISM: Artificial Sequence
<220> FEATURE:
<223> OTHER INFORMATION: Description of Artificial Sequence: Construct encoding Methionine-truncated Shiga-A1 Subunit HIS6 fusion protein
<220> FEATURE:
<221> NAME/KEY: CDS
<222> LOCATION: (1)..(750)

<400> SEQUENCE: 65

```
atg aaa gaa ttc acc ctg gac ttt tcc act gca aaa act tac gtc gat       48
Met Lys Glu Phe Thr Leu Asp Phe Ser Thr Ala Lys Thr Tyr Val Asp
  1               5                  10                  15 agc ctg aat gtg att cgt tcc gcg atc ggt acg ccg ctg caa acg att       96
Ser Leu Asn Val Ile Arg Ser Ala Ile Gly Thr Pro Leu Gln Thr Ile
             20                  25                  30 tcc agc ggt ggt act tcc ctc ctg atg att gat tcc ggt acg ggt gat      144
Ser Ser Gly Gly Thr Ser Leu Leu Met Ile Asp Ser Gly Thr Gly Asp
         35                  40                  45 aac ttg ttt gct gtt gat gtg cgc ggc att gac ccg gaa gaa ggc cgt      192
Asn Leu Phe Ala Val Asp Val Arg Gly Ile Asp Pro Glu Glu Gly Arg
     50                  55                  60 ttt aat aat ctg cgt ctg atc gtc gaa cgc aac aac ctg tat gtg acg      240
Phe Asn Asn Leu Arg Leu Ile Val Glu Arg Asn Asn Leu Tyr Val Thr
 65                  70                  75                  80 ggt ttt gtg aac cgt acg aac aac gtc ttc tat cgt ttc gct gat ttc      288
Gly Phe Val Asn Arg Thr Asn Asn Val Phe Tyr Arg Phe Ala Asp Phe
                 85                  90                  95 tcc cac gta acg ttt ccg ggc acc act gct gtt act ctg agc ggc gat      336
Ser His Val Thr Phe Pro Gly Thr Thr Ala Val Thr Leu Ser Gly Asp
            100                 105                 110 tct tct tat act acg tta cag cgt gtg gct ggt atc agc cgc act ggt      384
Ser Ser Tyr Thr Thr Leu Gln Arg Val Ala Gly Ile Ser Arg Thr Gly
        115                 120                 125 atg caa atc aat cgc cat tct ctg acg acc agc tat ctg gac tta atg      432
Met Gln Ile Asn Arg His Ser Leu Thr Thr Ser Tyr Leu Asp Leu Met
    130                 135                 140 agc cat tct ggc acc agc ctg acc cag tct gtt gcc cgt gcg atg ctg      480
Ser His Ser Gly Thr Ser Leu Thr Gln Ser Val Ala Arg Ala Met Leu
145                 150                 155                 160 cgc ttc gtg acg gtc acc gcc gaa gcc ctg cgt ttc cgt caa atc caa      528
Arg Phe Val Thr Val Thr Ala Glu Ala Leu Arg Phe Arg Gln Ile Gln
                165                 170                 175 cgc ggc ttc cgc acc act tta gac gat ctg tct ggc cgc agc tat gtg      576
Arg Gly Phe Arg Thr Thr Leu Asp Asp Leu Ser Gly Arg Ser Tyr Val
            180                 185                 190 atg act gcc gaa gat gtc gat ctg acc ctg aac tgg ggt cgc ttg tct      624
Met Thr Ala Glu Asp Val Asp Leu Thr Leu Asn Trp Gly Arg Leu Ser
        195                 200                 205 tcc gtt ctg ccg gat tat cac ggt cag gat tct gtc cgt gtt ggc cgt      672
Ser Val Leu Pro Asp Tyr His Gly Gln Asp Ser Val Arg Val Gly Arg
    210                 215                 220 atc agc ttt ggc tct att aat gcc atc cta ggc tcc gtc gca ctg att      720
Ile Ser Phe Gly Ser Ile Asn Ala Ile Leu Gly Ser Val Ala Leu Ile
225                 230                 235                 240 ctc aat tgc cac cac cac cat cat cat taa                              750
Leu Asn Cys His His His His His His
                245                 250
```

```
<210> SEQ ID NO 66
<211> LENGTH: 765
<212> TYPE: DNA
<213> ORGANISM: Artificial Sequence
<220> FEATURE:
<223> OTHER INFORMATION: Description of Artificial Sequence: Construct
      encoding Methionine-Saporin fusion protein
<220> FEATURE:
<221> NAME/KEY: CDS
<222> LOCATION: (1)..(765)

<400> SEQUENCE: 66 atg gtt act agt att acc ctg gac ctg gtc aat ccg acc gcc ggc caa      48
Met Val Thr Ser Ile Thr Leu Asp Leu Val Asn Pro Thr Ala Gly Gln
 1               5                  10                  15 tat agc agc ttc gtg gat aag att cgt aac aac gta aaa gat ccg aat      96
Tyr Ser Ser Phe Val Asp Lys Ile Arg Asn Asn Val Lys Asp Pro Asn
             20                  25                  30 ctg aaa tac ggt ggt act gat att gcg gtc atc ggt ccg ccg agc aaa     144
Leu Lys Tyr Gly Gly Thr Asp Ile Ala Val Ile Gly Pro Pro Ser Lys
         35                  40                  45 gaa aag ttc ctg cgc att aac ttt caa agc tcc cgt ggc act gtt tct     192
Glu Lys Phe Leu Arg Ile Asn Phe Gln Ser Ser Arg Gly Thr Val Ser
     50                  55                  60 ctg ggc ctg aag cgc gat aac ctg tat gtt gtt gcc tat ctg gcg atg     240
Leu Gly Leu Lys Arg Asp Asn Leu Tyr Val Val Ala Tyr Leu Ala Met
 65                  70                  75                  80 gat aat acg aac gtg aac cgc gcc tac tac ttt cgt agc gag att acg     288
Asp Asn Thr Asn Val Asn Arg Ala Tyr Tyr Phe Arg Ser Glu Ile Thr
                 85                  90                  95 agc gcg gaa tcc act gct ctg ttc ccg gag gcg acc act gca aac caa     336
Ser Ala Glu Ser Thr Ala Leu Phe Pro Glu Ala Thr Thr Ala Asn Gln
            100                 105                 110 aaa gca ctg gaa tat acg gaa gat tac cag tcc atc gag aag aac gcg     384
Lys Ala Leu Glu Tyr Thr Glu Asp Tyr Gln Ser Ile Glu Lys Asn Ala
        115                 120                 125 cag atc acc cag ggc gat caa tcc cgc aaa gaa ctg ggt ctg ggt att     432
Gln Ile Thr Gln Gly Asp Gln Ser Arg Lys Glu Leu Gly Leu Gly Ile
    130                 135                 140 gat ctg ctg agc acg agc atg gaa gcg gtc aac aaa aaa gct cgc gtg     480
Asp Leu Leu Ser Thr Ser Met Glu Ala Val Asn Lys Lys Ala Arg Val
145                 150                 155                 160 gtt aaa gac gaa gcc cgc ttc ctg ctg atc gcc att cag atg acg gca     528
Val Lys Asp Glu Ala Arg Phe Leu Leu Ile Ala Ile Gln Met Thr Ala
                165                 170                 175 gaa gcc gcc cgt ttc cgc tac att cag aac ctg gtc atc aaa aac ttc     576
Glu Ala Ala Arg Phe Arg Tyr Ile Gln Asn Leu Val Ile Lys Asn Phe
            180                 185                 190 ccg aac aag ttc aat tcc gag aat aaa gtc att cag ttc gag gtt aat     624
Pro Asn Lys Phe Asn Ser Glu Asn Lys Val Ile Gln Phe Glu Val Asn
        195                 200                 205 tgg aaa aaa att tcc acc gcc att tat ggt gac gcg aag aac ggt gtt     672
Trp Lys Lys Ile Ser Thr Ala Ile Tyr Gly Asp Ala Lys Asn Gly Val
    210                 215                 220 ttc aat aaa gat tat gat ttt ggt ttc ggt aag gta cgt cag gtg aaa     720
Phe Asn Lys Asp Tyr Asp Phe Gly Phe Gly Lys Val Arg Gln Val Lys
225                 230                 235                 240 gac ctg caa atg ggt ctg ctg atg tac cta gga aaa ccg aag taa         765
Asp Leu Gln Met Gly Leu Leu Met Tyr Leu Gly Lys Pro Lys
                245                 250                 255
```

```
<210> SEQ ID NO 67
<211> LENGTH: 231
<212> TYPE: DNA
<213> ORGANISM: Artificial Sequence
<220> FEATURE:
<221> NAME/KEY: CDS
<222> LOCATION: (1)..(231)
<220> FEATURE:
<223> OTHER INFORMATION: Description of Artificial Sequence: Construct
      encoding Methionine-MCP3 protein

<400> SEQUENCE: 67 atg caa ccg gta ggc atc aac acg tcg acc acg tgc tgt tat cgc ttt      48
Met Gln Pro Val Gly Ile Asn Thr Ser Thr Thr Cys Cys Tyr Arg Phe
 1               5                  10                  15 atc aac aag aaa atc ccg aaa caa cgc ctg gaa tcc tat cgt cgc acc      96
Ile Asn Lys Lys Ile Pro Lys Gln Arg Leu Glu Ser Tyr Arg Arg Thr
             20                  25                  30 act agc agc cac tgt ccg cgc gaa gca gtc atc ttc aaa acc aag ctc     144
Thr Ser Ser His Cys Pro Arg Glu Ala Val Ile Phe Lys Thr Lys Leu
         35                  40                  45 gat aag gaa atc tgt gca gac ccg act cag aaa tgg gtg caa gat ttt     192
Asp Lys Glu Ile Cys Ala Asp Pro Thr Gln Lys Trp Val Gln Asp Phe
 50                  55                  60 atg aaa cat ctg gat aag aaa act cag acc ccg aag ctt                 231
Met Lys His Leu Asp Lys Lys Thr Gln Thr Pro Lys Leu
 65                  70                  75

<210> SEQ ID NO 68
<211> LENGTH: 4
<212> TYPE: PRT
<213> ORGANISM: Pseudomonas aeruginosa
<220> FEATURE:
<221> NAME/KEY: MOD_RES
<222> LOCATION: (1)
<223> OTHER INFORMATION: Lys or Arg
<220> FEATURE:
<221> NAME/KEY: REPEAT
<222> LOCATION: (1)...(4)
<223> OTHER INFORMATION: repeat unit 1-6 times
<220> FEATURE:
<223> OTHER INFORMATION: Pseudomonas toxin carboxy-terminal endoplasmic
      reticulum retention signal

<400> SEQUENCE: 68

Xaa Asp Glu Leu
 1

<210> SEQ ID NO 69
<211> LENGTH: 393
<212> TYPE: DNA
<213> ORGANISM: Mus musculus
<220> FEATURE:
<223> OTHER INFORMATION: Mouse chemokine ALP cDNA
<220> FEATURE:
<221> NAME/KEY: CDS
<222> LOCATION: (11)..(373)

<400> SEQUENCE: 69
ctgagtgagc atg atg gag ggg ctc tcc ccc gcc agc agc ctc ccg ctg       49
           Met Met Glu Gly Leu Ser Pro Ala Ser Ser Leu Pro Leu
            1               5                  10 tta ctg ttg ctt ctg agc ccg gct cct gaa gca gcc ttg cct ctg ccc      97
Leu Leu Leu Leu Leu Ser Pro Ala Pro Glu Ala Ala Leu Pro Leu Pro
         15                  20                  25 tcc agc act agc tgc tgt act cag ctc tat aga cag cca ctc cca agc     145
Ser Ser Thr Ser Cys Cys Thr Gln Leu Tyr Arg Gln Pro Leu Pro Ser
 30                  35                  40                  45
```

```
agg ctg ctg agg agg att gtc cac atg gaa ctg cag gag gcc gat ggg      193
Arg Leu Leu Arg Arg Ile Val His Met Glu Leu Gln Glu Ala Asp Gly
            50                  55                  60 gac tgt cac ctc cag gct gtc gtg ctt cac ctg gct cgg cgc agt gtc      241
Asp Cys His Leu Gln Ala Val Val Leu His Leu Ala Arg Arg Ser Val
        65                  70                  75 tgt gtt cat ccc cag aac cgc agc ctg gct cgg tgg tta gaa cgc caa      289
Cys Val His Pro Gln Asn Arg Ser Leu Ala Arg Trp Leu Glu Arg Gln
    80                  85                  90 ggg aaa agg ctc caa ggg act gta ccc agt tta aat ctg gta cta caa      337
Gly Lys Arg Leu Gln Gly Thr Val Pro Ser Leu Asn Leu Val Leu Gln
95                  100                 105 aag aaa atg tac tca aac ccc caa cag caa aac taa taaagcaaca           383
Lys Lys Met Tyr Ser Asn Pro Gln Gln Gln Asn
110             115                 120 ttagacgaca                                                            393

<210> SEQ ID NO 70
<211> LENGTH: 912
<212> TYPE: DNA
<213> ORGANISM: Mus musculus
<220> FEATURE:
<223> OTHER INFORMATION: Mouse Lungkine cDNA
<220> FEATURE:
<221> NAME/KEY: CDS
<222> LOCATION: (1)..(504)
<300> PUBLICATION INFORMATION:
<308> DATABASE ACCESSION NUMBER: AF082859/GenBank

<400> SEQUENCE: 70 atg gct gct caa ggc tgg tcc atg ctc ctg ctg gct gtc ctt aac cta       48
Met Ala Ala Gln Gly Trp Ser Met Leu Leu Leu Ala Val Leu Asn Leu
1               5                   10                  15 ggc atc ttc gtc cgt ccc tgt gac act caa gag cta cga tgt ctg tgt       96
Gly Ile Phe Val Arg Pro Cys Asp Thr Gln Glu Leu Arg Cys Leu Cys
            20                  25                  30 att cag gaa cac tct gaa ttc att cct ctc aaa ctc att aaa aat ata      144
Ile Gln Glu His Ser Glu Phe Ile Pro Leu Lys Leu Ile Lys Asn Ile
        35                  40                  45 atg gtg ata ttc gag acc att tac tgc aac aga aag gaa gtg ata gca      192
Met Val Ile Phe Glu Thr Ile Tyr Cys Asn Arg Lys Glu Val Ile Ala
    50                  55                  60 gtc cca aaa aat ggg agt atg att tgt ttg gat cct gat gct cca tgg      240
Val Pro Lys Asn Gly Ser Met Ile Cys Leu Asp Pro Asp Ala Pro Trp
65                  70                  75                  80 gtg aag gct act gtt ggc cca att act aac agg ttc cta cct gag gac      288
Val Lys Ala Thr Val Gly Pro Ile Thr Asn Arg Phe Leu Pro Glu Asp
                85                  90                  95 ctc aaa caa aag gaa ttt cca ccg gca atg aag ctt ctg tat agt gtt      336
Leu Lys Gln Lys Glu Phe Pro Pro Ala Met Lys Leu Leu Tyr Ser Val
            100                 105                 110 gag cat gaa aag cct cta tat ctt tca ttt ggg aga cct gag aac aag      384
Glu His Glu Lys Pro Leu Tyr Leu Ser Phe Gly Arg Pro Glu Asn Lys
        115                 120                 125 aga ata ttt ccc ttt cca att cgg gag acc tct aga cac ttt gct gat      432
Arg Ile Phe Pro Phe Pro Ile Arg Glu Thr Ser Arg His Phe Ala Asp
    130                 135                 140 tta gct cac aac agt gat agg aat ttt cta cgg gac tcc agt gaa gtc      480
Leu Ala His Asn Ser Asp Arg Asn Phe Leu Arg Asp Ser Ser Glu Val
145                 150                 155                 160 agc ttg aca ggc agt gat gcc taa aagccactca tgaggcaaag agtttcaagg     534
Ser Leu Thr Gly Ser Asp Ala
```

```
Ser Leu Thr Gly Ser Asp Ala
            165 aagctctcct cctggagttt tggcgttctc attcttatac tctattcccg cgttagtctg      594 gtgtatggat ctatgagctc tcttttaata ttttattata aatgttttat ttacttaact      654 tcctagtgaa tgttcacagg tgactgctcc cccatcccca tttcttgata ttacatataa      714 tggcatcata taccccttta ttgactgaca aactactcag attgcttaac attttgtgct      774 tcaaagtctt atcccactcc actatgggct gttacagagt gcatctcggt gtagagcaag      834 gctccttgtc ttcagtgccc cagggtgaaa tacttctttg aaaaattttc attcatcaga      894 raatctgaaa taaatatt                                                    912

<210> SEQ ID NO 71
<211> LENGTH: 325
<212> TYPE: PRT
<213> ORGANISM: Artificial Sequence
<220> FEATURE:
<223> OTHER INFORMATION: Description of Artificial Sequence:
      Chemokine-toxin fusion protein MCP1-AM-truncated Shiga-A1 Subunit

<400> SEQUENCE: 71

Met Gln Pro Asp Ala Ile Asn Ala Pro Val Thr Cys Cys Tyr Asn Phe
  1               5                  10                  15

Thr Asn Arg Lys Ile Ser Val Gln Arg Leu Ala Ser Tyr Arg Arg Ile
                 20                  25                  30

Thr Ser Ser Lys Cys Pro Lys Glu Ala Val Ile Phe Lys Thr Ile Val
             35                  40                  45

Ala Lys Glu Ile Cys Ala Asp Pro Lys Gln Lys Trp Val Gln Asp Ser
         50                  55                  60

Met Asp His Leu Asp Lys Gln Thr Gln Thr Pro Lys Thr Ala Met Lys
 65                  70                  75                  80

Glu Phe Thr Leu Asp Phe Ser Thr Ala Lys Thr Tyr Val Asp Ser Leu
                 85                  90                  95

Asn Val Ile Arg Ser Ala Ile Gly Thr Pro Leu Gln Thr Ile Ser Ser
                100                 105                 110

Gly Gly Thr Ser Leu Leu Met Ile Asp Ser Gly Thr Gly Asp Asn Leu
            115                 120                 125

Phe Ala Val Asp Val Arg Gly Ile Asp Pro Glu Glu Gly Arg Phe Asn
        130                 135                 140

Asn Leu Arg Leu Ile Val Glu Arg Asn Asn Leu Tyr Val Thr Gly Phe
145                 150                 155                 160

Val Asn Arg Thr Asn Asn Val Phe Tyr Arg Phe Ala Asp Phe Ser His
                165                 170                 175

Val Thr Phe Pro Gly Thr Thr Ala Val Thr Leu Ser Gly Asp Ser Ser
            180                 185                 190

Tyr Thr Thr Leu Gln Arg Val Ala Gly Ile Ser Arg Thr Gly Met Gln
        195                 200                 205

Ile Asn Arg His Ser Leu Thr Thr Ser Tyr Leu Asp Leu Met Ser His
    210                 215                 220

Ser Gly Thr Ser Leu Thr Gln Ser Val Ala Arg Ala Met Leu Arg Phe
225                 230                 235                 240

Val Thr Val Thr Ala Glu Ala Leu Arg Phe Arg Gln Ile Gln Arg Gly
                245                 250                 255

Phe Arg Thr Thr Leu Asp Asp Leu Ser Gly Arg Ser Tyr Val Met Thr
            260                 265                 270
```

```
Ala Glu Asp Val Asp Leu Thr Leu Asn Trp Gly Arg Leu Ser Ser Val
            275                 280                 285

Leu Pro Asp Tyr His Gly Gln Asp Ser Val Arg Val Gly Arg Ile Ser
        290                 295                 300

Phe Gly Ser Ile Asn Ala Ile Leu Gly Ser Val Ala Leu Ile Leu Asn
305                 310                 315                 320

Cys His His His Ala
                325

<210> SEQ ID NO 72
<211> LENGTH: 327
<212> TYPE: PRT
<213> ORGANISM: Artificial Sequence
<220> FEATURE:
<223> OTHER INFORMATION: Description of Artificial Sequence:
      Chemokine-toxin fusion protein MCP1-AM-truncated Shiga-A1 Subunit
      HIS6

<400> SEQUENCE: 72

Met Gln Pro Asp Ala Ile Asn Ala Pro Val Thr Cys Cys Tyr Asn Phe
  1               5                  10                  15

Thr Asn Arg Lys Ile Ser Val Gln Arg Leu Ala Ser Tyr Arg Arg Ile
             20                  25                  30

Thr Ser Ser Lys Cys Pro Lys Glu Ala Val Ile Phe Lys Thr Ile Val
         35                  40                  45

Ala Lys Glu Ile Cys Ala Asp Pro Lys Gln Lys Trp Val Gln Asp Ser
     50                  55                  60

Met Asp His Leu Asp Lys Gln Thr Gln Thr Pro Lys Thr Ala Met Lys
 65                  70                  75                  80

Glu Phe Thr Leu Asp Phe Ser Thr Ala Lys Thr Tyr Val Asp Ser Leu
                 85                  90                  95

Asn Val Ile Arg Ser Ala Ile Gly Thr Pro Leu Gln Thr Ile Ser Ser
            100                 105                 110

Gly Gly Thr Ser Leu Leu Met Ile Asp Ser Gly Thr Gly Asp Asn Leu
        115                 120                 125

Phe Ala Val Asp Val Arg Gly Ile Asp Pro Glu Glu Gly Arg Phe Asn
130                 135                 140

Asn Leu Arg Leu Ile Val Glu Arg Asn Asn Leu Tyr Val Thr Gly Phe
145                 150                 155                 160

Val Asn Arg Thr Asn Asn Val Phe Tyr Arg Phe Ala Asp Phe Ser His
                165                 170                 175

Val Thr Phe Pro Gly Thr Thr Ala Val Thr Leu Ser Gly Asp Ser Ser
            180                 185                 190

Tyr Thr Thr Leu Gln Arg Val Ala Gly Ile Ser Arg Thr Gly Met Gln
        195                 200                 205

Ile Asn Arg His Ser Leu Thr Thr Ser Tyr Leu Asp Leu Met Ser His
    210                 215                 220

Ser Gly Thr Ser Leu Thr Gln Ser Val Ala Arg Ala Met Leu Arg Phe
225                 230                 235                 240

Val Thr Val Thr Ala Glu Ala Leu Arg Phe Arg Gln Ile Gln Arg Gly
                245                 250                 255

Phe Arg Thr Thr Leu Asp Asp Leu Ser Gly Arg Ser Tyr Val Met Thr
            260                 265                 270

Ala Glu Asp Val Asp Leu Thr Leu Asn Trp Gly Arg Leu Ser Ser Val
        275                 280                 285

Leu Pro Asp Tyr His Gly Gln Asp Ser Val Arg Val Gly Arg Ile Ser
```

```
                  290            295                300
Phe Gly Ser Ile Asn Ala Ile Leu Gly Ser Val Ala

Gln Met Gly Leu Leu Met Tyr Leu Gly Lys Pro Lys
            325                 330

<210> SEQ ID NO 74
<211> LENGTH: 325
<212> TYPE: PRT
<213> ORGANISM: Artificial Sequence
<220> FEATURE:
<223> OTHER INFORMATION: Description of Artificial Sequence:
      Chemokine-toxin fusion protein MCP3-AM-truncated Shiga-A1 Subunit

<400> SEQUENCE: 74

Met Gln Pro Val Gly Ile Asn Thr Ser Thr Cys Cys Tyr Arg Phe
1               5                   10                  15

Ile Asn Lys Lys Ile Pro Lys Gln Arg Leu Glu Ser Tyr Arg Arg Thr
                20                  25                  30

Thr Ser Ser His Cys Pro Arg Glu Ala Val Ile Phe Lys Thr Lys Leu
            35                  40                  45

Asp Lys Glu Ile Cys Ala Asp Pro Thr Gln Lys Trp Val Gln Asp Phe
    50                  55                  60

Met Lys His Leu Asp Lys Lys Thr Gln Thr Pro Lys Leu Ala Met Lys
65                  70                  75                  80

Glu Phe Thr Leu Asp Phe Ser Thr Ala Lys Thr Tyr Val Asp Ser Leu
                85                  90                  95

Asn Val Ile Arg Ser Ala Ile Gly Thr Pro Leu Gln Thr Ile Ser Ser
                100                 105                 110

Gly Gly Thr Ser Leu Leu Met Ile Asp Ser Gly Thr Gly Asp Asn Leu
            115                 120                 125

Phe Ala Val Asp Val Arg Gly Ile Asp Pro Glu Glu Gly Arg Phe Asn
130                 135                 140

Asn Leu Arg Leu Ile Val Glu Arg Asn Asn Leu Tyr Val Thr Gly Phe
145                 150                 155                 160

Val Asn Arg Thr Asn Asn Val Phe Tyr Arg Phe Ala Asp Phe Ser His
                165                 170                 175

Val Thr Phe Pro Gly Thr Thr Ala Val Thr Leu Ser Gly Asp Ser Ser
            180                 185                 190

Tyr Thr Thr Leu Gln Arg Val Ala Gly Ile Ser Arg Thr Gly Met Gln
        195                 200                 205

Ile Asn Arg His Ser Leu Thr Thr Ser Tyr Leu Asp Leu Met Ser His
    210                 215                 220

Ser Gly Thr Ser Leu Thr Gln Ser Val Ala Arg Ala Met Leu Arg Phe
225                 230                 235                 240

Val Thr Val Thr Ala Glu Ala Leu Arg Phe Arg Gln Ile Gln Arg Gly
                245                 250                 255

Phe Arg Thr Thr Leu Asp Asp Leu Ser Gly Arg Ser Tyr Val Met Thr
            260                 265                 270

Ala Glu Asp Val Asp Leu Thr Leu Asn Trp Gly Arg Leu Ser Ser Val
        275                 280                 285

Leu Pro Asp Tyr His Gly Gln Asp Ser Val Arg Val Gly Arg Ile Ser
    290                 295                 300

Phe Gly Ser Ile Asn Ala Ile Leu Gly Ser Val Ala Leu Ile Leu Asn
305                 310                 315                 320

Cys His His His Ala
            325

<210> SEQ ID NO 75

```
<211> LENGTH: 327
<212> TYPE: PRT
<213> ORGANISM: Artificial Sequence
<220> FEATURE:
<223> OTHER INFORMATION: Description of Artificial Sequence:
      Chemokine-toxin fusion protein MCP3-AM-truncated Shiga-A1 subunit
      HIS6

<400> SEQUENCE: 75

Met Gln Pro Val Gly Ile Asn Thr Ser Thr Thr Cys Cys Tyr Arg Phe
  1               5                  10                  15

Ile Asn Lys Lys Ile Pro Lys Gln Arg Leu Glu Ser Tyr Arg Arg Thr
             20                  25                  30

Thr Ser Ser His Cys Pro Arg Glu Ala Val Ile Phe Lys Thr Lys Leu
         35                  40                  45

Asp Lys Glu Ile Cys Ala Asp Pro Thr Gln Lys Trp Val Gln Asp Phe
     50                  55                  60

Met Lys His Leu Asp Lys Lys Thr Gln Thr Pro Lys Leu Ala Met Lys
 65                  70                  75                  80

Glu Phe Thr Leu Asp Phe Ser Thr Ala Lys Thr Tyr Val Asp Ser Leu
                 85                  90                  95

Asn Val Ile Arg Ser Ala Ile Gly Thr Pro Leu Gln Thr Ile Ser Ser
            100                 105                 110

Gly Gly Thr Ser Leu Leu Met Ile Asp Ser Gly Thr Gly Asp Asn Leu
        115                 120                 125

Phe Ala Val Asp Val Arg Gly Ile Asp Pro Glu Glu Gly Arg Phe Asn
    130                 135                 140

Asn Leu Arg Leu Ile Val Glu Arg Asn Asn Leu Tyr Val Thr Gly Phe
145                 150                 155                 160

Val Asn Arg Thr Asn Asn Val Phe Tyr Arg Phe Ala Asp Phe Ser His
                165                 170                 175

Val Thr Phe Pro Gly Thr Thr Ala Val Thr Leu Ser Gly Asp Ser Ser
            180                 185                 190

Tyr Thr Thr Leu Gln Arg Val Ala Gly Ile Ser Arg Thr Gly Met Gln
        195                 200                 205

Ile Asn Arg His Ser Leu Thr Thr Ser Tyr Leu Asp Leu Met Ser His
    210                 215                 220

Ser Gly Thr Ser Leu Thr Gln Ser Val Ala Arg Ala Met Leu Arg Phe
225                 230                 235                 240

Val Thr Val Thr Ala Glu Ala Leu Arg Phe Arg Gln Ile Gln Arg Gly
                245                 250                 255

Phe Arg Thr Thr Leu Asp Asp Leu Ser Gly Arg Ser Tyr Val Met Thr
            260                 265                 270

Ala Glu Asp Val Asp Leu Thr Leu Asn Trp Gly Arg Leu Ser Ser Val
        275                 280                 285

Leu Pro Asp Tyr His Gly Gln Asp Ser Val Arg Val Gly Arg Ile Ser
    290                 295                 300

Phe Gly Ser Ile Asn Ala Ile Leu Gly Ser Val Ala Leu Ile Leu Asn
305                 310                 315                 320

Cys His His His His His
                325

<210> SEQ ID NO 76
<211> LENGTH: 332
<212> TYPE: PRT
<213> ORGANISM: Artificial Sequence
<220> FEATURE:
```

-continued

<223> OTHER INFORMATION: Description of Artificial Sequence:
    Chemokine-toxin Fusion Protein MCP3-AM-SAPORIN

<400> SEQUENCE: 76

```
Met Gln Pro Val Gly Ile Asn Thr Ser Thr Thr Cys Cys Tyr Arg Phe
 1               5                  10                  15

Ile Asn Lys Lys Ile Pro Lys Gln Arg Leu Glu Ser Tyr Arg Arg Thr
             20                  25                  30

Thr Ser Ser His Cys Pro Arg Glu Ala Val Ile Phe Lys Thr Lys Leu
         35                  40                  45

Asp Lys Glu Ile Cys Ala Asp Pro Thr Gln Lys Trp Val Gln Asp Phe
     50                  55                  60

Met Lys His Leu Asp Lys Lys Thr Gln Thr Pro Lys Leu Ala Met Val
 65                  70                  75                  80

Thr Ser Ile Thr Leu Asp Leu Val Asn Pro Thr Ala Gly Gln Tyr Ser
                 85                  90                  95

Ser Phe Val Asp Lys Ile Arg Asn Asn Val Lys Asp Pro Asn Leu Lys
             100                 105                 110

Tyr Gly Gly Thr Asp Ile Ala Val Ile Gly Pro Pro Ser Lys Glu Lys
         115                 120                 125

Phe Leu Arg Ile Asn Phe Gln Ser Ser Arg Gly Thr Val Ser Leu Gly
     130                 135                 140

Leu Lys Arg Asp Asn Leu Tyr Val Val Ala Tyr Leu Ala Met Asp Asn
145                 150                 155                 160

Thr Asn Val Asn Arg Ala Tyr Tyr Phe Arg Ser Glu Ile Thr Ser Ala
                 165                 170                 175

Glu Ser Thr Ala Leu Phe Pro Glu Ala Thr Thr Ala Asn Gln Lys Ala
             180                 185                 190

Leu Glu Tyr Thr Glu Asp Tyr Gln Ser Ile Glu Lys Asn Ala Gln Ile
         195                 200                 205

Thr Gln Gly Asp Gln Ser Arg Lys Glu Leu Gly Leu Gly Ile Asp Leu
     210                 215                 220

Leu Ser Thr Ser Met Glu Ala Val Asn Lys Lys Ala Arg Val Val Lys
225                 230                 235                 240

Asp Glu Ala Arg Phe Leu Leu Ile Ala Ile Gln Met Thr Ala Glu Ala
                 245                 250                 255

Ala Arg Phe Arg Tyr Ile Gln Asn Leu Val Ile Lys Asn Phe Pro Asn
             260                 265                 270

Lys Phe Asn Ser Glu Asn Lys Val Ile Gln Phe Glu Val Asn Trp Lys
         275                 280                 285

Lys Ile Ser Thr Ala Ile Tyr Gly Asp Ala Lys Asn Gly Val Phe Asn
     290                 295                 300

Lys Asp Tyr Asp Phe Gly Phe Gly Lys Val Arg Gln Val Lys Asp Leu
305                 310                 315                 320

Gln Met Gly Leu Leu Met Tyr Leu Gly Lys Pro Lys
                 325                 330
```

<210> SEQ ID NO 77
<211> LENGTH: 320
<212> TYPE: PRT
<213> ORGANISM: Artificial Sequence
<220> FEATURE:
<223> OTHER INFORMATION: Description of Artificial Sequence:
    Chemokine-toxin fusion protein SDF-1-Beta-AM-truncated Shiga-A1
    Subunit

<400> SEQUENCE: 77

```
Lys Pro Val Ser Leu Ser Tyr Arg Cys Pro Cys Arg Phe Phe Glu Ser
  1               5                  10                  15

His Val Ala Arg Ala Asn Val Lys His Leu Lys Ile Leu Asn Thr Pro
             20                  25                  30

Asn Cys Ala Leu Gln Ile Val Ala Arg Leu Lys Asn Asn Arg Gln
         35                  40                  45

Val Cys Ile Asp Pro Lys Leu Lys Trp Ile Gln Glu Tyr Leu Glu Lys
     50                  55                  60

Ala Leu Asn Lys Arg Phe Lys Met Ala Met Lys Glu Phe Thr Leu Asp
 65                  70                  75                  80

Phe Ser Thr Ala Lys Thr Tyr Val Asp Ser Leu Asn Val Ile Arg Ser
                 85                  90                  95

Ala Ile Gly Thr Pro Leu Gln Thr Ile Ser Ser Gly Gly Thr Ser Leu
             100                 105                 110

Leu Met Ile Asp Ser Gly Thr Gly Asp Asn Leu Phe Ala Val Asp Val
         115                 120                 125

Arg Gly Ile Asp Pro Glu Glu Gly Arg Phe Asn Asn Leu Arg Leu Ile
     130                 135                 140

Val Glu Arg Asn Asn Leu Tyr Val Thr Gly Phe Val Asn Arg Thr Asn
145                 150                 155                 160

Asn Val Phe Tyr Arg Phe Ala Asp Phe Ser His Val Thr Phe Pro Gly
                 165                 170                 175

Thr Thr Ala Val Thr Leu Ser Gly Asp Ser Ser Tyr Thr Thr Leu Gln
             180                 185                 190

Arg Val Ala Gly Ile Ser Arg Thr Gly Met Gln Ile Asn Arg His Ser
         195                 200                 205

Leu Thr Thr Ser Tyr Leu Asp Leu Met Ser His Ser Gly Thr Ser Leu
     210                 215                 220

Thr Gln Ser Val Ala Arg Ala Met Leu Arg Phe Val Thr Val Thr Ala
225                 230                 235                 240

Glu Ala Leu Arg Phe Arg Gln Ile Gln Arg Gly Phe Arg Thr Thr Leu
                 245                 250                 255

Asp Asp Leu Ser Gly Arg Ser Tyr Val Met Thr Ala Glu Asp Val Asp
             260                 265                 270

Leu Thr Leu Asn Trp Gly Arg Leu Ser Ser Val Leu Pro Asp Tyr His
         275                 280                 285

Gly Gln Asp Ser Val Arg Val Gly Arg Ile Ser Phe Gly Ser Ile Asn
     290                 295                 300

Ala Ile Leu Gly Ser Val Ala Leu Ile Leu Asn Cys His His His Ala
305                 310                 315                 320
```

<210> SEQ ID NO 78
<211> LENGTH: 322
<212> TYPE: PRT
<213> ORGANISM: Artificial Sequence
<220> FEATURE:
<223> OTHER INFORMATION: Description of Artificial Sequence:
      Chemokine-toxin fusion protein SDF-1-Beta-AM-truncated Shiga-A1
      Subunit HIS6

<400> SEQUENCE: 78

```
Lys Pro Val Ser Leu Ser Tyr Arg Cys Pro Cys Arg Phe Phe Glu Ser
  1               5                  10                  15

His Val Ala Arg Ala Asn Val Lys His Leu Lys Ile Leu Asn Thr Pro
             20                  25                  30
```

-continued

```
Asn Cys Ala Leu Gln Ile Val Ala Arg Leu Lys Asn Asn Arg Gln
         35                  40                  45

Val Cys Ile Asp Pro Lys Leu Lys Trp Ile Gln Glu Tyr Leu Glu Lys
 50                  55                  60

Ala Leu Asn Lys Arg Phe Lys Met Ala Met Lys Glu Phe Thr Leu Asp
 65                  70                  75                  80

Phe Ser Thr Ala Lys Thr Tyr Val Asp Ser Leu Asn Val Ile Arg Ser
                 85                  90                  95

Ala Ile Gly Thr Pro Leu Gln Thr Ile Ser Ser Gly Gly Thr Ser Leu
                100                 105                 110

Leu Met Ile Asp Ser Gly Thr Gly Asp Asn Leu Phe Ala Val Asp Val
            115                 120                 125

Arg Gly Ile Asp Pro Glu Glu Gly Arg Phe Asn Asn Leu Arg Leu Ile
        130                 135                 140

Val Glu Arg Asn Asn Leu Tyr Val Thr Gly Phe Val Asn Arg Thr Asn
145                 150                 155                 160

Asn Val Phe Tyr Arg Phe Ala Asp Phe Ser His Val Thr Phe Pro Gly
                165                 170                 175

Thr Thr Ala Val Thr Leu Ser Gly Asp Ser Ser Tyr Thr Thr Leu Gln
            180                 185                 190

Arg Val Ala Gly Ile Ser Arg Thr Gly Met Gln Ile Asn Arg His Ser
        195                 200                 205

Leu Thr Thr Ser Tyr Leu Asp Leu Met Ser His Ser Gly Thr Ser Leu
    210                 215                 220

Thr Gln Ser Val Ala Arg Ala Met Leu Arg Phe Val Thr Val Thr Ala
225                 230                 235                 240

Glu Ala Leu Arg Phe Arg Gln Ile Gln Arg Gly Phe Arg Thr Thr Leu
                245                 250                 255

Asp Asp Leu Ser Gly Arg Ser Tyr Val Met Thr Ala Glu Asp Val Asp
            260                 265                 270

Leu Thr Leu Asn Trp Gly Arg Leu Ser Ser Val Leu Pro Asp Tyr His
        275                 280                 285

Gly Gln Asp Ser Val Arg Val Gly Arg Ile Ser Phe Gly Ser Ile Asn
    290                 295                 300

Ala Ile Leu Gly Ser Val Ala Leu Ile Leu Asn Cys His His His His
305                 310                 315                 320

His His
```

<210> SEQ ID NO 79
<211> LENGTH: 327
<212> TYPE: PRT
<213> ORGANISM: Artificial Sequence
<220> FEATURE:
<223> OTHER INFORMATION: Description of Artificial Sequence:
      Chemokine-toxin fusion protein SDF-1-Beta-AM-SAPORIN

<400> SEQUENCE: 79

```
Lys Pro Val Ser Leu Ser Tyr Arg Cys Pro Cys Arg Phe Phe Glu Ser
 1                   5                  10                  15

His Val Ala Arg Ala Asn Val Lys His Leu Lys Ile Leu Asn Thr Pro
                 20                  25                  30

Asn Cys Ala Leu Gln Ile Val Ala Arg Leu Lys Asn Asn Asn Arg Gln
         35                  40                  45

Val Cys Ile Asp Pro Lys Leu Lys Trp Ile Gln Glu Tyr Leu Glu Lys
 50                  55                  60
```

```
Ala Leu Asn Lys Arg Phe Lys Met Ala Met Val Thr Ser Ile Thr Leu
 65                  70                  75                  80

Asp Leu Val Asn Pro Thr Ala Gly Gln Tyr Ser Ser Phe Val Asp Lys
                 85                  90                  95

Ile Arg Asn Asn Val Lys Asp Pro Asn Leu Lys Tyr Gly Gly Thr Asp
                100                 105                 110

Ile Ala Val Ile Gly Pro Pro Ser Lys Glu Lys Phe Leu Arg Ile Asn
                115                 120                 125

Phe Gln Ser Ser Arg Gly Thr Val Ser Leu Gly Leu Lys Arg Asp Asn
            130                 135                 140

Leu Tyr Val Val Ala Tyr Leu Ala Met Asp Asn Thr Asn Val Asn Arg
145                 150                 155                 160

Ala Tyr Tyr Phe Arg Ser Glu Ile Thr Ser Ala Glu Ser Thr Ala Leu
                165                 170                 175

Phe Pro Glu Ala Thr Thr Ala Asn Gln Lys Ala Leu Glu Tyr Thr Glu
                180                 185                 190

Asp Tyr Gln Ser Ile Glu Lys Asn Ala Gln Ile Thr Gln Gly Asp Gln
            195                 200                 205

Ser Arg Lys Glu Leu Gly Leu Gly Ile Asp Leu Leu Ser Thr Ser Met
210                 215                 220

Glu Ala Val Asn Lys Lys Ala Arg Val Val Lys Asp Glu Ala Arg Phe
225                 230                 235                 240

Leu Leu Ile Ala Ile Gln Met Thr Ala Glu Ala Ala Arg Phe Arg Tyr
                245                 250                 255

Ile Gln Asn Leu Val Ile Lys Asn Phe Pro Asn Lys Phe Asn Ser Glu
                260                 265                 270

Asn Lys Val Ile Gln Phe Glu Val Asn Trp Lys Lys Ile Ser Thr Ala
            275                 280                 285

Ile Tyr Gly Asp Ala Lys Asn Gly Val Phe Asn Lys Asp Tyr Asp Phe
            290                 295                 300

Gly Phe Gly Lys Val Arg Gln Val Lys Asp Leu Gln Met Gly Leu Leu
305                 310                 315                 320

Met Tyr Leu Gly Lys Pro Lys
                325

<210> SEQ ID NO 80
<211> LENGTH: 323
<212> TYPE: PRT
<213> ORGANISM: Artificial Sequence
<220> FEATURE:
<223> OTHER INFORMATION: Description of Artificial Sequence:
      Chemokine-toxin fusion protein EOTAXIN-AM-truncated Shiga-A1
      Subunit

<400> SEQUENCE: 80

Met Gly Pro Ala Ser Val Pro Thr Thr Cys Cys Phe Asn Leu Ala Asn
  1               5                  10                  15

Arg Lys Ile Pro Leu Gln Arg Leu Glu Ser Tyr Arg Arg Ile Thr Ser
                 20                  25                  30

Gly Lys Cys Pro Gln Lys Ala Val Ile Phe Lys Thr Lys Leu Ala Lys
             35                  40                  45

Asp Ile Cys Ala Asp Pro Lys Lys Lys Trp Val Gln Asp Ser Met Lys
 50                  55                  60

Tyr Leu Asp Gln Lys Ser Pro Thr Pro Lys Pro Ala Met Lys Glu Phe
 65                  70                  75                  80

Thr Leu Asp Phe Ser Thr Ala Lys Thr Tyr Val Asp Ser Leu Asn Val
```

-continued

```
                85                  90                  95
Ile Arg Ser Ala Ile Gly Thr Pro Leu Gln Thr Ile Ser Ser Gly Gly
            100                 105                 110
Thr Ser Leu Leu Met Ile Asp Ser Gly Thr Gly Asp Asn Leu Phe Ala
        115                 120                 125
Val Asp Val Arg Gly Ile Asp Pro Glu Glu Gly Arg Phe Asn Asn Leu
    130                 135                 140
Arg Leu Ile Val Glu Arg Asn Asn Leu Tyr Val Thr Gly Phe Val Asn
145                 150                 155                 160
Arg Thr Asn Asn Val Phe Tyr Arg Phe Ala Asp Phe Ser His Val Thr
                165                 170                 175
Phe Pro Gly Thr Thr Ala Val Thr Leu Ser Gly Asp Ser Ser Tyr Thr
            180                 185                 190
Thr Leu Gln Arg Val Ala Gly Ile Ser Arg Thr Gly Met Gln Ile Asn
        195                 200                 205
Arg His Ser Leu Thr Thr Ser Tyr Leu Asp Leu Met Ser His Ser Gly
    210                 215                 220
Thr Ser Leu Thr Gln Ser Val Ala Arg Ala Met Leu Arg Phe Val Thr
225                 230                 235                 240
Val Thr Ala Glu Ala Leu Arg Phe Arg Gln Ile Gln Arg Gly Phe Arg
                245                 250                 255
Thr Thr Leu Asp Asp Leu Ser Gly Arg Ser Tyr Val Met Thr Ala Glu
            260                 265                 270
Asp Val Asp Leu Thr Leu Asn Trp Gly Arg Leu Ser Ser Val Leu Pro
        275                 280                 285
Asp Tyr His Gly Gln Asp Ser Val Arg Val Gly Arg Ile Ser Phe Gly
    290                 295                 300
Ser Ile Asn Ala Ile Leu Gly Ser Val Ala Leu Ile Leu Asn Cys His
305                 310                 315                 320

His His Ala

<210> SEQ ID NO 81
<211> LENGTH: 325
<212> TYPE: PRT
<213> ORGANISM: Artificial Sequence
<220> FEATURE:
<223> OTHER INFORMATION: Description of Artificial Sequence:
      Chemokine-toxin fusion protein EOTAXIN-AM-truncated Shiga-A1
      Subunit HIS6

<400> SEQUENCE: 81

Met Gly Pro Ala Ser Val Pro Thr Thr Cys Cys Phe Asn Leu Ala Asn
1               5                   10                  15
Arg Lys Ile Pro Leu Gln Arg Leu Glu Ser Tyr Arg Arg Ile Thr Ser
                20                  25                  30
Gly Lys Cys Pro Gln Lys Ala Val Ile Phe Lys Thr Lys Leu Ala Lys
            35                  40                  45
Asp Ile Cys Ala Asp Pro Lys Lys Lys Trp Val Gln Asp Ser Met Lys
        50                  55                  60
Tyr Leu Asp Gln Lys Ser Pro Thr Pro Lys Pro Ala Met Lys Glu Phe
65                  70                  75                  80
Thr Leu Asp Phe Ser Thr Ala Lys Thr Tyr Val Asp Ser Leu Asn Val
                85                  90                  95
Ile Arg Ser Ala Ile Gly Thr Pro Leu Gln Thr Ile Ser Ser Gly Gly
            100                 105                 110
```

```
Thr Ser Leu Leu Met Ile Asp Ser Gly Thr Gly Asp Asn Leu Phe Ala
        115                 120                 125

Val Asp Val Arg Gly Ile Asp Pro Glu Glu Gly Arg Phe Asn Asn Leu
130                 135                 140

Arg Leu Ile Val Glu Arg Asn Asn Leu Tyr Val Thr Gly Phe Val Asn
145                 150                 155                 160

Arg Thr Asn Asn Val Phe Tyr Arg Phe Ala Asp Phe Ser His Val Thr
                165                 170                 175

Phe Pro Gly Thr Thr Ala Val Thr Leu Ser Gly Asp Ser Ser Tyr Thr
            180                 185                 190

Thr Leu Gln Arg Val Ala Gly Ile Ser Arg Thr Gly Met Gln Ile Asn
        195                 200                 205

Arg His Ser Leu Thr Thr Ser Tyr Leu Asp Leu Met Ser His Ser Gly
    210                 215                 220

Thr Ser Leu Thr Gln Ser Val Ala Arg Ala Met Leu Arg Phe Val Thr
225                 230                 235                 240

Val Thr Ala Glu Ala Leu Arg Phe Arg Gln Ile Gln Arg Gly Phe Arg
                245                 250                 255

Thr Thr Leu Asp Asp Leu Ser Gly Arg Ser Tyr Val Met Thr Ala Glu
            260                 265                 270

Asp Val Asp Leu Thr Leu Asn Trp Gly Arg Leu Ser Ser Val Leu Pro
        275                 280                 285

Asp Tyr His Gly Gln Asp Ser Val Arg Val Gly Arg Ile Ser Phe Gly
    290                 295                 300

Ser Ile Asn Ala Ile Leu Gly Ser Val Ala Leu Ile Leu Asn Cys His
305                 310                 315                 320

His His His His His
            325

<210> SEQ ID NO 82
<211> LENGTH: 330
<212> TYPE: PRT
<213> ORGANISM: Artificial Sequence
<220> FEATURE:
<223> OTHER INFORMATION: Description of Artificial Sequence:
      Chemokine-toxin fusion protein EOTAXIN-AM-SAPORIN

<400> SEQUENCE: 82

Met Gly Pro Ala Ser Val Pro Thr Thr Cys Cys Phe Asn Leu Ala Asn
 1               5                  10                  15

Arg Lys Ile Pro Leu Gln Arg Leu Glu Ser Tyr Arg Arg Ile Thr Ser
                20                  25                  30

Gly Lys Cys Pro Gln Lys Ala Val Ile Phe Lys Thr Lys Leu Ala Lys
            35                  40                  45

Asp Ile Cys Ala Asp Pro Lys Lys Lys Trp Val Gln Asp Ser Met Lys
        50                  55                  60

Tyr Leu Asp Gln Lys Ser Pro Thr Pro Lys Pro Ala Met Val Thr Ser
 65                 70                  75                  80

Ile Thr Leu Asp Leu Val Asn Pro Thr Ala Gly Gln Tyr Ser Ser Phe
                85                  90                  95

Val Asp Lys Ile Arg Asn Asn Val Lys Asp Pro Asn Leu Lys Tyr Gly
            100                 105                 110

Gly Thr Asp Ile Ala Val Ile Gly Pro Pro Ser Lys Glu Lys Phe Leu
        115                 120                 125

Arg Ile Asn Phe Gln Ser Ser Arg Gly Thr Val Ser Leu Gly Leu Lys
    130                 135                 140
```

```
Arg Asp Asn Leu Tyr Val Val Ala Tyr Leu Ala Met Asp Asn Thr Asn
145                 150                 155                 160

Val Asn Arg Ala Tyr Tyr Phe Arg Ser Glu Ile Thr Ser Ala Glu Ser
            165                 170                 175

Thr Ala Leu Phe Pro Glu Ala Thr Thr Ala Asn Gln Lys Ala Leu Glu
            180                 185                 190

Tyr Thr Glu Asp Tyr Gln Ser Ile Glu Lys Asn Ala Gln Ile Thr Gln
            195                 200                 205

Gly Asp Gln Ser Arg Lys Glu Leu Gly Leu Gly Ile Asp Leu Leu Ser
            210                 215                 220

Thr Ser Met Glu Ala Val Asn Lys Lys Ala Arg Val Val Lys Asp Glu
225                 230                 235                 240

Ala Arg Phe Leu Leu Ile Ala Ile Gln Met Thr Ala Glu Ala Ala Arg
            245                 250                 255

Phe Arg Tyr Ile Gln Asn Leu Val Ile Lys Asn Phe Pro Asn Lys Phe
            260                 265                 270

Asn Ser Glu Asn Lys Val Ile Gln Phe Glu Val Asn Trp Lys Lys Ile
            275                 280                 285

Ser Thr Ala Ile Tyr Gly Asp Ala Lys Asn Gly Val Phe Asn Lys Asp
            290                 295                 300

Tyr Asp Phe Gly Phe Gly Lys Val Arg Gln Val Lys Asp Leu Gln Met
305                 310                 315                 320

Gly Leu Leu Met Tyr Leu Gly Lys Pro Lys
            325                 330
```

<210> SEQ ID NO 83
<211> LENGTH: 247
<212> TYPE: PRT
<213> ORGANISM: Artificial Sequence
<220> FEATURE:
<223> OTHER INFORMATION: Description of Artificial Sequence:
      Methionine-truncated Shiga-A1 Subunit fusion protein

<400> SEQUENCE: 83

```
Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
            20                  25                  30

Ser Ser Gly Gly Thr Ser Leu Leu Met Ile Asp Ser Gly Thr Gly Asp
            35                  40                  45

Asn Leu Phe Ala Val Asp Val Arg Gly Ile Asp Pro Glu Glu Gly Arg
    50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
            85                  90                  95

Ser His Val Thr Phe Pro Gly Thr Thr Ala Val Thr Leu Ser Gly Asp
            100                 105                 110

Ser Ser Tyr Thr Thr Leu Gln Arg Val Ala Gly Ile Ser Arg Thr Gly
            115                 120                 125

Met Gln Ile Asn Arg His Ser Leu Thr Thr Ser Tyr Leu Asp Leu Met
            130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
```

```
                      165                 170                 175
Arg Gly Phe Arg Thr Thr Leu Asp Asp Leu Ser Gly Arg Ser Tyr Val
                180                 185                 190
Met Thr Ala Glu Asp Val Asp Leu Thr Leu Asn Trp Gly Arg Leu Ser
                195                 200             205
Ser Val Leu Pro Asp Tyr His Gly Gln Asp Ser Val Arg Val Gly Arg
                210                 215                 220
Ile Ser Phe Gly Ser Ile Asn Ala Ile Leu Gly Ser Val Ala Leu Ile
225                 230                 235                 240
Leu Asn Cys His His His Ala
                245

<210> SEQ ID NO 84
<211> LENGTH: 249
<212> TYPE: PRT
<213> ORGANISM: Artificial Sequence
<220> FEATURE:
<223> OTHER INFORMATION: Description of Artificial Sequence:
      Methionine-truncated Shiga-A1 Subunit HIS6

```
<212> TYPE: PRT
<213> ORGANISM: Artificial Sequence
<220> FEATURE:
<223> OTHER INFORMATION: Description of Artificial Sequence:
      Methionine-Saporin fusion protein

<400> SEQUENCE: 85

Met Val Thr Ser Ile Thr Leu Asp Leu Val Asn Pro Thr Ala Gly Gln
 1               5                  10                  15

Tyr Ser Ser Phe Val Asp Lys Ile Arg Asn Asn Val Lys Asp Pro Asn
                20                  25                  30

Leu Lys Tyr Gly Gly Thr Asp Ile Ala Val Ile Gly Pro Pro Ser Lys
             35                  40                  45

Glu Lys Phe Leu Arg Ile Asn Phe Gln Ser Ser Arg Gly Thr Val Ser
         50                  55                  60

Leu Gly Leu Lys Arg Asp Asn Leu Tyr Val Val Ala Tyr Leu Ala Met
 65                  70                  75                  80

Asp Asn Thr Asn Val Asn Arg Ala Tyr Tyr Phe Arg Ser Glu Ile Thr
                 85                  90                  95

Ser Ala Glu Ser Thr Ala Leu Phe Pro Glu Ala Thr Thr Ala Asn Gln
            100                 105                 110

Lys Ala Leu Glu Tyr Thr Glu Asp Tyr Gln Ser Ile Glu Lys Asn Ala
        115                 120                 125

Gln Ile Thr Gln Gly Asp Gln Ser Arg Lys Glu Leu Gly Leu Gly Ile
    130                 135                 140

Asp Leu Leu Ser Thr Ser Met Glu Ala Val Asn Lys Lys Ala Arg Val
145                 150                 155                 160

Val Lys Asp Glu Ala Arg Phe Leu Leu Ile Ala Ile Gln Met Thr Ala
                165                 170                 175

Glu Ala Ala Arg Phe Arg Tyr Ile Gln Asn Leu Val Ile Lys Asn Phe
            180                 185                 190

Pro Asn Lys Phe Asn Ser Glu Asn Lys Val Ile Gln Phe Glu Val Asn
        195                 200                 205

Trp Lys Lys Ile Ser Thr Ala Ile Tyr Gly Asp Ala Lys Asn Gly Val
    210                 215                 220

Phe Asn Lys Asp Tyr Asp Phe Gly Phe Gly Lys Val Arg Gln Val Lys
225                 230                 235                 240

Asp Leu Gln Met Gly Leu Leu Met Tyr Leu Gly Lys Pro Lys
                245                 250

<210> SEQ ID NO 86
<211> LENGTH: 77
<212> TYPE: PRT
<213> ORGANISM: Artificial Sequence
<220> FEATURE:
<223> OTHER INFORMATION: Description of Artificial Sequence:
      Methionine-MCP3 fusion protein

<400> SEQUENCE: 86

Met Gln Pro Val Gly Ile Asn Thr Ser Thr Thr Cys Cys Tyr Arg Phe
 1               5                  10                  15

Ile Asn Lys Lys Ile Pro Lys Gln Arg Leu Glu Ser Tyr Arg Arg Thr
                20                  25                  30

Thr Ser Ser His Cys Pro Arg Glu Ala Val Ile Phe Lys Thr Lys Leu
             35                  40                  45

Asp Lys Glu Ile Cys Ala Asp Pro Thr Gln Lys Trp Val Gln Asp Phe
         50                  55                  60
```

```
Met Lys His Leu Asp Lys Lys Thr Gln Thr Pro Lys Leu
 65                  70                  75
```

```
<210> SEQ ID NO 87
<211> LENGTH: 120
<212> TYPE: PRT
<213> ORGANISM: Mus musculus
<220> FEATURE:
<223> OTHER INFORMATION: Mouse chemokine ALP

<400> SEQUENCE: 87

Met Met Glu Gly Leu Ser Pro Ala Ser Ser Leu Pro Leu Leu Leu
 1               5                  10                  15

Leu Leu Ser Pro Ala Pro Glu Ala Ala Leu Pro Leu Pro Ser Ser Thr
                 20                  25                  30

Ser Cys Cys Thr Gln Leu Tyr Arg Gln Pro Leu Pro Ser Arg Leu Leu
             35                  40                  45

Arg Arg Ile Val His Met Glu Leu Gln Glu Ala Asp Gly Asp Cys His
         50                  55                  60

Leu Gln Ala Val Val Leu His Leu Ala Arg Arg Ser Val Cys Val His
 65                  70                  75                  80

Pro Gln Asn Arg Ser Leu Ala Arg Trp Leu Glu Arg Gln Gly Lys Arg
                 85                  90                  95

Leu Gln Gly Thr Val Pro Ser Leu Asn Leu Val Leu Gln Lys Lys Met
            100                 105                 110

Tyr Ser Asn Pro Gln Gln Gln Asn
            115                 120
```

```
<210> SEQ ID NO 88
<211> LENGTH: 167
<212> TYPE: PRT
<213> ORGANISM: Mus musculus
<220> FEATURE:
<223> OTHER INFORMATION: Mouse Lungkine

<400> SEQUENCE: 88

Met Ala Ala Gln Gly Trp Ser Met Leu Leu Ala Val Leu Asn Leu
 1               5                  10                  15

Gly Ile Phe Val Arg Pro Cys Asp Thr Gln Glu Leu Arg Cys Leu Cys
                 20                  25                  30

Ile Gln Glu His Ser Glu Phe Ile Pro Leu Lys Leu Ile Lys Asn Ile
             35                  40                  45

Met Val Ile Phe Glu Thr Ile Tyr Cys Asn Arg Lys Glu Val Ile Ala
         50                  55                  60

Val Pro Lys Asn Gly Ser Met Ile Cys Leu Asp Pro Asp Ala Pro Trp
 65                  70                  75                  80

Val Lys Ala Thr Val Gly Pro Ile Thr Asn Arg Phe Leu Pro Glu Asp
                 85                  90                  95

Leu Lys Gln Lys Glu Phe Pro Ala Met Lys Leu Leu Tyr Ser Val
                100                 105                 110

Glu His Glu Lys Pro Leu Tyr Leu Ser Phe Gly Arg Pro Glu Asn Lys
            115                 120                 125

Arg Ile Phe Pro Phe Pro Ile Arg Glu Thr Ser Arg His Phe Ala Asp
        130                 135                 140

Leu Ala His Asn Ser Asp Arg Asn Phe Leu Arg Asp Ser Ser Glu Val
145                 150                 155                 160

Ser Leu Thr Gly Ser Asp Ala
                165
```

<210> SEQ ID NO 89
<211> LENGTH: 70
<212> TYPE: PRT
<213> ORGANISM: Homo sapiens
<220> FEATURE:
<223> OTHER INFORMATION: Human Chemokine polypeptide: NAP-2
<300> PUBLICATION INFORMATION:
<301> AUTHORS: Clark-Lewis et. al.,
<303> JOURNAL: J. Leukoc. Biol.
<304> VOLUME: 57
<306> PAGES: 703-711
<307> DATE: 1995

<400> SEQUENCE: 89

Ala Glu Leu Arg Cys Met Cys Ile Lys Thr Thr Ser Gly Ile His Pro
 1               5                  10                  15

Lys Asn Ile Gln Ser Leu Glu Val Ile Gly Lys Gly Thr His Cys Asn
            20                  25                  30

Gln Val Glu Val Ile Ala Thr Leu Lys Asp Gly Arg Lys Ile Cys Leu
        35                  40                  45

Asp Pro Asp Ala Pro Arg Ile Lys Lys Ile Val Gln Lys Lys Leu Ala
    50                  55                  60

Gly Asp Glu Ser Ala Asp
65                  70

<210> SEQ ID NO 90
<211> LENGTH: 78
<212> TYPE: PRT
<213> ORGANISM: Homo sapiens
<220> FEATURE:
<223> OTHER INFORMATION: Human Chemokine Polypepetide: ENA-78
<300> PUBLICATION INFORMATION:
<301> AUTHORS: Clark-Lewis et. al.,
<303> JOURNAL: J. Leukoc. Biol.
<304> VOLUME: 57
<306> PAGES: 703-711
<307> DATE: 1995

<400> SEQUENCE: 90

Ala Gly Pro Ala Ala Ala Val Leu Arg Glu Leu Arg Cys Val Cys Leu
 1               5                  10                  15

Gln Thr Thr Gln Gly Val His Pro Lys Met Ile Ser Asn Leu Gln Val
            20                  25                  30

Phe Ala Ile Gly Pro Gln Cys Ser Lys Val Glu Val Val Ala Ser Leu
        35                  40                  45

Lys Asn Gly Lys Glu Ile Cys Leu Asp Pro Glu Ala Pro Phe Leu Lys
    50                  55                  60

Lys Val Ile Gln Lys Ile Leu Asp Gly Gly Asn Lys Glu Asn
65                  70                  75

<210> SEQ ID NO 91
<211> LENGTH: 70
<212> TYPE: PRT
<213> ORGANISM: Homo sapiens
<220> FEATURE:
<223> OTHER INFORMATION: Human Chemokine polypeptide: PF-4
<300> PUBLICATION INFORMATION:
<301> AUTHORS: Clark-Lewis et. al.,
<303> JOURNAL: J. Leukoc. Biol.
<304> VOLUME: 57
<306> PAGES: 703-711
<307> DATE: 1995

<400> SEQUENCE: 91

```
Glu Ala Glu Glu Asp Gly Asp Leu Gln Cys Leu Cys Val Lys Thr Thr
 1               5                  10                  15

Ser Gln Val Arg Pro Arg His Ile Thr Ser Leu Glu Val Ile Lys Ala
            20                  25                  30

Gly Pro His Cys Pro Thr Ala Gln Leu Ile Ala Thr Leu Lys Asn Gly
        35                  40                  45

Arg Lys Ile Cys Leu Asp Leu Gln Ala Pro Leu Tyr Lys Lys Ile Ile
    50                  55                  60

Lys Lys Leu Leu Glu Ser
 65              70

<210> SEQ ID NO 92
<211> LENGTH: 74
<212> TYPE: PRT
<213> ORGANISM: Homo sapiens
<220> FEATURE:
<223> OTHER INFORMATION: Human Chemokine Polypeptide: gamma-IP-10
<300> PUBLICATION INFORMATION:
<301> AUTHORS: Clark-Lewis et. al.,
<303> JOURNAL: J. Leukoc. Biol.
<304> VOLUME: 57
<306> PAGES: 703-711
<307> DATE: 1995

<400> SEQUENCE: 92

Ser Arg Thr Val Arg Cys Thr Cys Ile Ser Ile Ser Asn Gln Pro Val
 1               5                  10                  15

Asn Pro Arg Ser Leu Glu Lys Leu Glu Ile Ile Pro Ala Ser Gln Phe
            20                  25                  30

Cys Pro Arg Val Glu Ile Ile Ala Thr Met Lys Lys Lys Gly Glu Lys
        35                  40                  45

Arg Cys Leu Asn Pro Glu Ser Lys Ala Ile Lys Asn Leu Leu Lys Ala
    50                  55                  60

Val Ser Lys Glu Met Ser Lys Arg Ser Pro
 65              70

<210> SEQ ID NO 93
<211> LENGTH: 93
<212> TYPE: PRT
<213> ORGANISM: Homo sapiens
<220> FEATURE:
<223> OTHER INFORMATION: Human Chemokine Polypeptide:  Stromal
      cell-derived Factor-1-Beta (SDF-1-Beta)
<300> PUBLICATION INFORMATION:
<303> JOURNAL: Genomics
<304> VOLUME: 28
<306> PAGES: 495-500
<307> DATE: 1995

<400> SEQUENCE: 93

Met Asn Ala Lys Val Val Val Val Leu Val Leu Val Leu Thr Ala Leu
 1               5                  10                  15

Cys Leu Ser Asp Gly Lys Pro Val Ser Leu Ser Tyr Arg Cys Pro Cys
            20                  25                  30

Arg Phe Phe Glu Ser His Val Ala Arg Ala Asn Val Lys His Leu Lys
        35                  40                  45

Ile Leu Asn Thr Pro Asn Cys Ala Leu Gln Ile Val Ala Arg Leu Lys
    50                  55                  60
```

```
Asn Asn Asn Arg Gln Val Cys Ile Asp Pro Lys Leu Lys Trp Ile Gln
65                  70              75                  80

Glu Tyr Leu Glu Lys Ala Leu Asn Lys Arg Phe Lys Met
                85                  90
```

METHODS AND COMPOSITIONS FOR TREATING SECONDARY TISSUE DAMAGE AND OTHER INFLAMMATORY CONDITIONS AND DISORDERS

RELATED APPLICATIONS

This application claims the benefit of priority under 35 U.S.C. §119(e) to U.S. provisional application Ser. No. 60/155,186 to McDONALD, John R. and COGGINS, Philip J., entitled "METHODS AND COMPOSITIONS FOR TREATING SECONDARY TISSUE DAMAGE", filed Jul. 22, 1998. This application is a continuation-in-part of International PCT application No. PCT/CA99/00659, filed Jul. 21, 1999, by Osprey Pharmaceuticals Limited, McDONALD, John R. and COGGINS, Philip J. entitled "METHODS AND COMPOSITIONS FOR TREATING SECONDARY TISSUE DAMAGE AND OTHER INFLAMMATORY CONDITIONS AND DISORDERS".

The subject matter of each of U.S. application Ser. No. 09/120,523, U.S. Provisional Application Ser. No. 60/155,186 and of International PCT application No. PCT/CA99/00659 is herein incorporated by reference in its entirety.

BACKGROUND OF THE INVENTION

Chemokines

Chemokines are a superfamily of forty or more small (approximately about 4 to about 14 kDa) inducible and secreted pro-inflammatory cytokines that act primarily as chemoattractants and activators of specific leukocyte cell subtypes. Together, chemokines target the entire spectrum of leukocyte subtypes; individually each targets only part of the spectrum. Chemokines, which are basic heparin-binding proteins, have four cysteines shared among almost all family members. There are four major groups of chemokines, three of which include the four conserved cysteines. The groups are defined by the arrangement of the first two cysteines. If the first two cysteines are separated by a single amino acid they are members of the CXC family (also called $\alpha$); if the cysteines are adjacent, they are classified in the CC family (also called $\beta$). If they are separated by three amino acids $CX_3C$, they are members of the third group. The fourth group of chemokines contains two cysteines, corresponding to the first and third cysteines in the other groups. Structural analysis demonstrates that most chemokines function as monomers and that the two regions necessary for receptor binding reside within the first 35 amino acids of the flexible N-terminus (Clark-Lewis et al. (1995) *J Leukoc Biol* 57, 703–11; Beall et al. (1996) *Biochem J* 313, 633–40; and Steitz et al. (1998) *FEBS Lett* 430, 158–64).

Chemokines, in association with adhesion molecules, recruit subsets of leukocytes to specific sites of inflammation and tissue injury. Generally, chemokines and chemokine receptor expression are up-regulated in disease, with chemokines acting in an autocrine or paracrine manner (Glabinski et al., *Int. J. Dev. Neurosci.*, 13: 153–65, 1995; Furie and Randolph, *Am. J. Pathol.*, 146: 1287–301, 1995; Benveniste, E. N., *J. Mol. Med.*, 75: 165–73, 1997; Schall et al., *Current Biol.*, 6: 865–73, 1994; Taub et al., *Ther. Immunol.*, 1: 229–46, 1994; Baggiolini et al., *Adv. Immunol.*, 55: 97–179, 1994; and Haelens et al., *Immunobiol.*, 195: 499–521, 1996). Several cytokines and chemokines work together to regulate most functions of mononuclear phagocytes (MNPs; monocytes), including the release of neurotoxic and cytotoxic factors.

Once secreted by infiltrating mononuclear phagocytes (MNPs), particularly, such as activated microglia, a distinct class of mononuclear phagocytes (MNPs) found in the CNS, chemokines are responsible for the chemoattraction of several other leukocyte cell types, including neutrophils, eosinophils, basophils, T-lymphocytes, and natural killer cells. In vitro studies have shown that various stimuli, including lipopolysaccharide (LPS), IL-1, IFN-$\gamma$ and TNF-$\alpha$ induce the expression and secretion of chemokines from various central nervous system (CNS) and other cell types (Proost et al., *J. Leukoc. Biol.*, 59: 67–74, 1996; Graves et al., *Crit. Rev. Oral Biol. Med.*, 6: 109–18, 1995; Hayashi et al., *J. Neurommunol.* 60: 143–50, 1995; and Hurwitz et al., *J Neuroimmunol.*, 57: 193–8, 1995). For example, production of chemokines such as monocyte chemotactic protein-1 (MCP-1), macrophage inflammatory protein-1 (MIP-1$\beta$), and RANTES (Regulated on Activation, Normal T cell Expressed and Secreted) can be induced from astrocytes, microglia and leukocytes (Proost et al., *J. Leukoc. Biol.*, 59: 67–74, 1996; Graves et al., *Crit. Rev. Oral Biol. Med.*, 6: 109–18, 1995; Hayashi et al., *J. Neurommunol.* 60: 143–50, 1995; and Hurwitz et al., *J Neuroimmunol.*, 57: 193–8, 1995). These chemokines have been shown to induce chemotaxis and activation of microglia and macrophages in cell culture studies (Graves et al., *Crit. Rev. Oral Biol. Med.*, 6: 109–18, 1995; Hayashi et al., *J. Neurommunol.* 60: 143–50, 1995; and Hurwitz et al., *J Neuroimmunol.*, 57: 193–8, 1995; Sun et al., *J. Neurosci. Res.*, 48: 192–200, 1997; and Peterson et al., *J. Infect. Dis.*, 175: 478–81, 1997). Thus, chemokines are thought to induce the production and release of reactive oxygen species, degradative enzymes, and inflammatory and toxic cytokines from various leukocyte and MNP cell populations (Glabinski et al., *Int. J. Dev. Neurosci.*, 13: 153–65, 1995; Furie and Randolph, *Am. J. Pathol.*, 146: 1287–301, 1995; Benveniste, E. N., *J. Mol. Med.*, 75: 165–73, 1997; Schall et al., *Current Biol.*, 6: 865–73, 1994; Taub et al., *Ther. Immunol.*, 1: 229–46, 1994; Proost et al., *J. Leukoc. Biol.*, 59: 67–74, 1996; Graves et al., *Crit. Rev. Oral Biol. Med.*, 6: 109–18, 1995; Hayashi et al., *J. Neurommunol.* 60: 143–50, 1995; Hurwitz et al., *J Neuroimmunol.*, 57: 193–8, 1995; Sun et al., *J. Neurosci. Res.*, 48: 192–200, 1997; Peterson et al., *J. Infect. Dis.*, 175: 478–81, 1997; Leonard et al., *Immunol. Today*, 11: 97–103, 1990 and Fahey et al., *J. Immunol.*, 148: 2764–9, 1992; Ali et al., *Adv. Rheumatol.*, 81: 1–28, 1997).

The chemokine members MCP-1, MIP-1$\beta$, and RANTES have been shown to be expressed in astrocytes and macrophages after mechanical injury to the brain (Glabinski et al., *Int. J. Dev. Neurosci.*, 13: 153–65, 1995; and Ghirnikar et al., *J. Neurosci. Res.*, 46: 727–33, 1996). In these studies, the expression of the chemokines under investigation correlated with the onset of reactive gliosis and the appearance of MNPs at the site of injury. MCP-1 and MIP-1$\alpha$ expression has been detected in MNPs and astrocytes after focal cerebral ischemia in the rat (Kim et al., *J. Neuroimmunol.*, 56: 127–34, 1995; Gourmala et al., *J. Neuroimmunol.*, 74: 35–44, 1997; and Takami et al., *Neurosci. Lett.*, 277: 173–6, 1997), and several investigators have studied the expression of various chemokines in EAE, an animal model for multiple sclerosis (Berman et al., *J. Immunol.*, 156: 3017–23, 1996; and Adamus et al., *J. Neurosci. Res.*, 50: 531–8, 1997). Also, transgenic mice that over-express MCP-1 have been shown to exhibit pronounced MNP and leukocyte infiltration into the CNS (Fuentes et al., *J. Immunol.*, 155: 5769–76, 1995).

The expression levels of numerous cytokines and chemokines have been reported to be elevated in and modulate the progression of countless cancer types (Van Mier,

*Glia*, 15:264–88, 1995). For example, leukemic human mast cells appear to be the source of multiple chemokines including; MCP-1; I-309; MIP-1α; MIP-1β; RANTES and IL-8. One study reports that normal human adult tissues express very low levels of RANTES, but expression was greatly increased in numerous types of cancers including lymphomas (von Luettichau, et al., *Cytokine*, 8:89–98). Similarly, MCP-3 expressions levels are increased in many tumor cell lines (Murakami, et al., *DNA Cell Biol.* 16:173–83).

Cytokines (e.g., IL-1, IL-6, and TNF-α) and chemokines (e.g., IL-8, MCP-1, MIP-1α, MIP-1β and RANTES) have been implicated in the pathology of numerous conditions and diseases, including secondary cellular damage. They have been implicated in the pathology of inflammatory joint diseases including rheumatoid arthritis (Rathanaswami et al., *J. Biol. Chem.* 268: 5834–9, 1993; Badolato and Oppenhiem, *Semin. Arthritis Rheum.*, 2: 526–38, 1996; De Benedetti et al., *Curr. Opin. Rheumatol.*, 9: 428–33, 1997; Viliger et al., *J. Immunol.*, 149: 722–27, 1992; Hosaka et al., *Clin. Exp Immunol.*, 97: 451–7, 1994; Kunkel et al., *J. Leukoc. Biol.*, 59: 6–12, 1996). The release of inflammatory mediators including reactive oxygen species, proteolytic enzymes, and a variety of cytokines from MNPs are associated with the initiation and maintenance of tissue damage in the arthritic state (Kunkel et al., *J. Leukoc. Biol.*, 59: 6–12, 1996; Badolato and Oppenhiem, *Semin. Arthritis Rheum.*, 2: 526–38, 1996).

Chemokine Receptors

Chemokines mediate their activities via G-protein-coupled cell surface receptors. Five receptors (CXCR1–5) to which CXC chemokines bind and ten receptors (CCR1–9, including CCR-2A and CCR-2B) to which CC chemokines bind have been identified. One member, designated Duffy antigen receptor, binds to CC and CXC chemokines.

Inflammatory cells, such as microglia, express several chemokine receptors, and more than one chemokine may bind to one receptor. For example, the β-chemokine receptor CCR3 (He et al., *Nature*, 385: 645–49, 1997) binds to not only MCP-3, MCP-4 and RANTES, but also to two other CC chemokines, eotaxin and eotaxin-2 (Jose et al., *J. Exp. Med.*, 179: 881–7, 1994; Jose et al., *Biochem. Biophys. Res. Commun.*, 205: 788–94, 1994; Ponath et al., *J. Clin. Invest.*, 97: 604–12, 1996; Daugherty et al., *J. Exp. Med.* 183: 2349–54, 1996; and Forssman et al., *J. Exp. Med.*, 185: 2171–6, 1997). Eotaxin and eotaxin-2 are CCR3-specific (Ponath et al., *J. Clin. Invest.*, 97: 604–12, 1996; Daugherty et al., *J. Exp. Med.* 183: 2349–54, 1996; and Forssman et al., *J. Exp. Med.*, 185: 2171–6, 1997).

A second example is the α-chemokine CXCR4 (fusin) HIV co-receptor. Three chemokines (stromal cell-derived factors SDF-1α, SDF-1β (SEQ ID NO. 93), and SDF-2) have been identified that specifically bind to this receptor, which is present on various subsets of inflammatory cells and are highly potent MNP cell attractants (Ueda et al., *J. Biol. Chem.*, 272: 24966–70, 1997; Yi et al., *J. Virol.*, 72: 772–7, 1998; Shirozu et al., *Genomics*, 28: 495–500. 1995; Shirozu et al., *Genomics*, 37: 273–80, 1996; Bleul et al., *J. Exp. Med.*, 184: 1101–9, 1996; Tanabe et al., *J. Immunol.* 159: 905–11, 1997; and Hamada et al., *Gene*, 176: 211–4, 1996).

Inflammatory Disease, Secondary Tissue Damage and Chemokines

Chemokines have a variety of biological activities. They were initially isolated by their ability to stimulate leukocyte migration and activation. They have been shown to regulate negative hematopoietic progenitor proliferation, and several CXC chemokines can regulate angiogenesis. They may play a role in many diseases that involve inflammatory tissue destruction, such as adult respiratory distress syndrome, myocardial infarction, rheumatoid arthritis, and atherosclerosis.

Inflammatory responses are mediated by immune defense cells that accumulate at the site of tissue injury or trauma to rid the body of unwanted exogenous agents (e.g., microbes) or endogenous agents (e.g., cancer cell clones); to clean up cellular debris, and to participate in tissue and wound healing. Unfortunately, the molecular mechanisms involved in these reparatory (inflammatory) processes can initiate secondary tissue damage, which, in turn, contributes to the pathogenesis and persistent pathology of several inflammatory diseases. The molecular mechanisms and the cellular and chemical mediators involved in secondary tissue damage are similar, if not identical, in most inflammatory diseases of man. As an example, the processes involved in secondary tissue damage in central nervous system (CNS) trauma and disease are outlined below.

Studies on spinal cord injury (SCI) and generalized central nervous system (CNS) trauma have demonstrated a clear onset of secondary tissue damage that is observed within a matter of hours, may proceed for several weeks, and is followed by a period of partial recovery. Numerous factors are involved in the spread of secondary damage in spinal cord after traumatic injury, including ischemia, edema, increased excitatory amino acids, and oxidative damage to the tissue from reactive oxygen species. Neutrophils and macrophages can produce reactive oxygen species when activated and thus may contribute to the lipid peroxidation that occurs after spinal cord injury. Secondary tissue damage is detectable as cell death, astrogliosis that leads to glial scarring, neovascularization, demyelination, and loss of sensory and motor functions, i.e., paralysis. The time course of secondary damage and partial recovery are correlated with the degree of inflammation at the site of injury (Blight, A. R., *J. Neurol. Sci.* 103: 156–71, 1991; Dusart et al., *Eur. J. Neurosci.* 6: 712–14, 1994; and Gehrmann et al., *Brain Res. Rev.*, 20: 269–87, 1995), and the molecular mechanisms that underlie these events appear to be similar to those that mediate the damage associated with other inflammatory diseases of the CNS, including multiple sclerosis (MS), encephalomyelitis, Alzheimer's disease (AD), AIDS dementia complex, spongiform encephalopathies, and adrenoleukodystrophy (Raine, C. S., *J. Neuropathol. Exp. Neurol.*, 53: 328–37, 1994; Sobel, R. A., *Neurol Clin.*, 13: 1–21, 1995; Dickson et al., *Glia* 7: 75–83, 1993; Benveniste, E. N., *Res. Publ. Assoc. Res. Nerv. Ment. Dis.*, 72: 71–88, 1994; Benveniste, E. N., *J. Mol. Med.*, 75: 165–73, 1997; Sippy et al., *J. Acquir. Defic. Syndr. Hum. Retrovirol.*, 10: 511–21, 1995; Giulian et al., *Neurochem, Int.*, 27: 119–37, 1995a; Christie et al., *Am. J. Pathol.*, 148: 399–403, 1996; El Khoury et al., *Nature* 382: 716–19, 1996; Powers, J. M., *J. Neuropathol. Exp. Neurol.*, 54: 710–9, 1995; and Ühleisen et al., *Neuropathol. App. Neurobiol.*, 21:505–517, 1995).

It is generally accepted that microglia are the resident immunoeffector cells of the CNS (Gehrmann et al., *Brain Res. Rev.*, 20: 269–87, 1995; Giulian, D., *J. Neurosci. Res.*, 18: 155–171, 1987; and Giulian et al., *J. Neurosci.*, 15: 7712–26, 1995b). Microglia and infiltrating macrophages, another class of MNP activated after injury, lead to secondary cellular damage (Giulian et al., *J. Neurosci.*, 9: 4416–29, 1989; Giulian et al., *Ann. Neurol.*, 27: 33–42, 1990; Gehrmann et al., *Brain Res. Rev.*, 20: 269–87, 1995; Sobel, R. A., *Neurol. Clin.*, 13: 1–21, 1995; Dickson et al., *Glia* 7: 75–83, 1993; Benveniste, E. N., *Res. Publ. Assoc. Res. Nerv. Ment. Dis.*, 72: 71–88, 1994; Sippy et al., *J. Acquir. Defic. Syndr.*

*Hum. Retrovirol.,* 10: 511–21, 1995; and Giulian et al., *Neurochem, Int.,* 27: 119–37, 1995a) by production and secretion of a number of pro-inflammatory cytokines and neurotoxic and other cytotoxic factors, and by de novo expression of cell surface immunomolecules.

Microglia produce and secrete the cytokine interleukin 1 (IL-1), which promotes the proliferation of astroglia in vitro (Giulian et al., *J. Neurosci.,* 8: 709–14, 1988). Studies have shown that intracerebral infusion of IL-1 can stimulate astrogliosis and neovascularization that can only be detected after the appearance of microglia and macrophages at the site of injury (Giulian et al., *J. Neurosci.,* 8: 2485–90, 1988; and Giulian et al., *J. Neurosci.,* 8: 709–14, 1988). The greatest number of microglia and blood-borne macrophages appear 1–2 days after CNS trauma, which is the time period that has been associated with the peak production of IL-1 (Giulian et al., *J. Neurosci.,* 9: 4416–29, 1989). Collectively, this evidence suggests that MNPs are responsible for stimulating astrogliosis via IL-1. In addition, activated microglia secrete tumor necrosis factor alpha (TNF-$\alpha$), a cytokine that has been shown to play several prominent roles in a number of inflammatory diseases of the CNS (Gehrmann et al., *Brain Res. Rev.,* 20: 269–87, 1995). TNF-$\alpha$ and IL-1 induce astrocytes to produce and secrete several cytokines, including TNF-$\alpha$ and granulocyte-macrophage colony stimulating factor (GM-CSF). Reactive microglia, but not astrocytes, also synthesize and secrete interleukin-3 (IL-3). GM-CSF, IL-3 and interleukin-4 (IL-4) are potent mitogens for MNPs (Giulian et al., *J. Neurosci.,* 12: 4707–17, 1988; Giulian et al., *Dev. Neurosci.,* 16: 128–36, 1994; Gebicke-Haerter et al., *J. Neuroimmunol.* 50: 203–14, 1994; Lee et al., *Glia* 12: 309–18, 1994; and Suzumura et al., *J. Neuroimmunol.,* 53: 209–18, 1994). Physiologically, a positive feedback loop is established whereby proliferating MNPs produce more astroglial factors, which leads to glial scarring at the site of injury. The astroglial scar seals the wound at the site of injury, but may eventually prevent axonal regeneration of the surrounding neurons.

MNPs also secrete a number of neurotoxic agents that appear to exert their effects via the excitatory amino acid N-methyl-D-aspartate (NMDA) receptor. These neurotoxins include aspartate, glutamate, and quinolinic acid. The first two compounds are found in elevated concentration in models of traumatic brain injury (Faden et al., *Science* 244: 798–800, 1989; and Panter et al., *Ann. Neurol.,* 27: 96–99, 1990), and quinolinic acid is found in models of spinal cord contusion injury (Blight et al., *Brain Res.,* 632: 314–16, 1993; and Popovich et al., *Brain Res.,* 633: 348–52, 1994). Another neurotoxic NMDA receptor ligand has been reported that appears to be specific for neurons, but has no effect on astroglia or oligodendroglia (Giulian et al., *J. Neurosci.,* 13: 29–37, 1993; and Giulian et al., *J. Neurosci. Res.,* 36: 681–93, 1993). In addition, a neurotoxic amine (Ntox) has been shown to be produced from microglia and peripheral MNPs isolated from HIV-1 positive patients (Giulian et al., *J. Neurosci.,* 16: 3139–53, 1996).

Activated microglia and MNPs release several other harmful substances, including proteinases, reactive oxygen species, and nitric oxide (NO) (Hartung et al., *J. Neuroimmunol.,* 40: 197–210, 1992; and Banati et al., *Glia* 7: 111–8, 1993; and Ali et al., *Adv. Rheumatol.,* 81: 1–28, 1997). Proteinases may directly degrade myelin and have been implicated in the proteolysis of extracellular matrix proteins (Hartung et al., *J. Neuroimmunol.,* 40: 197–210, 1992; and Romanic et al., *Brain Pathol.,* 4: 145–46, 1994). Thus, the elevated release of MNP-derived proteases appears to contribute to the breakdown of the extracellular matrix and myelin, thereby widening the zone of secondary tissue damage. Also, reactive oxygen intermediates are released by microglia in response to interferon-gamma (IFN-$\gamma$) and TNF-$\alpha$. These oxygen radicals are responsible for lipid peroxidation, which leads to the breakdown of cell membranes, the specific targets being neurons, oligodendrocytes, and the myelin sheath itself. Human microglia may regulate the production of NO by astrocytes by providing IL-1, IFN-$\gamma$ and TNF-$\alpha$ (Chao et al., *J. Leukoc. Biol.* 1: 65–70, 1995).

MNPs produce, secrete, and respond to several cytokines, including IL-1, TNF-$\alpha$, IL-3, IL-4, GM-CSF, and IFN-$\gamma$. These cytokines can modulate most functions of MNPs, particularly the expression of cell surface markers on MNPs. In vitro studies have demonstrated that TNF-$\alpha$ is directly cytotoxic to oligodendrocytes and stimulates microglial phagocytosis of myelin (Zajicek et al., *Brain* 115: 1611–31, 1992; and Soliven and Szuchet, *Int. J. Dev. Neurosci.,* 13: 351–67, 1995). In addition, TNF-$\alpha$ has been implicated in the pathogenesis of experimental autoimmune encephalomyelitis (EAE) and several other demyelinating diseases (Selmaj et al., *J. Neuroimmunol.,* 56: 135–41, 1995; Renno et al., *J. Immunol.,* 154: 944–53, 1995; Redford et al., *Brain,* 118: 869–78, 1995; Probert et al., *Proc. Natl. Acad. Sci. USA,* 92: 11294–8, 1995; and Probert et al., *J. Leukoc. Biol.,* 59: 518–25, 1996).

GM-CSF, IL-3, and IL-4 are potent mitogens for MNPs (Giulian et al., *J. Neurosci.,* 12: 4707–17, 1988c; Giulian et al., *Dev. Neurosci.,* 16: 128–36, 1994; Gebicke-Haerter et al., *J. Neuroimmunol.* 50: 203–14, 1994; Lee et al., *Glia* 12: 309–18, 1994; and Suzumura et al., *J. Neuroimmunol.,* 53: 209–18, 1994) and are thought to induce a more rapid phagocytosis of myelin (Giulian et al., *J. Neurosci.,* 12: 4707–17, 1988c and Smith, M. E., *J. Neurosci. Res.,* 5: 480–487, 1993), which contributes to the pathogenesis of autoimmune inflammatory diseases (Giulian et al., *J. Neurosci.,* 12: 4707–17, 1988c; Giulian et al., *Dev. Neurosci.,* 16: 128–36, 1994; Gebicke-Haerter et al., *J. Neuroimmunol.* 50: 203–14, 1994; Lee et al., *Glia* 12: 309–18, 1994; Suzumura et al., *J. Neuroimmunol.,* 53: 209–18, 1994; and Smith, M. E., *J. Neurosci. Res.,* 5: 480–487, 1993). For example, MNP-specific up-regulation of TNF-$\alpha$ receptors has been demonstrated in AIDS patients (Dickson et al., *Glia* 7: 75–83, 1993; and Sippy et al., *J. Acquir. Defic. Syndr. Hum. Retrovirol.,* 10: 511–21, 1995) and up-regulation of GM-CSF receptors has been demonstrated in an animal model of facial nerve injury (Raivich et al., *J. Neurosci. Res.* 30: 682–6, 1991). In addition, newly activated microglia and infiltrating macrophages increase the expression of the low density lipoprotein (LDL)/macrophage scavenger receptor in CNS trauma or disease (Christie et al., *Am. J. Pathol.,* 148: 399–403, 1996; Elkhoury et al., *Nature* 382: 716–19, 1996; Giulian, D., *J. Neurosci. Res.,* 18: 155–171, 1987; Giulian et al., *J. Neurosci.,* 13: 29–37, 1993a; and Bell et al., *J. Neurocytol.,* 23 605–13, 1994), which is thought to account for increased phagocytotic activity in these conditions.

MNPs and leukocytes are also implicated in the pathophysiology (which involves secondary tissue damage) associated with several non-CNS inflammatory diseases, including various neoplastic, skin, eye, renal, pulmonary and inflammatory joint diseases. Cytokines and chemokines are instrumental in modulating these responses (Furie and Randolph, *Am. J. Pathol.,* 146: 1287–301, 1995; Baggiolini et al., *Adv. Immunol.,* 55: 97–179, 1994; Schall et al., *Current Biol.,* 6: 865–73, 1994; Howard et al., *Trends Biotechnol.,* 14: 46–51, 1996; Strieter et al., *J. Immunol.,* 156:3583–86, 1997; Taub et al., *Ther. Immunol.*, 1: 229–46, 1994; Driscoll et al., *Environ. Health Perspect.*, 105: Suppl 5: 64: 1159–64, 1997).

In solid tumor disease, MNPs have been shown to induce tumor angiogenesis (Leek et al., *J. Leukoc. Biol.*, 56: 423–35, 1994; Sunderkotter et al., *J. Leukoc. Biol.*, 55: 410–22, 1994) and have been found to be the major component of the lymphoreticular infiltrate of various forms of solid tumor, and close to 50% of the cell mass in breast carcinomas (Lewis et al., *J. Leukoc. Biol.* 57:747–51, 1995).

MNPs, including microglia, are also implicated in the pathogenesis of eye diseases including proliferative vitreo-retinal retinopathies (Weller et al., *Exp. Eye Res.*, 53: 275–81, 1991; Charteris et al., *Ophthalmology*, 100: 43–46, 1993) as are elevated levels of cytokines and chemokines, including IL-2, IL-6, IFN-(, IL-8, and MCP-1 (Abu el Asrar et al., *Am. J. Ophthalmol.*, 123: 599–606, 1997; Aksunger et al., *Ophthalmologica*, 211: 223–5, 1997; Kernova et al., *Eur. J. Ophthalmol.*, 7: 64–67, 1997). The observations described above demonstrate that a number of inflammatory disease states, including the pathology of spinal cord injury, are associated with the proliferation, migration, or physiological activity of cells types that promote secondary tissue damage.

Treatment of Secondary Tissue Damage and Other Inflammatory Pathologies

The present treatment of secondary tissue damage and other associated disease states and inflammatory disease states is not well developed. Animal models have demonstrated that colchicine treatment decreases the number of MNPs in damaged tissue and helps to block astrogliosis and neovascularization in addition to the inhibition of phagocytosis and secretory functions (Giulian et al., *J. Neurosci.*, 9: 4416–29, 1989; Giulian et al., *Ann. Neurol.*, 27: 33–42, 1990; and Giulian et al., *J. Neurosci.*, 13: 29–37, 1993). Colchicine, however, is not a selective toxin, and, consequently, it is not considered a viable therapeutic for the treatment of humans. Current pharmacological approaches to the treatment of SCI and prevention of secondary tissue damage center around single biochemical events that occur at the cellular level, for example, inhibiting the cytotoxic actions of excitatory amino acids or reactive oxygen species using NMDA antagonists and free radical scavengers (Faden et al., *Trends Pharmacol Sci* 13: 29–35, 1992; and McIntosh, T. K., *J. Neurotrauma*, 10: 215–61, 1993). Few drugs have demonstrated a profound effect on secondary tissue damage. The drugs currently used to address secondary damage in SCI are the steroid methylprednisolone and its synthetic 21 aminosteroid (lazaroid) derivatives (e.g., trisilazad), which act as oxygen free radical scavengers. These drugs are used to inhibit membrane lipid peroxidation. The unwanted side effects of lazaroids, however, are believed to include the induction of gliosis, which has been observed in one animal model of SCI (Gonzalez-Deniselle et al., *Cell Mol. Neurobiol.*, 16: 61–72, 1996), and loss of motor and sensory function as observed in humans with penetrating wounds to the spinal cord (Prendergast et al., *J. Trauma*, 37: 576–9, 1994). Steroids are also the therapeutic drug of choice for most inflammatory diseases, but their beneficial effects are largely hindered by debilitating side effects, so that long term steroid treatment is not a viable clinical option. Thus, none of the available treatments satisfactorily treat these diseases and disorders.

Hence, there is a need for a more encompassing approach to effectively treat inflammatory disease states associated with the proliferation, migration and/or physiological activity of cells that promote inflammatory responses, including secondary tissue damage, and to treat secondary tissue damage. Therefore, it is an object herein to provide such treatments.

SUMMARY OF THE INVENTION

Provided herein are methods for treating disease states associated with activation, proliferation and migration of immune effector cells, including secondary tissue damage-promoting cells. In particular, the methods provided herein are for treating these disease states by administration of an effective amount of a therapeutic agent that inhibits the activation, proliferation and/or migration of these targeted immune effector cells. Preferably the therapeutic agent is directly toxic to such cells. Targeted immune effector cells include, but are not limited to, mononuclear phagocytes (MNPs), such as dendritic, microglial, monocyte and macrophage cells; leukocytes, such as basophils, neutrophils, and eosinophils; and lymphocytes, such as natural killer cells and T and B lymphocytes.

Also provided are therapeutic agents that can be used in these methods. These agents are ligand-toxin conjugates containing a chemokine receptor targeting agent and a targeted agent. The chemokine receptor targeting agent targets cells that express chemokine receptors. Chemokine receptors constitute a family of receptors that are expressed on activated cells of the leukocyte lineage, and hence are associated with the inflammatory response. Such cells include immune effector cells involved in inflammatory responses, including cells that promote secondary tissue damage. It is these cells that are targeted herein. In addition to targeting the chemokine receptors, methods are provided in which other receptors on these cells are targeted.

In one embodiment, the chimeric ligand-toxin includes a cell toxin and a proteinaceous ligand moiety, or a biologically functional fragment thereof, such as a chemokine or a non-chemokine cytokine specific for one or more secondary tissue damage-promoting cells. Some conjugates that contain a non-chemokine cytokine, such as IL-4, conjugated to a toxin are known in the art. The conjugates that contain a chemokine receptor targeting agent are provided herein.

Conjugates that contain one or more chemokine-receptor targeting agents linked, either directly or via a linker, to one or more targeted agents are provided. In particular, conjugates provided herein contain the following components: (chemokine receptor targeting agent)$_n$, (L)$_q$, and (targeted agent)$_m$ in which at least one chemokine receptor targeting agent, such as a chemokine peptide or chemokine receptor-specific antibody, or an effective portion thereof, is linked directly or via one or more linkers (L) to at least one targeted agent. L refers to a linker. Any suitable association among the elements of the conjugate is contemplated as long as the resulting conjugates interacts with a targeted receptor such that internalization of an associated targeted agent is effected. In addition to a chemokine receptor targeting agent, these conjugates may also contain a non-chemokine cytokine. Such non-chemokine cytokines are generally selected from among those that bind to immune effector cells, particularly the leukocyte populations, to which a chemokine kind binds.

The variables n and m are integers of 1 or greater and q is 0 or any integer. The variables n, q and m are selected such that the resulting conjugate interacts with the targeted receptor and a targeted agent is internalized by a cell to which it has been targeted. Typically n is between 1 and 3; q is 0 or more, depending upon the number of linked targeting and targeted agents and/or functions of the linker, q is generally 1 to 4; m is 1 or more, generally 1 or 2. When more than one targeted agent is present in a conjugate the targeted agents may be the same or different. Similarly, when more than one chemokine receptor targeting agent is present in the conjugates they may be the same or different.

The conjugates provided herein may be produced as fusion proteins, may be chemically coupled or include a fusion protein portion and a chemically linked portion or any combination thereof. For purposes herein, the chemokine receptor targeting agent is any agent, typically a polypeptide, that specifically interacts with a chemokine receptor, such as those on leukocytes, and that, upon interacting with the receptor, internalizes a linked or otherwise associated targeted agent, such as a cytotoxic agent or other therapeutic product intended to be internalized by the targeted cell. The presently preferred chemokine receptor targeting agents, include, but are not limited to, those set forth in Table 1 below.

The conjugates provided herein exploit the limited distribution of chemokine receptors and their localization on cells associated with inflammatory responses, particularly those associated with secondary tissue damage, and pathological responses associated with certain disease states. The advantages of the conjugates provided herein include selection of the chemokines and other such agents as the targeting agents, which bind to relatively small cell populations that are associated with inflammatory disorders or inflammatory processes. By virtue of the distribution and specificity of such receptors on such cell populations, the conjugates can be used to provide targeted delivery to selected cells and tissues of any linked agent, including toxic agents to effect death of the cells, inhibit proliferation, or to enhance or aid in survival of targeted cells.

It is understood that the above description does not represent the order in which each component is linked or the manner in which each component is linked. The chemokine receptor targeting agent and targeted agent (or linker and targeted agent) may be linked in any order and through any appropriate linkage, as long as the resulting conjugate binds to a receptor to which a chemokine binds and internalizes the targeted agent(s) in cells bearing the receptor. The chemokine receptor targeting agent is typically a polypeptide and may be linked to the targeted agent or linker at or near its N-terminus or at or near its C-terminus or at any internal locus. Presently, conjugates in which the targeted agent is linked, either directly or via a linker, at or near, within about twenty, preferably ten, amino acids of the amino-terminus of the chemokine are preferred. A chemokine receptor targeting agent may be linked to more than one targeted agent; alternatively, more than one targeted agents may be linked to more than one chemokine receptor targeting agent. When multiple targeting agents and/or targeted agents are linked, they may be the same or different. Preferably, when a chemokine is a targeting agent, the targeted agent is linked to the C-terminus of the chemokine.

Conjugates containing a plurality of targeting agents and/or targeted agents are provided. Conjugates that contain a plurality, generally at least two, chemokines targeting agents linked to one or more targeted agents, thus, are also provided. These conjugates that contain several chemokine receptor targeting agents and targeted agents can be produced by linking multiple copies of nucleic acid encoding the chemokine receptor-targeting agent as a fusion protein, preferably head-to-head and/or tail-to-tail, under the transcriptional control of a single promoter region. For example (see, e.g., FIG. 1), fusion proteins in which a toxin is linked at its amino-terminus to the carboxy-terminus of a chemokine moiety, represented by formula: chemokine receptor targeting agent-linker-toxin are provided. Also provided, for example, are fusion proteins in which a toxin is linked at its amino-terminus and at its carboxy-terminus to the carboxy-terminus of a chemokine receptor targeting agent. The two chemokine receptor targeting agents may be the same or different. These fusion proteins are represented by formula: chemokine receptor targeting agent-linker-toxin-chemokine receptor targeting agent. Conjugates containing one or two chemokine receptor-binding proteins are presently preferred. Where a second chemokine receptor-binding protein is employed it is attached via its carboxy-terminus to the vacant terminus of the toxin. Other combination of elements in which one or a plurality of chemokine receptor targeting agents is linked to one or a plurality of targeted agents are provided. As noted above, the conjugates may further include a non-chemokine cytokine.

The conjugates can be produced by chemical conjugation or by expression of fusion proteins in which, for example, DNA encoding a targeted agent, such as a ribosome inactivating protein (RIP), with or without a linker region to DNA encoding a chemokine receptor targeting agent linked. The conjugates may also be produced by chemical coupling, typically through disulfide bonds between cysteine residues present in or added to the components, or through amide bonds or other suitable bonds. Ionic or other linkages are also contemplated. Conjugates of the form targeted agent-$(L)_q$-chemokine receptor-binding moiety-$(L)_q$-chemokine receptor-binding moiety are of particular interest.

The chemokine receptor targeting agent is any agent that specifically binds to a receptor to which chemokines specifically bind. These agents include, but are not limited to, chemokines, antibodies and fragments of chemokines and antibodies that retain the ability to interact with the receptor and effect internalization of an associated or linked targeted agent. These agents do not include non-chemokine cytokines, such as IL-4, CSFs and other cytokines that do not typically specifically bind to chemokine receptors.

When antibodies are the targeting agents, the antibodies are selected from among those specific for chemokine receptors, and preferably from among those that antagonize binding of a chemokine to a chemokine receptor, thereby not only serving to internalize linked agents, but also to competitively inhibit binding of a chemokine.

The targeted agent is any agent for which targeted delivery to a selected population of cells or to a tissue is desired. These agent include, but are not limited to, a cytotoxic agent, particularly, ribosome inactivating proteins (RIPs), DNA and RNA nucleases, including certain RIPs and bacteriocins, such as the E. coli colicins, and other toxins, or a nucleic acid, or a drug, such as methotrexate, intended for internalization by a cell that expresses a receptor to which a chemokine receptor targeting agent binds, and internalizes a linked or associated targeted agent, any molecule that, when internalized, alters metabolism or gene expression in the cell, regulates or alters protein synthesis, inhibits proliferation or kills the cell. Other such agents include, but are not limited to, light activated porphyrins, and antisense nucleic acids, that result in inhibition of growth or cell death; and antisense RNA, DNA, and truncated proteins that alter gene expression via interactions with the DNA, or co-suppression or other mechanism. In certain embodiments, the cytotoxic agent is a ribosome-inactivating protein (RIP), such as, for example, saporin, ricin, shiga toxin, although other cytotoxic agents can also be advantageously used. Hence the targeted agent is any agent intended for internalization by a selected cell that expresses a receptor with which a chemokine receptor targeting agent interacts, typically binds, and upon such interaction effects internalization of the linked or associated targeted agent.

The targeted agents may also be modified to render them more suitable for conjugation with the linker and/or a chemokine receptor-targeting agent or to increase their intracellular activity. Such modifications include, but are not limited to, the introduction of a Cys residue at or near the N-terminus or C-terminus, derivatization to introduce reactive groups, such as thiol groups, and addition of sorting signals, such as (XaaAspGluLeu)$_n$ (SEQ ID NO. 68 where Xaa is Lys or Arg, preferably Lys, and n is 1 to 6, preferably 1–3, at, preferably, the carboxy-terminus (see, e.g., Seetharam et al. (1991) *J. Biol. Chem.* 266:17376–17381; and Buchner et al. (1992) *Anal. Biochem.* 205:263–270), that direct the targeted agent to the endoplasmic reticulum.

The linker is a peptide or a non-peptide and can be selected to relieve or decrease stearic hindrance caused by proximity of the targeted agent to the chemokine receptor targeting agent and/or increase or alter other properties of the conjugate, such as the specificity, toxicity, solubility, serum stability and/or intracellular availability of the targeted moiety and/or to increase the flexibility of the linkage between the chemokine receptor-binding moiety polypeptide and the targeted agent or to reduce stearic hindrance.

When fusion proteins are contemplated, the linker is selected such that the resulting nucleic encodes a fusion protein that binds to and is internalized by cells that express a chemokine receptor and all or a portion of the internalized protein preferably traffics to the cytoplasm. It is also contemplated that several linkers can be joined in order to employ the advantageous properties of each linker. In such instance, the linker portion of conjugate may contain more than 50 amino acid residues. The number of residues is not important as long as the resulting fusion protein binds to a chemokine receptor and internalizes the linked targeted agent via a pathway that traffics the targeted agent to the cytoplasm and/or nucleus.

More preferred linkers are those that can be incorporated in fusion proteins and expressed in a host cell, such as *E. coli*. Such linkers include: enzyme substrates, such as cathepsin B substrate, cathepsin D substrate, trypsin substrate, thrombin substrate, subtilisin substrate, Factor Xa substrate, and enterokinase substrate; linkers that increase solubility, flexibility, and/or intracellular cleavability include linkers, such as (gly$_m$ser)$_n$ and (ser$_m$gly)$_n$, in which m is 1 to 6, preferably 1 to 4, more preferably 2 to 4, and n is 1 to 6, preferably 1 to 4, more preferably 2 to 4 (see, e.g., International PCT application No. WO 96/06641, which provides exemplary linkers for use in conjugates). In some embodiments, several linkers may be included in order to take advantage of desired properties of each linker.

Conjugates in which the chemokine receptor targeting agents, such as chemokines, have been modified, such as by elimination of one or more cysteine residues, are also provided. In general, the conserved cysteines near the N-termini of chemokines are important for activity; other cysteines, may be replaced. Care must be taken to avoid altering specificity of the resulting modified chemokine, unless such alteration is desired. In all instances, particular modifications can be determined empirically.

Compositions containing such conjugates should exhibit reduced aggregation. Conjugates in which the chemokine receptor-targeting moiety and/or the targeted agent has been modified by addition of a cysteine (Cys)3, at or near one terminus, that is linked to a linker or targeted agent by chemical methods, are also provided.

Methods for the preparation of the conjugates are provided. These methods include chemical conjugation methods and methods that rely on recombinant production of the conjugates. The chemical methods rely on derivatization of the targeted agent with the desired linking agent, and then reaction with a chemokine receptor targeting agent. The chemical methods of derivatization are particularly useful for linking a chemokine receptor targeting moiety protein to DNA or RNA and for producing conjugates of the form targeted agent-(L)$_q$-chemokine receptor targeting agent. In practicing the chemical method, a chemokine receptor targeting agent that is produced by any means, typically by expression of DNA in a bacterial or eukaryotic host, is chemically coupled with the targeted agent. If the targeting agent or targeted agent does not contain suitable moieties for effecting chemical linkage it can be derivatized. For example, the agent, such as shiga toxin, gelonin or other such agent, can be derivatized such as by reaction with a linking agent, such as N-succinimidyl-3-(2-pyridyidithio) propionate (SPDP). In other embodiments, the targeted agent, such as shiga A chain, is modified at or near the N-terminus to include a cysteine residue, so that the resulting modified agent can react with the chemokine receptor-binding moiety protein without further derivatization.

The recombinant method of production of conjugates relies on expression of nucleic acid that encodes a chemokine receptor targeting agent peptide linked to nucleic encoding a linker, or, in instances in which the targeted agent is a protein or polypeptide, nucleic acid encoding chemokine receptor targeting agent linked either directly or via nucleic acid encoding a linker to nucleic acid encoding a targeted agent. Upon introduction into a suitable host and expression of the nucleic acid, the chemokine receptor targeting agent polypeptide, chemokine receptor-targeting agent with linker or chemokine receptor targeting agent linked via a linker or directly to a targeted polypeptide or polypeptide agent is expressed. The combination of the chemokine receptor targeting protein, linker and linked agent, or any subset or variation thereof, is prepared as a chimera, using recombinant DNA techniques. The fusion protein molecule is designed and produced in such a way that the chemokine receptor targeting agent portion is available for recognition of its respective cell-surface receptor and can target the conjugate to cells bearing such cell-surface receptor and effect internalization of any linked or associated targeted agent. When recombinant expression is employed, particularly when bacterial hosts are used, the preferred form of the conjugates is chemokine targeting agent-(L)$_q$-targeted-agent (i.e., ligand-optional linker-toxin), in which the targeted agent is linked to the C-terminus of a chemokine receptor targeting agent, with or without one or more linker moieties, and with or without one or more additional chemokine receptor targeting agents linked to the chemokine receptor targeting agent and/or to the targeted agent. In an exemplary embodiment, a conjugate with a plurality of chemokine targeting agents and/or targeted agents, is of the form N-ligand-C-(optional linker)-N-targeted agent-C-(optional linker)-C-ligand-N, where N and C refer to the amino-termini and carboxy-termini of a polypeptide, respectively, and the ligand refers to the chemokine targeting agent.

The resulting conjugates provided herein can be used in pharmaceutical compositions and in methods of treatment. Preferred disorders to be treated are pathophysiological inflammatory conditions. In such conditions the conjugates, by virtue of the linked chemokine receptor targeting agent, are targeted to cells that bear selected chemokine receptors. If a cytotoxic moiety is targeted, internalization of the conjugate results inhibition of proliferation or death of the cells. Such pathophysiological conditions include, for example, leukocytes associated with secondary tissue damage, leukocytes associated with solid tumors, and leukocytes and cells associated with other undesirable inflammatory responses. In particular, secondary tissue damage and associated disease states can be treated by administering to subjects in need thereof an effective amount of the conjugates provided herein that inhibit the proliferation, migration, or physiological activity of secondary tissue damage-promoting cells, such as mononuclear phagocytes (MNP), leukocytes, natural killer cells, dendritic cells, and T and B lymphocytes. Conjugates provided herein can be designed to be directly toxic to such cells and specific for a targeted G-protein coupled, seven transmembrane-domain, rhodopsin-like receptor, particularly a selected chemokine receptor, on the surface of such cells. The conjugates bind to these receptors and are taken up by the target cells. Once inside the cells, the therapeutic agent can disrupt normal cellular activities and thereby suppress the biologic activities of such cells, or cause cell death. Methods of treatment using such conjugates are provided.

The treatment is effected by administering a therapeutically effective amount a conjugate, for example, in a physiologically acceptable excipient. The conjugates may also be used in methods of genetic therapy to deliver nucleic acid encoding correct copies of defective genes or therapeutic agents, such as TNF, to cells that bear chemokine receptors.

A typical conjugate is a fusion protein containing a receptor-binding ligand moiety connected to a cellular toxin via a peptide linker. The ligand can be attached to either the carboxy or the amino terminus of the toxin. On binding to the appropriate cell surface receptor, the fusion protein is internalized and the toxin moiety is enzymatically released to kill the host cell. The fusion protein must reach the intracellular domain to exhibit cytotoxicity, and the free toxin has no inherent functional capacity to traverse the cell membrane.

The disease states suitable for treatment using the methods and conjugates provided herein include, but are not limited to, CNS injury, CNS inflammatory diseases, neurodegenerative disorders, inflammatory eye diseases, inflammatory bowel diseases, inflammatory joint diseases, inflammatory kidney or renal diseases, inflammatory lung diseases, inflammatory nasal diseases, inflammatory thyroid diseases, cytokine-regulated cancers. Treatment of spinal cord injury and trauma are of particular interest.

Accordingly, in one aspect of methods provided herein, the therapeutic agents used are chimeric ligand-toxins that include a proteinaceous ligand moiety, such as a chemokine, interleukin, lymphokine, monokine, colony-stimulating factor, or receptor associated protein that specifically recognized the contemplated receptors, linked to a cell toxin, such as a DNA cleaving agent, an antimetabolite, or a proteinaceous cell toxin, for example a bacterial, plant, insect, snake, or spider toxin. The chimeric ligand-toxins are formulated for selected delivery routes including, but are not limited to, topically, intraarticularly, intracisternally, intraocularly, intraventricularly, intrathecally, intravenously, intramuscularly, intratracheally, intraperitoneally and intradermally.

Hence provided herein are chemokine receptor targeting agent-toxin conjugates, referred to herein as chemokine-toxin conjugates, where the ligand moiety is preferably a chemokine, or a biologically active fragment thereof, that is linked to a targeted agent that this preferably a cell toxin. For example, the conjugate can be a fusion protein having a chemokine ligand linked to a proteinaceous cell toxin by a polypeptide linker of a size selected such that the conjugate interacts with the selected receptor and effects internalization of the linked targeted agents. Such linker when peptides are typically about 2 to about 60 amino acid residues.

Conjugates of non-chemokine cytokines may also be used in the methods herein. These non-chemokine cytokines are selected from among those that bind to receptors present on cells, such as leukocytes, involved in the undesirable inflammatory responses, such as secondary tissue damage, for which treatment is contemplated herein.

In addition, the conjugates that contain the chemokine receptor targeting agents may be administered in combination with other therapies for the inflammatory response and/or the underlying disorder. For example, a conjugate provided herein, which targets leukocytes that infiltrate tumors may be administered in combination with a conjugate, such as an IL-4-toxin conjugate, that treats the tumors. Combination therapy may be effected simultaneously, sequentially or intermittently.

The methods and compositions provide herein possess numerous advantages, among these is the advantage that the cell toxin is targeted specifically to the cells responsible for the inflammatory disease states, such as secondary tissue damage, thereby minimizing damage and toxicity to non-involved cells. Since the compositions can be delivered locally and specifically, a higher and more efficacious concentration of the cell toxin can be attained in the region to be treated than with systemic administration of a cell toxin.

As noted above, the conjugates provided herein, may also be used to deliver other agents to cells that express chemokine receptors or receptors to which chemokines selectively bind and effect or facilitate internalization of associated agents.

BRIEF DESCRIPTION OF THE FIGURES

FIG. 1 is a schematic drawing showing a fusion protein provided herein in which the "Ligand" is a proteinaceous ligand selected from one of the amino acid sequences of the type listed in Table 3, the "Linker" is a proteinaceous linker moiety having the amino acid sequence Ala-Met, or is selected from a polypeptides such as those disclosed herein as SEQ. ID NOS: 1–12, (see also International PCT application No. WO 96/06641, which provides exemplary linkers for use in conjugates), and the "Toxin" is a proteinaceous cell toxin, such as a cell toxins whose amino acid sequence is listed in Table 4.

DETAILED DESCRIPTION OF THE INVENTION

Figure 2:
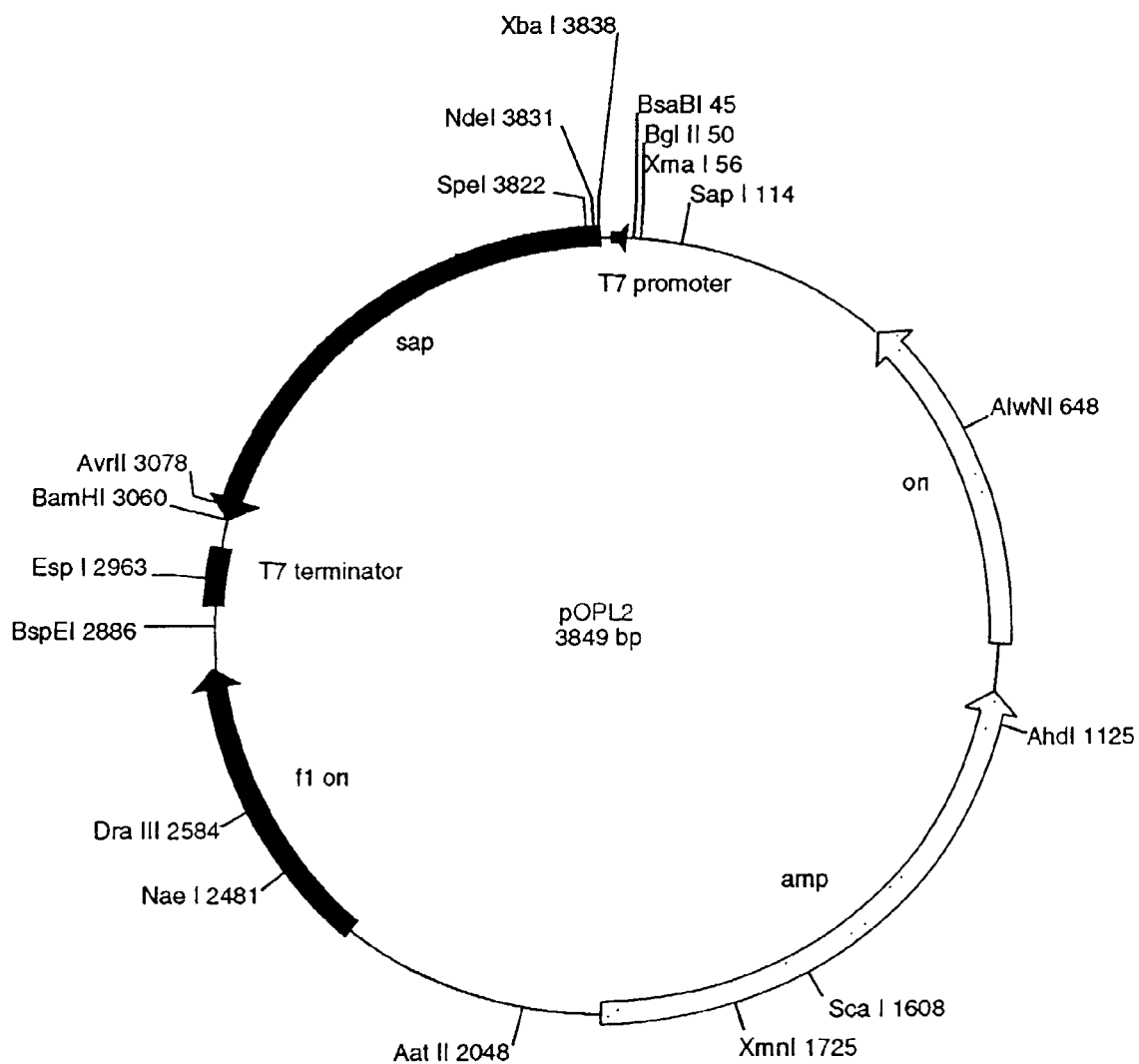
FIG. 2 is a schematic map of an exemplary plasmid designated pGEMEX-SAP encoding a saporin cloned into a pGEMEX vector fusion protein as described in the EXAMPLES.

CONTENTS
A. DEFINITIONS
B. THE INFLAMMATORY RESPONSE
C. COMPONENTS OF THE CONJUGATES
 1. Summary
 2. Chemokine receptor targeting moieties
  a. Chemokines
  b. Selection of a chemokine
  c. Non-chemokine cytokines
  d. Antibody Ligand Moieties
 3. Targeted agents
  a. Cell Toxin Moieties
   (1) DNA cleaving agents
   (2) Antimetabolites
   (3) Proteinaceous cell toxins
   (4) Bacterial toxins
   (5) Porphyrins and other light activated toxins
  b. Nucleic acids for targeted delivery
   (1) Antisense nucleotides, including: antisense oligonucleotides; triplex molecules; dumbbell oligonucleotides; DNA; extracellular protein binding oligonucleotides; and small nucleotide molecules
   (2) Ribozymes
   (3) Nucleic acids encoding therapeutic products for targeted delivery
   (4) Coupling of nucleic acids to proteins
   (5) Summary
 4. Linker Moieties
  a. Heterobifunctional cross-linking reagents
  b. Acid cleavable, photocleavable and heat sensitive linkers
  c. Other linkers
  d. Peptide linkers
  e. Summary of linkers
D. PREPARATION OF CONJUGATES
 1. Production of Fusion Proteins
  a. Plasmids and host cells for expression of constructs encoding chemokine receptor targeting agent peptides, conjugates, linkers, fusion proteins and peptide targeted agents
  b. Cloning and expression of a chimeric ligand-toxin fusion protein
  c. Construction and expression of exemplary chemokine receptor targeting agent-toxin fusion genes
 2. Production of chemical conjugates
E. ANIMAL MODELS FOR TESTING OF CONJUGATES
F. FORMULATION AND ADMINISTRATION OF COMPOSITIONS CONTAINING THE CONJUGATES
G. DISEASE STATES ASSOCIATED WITH THE INFLAMMATORY RESPONSE AND SECONDARY TISSUE DAMAGE A. Definitions Unless defined otherwise, all technical and scientific terms used herein have the same meaning as is commonly understood by one of skill in the art to which the subject matter described herein belongs. All patents, pending patent applications, published applications and other publications and sequence data from GenBank and other data bases referred to herein are incorporated by reference, where permitted, in their entirety.

As used herein, a conjugate refers to the compounds provided herein that include one or more chemokine receptor targeting agent (also referred to herein as a chemokine receptor binding agent) and a targeted agent. These conjugates are also referred herein as chemokine-toxins, and includes those produced by recombinant means as fusion proteins, those produced by chemical means and those produced by any other method whereby at least one chemokine-receptor binding moiety is linked, directly or indirectly to a targeted agent, whereby upon binding to a chemokine receptor the targeted agent is internalized into the targeted cell. Hence, a conjugate refers to a molecule that contains at least one chemokine receptor targeting moiety and at least one targeted agent that are linked directly or via a linker and that are produced by chemical coupling methods or by recombinant expression of chimeric nucleic acid molecules to produce fusion proteins.

As used herein, a chemokine receptor targeting agent refers to any molecule or ligand that specifically binds to a chemokine receptor on a cell and effects internalization of a linked or otherwise associated targeted agent. Chemokine receptor binding moieties, include, but are not limited to, any polypeptide that is capable of binding to a cell-surface protein to which a chemokine would be targeted, and is capable of facilitating the internalization of a ligand-containing fusion protein into the cell. Such ligands include growth factors, antibodies or fragments thereof, hormones, chemokines, antibodies that specifically bind to chemokine receptors and effect internalization of any linked targeted agent, and fragments of chemokines or antibodies that achieve this. Identification of fragments or portions of antibodies that are effective in binding to receptors and internalizing linked targeted agents can be done empirically, by testing, for example, a fragment linked to a cytotoxic agent, and looking for cell death using any of the assays therefor described herein or known to those of skill in the art. Hence, a chemokine receptor targeting agent includes all of the peptides characterized and designated as chemokines, including, but not limited to, classes described herein, and truncated versions and portions thereof that are sufficient to direct a linked targeted agent to a cell surface receptor or protein to which the full-length peptide specifically binds and to facilitate or enable internalization by the cell on which the receptor or protein is present.

As used herein, reference to chemokines is intended to encompass the chemoattractant (chemotactic) cytokines that bind to chemokine receptors and includes proteins isolated from natural sources as well as those made synthetically, as by recombinant means or by chemical synthesis. Exemplary chemokines include, but are not limited to, IL-8, GCP-2, GRO-α, GRO-β, GRP-γ, ENA-78, PBP, CTAP III, NAP-2, LAPF-4, MIG, PF4, IP-10, SDF-1α, SDF-1β, SDF-2, MCP-1, MCP-2, MCP-3, MCP-4, MCP-5, MIP-1α, MIP-1β, MIP-1γ, MIP-2, MIP-2α, MIP-3α, MIP-3β, MIP-4, MIP-5, MDC, HCC-1, ALP, lungkine, Tim-1, eotaxin-1, eotaxin-2, I-309, SCYA17, TARC, RANTES, DC-CK-1, lymphotactin, ALP, and fractalkine, and others known to those of skill in the art.

Chemokine also encompasses muteins of chemokine that possess the ability to target a linked targeted agent to chemokine-receptor bearing cells. Muteins of chemokine receptor targeting agents are also contemplated for use in the conjugates. Such muteins will have conservative amino acid changes, such as those set forth below in the following Table. Nucleic acid encoding such muteins will, unless modified by replacement of degenerate codons, hybridize under conditions of at least low stringency to DNA, generally high stringency, to DNA encoding a wild-type protein.

Muteins and modifications of the proteins also include, but are not limited to, minor allelic or species variations and insertions or deletions of residues, particularly cysteine residues. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson et al. *Molecular Biology of the Gene,* 4th Edition, 1987, The Benjamin/Cummings Pub. co., p. 224). Such substitutions are preferably made in accordance with those set forth as follows:

| Original residue | Conservative substitution |
| --- | --- |
| Ala (A) | Gly; Ser |
| Arg (R) | Lys |
| Asn (N) | Gln; His |
| Cys (C) | Ser; neutral amino acid |
| Gln (Q) | Asn |
| Glu (E) | Asp |
| Gly (G) | Ala; Pro |
| His (H) | Asn; Gln |
| Ile (I) | Leu; Val |
| Leu (L) | ILe; Val |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

Other substitutions are also permissible and may be determined empirically or in accord with known conservative substitutions. Any such modification of the polypeptide may be effected by any means known to those of skill in this art.

Also contemplated are muteins produced by replacing one or more of the cysteines with serine as herein or those that have any other amino acids deleted or replaced, with the proviso that the resulting protein has the ability, either as a monomer or as a dimer, to bind to chemokine-receptor bearing cells and to be internalized upon such binding or to internalize a linked targeted agent. Typically, such muteins will have conservative amino acid changes, such as those set forth in the Table above Nucleic acid encoding such muteins will, unless modified by replacement of degenerate codons, hybridize under conditions of at least low stringency, generally high stringency to DNA encoding a chemokine, such as those set forth in SEQ ID NOs. 25–28 or an exon thereof (SEQ ID NOs. 16–24).

Various in vitro assays for identification of chemokines and chemokine activity, particularly chemotactic activities, are known to those of skill in the art (see, e.g., Walz et al. (1987) *Biochem. Biophys. Res. Commun.* 149:755 to identify chemotaxis of neutrophils; Larsen et al. (1989) *Science* 243:1464 and Carr et al. (1994) *Proc. Natl. Acad. Sci. U.S.A.* 91:3652 to assay chemotaxis of lymphocytes; see, also International PCT application No. WO 99/33990, which describes numerous assays and exemplifies means to identify chemokines). Such assays can be used to identify chemokines, modified chemokines and active fragments thereof. Binding assays, as described herein and known to those of skill in the art may be used to identify moieties that will specifically recognize chemokine receptors, and cytotoxic assays can be used to identify those that also internalize linked or associated targeted agents.

It is emphasized, that the chemokine targeting agents do not include agents, such as non-chemokine cytokines, such as the CSFs, TNFs, IL-2, IL-3, IL-4 and others, which do not have the properties of chemokines.

As used herein a portion of a chemokine refers to a fragment or piece of chemokine that is sufficient, either alone or as a dimer with another fragment or a chemokine monomer, to bind to a receptor to which chemokine dimers bind and internalize a linked targeted agent.

As used herein, an amino acid residue of chemokine is non-essential if a chemokine dimer in which one or both chemokine monomers have been modified by deletion of the residue possesses substantially the same ability to bind to a chemokine receptor and internalize a linked agent that the dimer has with the amino acid(s).

As used herein, nucleic acid encoding a chemokine peptide or polypeptide refers to any of the nucleic acid fragments set forth herein as coding such peptides, to any such nucleic acid fragments known to those of skill in the art, any nucleic acid fragment that encodes a chemokine that binds to a chemokine receptor and is internalized thereby and may be isolated from a human cell library using any of the preceding nucleic acid fragments as a probe or any nucleic acid fragment that encodes any of the known chemokine peptides, including those set forth in SEQ ID NOs. 25–28, and any DNA fragment that may be produced from any of the preceding nucleic acid fragments by substitution of degenerate codons. It is understood that once the complete amino acid sequence of a peptide, such as a chemokine peptide, and one nucleic fragment encoding such peptide are available to those of skill in this art, it is routine to substitute degenerate codons and produce any of the possible nucleic fragments that encode such peptide. It is also generally possible to synthesize nucleic encoding such peptide based on the amino acid sequence.

As used herein, chemokine-mediated pathophysiological condition refers to a deleterious condition characterized by or caused by proliferation of cells that are sensitive to chemokine mitogenic stimulation, proliferative stimulation and/or attractant activity.

As used herein, chemokine receptors refer to receptors that specifically interact with a naturally-occurring member of the chemokine family of proteins and transport it into a cell bearing such receptors. These include, but are not limited to, the five receptors (CXCR1–5) to which CXC chemokines bind and the nine receptors (CCR1–9) to which CC chemokines bind, and any other receptors to which any chemokine will specifically bind and facilitate internalization of a linked targeted agent.

As used herein, a targeted agent is any agent that is intended for internalization by linkage to a targeting moiety, as defined herein, and that upon internalization in some manner alter or affect cellular metabolism, growth, activity, viability or other property or characteristic of the cell. The targeted agents are preferably therapeutic agents, including cytotoxic agents, and include, but are not limited to, proteins, polypeptides, organic molecules, drugs, nucleic acids and other such molecules. Labels, such as fluorescent moities linked to a chemokine or portion thereof, are not contemplated to be within the definition of a targeted agent contemplated herein.

As used herein, to target a targeted agent means to direct it to a cell that expresses a selected receptor by linking the agent to a chemokine receptor targeting agent. Upon binding to the receptor the targeted agent or targeted agent linked to the chemokine-receptor binding moiety is internalized by the cell.

As used herein, a targeted agent is any agent that is intended for internalization by linkage to a targeting moiety, as defined herein, and that upon internalization in some manner alter or affect cellular metabolism, growth, activity, viability or other property or characteristic of the cell. The targeted agents include proteins, polypeptides, organic molecules, drugs, nucleic acids and other such molecules.

As used herein, although chemokines are recognized to be a family of cytokines, with the above-described structural properties and biological properties, for purposes herein, reference to "cytokines" as ligands refers to cytokines that are not chemokines. Chemokine receptor targeting agent refers to chemokines, to cytokines that selectively bind to chemokine receptors, to antibodies specific for such receptors, and to any other moiety that would mimic the receptor selectivity and ability to facilitate internalization of a linked targeted agent of any chemokine.

As used herein, the term cytotoxic agent refers to a targeted agent that is capable of inhibiting cell function. The agent may inhibit proliferation or may be toxic to cells. Any agents that when internalized by a cell interfere with or detrimentally alter cellular metabolism or in any manner inhibit cell growth or proliferation are included within the ambit of this term, including, but are not limited to, agents whose toxic effects are mediated when transported into the cell and also those whose toxic effects are mediated at the cell surface. A variety of cytotoxic agents can be used and include those that inhibit protein synthesis and those that inhibit expression of certain genes essential for cellular growth or survival. Cytotoxic agents include those that result in cell death and those that inhibit cell growth, proliferation and/or differentiation. Cytotoxic agents, include, but are not limited to, those set forth in the Tables and sequence listing herein, gelonin, saporin, the ricins, abrin and other ribosome-inactivating-proteins (RIPs), aquatic-derived cytotoxins, *Pseudomonas exotoxin*, inhibitors of DNA, RNA or protein synthesis, such as antisense nucleic acids, and other metabolic inhibitors, such as DNA cleaving molecules, and light activated porphyrins, that are known to those of skill in this art. Shiga toxin, particularly the modified shiga catalytic subunit as provided herein, is a preferred toxin herein, but other suitable RIPs include, but are not limited to, shiga-A1, ricin, ricin A chain, saporin, *E. coli*-produced colicins, shiga-like toxins, maize RIP, gelonin, diphtheria toxin, diphtheria toxin A chain, trichosanthin, tritin, pokeweed antiviral protein (PAP), mirabilis antiviral protein (MAP), Dianthins 32 and 30, abrin, monordin, bryodin, a catalytic inhibitor of protein biosynthesis isolated from cucumber seeds (see, e.g., WO 93/24620), cytotoxically active fragments of these cytotoxins and toxins, and others known to those of skill in this art. The term RIP is used herein to broadly include such cytotoxins, as well as other cytotoxic molecules that inhibit cellular metabolic process, including transcription, translation, biosynthetic or degradative pathways, DNA synthesis and other such process, or that kill cells or inhibit cell proliferation.

As used herein, a linker is a peptide or other molecule that links a chemokine polypeptide to the targeted agent. The linker may be bound via the N- or C-terminus or an internal reside near, typically within about 20 amino acids, of either terminus of a chemokine and/or targeted agent, if the agent is a polypeptide or peptide. The linkers used herein can serve merely to link the components of the conjugate, to increase intracellular availability, serum stability, specificity and solubility of the conjugate or provide increased flexibility or relieve stearic hindrance in the conjugate. For example, specificity or intracellular availability of the targeted agent of may be conferred by including a linker that is a substrate for certain proteases, such as a protease that is present at higher levels in tumor cells than normal cells.

As used herein, a mitotoxin is a cytotoxic molecule targeted to specific cells by a mitogen, such as chemokine.

As used herein, a fusion protein refers to a polypeptide that contains at least two components, such as a chemokine monomer and a targeted agent or a chemokine monomer and linker, and is produced by expression of DNA in a host cells.

As used herein, a modification that is effected substantially near the N-terminus or C-terminus of a cytotoxic agent, such as shiga-A subunit, or chemokine monomer, is generally effected within twenty, or preferably ten residues from the terminus. Such modifications, include the addition or deletion of residues, such as the addition of a cysteine to facilitate conjugation between the polypeptide reactive with a chemokine receptor or fragment of the polypeptide and the targeted agent portion to form conjugates that contain a defined molar ratio, preferably a ratio of 1:1, of targeted agent and polypeptide reactive with a chemokine receptor or fragment of the polypeptide.

As used herein, nucleic acids refer to RNA or DNA that are intended as targeted agents, which include, but are not limited to, DNA encoding therapeutic proteins, fragments of DNA for co-suppression, DNA encoding cytotoxic proteins, antisense nucleic acids and other such molecules.

Reference to nucleic acids includes duplex DNA, single-stranded DNA, RNA in any form, including triplex, duplex or single-stranded RNA, anti-sense RNA, polynucleotides, oligonucleotides, single nucleotides and derivatives thereof.

As used herein, a therapeutic nucleic acid refers to a nucleic acid that is used to effect genetic therapy by serving as a replacement for a defective gene or by encoding a therapeutic product, such as a hormone, cytokine, including non-chemokine cytokines and or a growth factor. The therapeutic nucleic acid may encode all or a portion of a gene, and may function by recombining with DNA already present in a cell, thereby replacing a defective portion of a gene. It may also encode a portion of a protein and exert its effect by virtue of co-suppression of a gene product.

As used herein, antisense describes any of several methods and the nucleic acids used in the methods, that employ sequence-specific nucleic acids to modify gene transcription or translation. This term also includes nucleic acids and methods that provide nucleic acids that bind to sites on proteins and to receptors. Antisense includes, but is not limited to, the following types of nucleic acids: antisense mRNA, DNA intended to form triplex molecules, extracellular protein binding oligonucleotides, and small nucleotide molecules, which are described below. As used herein, antisense encompasses the following molecules:

(a) Antisense mRNA and DNA

Antisense nucleic acids are single-stranded nucleic acid constructs that specifically bind to mRNA that has complementary sequences, thereby preventing translation of the mRNA (see, e.g., U.S. Pat. No. 5,168,053 to Altman et al. U.S. Pat. No. 5,190,931 to Inouye, U.S. Pat. No. 5,135,917 to Burch, and U.S. Pat. No. 5,087,617 to Smith).

Antisense nucleic also include double-stranded cyclic oligonucleotides, such as hammerhead or dumbbell oligonucleotides, which have been shown to specifically inhibit RNA synthesis (see, e.g., Clusel et al. (1993) *Nucl. Acids Res.* 21:3405–3411).

(b) Triplex Molecules

Triplex molecules refer to single DNA strands that target duplex DNA, forming co-linear triplexes by binding to the major groove, and thereby prevent or alter transcription (see, e.g., U.S. Pat. No. 5,176,996 to Hogan et al.). Triplex DNA has been designed that bind tightly and specifically to selected DNA sites.

(c) Ribozymes

A ribozyme is an enzyme that is made of RNA and that primarily acts on RNA substrates. As used herein, ribozymes refer to RNA (or RNA analogs) constructs that specifically cleave messenger RNA (see, e.g., U.S. Pat. Nos. 5,180,818, 5,116,742 and 5,093,246 to Cech et al.) and in particular refers to ribozymes that are designed to target RNA molecules for cleavage and that thereby in some manner inhibit or interfere with cell growth or with expression of a targeted mRNA or protein.

(d) Extracellular Protein Binding Oligonucleotides

Extracellular protein binding oligonucleotides refer to oligonucleotides that specifically bind to proteins.

(e) Small Nucleotide Molecules

Small nucleotide molecules refer to nucleic acids that target a receptor site.

As used herein, heterologous or foreign nucleic acid are used interchangeably and refer to DNA or RNA that does not occur naturally as part of the genome in which it is present or which is found in a location or locations in the genome that differs from that in which it occurs in nature. Heterologous nucleic acid is generally not endogenous to the cell into which it is introduced, but has been obtained from another cell or prepared synthetically. Generally, although not necessarily, such nucleic acid encodes RNA and proteins that are not normally produced by the cell in which it is expressed. Any DNA or RNA that one of skill in the art would recognize or consider as heterologous or foreign to the cell in which it is expressed is herein encompassed by heterologous DNA. Examples of heterologous DNA include, but are not limited to, DNA that encodes transcriptional and translational regulatory sequences and selectable or traceable marker proteins, such as a protein that confers drug resistance. Heterologous DNA may also encode DNA that mediates or encodes mediators that alter expression of endogenous DNA by affecting transcription, translation, or other regulatable biochemical processes.

As used herein, vector or plasmid refers to discrete elements that are used to introduce heterologous DNA into cells for either expression of the heterologous DNA or for replication of the cloned heterologous DNA. Selection and use of such vectors and plasmids are well within the level of skill of the art.

As used herein, expression refers to the process by which nucleic acid is transcribed into mRNA and translated into peptides, polypeptides, or proteins. If the nucleic acid is derived from genomic DNA, expression may, if an appropriate eukaryotic host cell or organism is selected, include splicing of the mRNA.

As used herein, expression vector includes vectors capable of expressing DNA fragments that are in operative linkage with regulatory sequences, such as promoter regions, that are capable of effecting expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or may integrate into the host cell genome.

As used herein, operative linkage or operative association of heterologous DNA to regulatory and effector sequences of nucleotides, such as promoters, enhancers, transcriptional and translational stop sites, and other signal sequences, refers to the functional relationship between such DNA and such sequences of nucleotides. For example, operative linkage of heterologous DNA to a promoter refers to the physical and functional relationship between the DNA and the promoter such that the transcription of such DNA is initiated from the promoter by an RNA polymerase that specifically recognizes, binds to and transcribes the DNA in reading frame.

As used herein, a promoter region refers to the portion of DNA of a gene that controls transcription of DNA to which it is operatively linked. A portion of the promoter region includes specific sequences of DNA that are sufficient for RNA polymerase recognition, binding and transcription initiation. This portion of the promoter region is referred to as the promoter. In addition, the promoter region includes sequences that modulate this recognition, binding and transcription initiation activity of the RNA polymerase. These sequences may be cis acting or may be responsive to trans acting factors. Promoters, depending upon the nature of the regulation, may be constitutive or regulated. For use herein, inducible promoters are preferred. The promoters are recognized by an RNA polymerase that is expressed by the host. The RNA polymerase may be endogenous to the host or may be introduced by genetic engineering into the host, either as part of the host chromosome or on an episomal element, including a plasmid containing the DNA encoding the shiga A subunit-containing polypeptide. Most preferred promoters for use herein are tightly regulated such that, absent induction, the DNA encoding the saporin-containing protein is not expressed.

As used herein, a transcription terminator region has either (a) a subsegment that encodes a polyadenylation signal and polyadenylation site in the transcript, and/or (b) a subsegment that provides a transcription termination signal that terminates transcription by the polymerase that recognizes the selected promoter. The entire transcription terminator may be obtained from a protein-encoding gene, which may be the same or different from the gene, which is the source of the promoter. Preferred transcription terminator regions are those that are functional in *E. coli*. Transcription terminators are optional components of the expression systems herein, but are employed in preferred embodiments.

As used, the term "nucleotide sequence coding for expression of" a polypeptide refers to a sequence that, upon transcription and subsequent translation of the resultant mRNA, produces the polypeptide. This can include sequences containing, e.g., introns.

As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, maintenance of the correct reading frame of a protein-encoding gene to permit proper translation of the mRNA, and stop condons. In addition, DNA sequences encoding a fluorescent indicator polypeptide, such as a green or blue fluorescent protein, can be included in order to select positive clones (i.e., those host cells expressing the desired polypeptide).

As used herein, "host cells" are cells in which a vector can be propagated and its nucleic acid expressed. The term also includes any progeny of the subject host cell. It is understood that all progeny may not be identical to the parental cell since there may be mutations that occur during replication. Such progeny are included when the term "host cell" is used.

As used herein, secretion signal refers to a peptide region within the precursor protein that directs secretion of the precursor protein from the cytoplasm of the host into the periplasmic space or into the extracellular growth medium. Such signals may be either at the amino terminus or carboxy terminus of the precursor protein. The preferred secretion signal is linked to the amino terminus and may be heterologous to the protein to which it is linked. Typically signal sequences are cleaved during transit through the cellular secretion pathway. Cleavage is not essential or need to be precisely placed as long as the secreted protein retains its desired activity.

As used herein, a nuclear translocation or targeting sequence (NTS) is a sequence of amino acids in a protein that are required for translocation of the protein into a cell nucleus. Comparison with known NTSs, and if necessary testing of candidate sequences, should permit those of skill in the art to readily identify other amino acid sequences that function as NTSs.

As used herein, heterologous NTS refers to an NTS that is different from the NTS that occurs in the wild-type peptide, polypeptide, or protein. For example, the NTS may be derived from another polypeptide, it may be synthesized, or it may be derived from another region in the same polypeptide.

As used herein, transfection refers to the taking up of DNA or RNA by a host cell. Transformation refers to this process performed in a manner such that the DNA is replicable, either as an extrachromosomal element or as part of the chromosomal DNA of the host. Methods and means for effecting transfection and transformation are well known to those of skill in this art (see, e.g., Wigler et al. (1979) *Proc. Natl. Acad. Sci. USA* 76:1373–1376; Cohen et al. (1972) *Proc. Natl. Acad. Sci. USA* 69:2110).

As used herein, biological activity refers to the in vivo activities of a compound or physiological responses that result upon in vivo administration of a compound, composition or other mixture. Biological activity, thus, encompasses therapeutic effects and pharmaceutical activity of such compounds, compositions and mixtures. Such biological activity may, however, defined with reference to particular in vitro activities, as measured in a defined assay. Thus, for example, reference herein to the biological activity of chemokine, a dimer thereof, monomer, or fragment thereof, or other combination of chemokine monomers and fragments, refers to the ability of the chemokine to bind to cells bearing chemokine receptors and internalize a linked agent. Such activity is typically assessed in vitro by linking the chemokine (dimer, monomer or fragment) to a cytotoxic agent, such as shiga-A subunit, contacting cells bearing chemokine receptors, such as leukocytes, with the conjugate and assessing cell proliferation or growth. Such in vitro activity should be extrapolative to in vivo activity. Numerous animal models are referenced and described below.

As used herein, the term biologically active, or reference to the biological activity of a conjugate of a chemokine receptor targeting agent, such as a conjugate containing a chemokine and a targeted agent, such as shiga-A subunit, refers in that instance to the ability of such polypeptide to enzymatically inhibit protein synthesis by inactivation of ribosomes either in vivo or in vitro or to inhibit the growth of or kill cells upon internalization of the toxin-containing polypeptide by the cells. Such biological or cytotoxic activity may be assayed by any method known to those of skill in the art including, but not limited to, the in vitro assays that measure protein synthesis and in vivo assays that assess cytotoxicity by measuring the effect of a test compound on cell proliferation or on protein synthesis. Particularly preferred, however, are assays that assess cytotoxicity in targeted cells.

As used herein, to bind to a receptor refers to the ability of a ligand to specifically recognize and detectably bind, as assayed by standard in vitro assays, to such receptors. For example, binding, as used herein, is measures the capacity of the a chemokine conjugate, chemokine monomer, or other mixture to recognize a chemokine receptor on leukocyte cell subtypes such as microglia, monocytes, macrophages, neutrophils, eosinophils, basophils, and T-cells using well described ligand-receptor binding assays, chemotaxis assays, histopathologic analyses, flow cytometry and confocal microscopic analyses, and other assays known to those of skill in the art and/or exemplified herein.

As used herein, substantially pure means sufficiently homogeneous to appear free of readily detectable impurities as determined by standard methods of analysis, such as thin layer chromatography (TLC), gel electrophoresis, high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein, isolated, substantially pure DNA refers to DNA fragments purified according to standard techniques employed by those skilled in the art (see, e.g., Maniatis et al. (1982) *Molecular Cloning: A Laboratory Manual*, Cold Spring Harbor Laboratory Press, Cold Spring Harbor, N.Y. and Sambrook et al. (1989) *Molecular Cloning: A Laboratory Manual*, Cold Spring Harbor Laboratory Press, Cold Spring Harbor, N.Y.).

As used herein, to hybridize under conditions of a specified stringency describes the stability of hybrids formed between two single-stranded DNA fragments and refers to the conditions of ionic strength and temperature at which such hybrids are washed, following annealing under conditions of stringency less than or equal to that of the washing step. Typically high, medium and low stringency encompass the following conditions or equivalent conditions thereto:

1) high stringency: 0.1×SSPE or SSC, 0.1% SDS, 65° C.
2) medium stringency: 0.2×SSPE or SSC, 0.1% SDS, 50° C.
3) low stringency: 1.0×SSPE or SSC, 0.1% SDS, 50° C.

Equivalent conditions refer to conditions that select for substantially the same percentage of mismatch in the resulting hybrids. Additions of ingredients, such as formamide, Ficoll, and Denhardt's solution affect parameters such as the temperature under which the hybridization should be conducted and the rate of the reaction. Thus, hybridization in 5×SSC, in 20% formamide at 42° C. is substantially the same as the conditions recited above hybridization under conditions of low stringency.

The recipes for SSPE, SSC and Denhardt's and the preparation of deionized formamide are described, for example, in Sambrook et al. (1989) *Molecular Cloning, A Laboratory Manual*, Cold Spring Harbor Laboratory Press, Chapter 8; see, Sambrook et al. vol. 3, p. B.13, see, also, numerous catalogs that describe commonly used laboratory solutions). SSPE is pH 7.4 phosphate-buffered 0.18 NaCl.

As used herein, a culture means a propagation of cells in a medium conducive to their growth, and all sub-cultures thereof. The term subculture refers to a culture of cells grown from cells of another culture (source culture), or any subculture of the source culture, regardless of the number of subculturings that have been performed between the subculture of interest and the source culture. The term "to culture" refers to the process by which such culture propagates.

As used herein an effective amount of a compound for treating a particular disease is an amount that is sufficient to ameliorate, or in some manner reduce the symptoms associated with the disease. Such amount may be administered as a single dosage or may be administered according to a regimen, whereby it is effective. The amount may cure the disease but, typically, is administered in order to ameliorate the symptoms of the disease. Repeated administration may be required to achieve the desired amelioration of symptoms.

As used herein, pharmaceutically acceptable salts, esters or other derivatives of the conjugates include any salts, esters or derivatives that may be readily prepared by those of skill in this art using known methods for such derivatization and that produce compounds that may be administered to animals or humans without substantial toxic effects and that either are pharmaceutically active or are prodrugs.

As used herein, treatment means any manner in which the symptoms of a conditions, disorder or disease are ameliorated or otherwise beneficially altered. Treatment also encompasses any pharmaceutical use of the compositions herein.

As used herein, amelioration of the symptoms of a particular disorder by administration of a particular pharmaceutical composition refers to any lessening, whether permanent or temporary, lasting or transient that can be attributed to or associated with administration of the composition.

As used herein, a prodrug is a compound that, upon in vivo administration, is metabolized or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach*, Oxford University Press, New York, pages 388–392).

As used herein, $ED_{50}$ refers to the concentration at which 50% of the cells are killed following a stipulated time period of incubation with a conjugate provided herein.

As used herein, $ID_{50}$ refers to the concentration of a conjugate provided herein required to reduce the number or eliminate 50% of cells exposed to the conjugate compared to untreated cells during after a stipulated time period.

As used herein, the term "cytokine" encompasses interleukins, chemokines, lymphokines, monokines, colony stimulating factors, and receptor associated proteins, and functional fragments thereof. For purposes herein, non-chemokine cytokines refer to all cytokines, except for chemokines, which have chemoattractant activity not generally exhibited by other cytokines.

As used herein, a chemokine refers to a member of the superfamily of forty or more small (approximately about 6 to about 14 kDa) inducible and secreted pro-inflammatory polypeptides that act primarily as chemoattractants and activators of specific leukocyte cell subtypes. Together, chemokines target the entire spectrum of leukocyte subtypes; individually each targets only part of the spectrum. Chemokines, which are basic heparin-binding proteins, typically, although not necessarily, have four cysteines shared among almost all family members. There are four major groups of chemokines, three of which include the four conserved cysteines; other groups may be identified. The groups are defined by the arrangement of the first two cysteines. If the first two cysteines are separated by a single amino acid they are members of the CXC family (also called α); if the cysteines are adjacent, they are classified in the CC family (also called β). If they are separated by three amino acids $CX_3C$, they are members of the third group. The fourth group of chemokines contains two cysteines, corresponding to the first and third cysteines in the other groups. For purposes herein, chemokines do not include cytokines, such as GM-CSF, IL-1, IL-4, that do not interact with CC-, CXC-, CX3C- and XC-receptors, do not primarily act as chemoattractants for leukocytes and do exhibit regulatory effects on the growth, differentiation and function of most cell types. Because some cytokines bind to receptors that are present on cells that also express chemokine receptors, certain cytokine-targeted agent conjugates, such as Il-4 conjugates, may be used in the methods of treating inflammatory conditions, particularly the inflammation associated with secondary tissue damage, provided herein.

As used herein, a chemokine-toxin is a conjugate that contains a chemokine and a toxin.

As used herein, the term "functional fragment" refers to a polypeptide which possesses biological function or activity that is identified through a defined functional assay and which is associated with a particular biologic, morphologic, or phenotypic alteration in a cell or cell mechanism.

As used herein, the term "enzymatic subunit" refers to the A subunit of a given toxin that is responsible for either N-glycosidase or ADP-ribosylation activity of the toxin (Pastan et al., *Annu. Rev. Biochem.* 61:331–54, 1992; Stirpe et al., *Bio/Technology* 10:405–12, 1992; and Sandvig and Van Deurs, *Physiol. Rev.* 76:949–66, 1996).

As used herein, the term "antibody" as used herein includes intact molecules as well as functional fragments thereof, such as Fab, F(ab')$_2$, and Fv that are capable of binding the epitopic determinant. These functional antibody fragments retain some ability to selectively bind with their respective antigen or receptor and are defined as follows:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule that can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of making these fragments are known in the art (see, for example, Harlow and Lane, *Antibodies: A Laboratory Manual*, Cold Spring Harbor Laboratory, New York, 1988, incorporated herein by reference).

As used herein, the term "epitope" means any antigenic determinant on an antigen to which the paratope of an antibody binds. Epitopic determinants contain chemically active surface groupings of molecules such as amino acids or carbohydrate side chains and usually have specific three dimensional structural characteristics, as well as specific charge characteristics.

As used herein, peptide and/or polypeptide means a polymer in which the monomers are amino acid residues which are joined together through amide bonds, alternatively referred to as a polypeptide. When the amino acids are alpha-amino acids, either the L-optical isomer or the D-optical isomer can be used, the L-isomers being preferred. Additionally, unnatural amino acids such as beta-alanine, phenylglycine, and homoarginine are meant to be included. Commonly encountered amino acids that are not gene-encoded can also be used in ligand-toiin chimeras provided herein, although preferred amino acids are those that are encodable.

As used herein, effective amount is the quantity of a therapeutic agent necessary to prevent, to cure, ameliorate, or at least partially arrest, a symptom of secondary tissue damage in a subject or of a disease state associated therewith. A subject is any mammal, preferably a human.

B. The Inflammatory Response

Inflammation is initiated by the activation and recruitment of several groups of immune system defense cells (leukocytes) to the site of injury or trauma. Pro-inflammatory leukocytes include; macrophages, monocytes, and microglia (collectively known as mononuclear phagocytes, MNPs), neutrophils, eosinophils, and subtypes of the T-lymphocyte lineage. These cells serve to rid the body of unwanted exogenous agents (e.g., microbes) or endogenous agents (e.g., cancer cell clones), remove cellular debris, and participate in tissue and wound repair.

Leukocytes are activated, and subsequently release a wide array of inflammatory mediators, as a response to soluble factors released by injured cells undergoing necrosis. The leukocytic-derived mediators are essential to the healing process but they also appear to be responsible for the secondary tissue damage that may eventually lead to organ dysfunction. The first wave of leukocyte-derived mediators include numerous members of the cytokine superfamily and several powerful leukocyte chemoattractants of the chemokine superfamily.

Cytokines and chemokines perpetuate their own production and are released from leukocytes via autocrine and paracrine mechanisms. They also induce the synthesis and release of a second wave of inflammatory mediators from the cells that they target. This second wave of inflammatory mediators includes, but are not limited to, neurotoxins, proteolytic enzymes, cationic proteins, arachidonic acid metabolites, and reactive oxygen species. Cytokines and chemokines also induce the expression of cell adhesion molecules and cell surface antigens on leukocytes, endothelial cells, and glial cells, and both events are integral components of the inflammatory response.

Spinal Cord and CNS Injury

The precipitating events, such as motor vehicle accidents, that leads to a spinal cord injury are is usefully delineated as the initial, or first injury. The traumatized spinal cord quickly responds by invoking a normal inflammatory response, which is designed to rid the injury site of any invading foreign material like bacteria or viruses, seal the wound, and promote tissue repair. To this extent the spinal inflammatory response is akin to the skin's response to a minor cut or abrasion and in both cases a permanent scar may be formed.

While the peripheral response to injury can be envisaged as a single contained event, the spinal response develops to a point where "normal" becomes "inappropriate" and in essence a second injury is inflicted. In short, the spinal inflammatory response constructs an environment at the site of injury that is too hostile to support nerve regeneration or repair, extends the perimeter of this region to include undamaged areas of the cord, and actually kills both healthy neurons and oligodendrocytes. Consequently, SCI is a two stage process comprised of an initial or precipitating injury that is followed by secondary tissue damage.

As described herein, inappropriate progression of spinal inflammation is the major contributor to the degree of paralysis and secondary medical conditions that are the typical outcome of SCI. From a clinical perspective this means that the spinal injured patient may have been far better served if the inflammatory response had never been initiated. Because of the on-going spinal inflammation, prospects of a successful therapeutic intervention are bleak.

Studies on SCI and generalized CNS trauma have demonstrated a clear onset of secondary tissue damage that is observed within a matter of hours, may proceed for several weeks, and is followed by a period of partial recovery. Secondary damage is detectable as cell death, astrogliosis, which leads to glial scarring, neovascularization, demyelination, and loss of sensory and motor function (i.e. paralysis). The time course of secondary damage and partial recovery are well correlated with the degree of inflammation at the site of injury.

The early events in CNS inflammation include activation and proliferation of resident microglia and infiltrating MNPs. Microglia are a distinct class of MNPs and the resident immunoeffector cells of the CNS It is the inflammatory activities of these cells that cause secondary damage at the cellular level. Furthermore, MNP-derived cytokines and chemokines aid in the activation and recruitment of monocytes, neutrophils and T-lymphocytes to the site of injury, a process that is initiated as a consequence of the upregulation of cell surface antigens and cell-adhesion molecules, including integrins, selectins and intercellular adhesion molecule-1 (I-CAM), on leukocyte subtypes, endothelial cells, and astrocytes. Neutrophils and T-cells contribute to secondary damage by releasing their own cytokines, chemokines, reactive oxygen species, and proteinases into the inflammatory milieu. These inflammatory events lead to the focal death of neurons and oligodendrocytes (the myelin producing cells of the CNS) combined with demyelination of surrounding axons.

Role Of Cytokines In Secondary Damage Of The CNS

MNPs, neutrophils, T-lymphocytes, and astrocytes produce, secrete, and respond to several cytokines including; IL-1, TNF-α, IL-3, IL-4, IL-6, IL-8 GM-CSF, and IFN. These cytokines modulate most leukocyte functions including; phagocytotic activity, the expression of cell surface antigens and cell-adhesion molecules, and the production of oxygen radicals. Furthermore, these cytokines can be directly linked to the glial scarring process, or in some instance, linked via the induced release of neurotoxic and cytotoxic factors. TNF-α has been implicated in the pathogenesis of EAE and several other demyelinating diseases. For example, MNP-specific upregulation of TNF-α, and TNF-α receptors, has been demonstrated in the nervous system of AIDS patients. In vitro studies demonstrate that TNF-α is directly cytotoxic to oligodendrocytes and stimulates microglial phagocytosis of myelin. In addition, TNF-α, potentiates the IFN-γ-induced cell death of oligodendrocyte progenitor cells.

Leukocytic and astroglial GM-CSF and IL3, together with T-lymphocytic IL-4, are potent mitogens and activators of MNPs. These factors, along with others, contribute to the pathogenesis of inflammatory autoimmune diseases, most likely by way of the more rapid phagocytosis of myelin discussed earlier In several interesting studies, transgenic mice were designed to produce chronically low levels of either IL-3, IL-6 or TNF-α in the CNS, which led to the proliferation and activation of MNPs in CNS white matter, and subsequently, to primary demyelination and motor disease.

Role Of Chemokines In Secondary Damage Of The CNS

Chemokines, as noted above, are a superfamily of small (approximately about 6 to about 14 kDa), inducible and secreted, chemoattractant cytokines that act primarily on leukocyte subtypes. The superfamily is divided into four sub-families based upon the position (or existence) of four conserved cysteine residues in the primary sequences. The members of the CXC, or "alpha" family, possess an intervening amino acid between the first two conserved cysteines, whereas the CC, or "beta" family, does not. The C, or "gamma," chemokines only have the second and fourth conserved cysteine residues. A fourth, "delta" family has been described. This family shares three intervening amino acids between the first two conserved cysteines (hence, they are referred to as the CX3C family). The CX3C chemokine fractalkine is different from members of the other families in that it exists in soluble and membrane bound forms The receptor binding of chemokines to their target cells is a complex and an ever-evolving area of investigation. The alpha-chemokine family has been shown to bind to one or more of five CXC-receptors (CXCR1–5), while the beta-chemokines family bind to one or more of ten CC-receptors (CC1–9). The receptor binding profiles for a selected exemplary non-limiting group of α and β chemokines is presented in Table 1. Notwithstanding the presence of appropriate receptors, the cell specificity of a given chemokine is largely, although not exclusively, a matter of whether it targets MNPs, or neutrophils, or both. In addition, eosinophils are prominent targets for the beta chemokines (see Table 1).

In general, the binding affinities, specificities, and the differential distribution of receptor subtypes across target cells determines the contribution that a given chemokine will make to the inflammatory process. The biological profile of a given chemokine determined in one setting may not hold true in another, most especially if the ratio and activation status of target cells changes during trauma or disease. Hence the biological profile of a given chemokine must be established on a case by case basis. For example, the effects of monocyte chemotactic protein-3 (MCP-3) are similar to those of MCP-1, but the former binds to a broader range of cells. Adding to an already complicated situation, chemokines also bind to cell surface heparin and glycosaminoglycans in a way that is thought to facilitate the maintenance of a gradient needed for leukocyte activation and transportation (extravasation) from the circulation into the inflamed tissue.

Chemokines act in an autocrine or paracrine manner and their receptors are upregulated in disease. In vitro studies have shown that various stimuli including; lipopolysaccharide (LPS), IL-1, IFN, and TNF-α induce the expression and secretion of chemokines from various CNS and non-CNS cell types. For example, MCP-1, macrophage inflammatory protein-1 beta (MIP-1β) and RANTES (Regulated on Activation, Normal T cell Expressed and Secreted) from astrocytes, microglia, and leukocytes. Once released chemokines concomitantly chemoattract and activate microglia, macrophages, neutrophils, and T-lymphocytes to the site of injury. Chemokine-mediated activation means the induced synthesis and secretion of reactive oxygen species, proteases, and cytokines from the appropriate target cells, with a subsequent increase in secondary damage that is directly attributable to the secreted agents.

Turning to more specific examples, the CC chemokines MCP-1, MIP-1α, MIP-1β, and RANTES are expressed by astrocytes and macrophages after mechanical injury to the brain, and their expression correlates with the onset of reactive gliosis and the appearance of MNPs at the site of injury. In a similar example, MCP-1 and MIP-1α expression has been detected in MNPs and astrocytes after focal cerebral ischemia in the rat. In a more complex example, a selective and time-dependent upregulation of growth-regulated oncogene (GRO-α) has been demonstrated. Interferon-γ-inducible protein (IP-10 SEQ ID NO. 92), and MCP-1 and 5 are observed within the first six to twenty four hours following spinal cord contusion injury in the rat. Gro-α expression and neutrophil chemoattraction is an early event (within 6 hours), IP-10 expression and T cell chemoattraction is an intermediate event (6–12 hours), and finally, MCP-1 and 5 expression and MNP chemoattraction is a late event (12–24 hours). In contrast, MIP-1α and RANTES expression appeared to be little affected in spinal cord contusion, which is not to say that the infiltrating and proliferating cells do not have receptors for these two beta-chemokines.

Several investigators have studied chemokines in experimental autoimmune encephalomyelitis (EAE) and shown that endothelial cells, MNPs, and astrocytes, express MCP-1 at the onset of the acute phase. Monocytes infiltrate the lesion sites twenty four hours later and this is followed by widespread expression of MCP-1 in the spinal cord. MIP-1α, MIP-1β, RANTES and MCP-3 expression fluctuates in accordance with the severity and state of EAE. The temporal and spatial patterns of chemokine expression regulate the pathogenesis of the disease, and MIP-1-α and MCP-1 control MNP infiltration during acute and relapsing EAE, respectively. Finally, transgenic mice over-expressing MCP-1 exhibit pronounced MNP infiltration into the CNS.

The Contribution Of Apoptosis To Secondary Damage

In the initial phase of CNS trauma, including SCI, severely damaged cells begin to die almost immediately; the passive process of necrosis. Following cell activation, mediators of inflammation initiate a second, delayed, and prolonged period of cell death that amounts to an active cellular suicide process sometimes called "programmed cell death", or more frequently, apoptosis. Apoptotic effects extend to both neurons and oligodendrocytes, and their contribution to secondary damage is progressive. Once induced, apoptosis can occur over an extended period of time and to areas that are anatomically distant from the initial site of injury. The temporal and spatial effect of apoptosis may also explain why cell death is still observed when immune cells are no longer detectable at or near the site of injury.

Apoptosis has been observed in a variety of inflammatory and traumatic conditions including SCI, AD, MS, traumatic brain injury and stroke, pulmonary disease, and cancer. For example, apoptosis of neurons and oligodendrocytes (associated with demyelination) is evident in a number of animal models of CNS trauma and SCI. Data from typical animal models of CNS trauma reveal that apoptosis starts fairly early (within a matter of hours) and extends for at least one week post injury. In some instances, the experimental protocol has been extended and apoptosis is still detectable three weeks after injury. In at least one published study, the data suggest that there may be two distinct apoptotic waves. Immunohistochemical examination of human spinal cords from patients who died between three hours and two months post-SCI revealed apoptosis of neurons and oligodendrocytes in 93% of cases. In the animal and post-mortem studies apoptotic events were detected at a distance from the site of injury.

Apoptotic mechanisms involve changes in intracellular signaling and gene expression. Activation of intracellular endonucleases and proteases (e.g., caspases) leads to DNA cleavage (the characteristic "DNA ladder" observed by gel electrophoresis), partial degradation of the intracellular cytoskeleton and organelles, and ultimately, to delayed cell death. In the CNS, apoptosis is initiated by leukocyte and astroglial-derived inflammatory mediators including; cytokines, chemokines, reactive oxygen species, NO, and excitatory amino acids. Once again, this underlines the contribution of these mediators to secondary tissue damage.

The emphasis and relative intensity of apoptosis and necrosis appear to be different for a given mediator, and for example, NMDA receptor agonists and NO kill neurons using both mechanisms. NMDA or NO-mediated apoptosis involves activation of the intracellular caspase cascade. Reactive oxygen species, a consequence of NMDA and NO activation, are also thought to be involved in apoptosis but it appears that oxygen radical formation and lipid peroxidation occur downstream to caspase activation. In contrast, leukocyte-derived cytokines may either activate or suppress apoptosis. For example, TNF-α induces apoptosis in a variety of cell types through at least two different intracellular signal pathways. Il-1β has a synergistic role with NO in the activation of apoptosis, but GM-CSF and IL-3 suppress apoptosis of human and rat leukocytes. GM-CSF suppresses the apoptosis of human neutrophils that follows the activation of the FAS, or so-called "death" receptor, and the cells retain their ability to produce oxygen radicals and proteases. IL-4, a potent mitogen for microglia, suppresses apoptosis in human neutrophils via a mechanism that may include induction of de novo protein synthesis. These examples suggest that suppression or activation of apoptosis leads to secondary tissue damage that is dependent on the exact mixture of inflammatory mediators at the site of injury.

Leukocyte-Mediated Inflammation in CNS and Non-CNS Diseases and Conditions

The distinction between a disease and a clinical condition is not always an easy one to make. For example, a prizefighter may sustain a number of closed head injuries (a condition) in the course of his career and may go onto develop a form of dementia (dementia pugilistica) in later life that is very similar to Alzheimer's disease. The similarities between traumatic injury of the nervous system, which are primarily dependent on aggressive inflammatory processes and secondary damage, and a number of neurodegenerative diseases are striking. Indeed, a recent report indicates that the inflammatory response triggered by head trauma predisposes a patient to AD, and that brain inflammation in AIDS patients favors amyloid plaque formation, a feature of AD. From this perspective, the diseases targeted by the conjugates provided herein, share a common etiology and/or pathology.

Secondary damage of the CNS is exemplary of the progression of events and role of chemokines and chemokine-receptor bearing cells in the progressive damage observed from pathophyosiological inflammatory responses. As described below and known to those of skilled in the art, immune effector cells play a role in the pathology of numerous disorders and inflammatory processes, including but not limited to, lung inflammatory disorder, cancers, particularly in solid tumors in which large quantities of infiltrating leukocytes are observed, angiogenesis, viral and bacterial infections, including HIV infection, autoimmune disorders, and others.

C. Components of the Conjugates

1 Summary

Provided herein are methods, compounds and compositions for treating pathological conditions associated with inflammatory responses, particularly inflammatory responses associated with activation, proliferation and migration of immune effector cells, including leukocyte cell types, neutrophils, macrophages, eosinophils and other such cells, and the pathophysiological conditions associated these inflammatory responses.

The following are provided:

(1) Methods of treatment of the pathophysiological conditions associated with inflammatory responses mediated by immune effector cells by targeting and delivering cytoxic agents these cells. These pathophysiological conditions, include, but are not limited to, the secondary tissue damage associated with or a consequence of these inflammatory responses. Depending upon the timing of the treatment, the duration of the treatment and the condition or disorder, the methods inhibit, ameliorate or block these responses.

Targeting and delivery are effected through receptors that are expressed on these cells. Such receptors include those for cytokines, and particularly, receptors for chemokines. Hence, chemokine receptors are specifically targeted. Also targeted are other receptors, such as receptors for non-chemokine cytokines, such as IL-4 and GM-CSF, that are expressed on these cells. The conjugates provided herein are intended for use in these methods. Other conjugates known to those of skill in the art, such as conjugates containing IL-4 and toxin may also be used to target to any of these cell types that express receptors specific therefor.

Hence, methods that use the chemokine receptor targeting agents provided herein and methods that use known conjugates, which contain ligands that bind to receptors present on cells that are involved in these pathophysiological inflammatory responses, are provided.

(2) Also provided are conjugates that contain a chemokine receptor targeting agent and a targeted agent. These conjugates are intended for use in the above methods, but may also be used to deliver any agent to cells that express receptors with which chemokines interact and effect or facilitate internalization of linked moieties.

(3) Also provided are methods of treatment in which the above methods are combined with other art-recognized methods for treatment of the disorders associated with the pathophysiological inflammatory conditions.

2. Chemokine Receptor Targeting Moieties

Any agent that selectively targets receptors found on the panoply of cells to which any chemokine selectively binds are intended for use herein. The chemokine receptor targeting agent is preferably selected from the family of chemokines (approximately about 6 to about 14 kDa), which constitutes forty or more polypeptides that promote activation, migration, proliferation of various immune effector cells involved in inflammatory responses. As noted above, this family is subdivided into at least four sub-groups based upon the position or existence of four conserved cysteine residues. The members of the CXC chemokine (or α) subfamily possess an intervening amino acid between the first two conserved cysteines, whereas the members of the CC (or β) subfamily do not. The C (or γ) chemokines lack the first and third cysteine residues. In general, the α chemokine members preferentially are active on neutrophils and T-lymphocytes, and the β chemokines are active on monocytes, macrophages and T-lymphocytes. Additionally, several members of the α and β chemokine sub-families are active on dendritic cells, which are migratory cells that exhibit potent antigen-presenting properties and are thought to participate in the pathophysiology of many inflammatory diseases (Xu et al., *J. Leukoc. Biol.*, 60: 365–71, 1996; and Sozzani et al., *J. Immunol.*, 159: 1993–2000, 1997). A fourth human CX3C-type chemokine referred to as fractalkine has recently been reported (Bazan et al., *Nature,* 385:640–4, 1997; Imai et al., *Cell,* 91:521–30, 1997; Mackay, *Curr. Biol.* 7: R384–6, 1997). Unlike other chemokines, fractalkine exists in membrane and soluble forms. The soluble form is a potent chemoattractant for monocytes and T-cells. The cell surface receptor for this chemokine is termed CX3CR1. It should be noted that there may be subtle differences between the chemical nature and physiological effects of chemokines derived from different species (Baggiolini et al., *Adv. Immunol.,* 55: 97–179, 1994; and Haelens et al., *Immunobiol.,* 195: 499–521, 1996).

a. Chemokines

As noted above, chemokines are expressed on activated cells of leukocyte lineage. Such cells are involved in various disease processes, and the particular cells that are activated are function of the disease as well as the disease progress. Consequently, targeting these receptors and the cells that express these receptors permits the therapy to be tailored to the particular disease and also to the progress of the disease.

Chemokines exert their effects by binding to specific target cell receptors (e.g., CXCR-1 through 5 and CCR-1 through 9, XCR1 and CX3CR-1). These receptors bind to the various chemokine ligands in an overlapping and complex manner (See Table 1 below). The receptor binding specificity (or specificities) and cellular distribution of given receptors determine the inflammatory cell types that a given chemokine will influence. For example, MCP-3 has similar effects to that of MCP-1, but binds to a broader range of cell sub-types (Combadiere et al,. *J. Biol. Chem.*, 270: 29671–5, 1995; Franci et al., *J. Immunol.,* 154: 6511–7, 1995; Weber et al., *J. Immunol.,* 154: 4166–72, 1995; Gong et al., *J. Biol. Chem.,* 271: 10521–27, 1996; and Proost et al., *J. Leukoc. Biol.,* 59: 67–74, 1996). In addition, chemokines bind to cell surface heparin and glycosaminoglycans in a manner that is thought to facilitate the maintenance of a chemokine gradient needed for leukocyte activation and trafficking (Schall et al., *Current Biol,* 6: 865–73, 1994; and Tanaka et al., *Immunology Today,* 14: 111–15, 1993).

Non-limiting examples of chemokines for use in the conjugates and methods provided herein include, but are not limited to, the α-, β-, and γ- sub-groups of chemokines. More particularly, chemokines presently preferred for use as the proteinaceous ligand moiety in the chimeric ligand-toxins include, but are not limited to, the α-chemokines known in the art as IL-8; granulocyte chemotactic protein-2 (GCP-2); growth-related oncogene-α (GRO-α) GRO-β, and GRO-γ; epithelial cell-derived neutrophil activating peptide-78 (ENA-78 SEQ ID NO. 90); platelet basic protein (PBP); connective tissue activating peptide III (CTAP III); neutrophil activating peptide-2 (NAP-2 SEQ ID NO. 89); low affinity platelet factor-4 (LAPF-4); monokine induced by interferon-γ (MIG); platelet factor 4 (PF4 SEQ ID NO. 92); interferon inducible protein 10 (IP-10 SEQ ID NO. 91, which possesses potent chemoattractant actions for monocytes, T cells, and smooth muscle cells); the stromal cell derived factors SDF-1α, SDF-1β, and SDF-2; the β-chemokines known in the art as the monocyte chemotactic proteins MCP-1, MCP-2, MCP-3, MCP-4, and MCP-5; the macrophage inhibitory proteins MIP-1α, MIP-1β, MIP-1γ, MIP-2, MIP-2α, MIP-2β, MIP-3α, MIP-3β, MIP-4, and MIP-5; macrophage-derived chemokine (MDC); human chemokine 1 (HCC-1); RANTES; eotaxin 1; eotaxin 2; TARC; SCYA17 and I-309; dendritic cell chemokine-1 (DC-CK-1); the γ-chemokine, lymphotactin; the soluble form of the CX3C chemokine fractalkine; any others known to those of skill in the art; and any synthetic or modified proteins designed to bind to the chemokine receptors. Chemokines may be isolated from natural sources using routine methods, or expressed using nucleic acid encoding the chemokine. Biologically active chemokines have been recombinantly expressed in *E. coli* (e.g., those commercially available from R&D Systems, Minneapolis, Minn.).

Chemokine receptors on secondary tissue damage-promoting cells generally belong to the superfamily of G-protein coupled, seven transmembrane-domain, rhodopsin-like receptors. It is preferred that the chemokine in the chimeric ligand toxin binds with specificity to at least one chemokine receptor on an immune effector cell involved in inflammatory processes, such as those that promote secondary tissue damage. Such receptors are generally members of the superfamily of G-protein coupled, seven transmembrane-domain, rhodopsin-like receptors, including but are not limited to, for example, one or more of the receptors known in the art as the Duffy antigen receptor for chemokines (DARC), CXCR-1, CXCR-2, CXCR-3, CXCR-4, CXCR-5, CCR-1, CCR-2A, CCR-2B, CCR-3, CCR-4, CCR-5, CCR-6, CCR-7, CCR-8, CCR-9, CX3CR-1, CD97, XCR1 and other chemokine receptors. The chemokine receptor is generally a member of the superfamily of G-protein coupled, seven transmembrane-domain, rhodopsin-like receptors, including but are not limited to, DARC, CXCR-1, CXCR-2, CXCR-3, CXCR-4, CXCR-5, CCR-1, CCR-2A, CCR-2B, CCR-3, CCR-4, CCR-5, CCR-6, CCR-7, CCR-8, CCR-9, CX3CR-1, XCR-1 and CD97.

Table 1 below shows a list of representative chemokines associated with pathophysiological inflammatory responses, including secondary tissue damage, the receptor(s) they bind to, and the cell types affected by each in humans.

TABLE 1

| Chemokine | Receptor Binding | Affected Cell Types |
|---|---|---|
| CXC(α) Chemokines | | |
| IL-8 | CXCR1 and 2 | N, T, E, B, and NK |
| GROα | CXCR2 | N and B |
| GCP-2 | CXCR1 and 2 | N and B |
| SDF-1α | CXCR4 | M, T, L and Dc |
| SDF-1β | CXCR4 | M, T, L and Dc |
| CC (β) Chemokines | | |
| MCP-1 | CCR1*, 2-A, 2-B**, 4 and 5* | M, T, N and B |
| MCP-2 | CCR1, 2B and 3 | M and T |
| MCP-3 | CCR1, 2-A, 2-B and 3 | M, T, E, B NK, Dc and N |
| MCP-4 | CCR2-B and 3 | M, E, B and Dc |
| MIP-1α | CCR1, 2B, 3, 4 and 5 | M, T, E, B NK, Dc and N |
| MIP-1β | CCR1*3, 5, 8 | M, T, E, B and Dc |
| MIP-5 | CCR1 and 3 | M, T, E* and Dc |
| Eotaxin | CCR3 | E, B and microglia |
| Eotaxin-2 | CCR3 | E, B and microglia |
| RANTES | CCR1, 2B, 3, 4 and 5 | M, T, E, B, NK and Dc |
| I-309 | CCR8 | M |

*indicates low-affinity binding only.
**CC-R2 A and B are spliced variants and specifically bind MCP-1 and 3.
M = MNP lineage cells (monocytes, macrophages and microglia).
N = neutrophils.
T = T lymphocyte cell sub-types.
L = Leukocyte cell sub-types.
E = eosinophils.
B = basophils.
NK = natural killer cells.
Dc = dendritic cells.

Other chemokines include ALP and Lungkine (see, e.g., SEQ ID Nos. 69 and 70, respectively; see, also, Hromas et al. (1999) *Biochem. Biophys. Res. Comm.* 258:737–740) and Lungkine (see, Rossi et al. (1999) *J. Immunol.* 162:5490–5497), Tim-1, a human CXC chemokine (see, e.g., International PCT application No. WO 99/33990, based on U.S. application Ser. No. 09/026,546 (now U.S. Pat. No. 5,977,879); see also EMBL database ID HS1301003, Accession number AA505654), chemokines and chemokine-line peptides described in International PCT application No. WO 99/32631, Lkn-1 described in International PCT application No. WO 99/28473.

The data in Table 1 pertains to humans. There may be species differences between chemokine receptor specificities, and chemokines may have different affinities for different receptors. Hence, species-specific conjugates may be prepared. There even may be allelic differences in receptors among members of a species, and, if necessary allele-specific conjugates may be prepared. In addition, different species may express homologs of the human chemokine. For example, TCA-3 is the murine homolog of human I-309 (Goya et al., *J. Immunol.* 160:1975–81, 1998).

It is understood that other chemokines are known and that such chemokines and receptors specific therefor may be identified, and where necessary produced and used to produce conjugates as described herein. The diseases for which the resulting conjugates may be used may be determined by the specificity and cell populations upon which receptors therefor are expressed, and also may be determined empirically using in vitro and in vivo models known to those of skill in the art, including those exemplified, described and/or reference herein.

b. Selection of a Chemokine

Chemokines for use in the conjugates are selected according to the disease or disorder to be treated and also according to the timing and duration of treatment. For example, a chemokine-fusion protein exhibiting a higher degree of receptor specificity may be desirable at an early stage of secondary tissue damage where, for example, microglia and/or macrophages are initiating inflammation. Removing these cells with a very specific agent may reduce the potential for activation of surrounding, and as yet benign cells. When other leukocyte sub-groups are recruited, at an intermediate or late stages of disease, a broader spectrum of cell specificity may be desirable. In addition, an appropriate broad spectrum chemokine-fusion protein would deliver a very strong blow to those restricted populations of leukocytes that express multiple types of the chemokine receptors. Certain chemokines appear to have more influence in specific disease states than do others. For example, MCP-1 expression appears to regulate acute EAE whereas MIP-1α expression correlates with the severity of relapsing EAE, and immunohistochemical staining of AD brain specimens indicates a predominance of MIP-1β expression over several other chemokines. Thus, for example, MIP-1α and MIP-1β would be the ligands of choice for a chemotoxin to treat MS and Alzheimer's disease, respectively. Ligands, such as IP-10 and RANTES, which are specific for receptors CXCR3 and CCR5 that are upregulated in cases of human MS, would be used for treatment of MS. Finally, Eotaxins 1 and 2 show high specificity for the CCR3 beta chemokine receptor, which is preferentially expressed by eosinophils. Therefore, Eotaxin chemotoxins may be used for eosinophilic diseases including various pulmonary diseases, eosinophylia-myalgia syndrome, nasal allergy and polyposis.

Eotaxin and SDF-1β are examples of chemokine ligands that exhibit a restricted and very specific receptor binding profile. A ligand that targets very specific cell types through a restricted subset of available receptors. MCP-3 and MCP-1 are examples of ligands broad cell and receptor binding profiles. Such chemokine ligands may be relevant to a single or broad range of clinical conditions. A ligand that targets a broad range of cell-types utilizing receptor subtypes may be expressed on all the cells or only certain cells. This is largely a function of the cell types that are specific to a given condition or common to a range of conditions.

The following table summarizes some exemplary ligands for treatment of selected diseases and conditions.

TABLE 2

EXEMPLARY LIGAND(S) AND DISEASE TREATED

| Ligand(s) | Disease/Condition |
|---|---|
| MCP-1 and 3, RANTES, *IP-10, IL-8, GROα* | Atherosclerosis and Restenosis |
| MCP-1 and 3, RANTES, *SDF-1β* | SCI, Traumatic Brain Injury, Stroke, AD |
| MCP-3 and 4, RANTES, *IP-10, Mig* | Multiple Sclerosis |
| Eotaxin, RANTES, MDC, *SDF-1β* | HIV |
| Eotaxin, MCP-1 and 4, MDC, *IL-8, ENA-78* | Inflammatory Bowel Diseases |
| MCP-3 and 4, RANTES, *IP-10, Mig, IL-8, ENA-78, GROα, I-TAC* | Inflammatory Joint Diseases (e.g., arthritis) |
| | Inflammatory Lung Diseases |
| MIP-1α, MIP-1β, MCP-1, 2, 3, 4, RANTES, *IP-10, IL-8, ENA-78* | Acute lung Injuries and Fibroses |

TABLE 2-continued

EXEMPLARY LIGAND(S) AND DISEASE TREATED

| Ligand(s) | Disease/Condition |
|---|---|
| Eotaxin, MCP-4, MDC | Allergic and Eosinophil-associated Diseases |
| MCP-1, *IL-8* | Inflammatory Eye Diseases |
| | Cancers |
| *SDF-1β, IP-10, Mig,* IL-8, ENA-78, *GROα* | Glioma |
| MCP-1, 3, and 4, RANTES, *SDF-1β* | Breast |
| MCP-1, *IL-8, ENA-78* | Lung |

Italicized ligands are α or CXC chemokine family members the others are β or other chemokine family members.
The ligands indicated can be used in combinations for the treatment of the indicated diseases.
Combination treatment may also be achieved by using molecules composed of two or more, such as two different chemokines attached at either end of a toxin moiety. In that case these dual chemokine fusions would preferably include one ligand from each of α and β chemokines family.

Amino acid sequences of exemplary chemokine receptor targeting agents (ligands) for incorporation in the conjugates provided herein are set forth, in Table 3.

TABLE 3

Exemplary amino Acid Sequences of Ligands

| Ligand* | Sequence | SEQ ID |
|---|---|---|
| Eotaxin | GPASVPTTCCFNLANRKIPLQRLESYRRITSGKCPQK AVIFKTKLAKDICADPKKKWVQDSMKYLDQKSPTPKP | 13 |
| GCP-2 | GPVSAVLTELRCTCLRVTLRVNPKTIGKLQVFPAGPQ CSKVEVVASLKNGKQVCLDPEAPFLKKVIQKILDSGN KKN | 14 |
| GM-CSF | APARSPSPSTQPWEHVNAIQEARRLLNLSRDTAAEMN ETVEVISEMFDLQEPTCLQTRLELYKQGLRGSLTKLK GPLTMMASHYKQHCPPTPETSCATQIITFESFKENLK DFLLVIPFDCWEPVQE | 15 |
| GRO-1α | ASVATELRCQCLQTLQGIHPKNIQSVNVKSPGPHCAQ TEVIATLKNGRKACLNPASPIVKKIIEKMLNSDKSN | 16 |
| I-309 | KSMQVPFSRCCFSFAEQEIPLRAILCYRNTSSICSNE GLIFKLKRGKEACALDTVGWVQRHRKMLRHCPSKRK | 17 |
| IL-3 | APMTQTTPLKTSWVNCSNMIDEIITHLKQPPLPLLDF NNLNGEDQDILMENNLRRPNLEAFNRAVKSLQNASAI ESILKNLLPCLPLATAAPTRHPIHIKDGDWNEFRRKL TFYLKTLENAQAQQTTLSLAIF | 18 |
| IL-8 | AVLPRSAKELRCQCIKTYSKPFHPKFIKELRVIESGP HCANTEIIVKLSDGRELCLDPKENWVQRVVEKFLKRA ENS | 19 |
| MCP-1 | QPDAINAPVTCCYNFTNRKISVQRLASYRRITSSKCP KEAVIFKTIVAKEICADPKQKWVQDSMDHLDKQTQTP KT | 20 |
| MCP-2 | QPDSVSIPITCCFNVINRKIPIQRLESYTRITNIQCP KEAVIFKTKRGKEVCADPKERWVRDSMKHLDQIFQNL KP | 21 |
| MCP-3 | QPVGINTSTTCCYRFINKKIPKQRLESYRRTTSSHCP REAVIFKTKLDKEICADPTQKWVQDFMKHLDKKTQTP KL | 22 |
| MCP-4 | QPDALNVPSTCCFTFSSKKISLQRLKSYVITTSRCPQ KAVIFRTKLGKEICADPKEKWVQNYMKHLGRKAHTLK T | 23 |

TABLE 3-continued

Exemplary amino Acid Sequences of Ligands

| Ligand* | Sequence | SEQ ID |
|---|---|---|
| MIP-1α | ASLAADTPTACCFSYTSRQIPQNFIADYFETSSQCSK PGVIFLTKRSRQVCADPSEEWVQKYVSDLELSA | 24 |
| IL-4 | HKCDITLQEIIKTLNSLTEQKTLCTELTVTDIFAASK NTTEKETFCRAATVLRQFYSHHEKDTRCLGATAQQFH RHKQLIRFLKRLDRNLWGLAGLNSCPVKEANQSTLEN FLERLKTIMREKYSKCSS | 25 |
| MIP-2α (GRO-β) | APLATELRCQCLQTLQGIHLKNIQSVKVKSPGPHCAQ TEVIATLKNGQKACLNPASPMVKKIIEKMLKNGKSN | 26 |
| MIP-2β (GRO-γ) | ASVVTELRCQCLQTLQGIHLKNIQSVNVRSPGPHGAQ TEVIATLKNGKKACLNPASPMVQKIIEKILNKGSTN | 27 |
| PARC (MIP-4) | AQVGTNKELCCLVYTSWQIPQKFIVDYSETSPQCPKP GVILLTKRGRQICADPNKKWVQKYISDLKLNA | 28 |
| RANTES | SPYSSDTTPCCFAYIARPLPRAHIKEYFYTSGKCSNP AVVFVTRKNRQVCANPEKKWVREYINSLEMS | 29 |
| MIP-1β | APMGSDPPTACCFSYTARKLPRNFVVDYYETSSLCSQ PAVVFQTKRSKQVCADPSESWVQEYVYDLELN | 30 |
| RAP | YSREKNQPKPSPKRESGEEFRMEKLNQLWEKAQRLHL PPVRLAELHADLKIQERDELAWKKLKLDGLDEDGEKE ARLIRNLNVILAKYGLDGKKDARQVTSNSLSGTQEDG LDDPRLEKLWHKAKTSGKFSGEELDKLWREFLHHKEK VHEYNVLLETLSRTEEIHENVISPSDLSDIKGSVLHS RHTELKEKLRSINQGLDRLRRVSHQGYSTEAEFEEPR VIDLWDLAQSANLTDKELEAFREELKHFEAKIEKHNH YQKQLEIAHEKLRHAESVGDGERVSRSREKHALLEGR TKELGYTVKKHLQDLSGRISRARHNEL | 31 |
| SDF-1 | DGKPVSLSYRCPCRFFESHVARANVKHLKILNTPNCA LQIVARLKNNNRQVCIDPKLKWIQEYLEKALNKRFKM | 32 |
| TARC | ARGTNVGRECCLEYFKGAIPLRKLKTWYQTSEDCSRD AIVFVTVQGRAICSDPNNKRVKNAVKYLQSLERS | 33 |

*All sequences, except for ALP (see, Hromas et al. (1999) Biochem. Biophys. Res. Comm. 258:737–740) and Lungkine (see, Rossi et al. (1999) J. Immunol. 162:5490–5497), set forth in the Table are sequences of the human protein.

A nucleotide sequence for MCP-3 is set forth in SEQ ID No. 67, and nucleotide sequences for mouse ALP and mouse Lungkine are set forth in SEQ ID Nos. 69 and 70, respectfully.

C. Non-Chemokine Cytokines

Conjugates that include non-chemokine cytokines that also bind to cell types that express chemokine receptors or to cell types involved in secondary tissue damage, may also be used in the methods provided herein. Conjugates that include such non-chemokine cytokines have been used for other treatments, such as treatment cancers by targeting the tumor cells. It is intended herein, that cytokines are selected for their ability to bind to chemokine-receptor bearing cells, such as leukocytes that infiltrate tumors, and other cells associated with undesirable inflammatory responses.

The non-chemokine cytokines, colony stimulating factors (CSF), and non-chemokine interleukins (IL) useful as a proteinaceous ligand moiety for targeting to receptors on cells that bear chemokine receptors, include, but are not limited to, endothelial monocyte activating polypeptide II (EMAP-II), granulocyte-macrophage-CSF (GM-CSF), granulocyte-CSF (G-CSF), macrophage-CSF (M-CSF), IL-1, IL-2, IL-3, IL-4, IL-5, IL-6, IL-12, and IL-13 which bind, respectively, to the EMAP-II, GM-CSF, G-CSF, M-CSF, IL-1, IL-2, IL-3, IL-4, IL-5, IL-6, IL-12, IL-13 families of cytokine receptors on cells involved in an inflammatory response, such as on secondary tissue damage-promoting cells.

Examples of other receptor associated proteins that can be used as targeting agents for treating or inhibit pathophysiological conditions associated with inflammatory responses, are those that bind to non-chemokine receptors on and/or activate one or more of the secondary tissue damage-promoting cells, such as, but are not limited to, the acylated LDL scavenger receptors 1 and 2, and the receptors for the LDL, very low density lipoprotein-1 (VLDL-1), VLDL-2, glycoprotein 330/megalin, lipoprotein receptor-related protein (LRP), alpha-2-macroglobulin, sorLA-1. A particularly useful receptor associated protein, as yet unnamed, has a molecular weight of about 39,000 daltons and binds to and modulates the activity proteins, such as members of the low density lipoprotein (LDL)-receptor family.

d. Antibody Ligand Moieties

The proteinaceous ligand moiety in the chemokine receptor targeting conjugate also can be an antibody, particularly a monoclonal antibody, or a functional fragment of thereof, that is specific for a receptor expressed on cells involved in the inflammatory response, particularly a chemokine receptor and receptors expressed on cells that express chemokine receptors. It is preferred that the monoclonal antibody be specific for a chemokine receptor, for example DARC, CXCR-1, CXCR-2, CXCR-3, CXCR-4, CXC4–5, CCR-1, CCR-2A, CCR-2B, CCR-3, CCR-4, CCR-5, CCR-6, CCR-7, CCR-8, CCR-9, XCR1, CX3CR-1, CD97 and other such receptors.

In some instances, the antibody can be specific for a non-chemokine cytokine receptor EMAPII, GM-CSF, G-CSF, M-CSF, IL-1, IL-2, IL-3, IL-4, IL-5, IL-6, IL-12, IL-13. Conjugates containing these antibodies will be used for targeting to cells that express chemokine receptors and also the targeted cytokine receptors or to cells involved in secondary tissue damage that express such non-chemokine receptors.

Non-limiting examples of monoclonal antibodies that can be used in the conjugates include, but are not limited to, MAC-1, MAC-3, ED-1, ED-2, ED-3, and monoclonal antibodies against the following antigens CD5, 14, 15, 19, 22, 34, 35, 54 and 68; OX4, 6, 7, 19 and 42; Ber-H2, BR96, Fib75, EMB-11, HLA-DR, LN-1, and *Ricinus communis* agglutinin-1.

Antibody fragments can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see, e.g., U.S. Pat. Nos. 4,036,945 and 4,331,647, and references contained therein, which patents are hereby incorporated in their entireties by reference; see, also Porter, R. R., *Biochem. J.*, 73: 119–126, 1959). Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments contain an association of $V_H$ and $V_L$ chains. This association may be noncovalent, as described in Inbar et al., *Proc. Nat'l Acad. Sci. USA* 69:2659–62, 1972. Alternatively, the variable chains can be linked by an intermolecular disulfide bond or cross-linked by chemicals such as glutaraldehyde. Preferably, the Fv fragments contain $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow and Filpula, *Methods*, 2: 97–105, 1991; Bird et al., *Science* 242:423–426, 1988; Pack et al., *Bio/Technology* 11:1271–77, 1993; and Ladner et al., U.S. Pat. No. 4,946, 778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, e.g., Larrick et al. *Methods*, 2: 106–10, 1991; and Orlandi et al. *Proc. Natl. Acad. Sci. U.S.A.* 86:3833–3837, 1989).

Antibodies that bind to a chemokine receptor or non-chemokine cytokine receptor on a secondary tissue damage-promoting cell can be prepared using an intact polypeptide or biologically functional fragment containing small peptides of interest as the immunizing antigen. The polypeptide or a peptide used to immunize an animal (derived, for example, from translated cDNA or chemical synthesis) can be conjugated to a carrier protein, if desired. Commonly used carriers that are chemically coupled to the peptide include, but are not limited to, keyhole limpet hemocyanin (KLH), thyroglobulin, bovine serum albumin (BSA), and tetanus toxoid. The coupled peptide is then used to immunize the animal (e.g., a mouse, a rat, or a rabbit).

The preparation of monoclonal antibodies is conventional and well known (see e.g., Kohler et al. *Nature* 256:495–7, 1975; and Harlow et al., in: *Antibodies: a Laboratory Manual*, (Cold Spring Harbor Pub., 1988). Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography and are well known to those of skill in the art (see, for example, *Pharmacia Monoclonal Antibody Purification Handbook* (e.g., Cat. # 18-1037-46)).

Antibodies may also be derived from subhuman primate antibodies. General techniques for raising therapeutically useful antibodies in baboons can be found, for example, in Goldenberg et al., International Patent Publication WO 91/11465 (1991) and Losman et al., *Int. J. Cancer,* 46:310–314, 1990, which are hereby incorporated by reference. Alternatively, a therapeutically useful antibody may be derived from a "humanized" monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Nat'l Acad. Sci. USA* 86:3833–7, 1989, which is hereby incorporated in its entirety by reference. Techniques for producing humanized monoclonal antibodies are described, for example, by Jones et al., *Nature* 321: 522–5, 1986; Riechmann et al., *Nature* 332:323–7, 1988; Verhoeyen et al., *Science* 239:1534–6, 1988; Carter et al., *Proc. Nat'l Acad. Sci. USA* 89:4285–9, 1992; Sandhu, *Crit. Rev. Biotech.* 12:437–62, 1992; and Singer et al., *J. Immunol.* 150:2844–67, 1993, which are hereby incorporated by reference.

It is also possible to use anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

3. Targeted Agents

Targeted agents included any agents whose deliver to a selected cell type that expresses a targeted chemokine receptor is desired. These agents include the cytotoxins, such as shiga A chain, ricin and saporin, drugs of substantially all classes, including, but are not limited to, for example, antibacterial, antivirals, antifungals, anticancer drugs, antimycoplasmals, nucleic acids and any other compounds whose targeted delivery to a cell of interest herein is desired. Drugs for cancer therapy include, in general, alkylating agents, anti-proliferative agents, tubulin binding agents and other such drugs. Other cytotoxic agents include, for example, nucleoside analogs, the anthracycline family of drugs, the vinca drugs, the mitomycins. The drug conjugates so constructed are effective for the usual purposes for which the corresponding drugs are effective, and have superior efficacy because of the ability to transport the drug to the cell where it is of particular benefit, thereby increasing the effective concentration at the site.

a. Cell Toxin Moieties

Cell toxins suitable for use the in the methods and compositions include small molecules, such as DNA cleaving agents, and proteinaceous cell toxins, including, but are not limited to, bacterial, fungal, plant, insect, snake and spider toxins.

Amino acid sequences of exemplary cell toxins contemplated for incorporation in the conjugates provided herein are set forth in Table 4.

TABLE 4

Exemplary Amino Acid Sequences of Toxins

| Toxin | Sequence | SEQ ID |
|---|---|---|
| Bryodin | DVSFRLSGATTTSYGVFIKNLREALPYERKVY NIPLLRSSISGRYTLLHLTNYADETISVAVDV | 34 |

TABLE 4-continued

Exemplary Amino Acid Sequences of Toxins

| Toxin | Sequence | SEQ ID |
|---|---|---|
| | TNVYIMGYLAGDVSYFFNEASATEAAKFVFKD AKKKVTLPYSGNYERLQTAAGKIRENIPLGLP ALDSAITTLYYYTASSAASALLVLIQSTAESA RYKFIEQQIGKRVDKTFLPSLATISLENNWSA LSKQIQIASTNNGQFESPVVLIDGNNQRVSIT NASARVVTSNIALLLNRNNIA | |
| Saporin-6 | VTSITLDLVNPTAGQYSSFVDKIRNNVKDPNL KYGGTDIAVIPPSKEKFLRINFQSSRGTVSLG LKRDNLYVVAYLAMDNTNVNRAYYFRSEITSA ESTALFPEATTANQKALEYTEDYQSIEKNAQI TQGDQSRKELGLGIDLLSTSMEAVNKKARVVK DEARFLLIAIQMTAEAARFRYIQNLVIKNFPN KFNSENKVIQFEVNWKKISTAIYGDAKNGVFN KDYDFGFGKVRQVKDLQMGLLMYLGKPKSSNE ANSTVRHYGPLKPTLLIT | 35 |
| Anti-Viral Protein MAP | APTLETIASLDLNNPTTYLSFITNIRTKVADK TEQCTIQKISKTFTQRYSYIDLIVSSTQKITL AIDMADLYVLGYSDIANNKGRAFFFKDVTEAV ANNFFPGATGTNRIKLTFTGSYGDLEKNGGLR KDNPLGIFRLENSIVNIYGKAGDVKKQAKFFL LAIQMVSEAARFKYISDKIPSEKYEEVTVDEY MTALENNWAKLSTAVYNSKPSTTTATKCQLAT SPVTISPWIFKTVEEIKLVMGLLKSS | 36 |
| Shiga Toxin A-Chain | KEFTLDFSTAKTYVDSLNVIRSAIGTPLQTIS SGGTSLLMIDSGTGDNLFAVDVRGIDPEEGRF NNLRLIVERNNLYVTGFVNRTNNVFYRFADFS HVTFPGTTAVTLSGDSSYTTLQRVAGISRTGM QINRHSLTTSYLDLMSHSGTSLTQSVARAMLR FVTVTAEALRFRQIORGFRTTLDDLSGRSYVM TAEDVDLTLNWGRLSSVLPDYHGQDSVRVGRI SFGSINAILGSVALILNCHHHASRVARMASDE FPSMCPADGRVRGITHNKILWDSSTLGAILMR RTISS | 37 |
| Shiga-Like Toxin Subunit A (Verotoxin 2) | MKCILFKWVLCLLLGFSSVSYSREFTIDFSTQ QSYVSSLNSIRTEISTPLEHISQGTTSVSVIN HTPPGSYFAVDIRGLDVYQARFDHLRLIIEQN NLYVAGFVNTATNTFYRFSDFTHISVPGVTTV SMTTDSSYTTLQRVAALERSGMQISRHSLVSS YLALMEFSGNTMTRDASRAVLRFVTVTAEALR FRQIQREFRQALSETAPVYTMTPGDVDLTLNW GRISNVLPEYRGEDGVRVGRISFNNISAILGT VAVILNGHHQGARSVRAVNEESQPECQITGDR PVIKINNTLWESNTAAAFLNRKSQFLYTTGK | 38 |
| Trichosanthin | DVSFRLSGATSSSYGVFISNLRKALPNERKLY DIPLLRSSLPGSQRYALIHLTNYADETISVAI DVTNVYIMGYRAGDTSYFFNEASATEAAKYVF KDAMRKVTLPYSGNYERLQTAAGKIRENIPLG LPALDSAITTLFYYNANSAASALMVLIQSTSE AARYKFIEQQIGKRVDKTFLPSLAIISLENSW SALSKQIQIASTNNGQFESPVVLINAQNQRVT ITNVDAGVVTSNIALLLNRNNMA | 39 |

(1) DNA Cleaving Agents

Examples of DNA cleaving agents suitable for inclusion as the cell toxin in the chimeric ligand-toxin used in practicing the methods include, but are not limited to, anthraquinone-oligopyrrol-carboxamide, benzimidazole, leinamycin; dynemycin A; enediyne; as well as biologically active analogs or derivatives thereof (i.e., those having a substantially equivalent biological activity). Known analogs and derivatives are disclosed, for examples in Islam et al., *J. Med. Chem.* 34 2954–61, 1991; Skibo et al., *J. Med. Chem.* 37:78–92, 1994; Behroozi et al., *Biochemistry* 35:1568–74, 1996; Helissey et al., *Anticancer Drug Res.* 1 1:527–51, 1996; Unno et al., *Chem. Pharm. Bull.* 45:125–33, 1997;

Unno et al., *Bioorg. Med. Chem.*, 5:903–19, 1997; Unno et al., *Bioorg. Med. Chem.*, 5: 883–901, 1997; and Xu et al., *Biochemistry* 37:1890–7, 1998). Other examples include, but are not limited to, endiyne quinone imines (U.S. Pat. No. 5,622,958); 2,2r-bis (2-aminoethyl)-4-4'-bithiazole (Lee et al., *Biochem. Mol. Biol. Int.* 40:151–7, 1996); epilliticine-salen.copper conjugates (Routier et al., *Bioconjug. Chem.*, 8: 789–92, 1997).

(2) Antimetabolites

Examples of antimetabolites useful for inclusion as the cell toxin in the chimeric ligand-toxin include, but are not limited to, 5-fluorouracil, methotrexate, melphalan, duanomycin, doxorubicin, nitrogen mustard and mitomycin c.

(3) Proteinaceous Cell Toxins

Examples of proteinaceous cell toxins useful for incorporation into the chimeric ligand-toxins used in the methods include, but are not limited to, type one and type two ribosome inactivating proteins (RIP). Useful type one plant RIPs include, but are not limited to, dianthin 30, dianthin 32, lychnin, saporins 1–9, pokeweed activated protein (PAP), PAP II, PAP-R, PAP-S, PAP-C, mapalmin, dodecandrin, bryodin-L, bryodin, Colicin 1 and 2, luffin-A, luffin-B, luffin-S, 19K-protein synthesis inhibitory protein (PSI), 15K-PSI, 9K-PSI, alpha-kirilowin, beta-kirilowin, gelonin, momordin, momordin-II, momordin-Ic, MAP-30, alpha-momorcharin, beta-momorcharin, trichosanthin, TAP-29, trichokirin; barley RIP; flax RIP, tritin, corn RIP, Asparin 1 and 2 (Stirpe et al., *Bio/Technology* 10:405–12, 1992). Useful type two RIPs include, but are not limited to, volkensin, ricin, nigrin-b, CIP-29, abrin, modeccin, ebulitin-α, ebulitin-β, ebulitin-γ, vircumin, porrectin, as well as the biologically active enzymatic subunits thereof (Stirpe et al., *Bio/Technology* 10:405–12, 1992; Pastan et al., *Annu. Rev. Biochem.* 61:331–54; Brinkmann and Pastan, *Biochim. et Biophys. Acta* 1198:27–45, 1994; and Sandvig and Van Deurs, *Physiol. Rev.* 76:949–66, 1996).

(4) Bacterial Toxins

Examples of bacterial toxins useful as cell toxins include, but are not limited to, shiga toxin and shiga-like toxins (ie,. toxins that have the same activity or structure), as well as the catalytic subunits and biologically functional fragments thereof. These bacterial toxins are also type two RIPs (Sandvig and Van Deurs, *Physiol. Rev.* 76:949–66, 1996; Armstrong, *J. Infect. Dis.*, 171:1042–5, 1995; Kim et al., *Microbiol. Immunol.* 41:805–8, 1997, and Skinner et al., *Microb. Pathog.* 24:117–22, 1998). Additional examples of useful bacterial toxins include, but are not limited to, *Pseudomonas* exotoxin and Diphtheria toxin (Pastan et al., *Annu. Rev. Biochem.* 61:331–54; and Brinkmann and Pastan, *Biochim. et Biophys. Acta* 1198:27–45, 1994). Truncated forms and mutants of the toxin enzymatic subunits can also be used as a cell toxin moiety (Pastan et al., *Annu. Rev. Biochem.* 61:331–54; Brinkmann and Pastan, *Biochim. et Biophys. Acta* 1198:27–45, 1994; Mesri et al., *J. Biol. Chem.* 268:4852–62, 1993; Skinner et al., *Microb. Pathog.* 24:117–22, 1998; and U.S. Pat. No. 5,082,927). Other targeted agents include, but are not limited to the more then 34 described Colicin family of RNase toxins which include colicins A, B, D, E1–9, cloacin DF13 and the fungal RNase, α-sarcin (Ogawa et al. *Science* 283: 2097–100, 1999; Smarda et al., *Folia Microbiol (Praha)* 43:563–82, 1998; Wool et al., *Trends Biochem. Sci.*, 17: 266–69, 1992).

(5) Porphyrins and Other Light Activated Toxins

Porphyrins are well known light activatable toxins that can be readily cross-linked to proteins (see, e.g., U.S. Pat. No. 5,257,970; U.S. Pat. No. 5,252,720; U.S. Pat. No. 5,238,940; U.S. Pat. No. 5,192,788; U.S. Pat. No. 5,171,749; U.S. Pat. No. 5,149,708; U.S. Pat. No. 5,202,317; U.S. Pat. No. 5,217,966; U.S. Pat. No. 5,053,423; U.S. Pat. No. 5,109,016; U.S. Pat. No. 5,087,636; U.S. Pat. No. 5,028,594; U.S. Pat. No. 5,093,349; U.S. Pat. No. 4,968,715; U.S. Pat. No. 4,920,143 and International Application WO 93/02192).

b. Nucleic Acids for Targeted Delivery

The conjugates provided herein are can also be used to deliver nucleic acids to targeted cells. The nucleic acids include DNA intended to modify the genome of a cell and thereby effect genetic therapy, and DNA and RNA for use as antisense agents. The nucleic acids include antisense RNA, DNA, ribozymes and other oligonucleotides that are intended to be used as antisense agents. The nucleic acids can also include RNA trafficking signals, such as viral packaging sequences (see, e.g., Sullenger et al. (1994) *Science* 262:1566–1569). The nucleic acids also include DNA molecules that encode intact genes or that encode proteins intended to be used in gene therapy.

DNA (or RNA) that may be delivered to a cell to effect genetic therapy includes DNA that encodes tumor-specific cytotoxic molecules, such as tumor necrosis factor, viral antigens and other proteins to render a cell susceptible to anti-cancer agents, and DNA encoding genes, such as the such as the defective gene (CFTR) associated with cystic fibrosis (see, e.g., International Application WO 93/03709, which is based on U.S. application Ser. No. 07/745,900 (now abandoned); and Riordan et al. (1989) *Science* 245:1066–1073), to replace defective genes. Of particular interest herein, for example, would be genes that express CNS growth factors, which could be delivered to cells in the CNS, such as those involved in SCI, and to aid in regeneration of damaged tissue.

Nucleic acids and oligonucleotides for use as described herein can be synthesized by any method known to those of skill in this art (see, e.g., Wo 93/01286, which is based on U.S. application Ser. No. 07/723,454 (now abandoned); U.S. Pat. No. 5,218,088; U.S. Pat. No. 5,175,269; U.S. Pat. No. 5,109,124). Identification of oligonucleotides and ribozymes for use as antisense agents is well within the skill in this art. Selection of DNA encoding genes for targeted delivery for genetic therapy is also well within the level of skill of those in this art. For example, the desirable properties, lengths and other characteristics of such oligonucleotides are well known. Antisense oligonucleotides are designed to resist degradation by endogenous nucleolytic enzymes and include, but are not limited to: phosphorothioate, methylphosphonate, sulfone, sulfate, ketyl, phosphorodithioate, phosphoramidate, phosphate esters, and other such linkages (see, e.g., Agrawal et al. (1987) *Tetrehedron Lett.* 28:3539–3542; Miller et al. (1971) *J. Am. Chem. Soc.* 93:6657–6665; Stec et al. (1985) *Tetrehedron Lett.* 26:2191–2194; Moody et al. (1989) *Nucl. Acids Res.* 17:4769–4782; Letsinger et al. (1984) *Tetrahedron* 40:137–143; Eckstein (1985) *Annu. Rev. Biochem.* 54:367–402; Eckstein (1989) *Trends Biol. Sci.* 14:97–100; Stein (1989) In: *Oligodeoxynucleotides. Antisense Inhibitors of Gene Expression*, Cohen, ed., Macmillan Press, London, pp. 97–117; Jager et al. (1988) *Biochemistry* 27:7237–7246).

(1) Antisense Nucleotides, Including: Antisense Oligonucleotides; Triplex Molecules; Dumbbell Oligonucleotides; DNA; Extracellular Protein Binding Oligonucleotides; and Small Nucleotide Molecules Antisense nucleotides are oligonucleotides that specifically bind to mRNA that has complementary sequences, thereby preventing translation of the mRNA (see, e.g., U.S. Pat. No. 5,168,053 to Altman et al. U.S. Pat. No. 5,190,931 to Inouye, U.S. Pat. No. 5,135,917 to Burch; U.S. Pat. No.

5,087,617 to Smith and Clusel et al. (1993) *Nucl. Acids Res.* 21:3405–3411, which describes dumbbell antisense oligonucleotides). Triplex molecules refer to single DNA strands that target duplex DNA and thereby prevent transcription (see, e.g., U.S. Pat. No. 5,176,996 to Hogan et al. which describes methods for making synthetic oligonucleotides that bind to target sites on duplex DNA).

(2) Ribozymes

Ribozymes are RNA constructs that specifically cleave messenger RNA. There are at least five classes of ribozymes that are known that are involved in the cleavage and/or ligation of RNA chains. Ribozymes can be targeted to any RNA transcript and can catalytically cleave such transcript (see, e.g., U.S. Pat. No. 5,272,262; U.S. Pat. No. 5,144,019; and U.S. Pat. Nos. 5,168,053, 5,180,818, 5,116,742 and 5,093,246 to Cech et al. which described ribozymes and methods for production thereof). Any such ribosome may be linked to the chemokine receptor targeting agent for delivery to chemokine-receptor bearing cells.

The ribozymes may be delivered to the targeted cells as DNA encoding the ribozyme linked to a eukaryotic promoter, such as a eukaryotic viral promoter, generally a late promoter, such that upon introduction into the nucleus, the ribozyme will be directly transcribed. In such instances, the construct will also include a nuclear translocation sequence, generally as part of the targeting agent or as part of a linker in order to render it form suitable for delivering linked nucleic acids to the nucleus.

(3) Nucleic Acids Encoding Therapeutic Products for Targeted Delivery

Among the DNA that encodes therapeutic products contemplated for use is DNA encoding correct copies of defective genes, such as the defective gene (CFTR) associated with cystic fibrosis (see, e.g., International Application WO 93/03709, which is based on U.S. application Ser. No. 07/745,900 (now abandoned); and Riordan et al. (1989) *Science* 245:1066–1073), and anticancer agents, such as tumor necrosis factors, and cytotoxic agents, such as shiga A1 toxin or saporin to chemokine-receptor bearing cells. The conjugate should include an NTS. If the conjugate is designed such that the targeting agent and linked DNA is cleaved in the cytoplasm, then the NTS should be included in a portion of the linker that remains bound to the DNA, so that, upon internalization, the conjugate will be trafficked to the nucleus. The nuclear translocation sequence (NTS) may be a heterologous sequence or a may be derived from the selected chemokine receptor targeting agent. A typical consensus NTS sequence contains an amino-terminal proline or glycine followed by at least three basic residues in a array of seven to nine amino acids (see, e.g., Dang et al. (1989) *J. Biol. Chem.* 264:18019–18023, Dang et al. (1988) *Mol. Cell. Biol.* 8:4048–4058 and Table 2, which sets forth examples of NTSs and regions of proteins that share homology with known NTSs).

(4) Coupling of Nucleic Acids to Proteins

To effect chemical conjugation herein, the targeting agent is linked to the nucleic acid either directly or via one or more linkers. Methods for conjugating nucleic acids, at the 5' ends, 3' ends and elsewhere, to the amino and carboxyl termini and other sites in proteins are known to those of skill in the art (for a review see e.g., Goodchild, (1993) In: *Perspectives in Bioconjugate Chemistry*, Mears, Ed., American Chemical Society, Washington, D.C. pp. 77–99). For example, proteins have been linked to nucleic acids using ultraviolet irradiation (Sperling et al. (1978) *Nucleic Acids Res.* 5:2755–2773; Fiser et al. (1975) *FEBS Lett.* 52:281–283), bifunctional chemicals (Bäumert et al. (1978) *Eur. J. Biochem.* 89:353–359; and Oste et al. (1979) *Mol. Gen. Genet.* 168:81–86) photochemical cross-linking (Vanin et al. (1981) *FEBS Lett.* 124:89–92; Rinke et al. (1980) *J. Mol. Biol.* 137:301–314; Millon et al. (1980) *Eur. J. Biochem.* 110:485–454).

In particular, the reagents (N-acetyl-N'-(p-glyoxylylbenzolyl)cystamine and 2-iminothiolane have been used to couple DNA to proteins, such as $\alpha_2$macroglobulin ($\alpha_2$M) via mixed disulfide formation (see, Cheng et al. (1983) *Nucleic Acids Res.* 11:659–669). N-acetyl-N'-(p-glyoxylylbenzolyl) cystamine reacts specifically with nonpaired guanine residues and, upon reduction, generates a free sulfhydryl group. 2-Iminothiolane reacts with proteins to generate sulfhydryl groups that are then conjugated to the derivatized DNA by an intermolecular disulfide interchange reaction. Any linkage may be used provided that, upon internalization of the conjugate the targeted nucleic acid is active. Thus, it is expected that cleavage of the linkage may be necessary, although it is contemplated that for some reagents, such as DNA encoding ribozymes linked to promoters or DNA encoding therapeutic agents for delivery to the nucleus, such cleavage may not be necessary.

Thiol linkages can be readily formed using heterbiofunctional reagents. Amines have also been attached to the terminal 5' phosphate of unprotected oligonucleotides or nucleic acids in aqueous solutions by reacting the nucleic acid with a water-soluble carbodiimide, such as 1-ethyl-3' [3-dimethylaminopropyl]carbodiimide (EDC) or N-ethyl-N' (3-dimethylaminopropylcarbodiimidehydrochloride (EDCI), in imidazole buffer at pH 6 to produce the 5'phosphorimidazolide. Contacting the 5'phosphorimidazolide with amine-containing molecules and ethylenediamine, results in stable phosphoramidates (see, e.g., Chu et al. (1983) *Nucleic Acids Res.* 11:6513–6529; and WO 88/05077 in which the U.S. is designated). In particular, a solution of DNA is saturated with EDC, at pH 6 and incubated with agitation at 4° C. overnight. The resulting solution is then buffered to pH 8.5 by adding, for example about 3 volutes of 100 mM citrate buffer, and adding about 5 μg—about 20 μg of a chemokine receptor targeting agent, and agitating the resulting mixture at 4° C. for about 48 hours. The unreacted protein may be removed from the mixture by column chromatography using, for example, SEPHADEX G75 (Pharmacia) using 0.1 M ammonium carbonate solution, pH 7.0 as an eluting buffer. The isolated conjugate may be lyophilized and stored until used.

U.S. Pat. No. 5,237,016 provides methods for preparing nucleotides that are bromacetylated at their 5' termini and reacting the resulting oligonucleotides with thiol groups. Oligonucleotides derivatized at their 5'-termini bromoacetyl groups can be prepared by reacting 5'-aminohexyl-phosphoramidate oligonucleotides with bromoacetic acid-N-hydroxysuccinimide ester as described in U.S. Pat. No. 5,237,016. U.S. Pat. No. 5,237,016 also describes methods for preparing thiol-derivatized nucleotides, which can then be reacted with thiol groups on the selected growth factor. Briefly, thiol-derivatized nucleotides are prepared using a 5'-phosphorylated nucleotide in two steps: (1) reaction of the phosphate group with imidazole in the presence of a diimide and displacement of the imidazole leaving group with cystamine in one reaction step; and reduction of the disulfide bond of the cystamine linker with dithiothreitol (see, also, Orgel et al. ((1986) *Nucl. Acids Res.* 14:651, which describes a similar procedure). The 5'-phosphorylated starting oligonucleotides can be prepared by methods known to those of skill in the art (see, e.g., Maniatis et al. (1982) Molecular Cloning: *A Laboratory Manual*, Cold Spring Harbor Laboratory, New York, p. 122).

The antisense oligomer or nucleic acid, such as a methylphosphonate oligonucleotide (MP-oligomer), may be derivatized by reaction with SPDP or SMPB. The resulting MP-oligomer may be purified by HPLC and then coupled to the chemokine receptor targeting agent. The MP-oligomer (about 0.1 µM) is dissolved in about 40–50 µl of 1:1 acetonitrile/water to which phosphate buffer (pH 7.5, final concentration 0.1 M) and a 1 mg MP-oligomer in about 1 ml phosphate buffered saline is added. The reaction is allowed to proceed for about 5–10 hours at room temperature and is then quenched with about 15 µL 0.1 iodoacetamide. The conjugates can be purified on heparin sepharose Hi Trap columns (1 ml, Pharmacia) and eluted with a linear or step gradient. The conjugate should elute in 0.6 M NaCl.

(5) Summary

Thus, targeted agents include any agents for which delivery into targeted cells is desired in order to effect a change in the cell' proliferative ability, genome, to effect cell death, to inhibit proliferation and for other therapeutic purposes. Targeted agents include, but are not limited to, toxins, nucleic acids and therapeutic moieties. Toxins include DNA cleaving agents, antimetabolites, bacterial, plant, insect, snake and spider toxins, and ribosome incactivating protines, including type one and type two RIPs and functional fragments thereof. Exemplary DNA cleaving agents include, but are not limited to, anthraquinone-oligopyrrolcarboxamide, benzimidazole, leinamycin, dynemycin A, enediyne, endiyne quinone imines, 2,2r-bis(2-aminoethyl)-4-4'-bithiazole, epillicitine-salen.copper conjugates, and functional analogs or derivatives thereof; antimetabolites include, but are not limited to 5-fluorouracil, methotrexate, melphalan, daunomycin, doxorubicin, nitrogen mustard, mitomycin c, and functional analogs or derivatives thereof; type one RIPs include, but are not limited to, dianthin 30, dianthin 32, lychnin, saporin-1, saporin-2, saporin-3, saporin-4, saporin-5, saporin-6, saporin-7, saporin-8 and saporin-9, PAP, PAP II, PAP-R, PAP-S, PAP-C, mapalmin, dodecandrin, bryodin-L, bryodin, colicin-1, colicin-2, luffin-A, luffin-B, luffin-S, 19K-PSI, 15K-PSI, 9K-PSI, alpha-kirilowin, beta-kirilowin, gelonin, momordin, momordin-II, momordin-Ic, MAP-30, alpha-momorcharin, beta-momorcharin, trichosanthin, TAP-29, trichokirin, barley RIP, tritin, flax RIP, corn RIP, asparin-1, and asparin-2; type two RIPs, include, but are not limited to, the catalytic subunit thereof, or a biologically functional subunit or fragment thereof, volkensin, ricin, nigrin-CIP-29, abrin, vircumin, modeccin, ebulitin-α, ebulitin-β, ebultin-γ, and porrectin; bacterial toxins include, but are not limited to, exotoxin, Diphtheria toxin, shiga toxin, shiga-like toxins, catalytic subunits thereof, and biologically functional fragments thereof.

4. Linker Moieties

In preparing the conjugates provided herein, the cell toxin is linked either directly or indirectly to the chemokine receptor targeting agent in the chimeric ligand toxin by any method presently known in the art for attaching two moieties, so long as the attachment of the linker moiety to the proteinaceous ligand does not substantially impede binding of the proteinaceous ligand to the target cell, that is, to a receptor on the target cell, or substantially impede the internalization or metabolism of the ligand-toxin so as to lower the toxicity of the cell toxin for the target cell. The linkage may be any type of linkage, including, but are not limited to, ionic and covalent bonds, and any other sufficiently stable association, whereby the targeted agent will be internalized by a cell to which the conjugated is targeted.

The chemokine receptor targeting agent is optionally linked to the targeted agent via one or more linkers. The linker moiety is selected depending upon the properties desired. For example, the length of the linker moiety can be chosen to optimize the kinetics and specificity of ligand binding, including any conformational changes induced by binding of the ligand to a target receptor. The linker moiety should be long enough and flexible enough to allow the proteinaceous ligand moiety and the target cell receptor to freely interact. If the linker is too short or too stiff, there may be steric hindrance between the proteinaceous ligand moiety and the cell toxin. If the linker moiety is too long, the cell toxin may be proteolysed in the process of production, or may not deliver its toxic effect to the target cell effectively. These chemical linkers can be attached to purified ligands using numerous protocols known in the art, such as those described in Examples 1 and 2 (see Pierce Chemicals "Solutions, Cross-linking of Proteins: Basic Concepts and Strategies," Seminar #12, Rockford, Ill.).

Exemplary Linkers

Any linker known to those of skill in the art may be used herein. Generally a different set of linkers will be used in conjugates that are fusion proteins from linkers in chemically-produced conjugates. Linkers and linkages that are suitable for chemically linked conjugates include, but are not limited to, disulfide bonds, thioether bonds, hindered disulfide bonds, and covalent bonds between free reactive groups, such as amine and thiol groups. These bonds are produced using heterobifunctional reagents to produce reactive thiol groups on one or both of the polypeptides and then reacting the thiol groups on one polypeptide with reactive thiol groups or amine groups to which reactive maleimido groups or thiol groups can be attached on the other. Other linkers include, acid cleavable linkers, such as bismaleimideothoxy propane, acid labile-transferrin conjugates and adipic acid diihydrazide, that would be cleaved in more acidic intracellular compartments; cross linkers that are cleaved upon exposure to UV or visible light and linkers, such as the various domains, such as $C_H1$, $C_H2$, and $C_H3$, from the constant region of human $IgG_1$ (see, Batra et al. (1993) *Molecular Immunol.* 30:379–386). In some embodiments, several linkers may be included in order to take advantage of desired properties of each linker. Chemical linkers and peptide linkers may be inserted by covalently coupling the linker to the chemokine receptor targeting agent (TA) and the targeted agent. The heterobifunctional agents, described below, may be used to effect such covalent coupling. Peptide linkers may also be linked by expressing DNA encoding the linker and TA, linker and targeted agent, or linker, targeted agent and TA as a fusion protein. Flexible linkers and linkers that increase solubility of the conjugates are contemplated for use, either alone or with other linkers are also contemplated herein.

a. Heterobifunctional Cross-Linking Reagents

Numerous heterobifunctional cross-linking reagents that are used to form covalent bonds between amino groups and thiol groups and to introduce thiol groups into proteins, are known to those of skill in this art (see, e.g., the PIERCE CATALOG, ImmunoTechnology Catalog & Handbook, 1992–1993, which describes the preparation of and use of such reagents and provides a commercial source for such reagents; see, also, e.g., Cumber et al. (1992) *Bioconjugate Chem.* 3:397–401; Thorpe et al. (1987) *Cancer Res.* 47:5924–5931; Gordon et al. (1987) *Proc. Natl. Acad Sci.* 84:308–312; Walden et al. (1986) *J. Mol. Cell Immunol.*

2:191–197; Carlsson et al. (1978) *Biochem. J.* 173: 723–737; Mahan et al. (1987) *Anal. Biochem.* 162:163–170; Wawryznaczak et al. (1992) *Br. J. Cancer* 66:361–366; Fattom et al. (1992) *Infection &Immun.* 60:584–589). These reagents may be used to form covalent bonds between the targeting agent, the chemokine, and the targeted agent. These reagents include, but are not limited to: N-succinimidyl-3-(2-pyridyldithio)propionate (SPDP; disulfide linker); sulfosuccinimidyl 6-[3-(2-pyridyidithio)propionamido]hexanoate (sulfo-LC-SPDP); succinimidyloxycarbonyl-α-methyl benzyl thiosulfate (SMBT, hindered disulfate linker); succinimidyl 6-[3-(2-pyridyidithio)propionamido]hexanoate (LC-SPDP); sulfosuccinimidyl 4-(N-maleimidomethyl)cyclohexane-1-carboxylate (sulfo-SMCC); succinimidyl 3-(2-pyridyidithio)butyrate (SPDB; hindered disulfide bond linker); sulfosuccinimidyl 2-(7-azido-4-methylcoumarin-3-acetamide)ethyl-1,3'-dithiopropionate (SAED); sulfo-succinimidyl 7-azido-4-methylcoumarin-3-acetate (SAMCA); sulfosuccinimidyl 6-[alpha-methyl-alpha-(2-pyridyldithio)toluamido]hexanoate (sulfo-LC-SMPT); 1,4-di-[3'-(2'-pyridyldithio)propionamido]butane (DPDPB); 4-succinimidyloxycarbonyl-α-methyl-α-(2-pyridylthio) toluene (SMPT, hindered disulfate linker);sulfo-succinimidyl6[α-methyl-α-(2-pyridyldithio)toluamido]hexanoate (sulfo-LC-SMPT); m-maleimidobenzoyl-N-hydroxysuccinimide ester (MBS); m-maleimidobenzoyl-N-hydroxysulfo-succinimide ester (sulfo-MBS); N-succinimidyl(4-iodoacetyl)aminobenzoate (SIAB; thioether linker); sulfosuccinimidyl(4-iodoacetyl)amino benzoate (sulfo-SIAB); succinimidyl4(p-maleimidophenyl)butyrate (SMPB); sulfosuccinimidyl-4-(p-maleimidophenyl)butyrate (sulfo-SMPB); azidobenzoyl hydrazide (ABH).

Other heterobifunctional cleavable cross-linkers include, N-succinimidyl (4-iodoacetyl)-aminobenzoate; sulfosuccinimydil (4-iodoacetyl)-aminobenzoate; 4-succinimidyl-oxycarbonyl-a-(2-pyridyidithio)-toluene; sulfosuccinimidyl-6-[a-methyl-a-(pyridyidithiol)-toluamido]hexanoate; N-succinimidyl-3-(-2-pyridyldithio)-proprionate; succinimidyl 6[3(-(-2-pyridyidithio)-proprionamido]hexanoate; sulfosuccinimidyl 6[3(-(-2-pyridyidithio)-propionamido]hexanoate; 3-(2-pyridyidithio)-propionyl hydrazide, Ellman's reagent, dichlorotriazinic acid, S-(2-thiopyridyl)-L-cysteine. Further exemplary bifunctional linking compounds are disclosed in U.S. Pat. Nos. 5,349,066. 5,618,528, 4,569,789, 4,952,394, and 5,137,877.

b. Acid Cleavable, Photocleavable and Heat Sensitive Linkers

Acid cleavable linkers, photocleavable and heat sensitive linkers may also be used, particularly where it may be necessary to cleave the targeted agent to permit it to be more readily accessible to reaction. Acid cleavable linkers include, but are not limited to, bismaleimideothoxy propane; and adipic acid dihydrazide linkers (see, e.g., Fattom et al. (1992) *Infection &Immun.* 60:584–589) and acid labile transferrin conjugates that contain a sufficient portion of transferrin to permit entry into the intracellular transferrin cycling pathway (see, e.g., Welhöner et al. (1991) *J. Biol. Chem.* 266:4309–4314).

Photocleavable linkers are linkers that are cleaved upon exposure to light (see, e.g., Goldmacher et al. (1992) *Bioconj. Chem.* 3:104–107, which linkers are herein incorporated by reference), thereby releasing the targeted agent upon exposure to light. Photocleavable linkers that are cleaved upon exposure to light are known (see, e.g., Hazum et al. (1981) in *Pept., Proc. Eur. Pept. Symp.*, 16th, Brunfeldt, K (Ed), pp. 105–110, which describes the use of a nitrobenzyl group as a photocleavable protective group for cysteine; Yen et al. (1989) *Makromol. Chem* 190:69–82, which describes water soluble photocleavable copolymers, including hydroxypropylmethacrylamide copolymer, glycine copolymer, fluorescein copolymer and methylrhodamine copolymer; Goldmacher et al. (1992) *Bioconj. Chem.* 3:104–107, which describes a cross-linker and reagent that undergoes photolytic degradation upon exposure to near UV light (350 nm); and Senter et al. (1985) *Photochem. Photobiol* 42:231–237, which describes nitrobenzyloxycarbonyl chloride cross linking reagents that produce photocleavable linkages), thereby releasing the targeted agent upon exposure to light. Such linkers would have particular use in treating dermatological or ophthalmic conditions that can be exposed to light using fiber optics. After administration of the conjugate, the eye or skin or other body part can be exposed to light, resulting in release of the targeted moiety from the conjugate. Such photocleavable linkers are useful in connection with diagnostic protocols in which it is desirable to remove the targeting agent to permit rapid clearance from the body of the animal.

c. Other Linkers for Chemical Conjugation

Other linkers, include trityl linkers, particularly, derivatized trityl groups to generate a genus of conjugates that provide for release of therapeutic agents at various degrees of acidity or alkalinity. The flexibility thus afforded by the ability to preselect the pH range at which the therapeutic agent will be released allows selection of a linker based on the known physiological differences between tissues in need of delivery of a therapeutic agent (see, e.g., U.S. Pat. No. 5,612,474). For example, the acidity of tumor tissues appears to be lower than that of normal tissues.

d. Peptide Linkers

The linker moieties can be peptides. Peptide linkers can be employed in fusion proteins and also in chemically linked conjugates. The peptide typically a has from about 2 to about 60 amino acid residues, for example from about 5 to about 40, or from about 10 to about 30 amino acid residues. The length selected will depend upon factors, such as the use for which the linker is included.

The proteinaceous ligand binds with specificity to a receptor(s) on one or more of the target cell(s) and is taken up by the target cell(s). In order to facilitate passage of the chimeric ligand-toxin into the target cell, it is presently preferred that the size of the chimeric ligand-toxin be no larger than can be taken up by the target cell of interest. Generally, the size of the chimeric ligand-toxin will depend upon its composition. In the case where the chimeric ligand toxin contains a chemical linker and a chemical toxin (i.e., rather than proteinaceous one), the size of the ligand toxin is generally smaller than when the chimeric ligand-toxin is a fusion protein. Peptidic linkers can conveniently be encoded by nucleic acid and incorporated in fusion proteins upon expression in a host cell, such as *E. coli*.

Peptide linkers are advantageous when the chemokine receptor targeting agent is proteinaceous. For example, the linker moiety can be a flexible spacer amino acid sequence, such as those known in single-chain antibody research. Examples of such known linker moieties include, but are not limited to, GGGGS (SEQ ID NO:1), (GGGGS)$_n$ (SEQ. ID NO:2), GKSSGSGSESKS (SEQ ID NO:3), GSTSGSGKS-SEGKG (SEQ. ID NO:4), GSTSGSGKSSEGSGSTKG (SEQ ID NO:5), GSTSGSGKSSEGKG (SEQ ID NO:6), GSTSGSGKPGSGEGSTKG (SEQ ID NO:7), EGKSSGSGSESKEF (SEQ ID NO:8), SRSSG (SEQ. ID NO:9), SGSSC (SEQ ID NO:10). A Diphtheria toxin trypsin sensitive linker having the sequence AMGRSGGGCAG-NRVGSSLSCGGLNLQAM (SEQ ID NO:11) is also useful.

Alternatively, the peptide linker moiety can be VM or AM, or have the structure described by the formula: AM(G$_2$ $_{to}$ $_4$S)$_x$AM wherein X is an integer from 1 to 11 (SEQ ID NO:12). Additional linking moieties are described, for example, in Huston et al., *Proc. Natl. Acad. Sci. U.S.A.* 85:5879–5883, 1988; Whitlow, M., et al., *Protein Engineering* 6:989–995, 1993; Newton et al., *Biochemistry* 35:545–553, 1996; A. J. Cumber et al., *Bioconj. Chem.* 3:397–401, 1992; Ladurner et al., *J. Mol. Biol.* 273:330–337, 1997; and U.S. Pat. No. 4,894,443.

Other linkers include, but are not limited to: enzyme substrates, such as cathepsin B substrate, cathepsin D substrate, trypsin substrate, thrombin substrate, subtilisin substrate, Factor Xa substrate, and enterokinase substrate; linkers that increase solubility, flexibility, and/or intracellular cleavability include linkers, such as (gly$_m$ser)$_n$ and (ser$_m$gly)$_n$, in which m is 1 to 6, preferably 1 to 4, more preferably 2 to 4, and n is 1 to 30, preferably 1 to 10, more preferably 1 to 4 (see, e.g., International PCT application No. WO 96/06641, which provides exemplary linkers for use in conjugates). In some embodiments, several linkers may be included in order to take advantage of desired properties of each linker.

e. Summary of Linkers

In summary, linkers can be any moiety suitable to associate a targeted agent and a chemokine receptor targeting agent. Such agents include, but are not limited to, peptidic linkages, amino acid and peptide linkages, typically containing between one and about 60 amino acids, more generally between about 10 and 30 amino acids, chemical linkers, such as heterobifunctional cleavable cross-linkers, including but are not limited to, N-succinimidyl(4-iodoacetyl)-aminobenzoate, sulfosuccinimydil (4-iodoacetyl)-aminobenzoate, 4-succinimidyl-oxycarbonyl-a-(2-pyridyidithio)toluene, sulfosuccinimidyl-6-[a-methyl-a-(pyridyidithiol)-toluamido]hexanoate, N-succinimidyl-3-(-2-pyridyldithio)-proprionate, succinimidyl 6[3(-(-2-pyridyldithio)-proprionamido]hexanoate, sulfosuccinimidyl 6[3(-(-2-pyridyldithio)-propionamido]hexanoate, 3-(2-pyridyldithio)-propionyl hydrazide, Ellman's reagent, dichlorotriazinic acid, and S-(2-thiopyridyl)-L-cysteine. Other linkers include, but are not limited to peptides and other moieties that reduce stearic hindrance between the targeted agent and chemokine receptor targeting agent, intracellular enzyme substrates, linkers that increase the flexibility of the conjugate, linkers that increase the solubility of the conjugate, linkers that increase the serum stability of the conjugate, photocleavable linkers and acid cleavable linkers.

D. Preparation of Conjugates

Conjugates with linked targeted agents can be prepared either by chemical conjugation, recombinant DNA technology, or combinations of recombinant expression and chemical conjugation. The methods herein are exemplified with particular reference to chemokines and shiga-A1 or saporin. It is understood, however, that the same methods may be used to prepare and use conjugates of any targeting agent with any targeted agent, such as a RIP, a nucleic acid or any other targeted agent either directly or via linkers as described herein. The targeting agent and targeted agent may be linked in any orientation and more than one targeting agent and/or targeted agent may be present in a conjugate.

1. Production of Fusion Proteins

The chemokine ligand and/or chimeric fusion proteins can be produced by well known techniques of protein synthesis if the amino acid sequence of the chemokine and/or cell toxin are known, or the sequence can first be determined by well known methods described below, if necessary. Some of the ligand genes are now commercially available. An advantage of obtaining commercially available genes is that they have generally been optimized for expression in *E. coli*. A polynucleotide encoding a protein, peptide or polynucleotide of interest, can be produced using DNA synthesis technology. Methods for obtaining the DNA encoding an unavailable gene and expressing a gene product therefrom are described below and are illustrated in Example 1 herein.

The chimeric ligand-toxin, including a chemokine ligand, a proteinaceous linker moiety, and a proteinaceous cell toxin can also be produced as a fusion protein having the general structure illustrated in FIG. 1. The fusion protein is produced using well known techniques wherein a host cell is transfected with an expression vector containing expression control sequences operably linked to a nucleic acid sequence coding for the expression of the fusion protein (*Molecular Cloning A Laboratory Manual*, Sambrook et al., eds., 2nd Ed., Cold Spring Harbor Laboratory, N.Y., 1989).

Table 5 below illustrates the theoretical size and pI of representative chemokine receptor targeting ligand conjugates and also conjugates that contain non-chemokine cytokines that bind to cell populations that express chemokine receptors. Conjugates with non-chemokine cytokines, such as IL-4-containing conjugates, have previously been used to provided targeted delivery to tumor cells, but have not been used to treat pathological inflammatory conditions such as secondary tissue damage.

TABLE 5

Theoretical Molecular Weights and Isoelectric Points of free Human Ligands and Ligand-Saporin 6 fusion proteins (linked by an ALA-MET Linker)

| Ligand | Free Ligand | | Ligand-AM-Saporin-6 | |
|---|---|---|---|---|
| | Theoretical pI | Theoretical Mol. Wt.(daltons) | Theoretical pI | Theoretical Mol. Wt.(daltons) |
| (A) | | | | |
| MCP-1 | 9.39 | 8,685 | 9.44 | 37,371 |
| MCP-2 | 9.49 | 8,914 | 9.47 | 37,600 |
| MCP-3 | 9.74 | 8,956 | 9.56 | 37,642 |
| MCP-4 | 9.98 | 8,599 | 9.64 | 37,285 |
| MIP-1α | 4.77 | 7,788 | 8.93 | 36,473 |
| MIP-1β | 4.77 | 7,819 | 8.91 | 36,505 |
| RANTES | 9.24 | 7,851 | 9.40 | 36,537 |
| EOTAXIN | 9.92 | 8,365 | 9.63 | 37,051 |
| (B) | | | | |
| SDF-1α | 9.97 | 8,698 | 9.63 | 37,384 |
| IL-8 | 9.24 | 8,922 | 9.43 | 39,999 |
| GROα | 9.51 | 7,865 | 9.51 | 38,932 |
| GCP-2 | 9.75 | 8,312 | 9.57 | 39,382 |
| (C) | | | | |
| RAP | 6.88 | 37,772 | 8.86 | 66,457 |
| (D) | | | | |
| AM-Sap-6 | | | 9.40 | 28,704 |
| (E) | | | | |
| IL-3 | 7.05 | 15,091 | 9.19 | 43,777 |
| IL-4 | 9.26 | 14,963 | 9.39 | 43,649 |
| GM-CSF | 5.21 | 14,477 | 8.47 | 43,163 |

KEY:
(A) C-C Chemokines;
(B) CXC Chemokines;
(C) Receptor Associated Protein to the LDL-Receptor;
(D) Toxin plus linker;
(E) Non-chemokine cytokines that target to cells associated with the inflammatory responses described herein.

a. Plasmids and Host Cells for Expression of Constructs Encoding Chemokine Receptor Targeting Agent Peptides, Conjugates, Linkers, Fusion Protesins and Peptide Targeted Agents The construction of expression vectors and the expression of genes in transfected cells involves the use of molecular cloning techniques also well known in the art (see, e.g., *Molecular Cloning—A Laboratory Manual*, Cold Spring Harbor Laboratory, Sambrook et al., eds., 2nd Ed., Cold Spring Harbor, N.Y., (1989) and *Current Protocols in Molecular Biology*, Vols. 1 and 2, Current Protocols in Molecular Biology, Vols. 1 and 2, Ausubel, et al. Eds., Current Protocols, 1987–1994; John Wiley and Sons, Inc., 1994–1999; Cloning Vectors—A Laboratory Manual, Vols I–IV, Pouwels, et al., Eds., and Supplements therein, Elsebier, N.Y., 1995–1998). Such methods include construction of expression vectors containing a fusion protein coding sequence and appropriate transcriptional/translational control signals as illustrated in FIGS. 2–5. These methods also include in vitro recombinant DNA techniques, synthetic techniques and in vivo recombination/genetic recombination. (see, for example, the techniques described in *Molecular Cloning A Laboratory Manual*, Sambrook et al., eds., 2nd Ed., Cold Spring Harbor Laboratory, N.Y., 1989; and *Current Protocols in Molecular Biology*, Vols. 1 and 2, Current Protocols in Molecular Biology, Vols. 1 and 2, Ausubel, et al. Eds., Current Protocols, 1987–1994; John Wiley and Sons, Inc., 1994–1999; Cloning Vectors—A Laboratory Manual, Vols I–IV, Pouwels, et al., Eds., and Supplements therein, Elsebier, N.Y., 1995–1998).

Nucleic acids used to transfect cells with sequences coding for expression of the polypeptide of interest generally will be in the form of an expression vector including expression control sequences operatively linked to a nucleotide sequence coding for expression of the polypeptide. Methods of obtaining stable transfer so that the foreign nucleic acid is continuously maintained in the host, are known in the art. Transformation of a host cell with recombinant DNA may be carried out by conventional techniques as are well known to those skilled in the art. When the host is prokaryotic, such as *E. coli*, competent cells that are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation. Preferably, a prokaryotic host is utilized as the host cell.

When the host is eukaryotic, methods of transfection of DNA include formation of calcium phosphate co-precipitates, and conventional mechanical procedures, such as microinjection, electroporation, and insertion of a plasmid encased in liposomes. Another method is to use a eukaryotic viral vector, such as simian virus 40 (SV40), bovine papilloma virus, or recombinant autonomous parvovirus vector (as described in U.S. Pat. No. 5,585,254) to transiently infect or transform eukaryotic cells and express the protein. (*Eukaryotic Viral Vectors*, Cold Spring Harbor Laboratory, Gluzman ed., 1982). Eukaryotic cells can also be cotransfected with DNA sequences encoding the fusion polypeptide and a second foreign DNA molecule encoding a selectable phenotype, such as the Herpes simplex thymidine kinase gene.

Eukaryotic expression systems can allow for further post-translational modifications of expressed mammalian proteins to occur. Such cells possess the cellular machinery for post-translational processing of the primary transcript, if so desired. Such modifications include, but are not limited to, glycosylation, phosphorylation, farnesylation. Such host cell lines may include but are not limited to CHO, VERO, BHK, HeLa, COS, MDCK, Jurkat, HEK-293, and WI38.

Techniques for the isolation and purification of expressed either by prokaryotes or eukaryotes may be effected by any conventional means such as, for example, preparative chromatographic separations and immunological separations such as those involving the use of monoclonal or polyclonal antibodies or antigen.

A variety of host-expression vector systems may be used to express the fusion protein coding sequence. These include, but are not limited to, microorganisms, such as bacteria, transformed with recombinant bacteriophage DNA, plasmid DNA, or cosmid DNA expression vectors containing a fusion protein coding sequence; yeast transformed with recombinant yeast expression vectors containing the fusion protein coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing a fusion protein coding sequence; insect cell systems infected with recombinant virus expression vectors (e.g., baculovirus) containing a fusion protein coding sequence; or animal cell systems infected with recombinant virus expression vectors (e.g., retroviruses, adenovirus, vaccinia virus) containing a fusion protein coding sequence, or transformed animal cell systems engineered for stable expression.

Depending on the host/vector system utilized, any of a number of suitable transcription and translation elements, including constitutive and inducible promoters, transcription enhancer elements, transcription terminators, etc. may be used in the expression vector (see, e.g., Bitter et al., *Methods in Enzymology* 153:516–544, 1987). For example, when cloning in bacterial systems, inducible promoters such as, but are not limited to, pL of bacteriophage S, plac, ptrp, ptac tac, T7 (ptrp-lac hybrid promoter) may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the inserted fusion protein coding sequence.

In bacterial systems, a number of expression vectors may be advantageously selected depending upon the desired attributes of the system. For example, when large quantities of the fusion protein are to be produced, vectors which direct the expression of high levels of fusion protein products that are readily purified may be desirable. Those which are engineered to contain a cleavage site to aid in recovering fusion protein are preferred. Excellent results can and have been obtained using several commercially available vectors, including pET 11a, b, c, or d (Novagen, Madison, Wis.).

Particularly preferred plasmids for transformation of *E. coli* cells include the pET expression vectors (see, U.S. Pat. No. 4,952,496; available from NOVAGEN, Madison, Wis.; see, also literature published by Novagen describing the system). Such plasmids include pET 11c and/or pET 11a, which contains the T7lac promoter, T7 terminator, the inducible *E. coli* lac operator, and the lac repressor gene; pET 12a–c, which contains the T7 promoter, T7 terminator, and the *E. coli* ompT secretion signal; and pET 15b (NOVAGEN, Madison, Wis.), which contains a His-Tag™ leader sequence (Seq. ID NO. 40) for use in purification with a His column and a thrombin cleavage site that permits cleavage following purification over the column; the T7-lac promoter region and the T7 terminator.

Nucleic acid encoding a chemokine receptor targeting agent linked to a targeted agnet with and without linkers, and other such constructs, can be into the pET vectors, pET11c, pET-11a and pET-15b expression vectors (NOVAGEN, Madison, Wis.), for intracellular and periplasmic expression, respectively, the fusion proteins.

Other plasmids include the pKK plasmids, particularly pKK 223-3, which contains the TAC promoter, (available from Pharmacia; see also, Brosius et al. (1984) *Proc. Natl. Acad. Sci.* 81:6929; Ausubel et al. Current Protocols in Molecular Biology; U.S. Pat. Nos. 5,122,463, 5,173,403, 5,187,153, 5,204,254, 5,212,058, 5,212,286, 5,215,907, 5,220,013, 5,223,483, and 5,229,279), which contain the TAC promoter. Plasmid pKK has been modified by insertion of a kanamycin resistance cassette with EcoRI sticky ends (purchased from Pharmacia; obtained from pUC4K, see, e.g., Vieira et al. (1982) *Gene* 19:259–268; and U.S. Pat. No. 4,719,179) into the ampicillin resistance marker gene.

Other preferred vectors include the $pP_L$-lambda inducible expression vector and the tac promoter vector pDR450 (see, e.g., U.S. Pat. Nos. 5,281,525, 5,262,309, 5,240,831, 5,231, 008, 5,227,469, 5,227,293, available from Pharmacia P.L. Biochemicals, see; also Mott, et al. (1985) *Proc. Natl. Acad. Sci. U.S.A.* 82:88; and De Boer et al. (1983) *Proc. Natl. Acad. Sci. U.S.A.* 80:21); and baculovirus vectors, such as a pBlueBac vector (also called pJVETL and derivatives thereof; see, e.g., U.S. Pat. Nos. 5,278,050, 5,244,805, 5,243,041, 5,242,687, 5,266,317, 4,745,051, and 5,169,784), including pBlueBac III.

Other plasmids include the pIN-IIIompA plasmids (see, U.S. Pat. No. 4,575,013 to Inouye; see, also, Duffaud et al. (1987) *Meth. Enz.* 153:492–507), such as pIN-IIIompA2. The pIN-IIIompA plasmids include an insertion site for heterologous DNA linked in transcriptional reading frame with functional fragments derived from the lipoprotein gene of *E. coli*. The plasmids also include a DNA fragment coding for the signal peptide of the ompA protein of *E. coli*, positioned such that the desired polypeptide is expressed with the ompA signal peptide at its amino terminus, thereby allowing efficient secretion across the cytoplasmic membrane. The plasmids further include DNA encoding a specific segment of the *E. coli* lac promoter-operator, which is positioned in the proper orientation for transcriptional expression of the desired polypeptide, as well as a separate functional *E. coli* lacI gene encoding the associated repressor molecule that, in the absence of lac operon inducer, interacts with the lac promoter-operator to prevent transcription therefrom. Expression of the desired polypeptide is under the control of the lipoprotein (lpp) promoter and the lac promoter-operator, although transcription from either promoter is normally blocked by the repressor molecule. The repressor is selectively inactivated by means of an inducer molecule thereby inducing transcriptional expression of the desired polypeptide from both promoters.

The repressor protein may be encoded by the plasmid containing the construct or a second plasmid that contains a gene encoding for a repressor-protein. The repressor-protein is capable of repressing the transcription of a promoter that contains sequences of nucleotides to which the repressor-protein binds. The promoter can be derepressed by altering the physiological conditions of the cell. The alteration can be accomplished by the addition to the growth medium of a molecule that inhibits, for example, the ability to interact with the operator or with regulatory proteins or other regions of the DNA or by altering the temperature of the growth media. Preferred repressor-proteins include, but are not limited to the *E. coli*. lacI repressor responsive to IPTG induction, the temperature sensitive cI857 repressor. The *E. coli* lacI repressor is preferred.

In certain embodiments, the constructs also include a transcription terminator sequence. The promoter regions and transcription terminators are each independently selected from the same or different genes. In some embodiments, the DNA fragment is replicated in bacterial cells, preferably in *E. coli*. The DNA fragment also typically includes a bacterial origin of replication, to ensure the maintenance of the DNA fragment from generation to generation of the bacteria. In this way, large quantities of the DNA fragment can be produced by replication in bacteria. Preferred bacterial origins of replication include, but are not limited to, the f1-ori and col E1 origins of replication.

For insect hosts, baculovirus vectors, such as a pBlueBac (also called pJVETL and derivatives thereof) vector, particularly pBlueBac III, (see, e.g., U.S. Pat. Nos. 5,278,050, 5,244,805, 5,243,041, 5,242,687, 5,266,317, 4,745,051, and 5,169,784; available from INVITROGEN, San Diego) may also be used for expression of the polypeptides. The pBlueBacIII vector is a dual promoter vector and provides for the selection of recombinants by blue/white screening as this plasmid contains the β-galactosidase gene (lacZ) under the control of the insect recognizable ETL promoter and is inducible with IPTG. A DNA construct is introduced into a baculovirus vector pBluebac III (INVITROGEN, San Diego, Calif.) and then co-transfected with wild type virus into insect cells *Spodoptera frugiperda* (sf9 cells; see, e.g., Luckow et al. (1988) *Bio/technology* 6:47–55 and U.S. Pat. No. 4,745,051).

Preferred bacterial hosts contain chromosomal copies of DNA encoding T7 RNA polymerase operably linked to an inducible promoter, such as the lacUV promoter (see, U.S. Pat. No. 4,952,496). Such hosts include, but are not limited to, lysogens *E. coli* strains HMS174(DE3)pLysS, BL21 (DE3)pLysS, HMS174(DE3) and BL21 (DE3). Strain BL21 (DE3) is preferred. The pLys strains provide low levels of T7 lysozyme, a natural inhibitor of T7 RNA polymerase. Preferred bacterial hosts are the insect cells *Spodoptera frugiperda* (sf9 cells; see, e.g., Luckow et al. (1988) *Bio/technology* 6:47–55 and U.S. Pat. No. 4,745,051).

An alternative expression system that can be used to express the fusion protein is an insect system. In one such system, *Autographa californica* nuclear polyhedrosis virus (AcNPV) is used as a vector to express foreign genes. The virus grows in *Spodoptera frugiperda* cells. The fusion protein coding sequence may be cloned into non-essential regions (for example, the polyhedrin gene) of the virus and placed under control of an AcNPV promoter (for example the polyhedrin promoter). Successful insertion of the fusion protein coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed, see U.S. Pat. No. 4,215,051.

The constructs provided herein are also inserted into the baculovirus vector sold commercially under the name pBLUEBACIII (INVITROGEN, San Diego Calif.; see the INVITROGEN CATALOG; see, Vialard et al. (1990) *J. Virol.* 64:37; see also, U.S. Pat. No. 5,270,458; U.S. Pat. No. 5,243,041; and published International PCT Application WO 93/10139, which is based on U.S. patent application Ser. No. 07/792,600. The pBlueBacIII vector is a dual promoter vector and provides for the selection of recombinants by blue/white screening as this plasmid contains the β-galactosidase gene (lacZ) under the control of the insect recognizable ETL promoter and is inducible with IPTG. The construct or other construct is inserted into this vector under control of the polyhedrin promoter. Blue occlusion minus viral plaques are selected and plaque purified and screened for the presence of the chemokine-toxin-encoding DNA by any standard methodology, such as western blots using appropriate anti-sera or Southern blots using an appropriate probe. Selected purified recombinant virus is then cotransfected, such as by $CaPO_4$ transfection or liposomes, into *Spodoptera frugiperda* cells (sf9 cells) with wild type baculovirus and grown in tissue culture flasks or in suspension cultures.

In yeast, a number of vectors containing constitutive or inducible promoters may be used. Such vectors are well known (for a review see, e.g., *Current Protocols in Molecular Biology, Vol.* 2, ed. Ausubel et al., eds., Ch 13, Current Protocols, 1987–1994; John Wiley and Sons, Inc., 1994–1999; Bitter, et al., *Methods in Enzymol.,* 153: 516–544, 1987; Rothstein In: *DNA Cloning*, Vol. II, Glover, D. M., Ed., IRL Press, Wash., D.C., Ch. 3, 1986; and Bitter et al., *Methods in Enzymol.,* 152: 673–684, 1987; and *The Molecular Biology of the Yeast Saccharomyces*, Strathern et al., Eds., Cold Spring Harbor Press, Vols. I and II, 1982). A constitutive yeast promoter such as ADH or LEU2 or an inducible promoter such as GAL may be used (*DNA Cloning*, Vol. II, Glover, D. M., Ed., IRL Press, Wash., D.C., Ch. 3, 1986. Alternatively, vectors that promote integration of foreign DNA sequences into the yeast chromosome may be used.

In cases where plant expression vectors are used, the expression of a fusion protein coding sequence may be driven by any of a number of promoters. For example, viral promoters such as the 35S RNA and 19S RNA promoters of CaMV (Brisson et al., *Nature* 310:511–514, 1984), or the coat protein promoter to TMV (Takamatsu et al., *EMBO J.* 6:307–311, 1987) may be used; alternatively, plant promoters such as the small subunit of RUBISCO (Coruzzi et al., *EMBO J.* 3:1671–1680, 1984; Broglie et al., *Science* 224: 838–843, 1984); or heat shock promoters, e.g., soybean hsp17.5-E or hsp17.3-B (Gurley, et al., *Mol. Cell. Biol.* 6:559–565, 1986) may be used. These constructs can be introduced into plant cells using Ti plasmids, Ri plasmids, plant virus vectors, direct DNA transformation, microinjection, electroporation, etc. For reviews of such techniques see, for example, Weissbach and Weissbach, *Methods for Plant Molecular Biology*, Academic Press, NY, Section VIII, pp. 421–463, 1988; and *Plant Molecular Biology,* 2d Ed., Covey, S. N., Ed., Ch. 7–9, Blackie, London 1988.

Mammalian cell systems that use recombinant viruses or viral elements to direct expression may be engineered. For example, when using adenovirus expression vectors, the fusion protein coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the fusion protein in infected hosts (e.g., see Logan and Shenk, *Proc. Natl. Acad. Sci. USA,* 81: 3655–3659, 1984). Alternatively, the vaccinia virus 7.5K promoter may be used. (e.g., see, Mackett et al., *Proc. Natl. Acad. Sci. USA,* 79: 7415–7419, 1982; Mackett et al., *J. Virol.,* 49: 857–864, 1984; Panicali et al., *Proc. Natl. Acad. Sci. USA,* 79: 4927–4931, 1982). Of particular interest are vectors based on bovine papilloma virus which have the ability to replicate as extrachromosomal elements (Sarver, et al., *Mol. Cell. Biol.* 1: 486–96, 1981). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as the neo gene. Alternatively, the retroviral genome can be modified for use as a vector capable of introducing and directing the expression of the fusion protein gene in host cells (Cone and Mulligan, *Proc. Natl. Acad. Sci. USA,* 81:6349–6353, 1984). High level expression may also be achieved using inducible promoters, including, but not limited to, the metallothionine IIA promoter and heat shock promoters.

For long-term, high-yield production of recombinant proteins, stable expression is preferred. Rather than using expression vectors which contain viral origins of replication, host cells can be transformed with cDNA encoding the fusion protein controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1–2 days in an enriched media, and then are switched to a selective media. A number of selection systems may be used, including but not limited to the Herpes simplex virus thymidine kinase (Wigler et al., *Cell,* 11: 223–32, 1977), hypoxanthine-guanine phosphoribosyltransferase (Szybalska and Szybalski, *Proc. Natl. Acad. Sci. USA,* 48:2026–30, 1962), and adenine phosphoribosyltransferase (Lowy et al., *Cell,* 22: 817–31, 1980) genes can be employed in $tk^-$, $hgprt^-$ or $aprt^-$ cells respectively. Also, antimetabolite resistance can be used as the basis of selection for dhfr, which confers resistance to methotrexate (Wigler et al., *Proc. Natl. Acad. Sci. USA,* 78: 3567–70, 1980; O'Hare et al., *Proc. Natl. Acad. Sci. USA,* 8: 1527–31, 1981); gpt, which confers resistance to mycophenolic acid (Mulligan and Berg, *Proc. Natl. Acad. Sci. USA,* 78: 2072–6, 1981; neo, which confers resistance to the aminoglycoside G-418 (Colberre-Garapin et al., *J. Mol. Biol.,* 150:1–14, 1981); and hygro, which confers resistance to hygromycin (Santerre et al., *Gene,* 30: 147–56, 1984) genes. Recently, additional selectable genes have been described, namely trpB, which allows cells to utilize indole in place of tryptophan; hisD, which allows cells to utilize histinol in place of histidine (Hartman and Mulligan, *Proc. Natl. Acad. Sci. USA,* 85:8047–51, 1988); and ODC (ornithine decarboxylase) which confers resistance to the ornithine decarboxylase inhibitor, 2-(difluoromethyl)-DL-ornithine, DFMO (McConlogue et al. *J. Biol. Chem.,* 258:8384–8388).

In one embodiment, the fusion protein is produced by recombinant DNA technology in which a single polypeptide includes a chemokine receptor targeting agent, a peptide linker moiety and a proteinaceous targeting agent, such as a cell toxin moiety. The chemokine receptor targeting moiety can be positioned at the amino-terminus relative to the cell toxin moiety in the polypeptide. Such a fusion protein has the generalized structure: (amino terminus) chemokine ligand moiety—peptide linker moiety—proteinaceous cell toxin moiety(carboxy terminus). Such a fusion protein has the generalized structure: (amino terminus) chemokine ligand moiety—peptide linker moiety—proteinaceous cell toxin moiety (carboxy terminus), and is illustrated in FIG. 1. Alternatively, the chemokine moiety can be positioned at the carboxy-terminus relative to the cell toxin moiety within the fusion protein. Also contemplated herein are fusion proteins that contain extra amino acid sequences at the amino and/or carboxy termini, for example, polyhistidine tags.

Following transformation, large amounts of the protein may be isolated and purified in accordance with conventional methods. For example, a lysate can be prepared from the expression host and the desired protein (or fusion-protein) purified using HPLC, exclusion chromatography, gel electrophoresis, affinity chromatography, or other purification techniques. The purified protein will generally be about 80% to about 90% pure, and may be up to and including 100% pure. Pure is intended to mean free of other proteins, as well as cellular debris.

b. Cloning and Expression of a Chimeric Ligand-Toxin Fusion Protein

Construction of a cDNA Library

Total RNA is isolated from a cell line known to produce the desired proteinaceous ligand and purified by fractionation over oligo(dT)-cellulose to bind RNA with a poly A tail. A first strand of cDNA synthesis is carried out using a reverse transcriptase and a primer with a suitable restriction site, such as NotI. Several reverse transcriptases are available, with avian and murine being most frequently used. This DNA-RNA hybrid molecule is then used to generate a double strand of cDNA by one of several different methods that are available. Linkers are attached to the DNA, and the DNA is then size fractionated by agarose gel electrophoresis. The DNA so obtained is cloned into a suitable vector directly, or first screened by probing. For probing, two oligonucleotides are made from the known gene sequence, one for each end of the gene, and the oligonucleotides are used to probe the gel. Any region of the gel that shows hybridization to both probes is excised, and the DNA is purified. This purified DNA is cloned and used to transform *E. coli*. Colonies obtained are re-probed and positive clones are selected.

Expression of the Gene Product

Secondly, the gene product is expressed. Once a positive clone is obtained, one sequencing reaction is carried out to ensure that the selected clone has the desired sequence. PCR oligonucleotides are made such that the ATG start codon of the gene is directly preceded by a restriction site in the expression vector pKK223-3 (Pharmacia, Piscataway, N.J.) Following the 3' end of the gene are two restriction sites. The first restriction site is recognized by an enzyme that cuts 10 to 12 bases before the recognition sequence to permit subsequent digestion to remove the stop codon and to allow fusion to a second gene. The second recognition site is used to clone the gene into the expression vector. PCR is carried out under standard conditions to extend the sequence, the resultant DNA is separated on agarose gel, and a clone having a band of the correct size is excised and cloned onto the expression vector. As PCR can introduce errors, the whole gene is now sequenced to confirm that it has the desired correct sequence. Once a clone having the correct sequence is isolated in this fashion, the vector is transfected into *E. coli*, and the clone is grown to mid log phase induced with isopropyl-β-D-thiogalactopyranoside for 4 to 6 hours.

Expressed proteins are separated by polyacrylamide gel electrophoresis and are stained by coomassie blue dye for isolation. At this stage the protein is expressed in a soluble phase in high yield. If the protein is insoluble or the yield is too low, various modifications to the ribosome binding site or to the growth conditions are made to correct the problem.

The second nucleic acid fragment to be fused to the ligand gene (e.g., a polynucleotide sequence encoding a proteinaceous linker) is obtained by synthesis from a known amino acid sequence, such as SEQ. ID Nos: 1–12 (International PCT application No. WO 96/06641, which provides exemplary linkers for use in conjugates), except that a PCR primer at the 5' end is added with dual restriction sites, one site to facilitate direct cloning for expression, and one site that would allow for cloning the oligonucleotide into an expression vector for making of a fusion protein. The second protein would be expressed either by itself, or in a fusion protein containing the products of both genes. A third gene (e.g., one encoding a proteinaceous cell toxin) is obtained from an appropriate cell line in the manner described above and added to the expression vector prior to its transfection into the host cell.

c. Construction and Expression of Exemplary Chemokine Receptor Targeting Agent-Toxin Fusion Genes Twelve ligand-toxin fusion genes (Table 6) have been constructed. The gene products contain four ligands genetically fused to each of three toxins. The HIS-tagged genes were constructed so that a small amount of each fusion could be expediently expressed, purified, and tested in vitro. The HIS tag also affords an alternative route for protein purification, should one be required. The Saporin-containing chemokine-toxin fusion serve as prototypes against which the other toxins can be compared and characterized.

Partially purified OPL898110 has been tested on target and non-target cells, in vitro. In a relatively quiescent state target cells (human primary peripheral blood monocytes and the human THP-1 cell line) are eradicated slowly, consistent with an apoptotic mechanism, whereas activated target cells (the human THP-1 cell line and human primary T-lymphocytes) were eradicated in a shorter time frame. The latter effect is presumably due, at least in part, to the cells upregulated metabolic rate, expression of suitable chemokine receptors and the inhibitory effect of OPL98110 on an increased rate of protein synthesis. Metabolically active non target cells (pre-activated human fetal neurons and human glioma cells) are not affected by the chemokine-toxin at concentrations where target cells look distinctly abnormal or dead. The chemokine-toxin fusion protein tested in tissue culture kills target cells of leukocyte lineage, but does not affect non target cells. These results indicate that OPL98110 would be useful in treating spinal cord injury.

This chemokine-toxin protein is used to eradicate the cells that cause secondary tissue damage while sparing the vital neuronal and astrocyte populations that are necessary for normal CNS survival and function.

As noted above, twelve exemplary constructs that encode a series of chemokine-toxin fusion proteins containing a chemokine attached to a cellular toxin via a peptide linker were constructed. The compositions, code designator, and selected theoretical characteristics of these fusion proteins are presented in Table 6.

TABLE 6

Composition, Designation, Theoretical Molecular Weight and Isoelectric Point of Chemokine-toxins and Free Toxins

| Ligand | Linker | Toxin Moiety | Designation | Mol. Wt. (Daltons) | pI | SEQ ID |
|---|---|---|---|---|---|---|
| (A) Conjugates | | | | | | |
| Eotaxin | AM | Shiga-A1 | OPL98104 | 35,603 | 9.63 | 61 |
| | AM | ShigaHIS | OPL98112 | 35,943 | 9.63 | 62 |
| | AM | Saporin | OPL98108 | 36,848 | 9.63 | 63 |
| MCP-1 | AM | Shiga-A1 | OPL98102 | 35,923 | 9.22 | 52 |
| | AM | ShigaHIS | OPL98110 | 36,263 | 9.22 | 53 |
| | AM | Saporin | OPL98106 | 37,168 | 9.44 | 54 |
| MCP-3 | AM | Shiga-A1 | OPL98101 | 36,194 | 9.49 | 55 |
| | AM | ShigaHIS | OPL98109 | 36,535 | 9.49 | 56 |
| | AM | Saporin | OPL98105 | 37,439 | 9.56 | 57 |
| SDF-1β | AM | Shiga-A1 | OPL98103 | 35,944 | 9.62 | 58 |
| | AM | ShigaHIS | OPL98111 | 36,263 | 9.62 | 59 |
| | AM | Saporin | OPL98107 | 37,257 | 9.63 | 60 |
| (B) Free toxin | | | | | | |
| | — | Shiga-A1 | OPL981 | 27,053 | 8.13 | 64 |
| | — | ShigaHIS | OPL983 | 27,394 | 8.15 | 65 |
| | — | Saporin | OPL982 | 28,501 | 9.40 | 66 |

KEY
(A) Chemokine-toxin conjugates composed of a chemokine, linker, and toxin moiety;
(B) Free toxin moieties.
"HIS6" indicates six carboxy terminal histidine residues.

The expression of each chemokine-toxin was clearly detectable but estimated to be substantially less than 0.1% of the total protein in the crude cell pastes. These low levels are entirely consistent with previously published observations that ribosome inactivating proteins (RIPs), including Shiga and Saporin toxins, are toxic to the bacterial host cells expressing them. More pertinently, the Shiga A1 subunit is the most powerful RIP toxin assayed against *E. coli* ribosomes. To improve levels of expressed proteins, a signal peptide is operatively linked to the expressed protein to transport it to the periplasmic space. Alternatively, and preferably, the fusion protein is introduced into tightly regulated expression vectors, and grown using optimized media and fermentation procedures.

The fusion proteins provided herein were expressed using the tightly-regulated pET11c vector (T7 promoter) but the fermentation conditions were not yet optimized for routine protein production. Consistent with this, chemokine-toxin-transformed *E. coli* start to die at approximately four hours post induction, and at a relatively low cell density. More recent experiments with OPL98110 and OPL98106 indicate that these chemokine-toxins are increasingly associated with the insoluble fraction as fermentation proceeds, which suggests that they are associated with inclusion bodies. Insoluble inclusion bodies are a practical advantage to protein isolation and purification. Optimization of the fermentation of the strains containing the chemokine-toxin conjugate-encoding proteins, including the adoption of automated fermentors, and more appropriate growth media and conditions will take full advantage of the pET11c system.

2. Production of Chemical Conjugates

To effect chemical conjugation herein, the targeting agent is linked via one or more selected linkers or directly to the targeted agent. Chemical conjugation must be used if the targeted agent is other than a peptide or protein, such a nucleic acid or a non-peptide drug. Any means known to those of skill in the art for chemically conjugating selected moieties may be used. Several methods are described in the EXAMPLES.

E. Animal Models for Testing of Conjugates

The conjugates provided herein and available conjugates, such as IL-2-, IL-4-, GM-CSF-, anti-CD4-, and anti-CD5-containing conjugates, used for other indications, may be used and tested in various animal models of the inflammatory diseases and conditions contemplated herein to confirm activity and/or to identify those suitable for treatment of a particular disease or condition contemplated herein.

Also, the chemokine-receptor targeting conjugates provided herein may also be tested models of diseases for which other conjugates have been used. For example, the mouse xenograft model for anti-tumor activity to identify (see, e.g., Beitz et al. (1992) *Cancer Research* 52:227–230; Houghton et al. (1982) *Cancer Res.* 42:535–539; Bogden et al. (1981) *Cancer* (*Philadelphia*) 48:10–20; Hoogenhout et al. (1983) *Int. J. Radiat. Oncol., Biol. Phys.* 9:871–879; Stastny et al. (1993) *Cancer Res.* 53:5740–5744).

Animal models for selecting candidates for treatment of mammals are well known and there are numerous recognized models. In addition, the role of activated immune cells in these diseases states have been demonstrated. Exemplary models for such diseases and conditions include, but are not limited to, those in the following discussion.

Spinal Cord Injury (SCI)

Some exemplary references that provide and use animal models of SCI that may be used to test chemokine receptor targeting conjugates include, but are not limited to, the following.

Bennett et al. (1999) Spasticity in rats with sacral spinal cord injury *J. Neurotrauma* 16:69–84 provides a rat model of muscular spasticity that is minimally disruptive, not interfering with bladder, bowel, or hindlimb locomotor function. Spinal transections were made at the S2 sacral level and, thus, only affected the tail musculature. After spinal transection, the muscles of the tail were inactive for 2 weeks. Following this initial period, hypertonia, hyperreflexia, and clonus developed in the tail, and grew more pronounced with time. These changes were assessed in the awake rat, since the tail is readily accessible and easy to manipulate. Muscle stretch or cutaneous stimulation of the tail produced muscle spasms and marked increases in muscle tone, as measured with force and electromyographic recordings. When the tail was unconstrained, spontaneous or reflex induced flexor and extensor spasms coiled the tail. Movement during the spasms often triggered clonus in the end of the tail. The tail hair and skin were extremely hyperreflexive to light touch, withdrawing quickly at contact, and at times clonus could be entrained by repeated contact of the tail on a surface. Segmental tail muscle reflexes, e.g., Hoffman reflexes (H-reflexes), were measured before and after spinalization, and increased significantly 2 weeks after transection. These results indicate that sacral spinal rats develop symptoms of spasticity in tail muscles with similar characteristics to those seen in limb muscles of humans with spinal cord injury, and thus provide a convenient preparation for studying this condition.

Taoka et al. (1998) Spinal cord injury in the rat, *Prog Neurobiol* 56:341–58 provides a review of the pathologic mechanisms of trauma-induced spinal cord injury in rats to further development of new therapeutic strategies. Spinal cord injury induced by trauma is a consequence of an initial physical insult and a subsequent progressive injury process that involves various pathochemical events leading to tissue destruction; the latter process should therefore be a target of pharmacological treatment. Recently, activated neutrophils have been shown to be implicated in the latter process of the spinal cord injury in rats. Activated neutrophils damage the endothelial cells by releasing inflammatory mediators such as neutrophil elastase and oxygen free radicals. Adhesion of activated neutrophils to the endothelial cell could also play a role in endothelial cell injury. This endothelial cell injury could in turn induce microcirculatory disturbances leading to spinal cord ischemia. Some therapeutic agents that inhibit neutrophil activation alleviate the motor disturbances observed in the rat model of spinal cord injury. Methylprednisolone (MPS) and GM1 ganglioside, which are the only two pharmacological agents currently clinically available for treatment of acute spinal cord injury, do not inhibit neutrophil activation in this rat model. Taken together, these observations raise a possibility that other pharmacological agents that inhibit neutrophil activation used in conjunction with MPS or GM1 ganglioside may have a synergistic effect in the treatment of traumatic spinal cord injury in humans.

Carlson et al. (1998) Acute inflammatory response in spinal cord following impact injury, *Exp Neurol* 151:77–88, provides a study examines the rostral-caudal distribution of neutrophils and macrophages/microglia at 4, 6, 24, and 48 h after contusion injury to the T10 spinal cord of rat (10 g weight, 50 mm drop). Neutrophils were located predominantly in necrotic regions, with a time course that peaked at 24 h as measured with assays of myeloperoxidase activity (MPO). The sharpest peak of MPO activity was localized between 4 mm rostral and caudal to the injury. Macrophages/microglia were visualized with antibodies against ED1 and OX-42. Numerous cells with a phagocytic morphology were present by 24 h, with a higher number by 48 h. These cells were predominantly located within the gray matter and dorsal funiculus white matter. The number of cells gradually declined through 6 mm rostral and caudal to the lesion. OX-42 staining also revealed reactive microglia with blunt processes, particularly at levels distant to the lesion. The number of macrophages/microglia was significantly correlated with the amount of tissue damage at each level.

Bartholdi et al. (1997) Expression of pro-inflammatory cytokine and chemokine mRNA upon experimental spinal cord injury in mouse: an in situ hybridization study, *Eur J Neurosci* 9:1422–38 describes a study of the expression pattern of pro-inflammatory and chemoattractant cytokines in an experimental spinal cord injury model in mouse. In situ hybridization shows that transcripts for the pro-inflammatory cytokines TNF alpha and IL-1 as well as the chemokines MIP-1α and MIP-1β are upregulated within the first hour following injury. In this early phase, the expression of the pro-inflammatory cytokines is restricted to cells in the surroundings of the lesion area probably resident CNS cells. While TNF alpha is expressed in a very narrow time window, IL-1 can be detected in a second phase in a subset of polymorphonuclear granulocytes which immigrate into the spinal cord around 6 h. Message for the chemokines MIP-1α and -β is expressed in a generalized way in the grey matter of the entire spinal cord around 24 h and gets again restricted to the cellular infiltrate at the lesion site at 4 days following injury. The data indicate that resident CNS cells, most probably microglial cells, and not peripheral inflammatory cells, are the main source for cytokine and chemokine mRNAs. The defined cytokine pattern observed indicates that the inflammatory events upon lesioning the CNS are tightly controlled. The very early expression of pro-inflammatory cytokine and chemokine messages may represent an important element of the recruitment of inflammatory cells.

Blight et al. (1991) Morphometric analysis of blood vessels in chronic experimental spinal cord injury: hypervascularity and recovery of function, *J Neurol Sci* 106: 158–74 provides a model of spinal cord trauma in guinea pigs, based on compression to a set thickness, was described previously. Compression injuries of the lower thoracic cord were produced in 11 anesthetized, adult guinea pigs, and the outcome monitored, using successive behavioral tests and morphometry of the lesion at 2–3 months. This report describes changes in the vascularity of the spinal cord, based on light microscopic analysis of 1 micron plastic transverse sections through the center of the lesion. Mean blood vessel density in these lesions was approximately twice that found in equivalent regions of normal, uninjured spinal cords, and hypervascularity of the white matter extended at least four spinal cord segments cranially and caudally from the lesion center. Capillary diameter distribution was significantly shifted to larger values and large perivascular spaces surrounded most capillaries and pre- and post-capillary vessels. Extent of hypervascularity was not correlated with the overall severity of the injury, but there was a significant positive correlation between the density of blood vessels in the outer 400 microns of the white matter and secondary loss of neurological function below the lesion, seen between one day and eight weeks after injury. These data indicate that hypervascularization of the lesion is related to secondary pathological mechanisms in spinal cord injury, possibly inflammatory responses, that are relatively independent of the primary mechanical injury but more closely connected with loss and recovery of function.

Blight et al. (1993) Increased levels of the excitotoxin quinolinic acid in spinal cord following contusion injury, *Brain Res* 632:314–6 shows that products of inflammatory phagocytes are potential contributors to secondary pathology following spinal cord trauma, and presents a study quantifying the levels of the neurotoxin and product of activated macrophages, quinolinic acid (QUIN), in the lower thoracic spinal cord of adult guinea pigs 5 days after brief compression injury. At the injured site (T13), elevations in tissue QUIN levels (>10-fold) accompanied proportional increases in the activity of indoleamine-2,3 dioxygenase (>2-fold) and the concentrations of L-kynurenine (>2.5-fold). In contrast, no significant changes occurred in two uninjured regions examined compared to controls, namely cervical spinal cord (C2) and the somatosensory cortex.

Forbes et al. (1994) Inhibition of neutrophil adhesion does not prevent ischemic spinal cord injury, *Ann Thorac Surg* 58:1064–8, relies on animal models to show that paraplegia may occur after transient aortic occlusion as a consequence of primary ischemia to the spinal cord or injury during the reperfusion period. In animal models of ischemia/reperfusion there is evidence that reperfusion injury may be modulated partially by neutrophils. The efficacy of the neutrophil adherence blocking murine monoclonal antibody (MAb 60.3) was assessed in spinal cord ischemia/reperfusion in rabbits. Spinal cord ischemia was accomplished by balloon catheter occlusion of the infrarenal aorta. Neurologic assessment was graded as normal, partial neurologic deficit, or complete paralysis. Electrophysiologic monitoring with somatosensory evoked potentials was used to determine the optimal length of time of occlusion. Animals were treated randomly with 2 mg/kg of intravenous Mab 60.3 (n=8) or saline solution (n=9) with the investigator unaware of treatment. Mean occlusion times were no different between groups (control, 32.7+/−3.6 minutes versus MAb, 32.4+/−6.0 minutes). Five (55%) saline-treated and four (50%) MAb 60.3-treated animals became paraplegic. Animals with initial paraparesis all progressed to flaccid paraplegia within 24 hours. The study concludes that spinal cord injury after transient aortic occlusion is independent of the CD11/CD18 glycoprotein complex of the neutrophil. Injury in this setting may occur during ischemia and thus may not be dependent on neutrophils or reperfusion.

Liu et al. (1997) Neuronal and glial apoptosis after traumatic spinal cord injury, *J Neurosci* 17:5395–406 examines the spinal cords of rats subjected to traumatic insults of mild to moderate severity. Within minutes after mild weight drop impact (a 10 gm weight falling 6.25 mm), neurons in the immediate impact area showed a loss of cytoplasmic Nissl substances. Over the next 7 d, this lesion area expanded and cavitated. Terminal deoxynucleotidyl transferase (TdT)-mediated deoxyuridine triphosphate-biotin nick end labeling (TUNEL)-positive neurons were noted primarily restricted to the gross lesion area 4–24 hr after injury, with a maximum presence at 8 hr after injury. TUNEL-positive glia were present at all stages studied between 4 hr and 14 d, with a maximum presence within the lesion area 24 hr after injury. Seven days after injury, a second wave of TUNEL-positive glial cells was noted in the white matter peripheral to the lesion and extending at least several millimeters away from the lesion center. The suggestion of apoptosis was supported by electron microscopy, as well as by nuclear staining with Hoechst 33342 dye, and by examination of DNA prepared from the lesion site. Furthermore, repeated intraperitoneal injections of cycloheximide, beginning immediately after a 12.5 mm weight drop insult, produced a substantial reduction in histological evidence of cord damage and in motor dysfunction assessed 4 weeks later. The data support the hypothesis that apoptosis dependent on active protein synthesis contributes to the neuronal and glial cell death, as well as to the neurological dysfunction, induced by mild-to-moderate severity traumatic insults to the rat spinal cord.

Traumatic Brain Injury and Stroke

Ghirnikar et al. (1996) Chemokine expression in rat stab wound brain injury, *J Neurosci Res* 46:727–33 describes that traumatic injury to the adult mammalian central nervous system (CNS) results in reactive astrogliosis and the migration of hematogenous cells into the damaged neural tissue. Chemokines, class of chemoattractant cytokines, are recognized as mediators of the inflammatory changes that occur following injury. The expression of MCP-1 (macrophage chemotactic peptide-1), a member of the β family of chemokines, has been demonstrated in trauma in the rat brain (Berman (1996) et al. *J Immunol* 156:3017–3023). Using a stab wound model for mechanical injury, expression of two other β chemokines: RANTES (Regulated on Activation, Normal T cell Expressed and Secreted) and MIP-1 beta (macrophage inflammatory protein-1β) in the rat brain is studied. The stab wound injury was characterized by widespread gliosis and infiltration of hematogenous cells. Immunohistochemical staining revealed the presence of RANTES and MIP-1 beta in the injured brain. RANTES and MIP-1 beta were both diffusely expressed in the necrotic tissue and were detected as early as 1 day post-injury (dpi). Double-labeling studies showed that MIP-1 beta, but not RANTES, was expressed by reactive astrocytes near the lesion site. In addition, MIP-1 beta staining was also detected on macrophages at the site of injury. The initial expression of the chemokines closely correlated with the appearance of inflammatory cells in the injured CNS, suggesting that RANTES and MIP-1 beta may play a role in the inflammatory events of traumatic brain injury. This study also demonstrates MIP-1β expression in reactive astrocytes following trauma to the rat CNS.

Wang et al. (1998) Prolonged expression of interferon-inducible protein-10 in ischemic cortex after permanent occlusion of the middle cerebral artery in rat, *J Neurochem* 71:1194–204 investigates the role of IP-10 in focal stroke, and studies temporal expression of IP-10 mRNA after occlusion of the middle cerebral artery in rat by means of northern analysis. IP-10 mRNA expression after focal stroke demonstrated a unique biphasic profile, with a marked increase early at 3 h (4.9-fold over control; p 0.01), a peak level at 6 h (14.5-fold; p 0.001) after occlusion of the middle cerebral artery, and a second wave induction 10–15 days after ischemic injury (7.2- and 9.3-fold increase for 10 and 15 days, respectively; p 0.001). In situ hybridization confirmed the induced expression of IP-10 mRNA and revealed its spatial distribution after focal stroke. Immunohistochemical studies demonstrated the expression of IP-10 peptide in neurons (3–12 h) and astroglial cells (6 h to 15 days) of the ischemic zone. A dose-dependent chemotactic action of IP-10 on C6 glial cells and enhanced attachment of rat cerebellar granule neurons was demonstrated. The data indicate that ischemia induces IP-10, which plays a pleiotropic role in prolonged leukocyte recruitment, astrocyte migration/activation, and neuron attachment/sprouting after focal stroke.

Galasso et al. (1998) Excitotoxic brain injury stimulates expression of the chemokine receptor CCR5 in neonatal rats, *Am J Pathol* 153:1631–40, evaluates the impact of intrahippocampal injections of NMDA on CCR5 expression in postnatal day 7 rats. Reverse transcription polymerase chain reaction revealed an increase in hippocampal CCR5mRNA expression 24 hours after lesioning, and in situ hybridization analysis demonstrated that CCR5 mRNA was expressed in the lesioned hippocampus and adjacent regions. Western blot analysis demonstrated increased CCR5 protein in hippocampal tissue extracts 32 hours after lesioning. Complementary immunocytochemistry studies identified infiltrating microglia/monocytes and injured neurons as the principal CCR5-immunoreactive cells. These results evidence that acute excitotoxic injury regulates CCR5 expression.

Vannucci et al. (1999) Rat model of perinatal hypoxic-ischemic brain damage, *J Neurosci Res* 55:158–63, uses an immature rat model to gain insights into the pathogenesis and management of perinatal hypoxic-ischemic brain damage. The model entails ligation of one common carotid artery followed thereafter by systemic hypoxia. The insult produces permanent hypoxic-ischemic brain damage limited to the cerebral hemisphere ipsilateral to the carotid artery occlusion. This model is used in investigations to identify therapeutic strategies to prevent or minimize hypoxic-ischemic brain damage.

Alzheimer's Disease

Hauss-Wegrzyniak et al. (1998) Chronic neuroinflammation in rats reproduces components of the neurobiology of Alzheimer's disease, *Brain Res* 780:294–303, describes that inflammatory processes play a role in the pathogenesis of the degenerative changes and cognitive impairments associated with Alzheimer's disease (AD) and describes use of lipopolysaccharide (LPS) from the cell wall of gram-negative bacteria to produce chronic, global inflammation within the brain of young rats. Chronic infusion of LPS (0.25 microgram/h) into the 4th ventricle for four weeks produced (1) an increase in the number of glial fibrillary acidic protein-positive activated astrocytes and OX-6-positive reactive microglia distributed throughout the brain, with the greatest increase occurring within the temporal lobe, particularly the hippocampus, (2) an induction in interleukin-1 beta, tumor necrosis factor-alpha and beta-amyloid precursor protein mRNA levels within the basal forebrain region and hippocampus, (3) the degeneration of hippocampal CA3 pyramidal neurons, and (4) a significant impairment in spatial memory as determined by decreased spontaneous alternation behavior on a T-maze.

Numerous other Alzheimer disease models, including rodents genetically engineered to express the mutated form of a human gene involved in production of Aβ in families with early onset AD, are known and available to those of skill in this art.

Multiple Sclerosis

Multiple sclerosis (MS) is an inflammatory disease of the central nervous system (CNS) characterized by localized areas of demyelination. Although the etiology and pathogenesis of MS remain largely unknown, it is generally assumed that immune responses to myelin antigens contribute to the disease process. The exact sequence of events, as well as the molecular mediators that lead to myelin destruction, is yet to be defined.

Liu et al. (1998) TNF is a potent anti-inflammatory cytokine in autoimmune-mediated demyelination, *Nat Med* 4:78–83, describes use of a rodent model, experimental autoimmune encephalomyelitis (EAE) for studying MS.

Arthritis and Autoimmune Disease

Barnes et al. (1998) Polyclonal antibody directed against human RANTES ameliorates disease in the Lewis rat adjuvant-induced arthritis model, *J Clin Invest* 101:2910–9, describes that adjuvant-induced arthritis (AIA) is one of many animal models of rheumatoid arthritis, a disease characterized by a T-lymphocyte and macrophage cellular infiltrate. Barnes et al. characterizes the development of this disease model with respect to chemokine expression, and shows that increased levels of two chemokines, RANTES, a T-lymphocyte and monocyte chemo-attractant, and KC a chemoattractant for neutrophils, were found in whole blood and in the joint. Levels of MIP-1 alpha, another T-lymphocyte and monocyte chemoattractant, were unchanged throughout the course of the disease in whole blood and only slightly elevated in the joint. RANTES expression plays an important role in the disease since a polyclonal antibody to RANTES greatly ameliorated symptoms in animals induced for AIA and was found to be as efficacious as treatment with indomethacin, a non-steroidal anti inflammatory. Polyclonal antibodies to either MIP-1 alpha or KC were ineffective.

Weinberg, A. D. (1998) Antibodies to OX-40 (CD134) can identify and eliminate autoreactive T cells: implications for human autoimmune disease, *Mol Med Today* 4:76–83, describes that autoantigen-specific CD4+ T cells have been implicated as the causative cell type in: multiple sclerosis, rheumatoid arthritis, autoimmune uveitis, diabetes mellitus, inflammatory bowel disease and graft-versus-host disease, describes use of experimentally induced autoimmune diseases to develop an effective therapy that deletes the autoreactive T cells at the site of autoimmune tissue destruction.

Schrier et al. (1998) Role of chemokines and cytokines in a reactivation model of arthritis in rats induced by injection with streptococcal cell walls, *J Leukoc Biol* 63:359–63, provides a study of the role of chemokines in an animal model of arthritis. Intraarticular injection of streptococcal cell wall (SCW) antigen followed by intravenous challenge results in a T cell-mediated monoarticular arthritis ill female Lewis rats. Initial studies showed that this reactivation response to intravenous SCW antigen is dependent on the presence of interleukin-1 (IL-1) and tumor necrosis factor alpha (TNF-alpha) and that the early phase of swelling is neutrophil-dependent. Neutrophil depletion or passive immunization with antibodies to P-selectin or macrophage inflammatory protein-2 reduced the intensity of ankle edema and the influx of neutrophils. After the first few days, however, the arthritic response is mediated primarily by mononuclear cells. Joint tissues showed up-regulation of mRNA for monocyte chemotactic protein-1 (MCP-1), which could be inhibited in part by anti-IL-4; treatment of rats with antibodies to IL-4 or MCP-1 significantly suppressed development of ankle edema and histopathological evidence of inflammation. Antibodies to interferon-=gamma or IL-10 had no effect. Treatment with anti-MCP-1 also suppressed influx of $^{(111)}$In-labeled T cells into the ankle joint. These data suggest that the late, mononuclear-dependent phase of SCW-induced arthritis in female Lewis rats requires cytokines that up-regulate MCP-1, which in turn may facilitate recruitment and extravasation of mononuclear cells into the joint.

Oppenheimer-Marks et al. (1998) Interleukin 15 is produced by endothelial cells and increases the transendothelial migration of T cells In vitro and in the SCID mouse-human rheumatoid arthritis model In vivo, *J Clin Invest* 101: 1261–72, examines the capacity of endothelial cells (EC) to produce IL-15 and the capacity of IL-15 to influence transendothelial migration of T cells. Human umbilical vein endothelial cells express IL-15 mRNA and protein. Endothelial-derived IL-15 enhanced transendothelial migration of T cells as evidenced by the inhibition of this process by blocking monoclonal antibodies to IL-15. IL-15 enhanced transendothelial migration of T cells by activating the binding capacity of the integrin adhesion molecule LFA-1 (CD11a/CD18) and also increased T cell motility. In addition, IL-15 induced expression of the early activation molecule CD69. The importance of IL-15 in regulating migration of T cells in vivo was documented by its capacity to enhance accumulation of adoptively transferred human T cells in rheumatoid arthritis synovial tissue engrafted into immune deficient SCID mice. These results demonstrate that EC produce IL-15, which plays a critical role in stimulation of T cells to extravasate into inflammatory tissue.

Kasama et al. (1995) Interleukin-10 expression and chemokine regulation during the evolution of murine type II collagen-induced arthritis *J Clin Invest* 95:2868–76, studies the expression and contribution of specific chemokines, macrophage inflammatory protein 1 alpha (MIP-1α) and macrophage inflammatory protein 2 (MIP-2), and interleukin 10 (IL-10) during the evolution of type II collagen-induced arthritis (CIA). Detectable levels of chemotactic cytokine protein for MIP-1 alpha and MIP-2 were first observed between days 32 and 36, after initial type II collagen challenge, while increases in IL-10 were found between days 36 and 44. CIA mice passively immunized with antibodies directed against either MIP-1 alpha or MIP-2 demonstrated a delay in the onset of arthritis and a reduction of the severity of arthritis. CIA mice receiving neutralizing anti-IL-10 antibodies demonstrated an acceleration of the onset and an increase in the severity of arthritis. Interestingly, anti-IL-10 treatment increased the expression of MIP-1α and MIP-2, as well as increased myeloperoxidase (MPO) activity and leukocyte infiltration in the inflamed joints. These data indicate that MIP-1α and MIP-2 play a role in the initiation and maintenance, while IL-10 appears to play a regulatory role during the development of experimental arthritis.

Keffer et al. (1991) Transgenic mice expressing human tumour necrosis factor: a predictive genetic model of arthritis, *Embo J* 10:4025–31, provide transgenic mouse lines carrying and expressing wild-type and 3'-modified human tumour necrosis factor (hTNF-alpha, cachectin) transgenes, shows correct, endotoxin-responsive and macrophage-specific hTNF gene expression can be established in transgenic mice and present evidence that the 3'-region of the hTNF gene may be involved in macrophage-specific transcription. Transgenic mice carrying 3'-modified hTNF transgenes shows deregulated patterns of expression and develop chronic inflammatory polyarthritis. Keffer et al. show that transgenic mice predictably develop arthritis represent a genetic model by which the pathogenesis and treatment of this disease in humans may be further investigated.

Sakai et al. (1998) Potential withdrawal of rheumatoid synovium by the induction of apoptosis using a novel in vivo model of rheumatoid arthritis, *Arthritis Rheum* 41:1251–7, investigates whether Fas-mediated apoptosis has potential as a therapeutic strategy in rheumatoid arthritis (RA) by use of a model of RA in which human RA tissue is grafted into SCID mice. Fresh rheumatoid synovial tissue including joint cartilage was grafted subcutaneously into the backs of SCID mice. Six weeks after engraftment, anti-Fas monoclonal antibody was injected intraperitoneally. Time-related apoptotic changes caused by anti-Fas monoclonal antibody in grafted synovium were evaluated by nick end-labeling histochemistry. Thirty-six hours after the injection, diffuse apoptotic changes were observed in the grafted synovia. Four weeks after the injection, rheumatoid synovial tissue diminished.

Smith et al. (1999) Diacerhein treatment reduces the severity of osteoarthritis in the canine cruciate-deficiency model of osteoarthritis, *Arthritis Rheum* 42:545–54, describe a canine model of osteoarthritis (OA). OA was induced in 20 adult mongrel dogs by transection of the anterior cruciate ligament of the left knee and use the model to test treatments for OA.

Inflammatory Lung Diseases

Kumagai et al. (1999) Inhibition of Matrix Metalloproteinases Prevents Allergen-induced Airway Inflammation in a Murine Model of Asthma, *J Immunol* 162:4212–4219. investigate the role of MMPs in the pathogenesis of bronchial asthma, using a murine model of allergic asthma. Using this model, an increase of the release of MMP-2 and MMP-9 in bronchoalveolar lavage fluids after Ag inhalation in the mice sensitized with OVA, which was accompanied by the infiltration of lymphocytes and eosinophils is reported. Administration of tissue inhibitor of metalloproteinase-2 to airways inhibited the Ag-induced infiltration of lymphocytes and eosinophils to airway wall and lumen, reduced Ag-induced airway hyperresponsiveness, and increased the numbers of eosinophils and lymphocytes in peripheral blood. The inhibition of cellular infiltration to airway lumen was observed also with tissue inhibitor of metalloproteinase-1 and a synthetic matrix metalloproteinase inhibitor. The data indicate that MMPS, especially MMP-2 and MMP-9, are crucial for the infiltration of inflammatory cells and the induction of airway hyperresponsiveness, which are pathophysiologic features of bronchial asthm.

Griffiths-Johnson et al. (1997) Animal models of asthma: role of chemokines, *Methods Enzymol* 288:241–66, describes that numerous chemokines have been discovered through the use of (1) bioassay of in vitro cell culture supernatants and in vivo exudates from animal models of inflammation and (2) molecular biology techniques. Any one chemokine can often be produced by a number of different cell types and exert its effects on different target cells. and that there is compelling evidence from animal and clinical studies that eosinophils are important effector cells in asthma. Griffiths-Johnson et al. identify two targets to prevent eosinophil recruitment to the lung: IL-5 and its receptor, which are important in several aspects of eosinophil biology, and eotaxin and its receptor, CCR3. The eotaxin receptor is expressed in high numbers on eosinophils, but not other leukocytes, and appears to be the major detector of the eosinophil for eotaxin and other chemokines such as MCP-4. They indicate that eotaxin and CCR3 knockout mice are being developed, and that animal models will continue to be invaluable.

Campbell et al. (1998) Temporal role of chemokines in a murine model of cockroach allergen-induced airway hyperreactivity and eosinophilia, *J Immunol* 161:7047–53, provides a murine model of cockroach allergen-induced airway disease and assesses specific mechanisms of the response, which resembles atopic human asthma. The allergic responses in this model include allergen-specific airway eosinophilia and significantly altered airway physiology, which directly correlates with inflammation. Specific roles for CC chemokines during these stages, with MIP-1alpha being an important eosinophil attractant during the primary stage and eotaxin during the secondary rechallenge stage are identified. These models allow the evaluation of mediators involved in both stages of cockroach allergen challenge, as well as the testing of specific therapeutic modalities.

Piguet et al (1989) Tumor necrosis factor/cachectin plays a key role in bleomycin-induced pneumopathy and fibrosis, *J Exp Med* 170:655–63 and Schrier et al. (1983) The effects of the nude (nu/nu) mutation on bleomycin-induced pulmonary fibrosis. A biochemical evaluation, *Am Rev Respir Dis* 127:614–617, describe a mouse model of pulmonary fibrosis.

Steinhauser et al. (1999) IL-10 is a major mediator of sepsis-induced impairment in lung antibacterial host defense, *J Immunol* 162:392–399, desribe a murine model of sepsis-induced *Pseudomonas aeruginosa* pneumonia to explore the mechanism of immunosuppression associated with sepsis. CD-1 mice underwent either cecal ligation and 26-gauge needle puncture (CLP) or sham surgery, followed by the intratracheal (i.t.) administration of *P. aeruginosa* or saline. Survival in mice undergoing CLP followed 24 h later by the i.t. administration of saline or *P. aeruginosa* was 58% and 10%, respectively, whereas 95% of animals undergoing sham surgery followed by *P. aeruginosa* administration survived. Increased mortality in the CLP/*P. aeruginosa* group was attributable to markedly impaired lung bacterial clearance and the early development of *P. aeruginosa* bacteremia. The i.t. administration of bacteria to CLP-, but not sham-, operated mice resulted in an impressive intrapulmonary accumulation of neutrophils. Furthermore, *P. aeruginosa* challenge in septic mice resulted in a relative shift toward enhanced lung IL-10 production concomitant with a trend toward decreased IL-12. The i.p., but not i.t., administration of IL-10 Abs given just before *P. aeruginosa* challenge in septic mice significantly improved both survival and clearance of bacteria from the lungs of septic animals administered *P. aeruginosa*. Finally, alveolar macrophages isolated from animals undergoing CLP displayed a marked impairment in the ability to ingest and kill *P. aeruginosa* ex vivo, and this defect was partially reversed by the in vivo neutralization of IL-10. Collectively, these observations indicate that the septic response substantially impairs lung innate immunity to *P. aeruginosa*, and this effect is mediated by endogenously produced IL-10.

Inflammation after Gene Therapy

Muruve et al. (1999) Adenoviral gene therapy leads to rapid induction of multiple chemokines and acute neutrophil-dependent hepatic injury in vivo [In Process Citation], *Hum Gene Ther* 10:965–76 studies the molecular mechanisms by which replication-deficient adenoviruses iduce acute injury and inflammation of infected tissues, which limits their use for human gene therapy. To characterize this response, chemokine expression was evaluated in DBA/2 mice following the intravenous administration of various adenoviral vectors. Administration of adCMVbeta gal, adCMV-GFP, or FG140 intravenously rapidly induced a consistent pattern of C-X-C and C—C chemokine expression in mouse liver in a dose-dependent fashion. One hour following infection with 10(10) PFU of adCMVbeta gal, hepatic levels of MIP-2 mRNA were increased >60-fold over baseline. MCP-1 and IP-10 mRNA levels were also increased immediately following infection with various adenoviral vectors, peaking at 6 hr with >25- and >100-fold expression, respectively. Early induction of RANTES and MIP-1 beta mRNA by adenoviral vectors also occurred, but to a lesser degree. The induction of chemokines occurred independently of viral gene expression since psoralen-inactivated adenoviral particles produced an identical pattern of chemokine gene transcription within the first 16 hr of administration. The expression of chemokines correlated as expected with the influx of neutrophils and CD11b+ cells into the livers of infected animals. At high titers, all adenoviral vectors caused significant hepatic necrosis and apoptosis following systemic administration to DBA/2 mice. To investigate the role of neutrophils in this adenovirus-induced hepatic injury, animals were pretreated with neutralizing anti-MIP-2 antibodies or depleted of neutrophils. MIP-2 antagonism and neutrophil depletion both resulted in reduced serum ALT/AST levels and attenuation of the adenovirus-induced hepatic injury histologically, confirming that this early injury is largely due to chemokine production and neutrophil recruitment. The results clarify the early immune response against replication-deficient adenoviral vectors and suggest a strategy to prevent adenovirus-mediated inflammation and tissue injury by interfering with chemokine or neutrophil function.

Angiogenesis, Including its Role in Arthritis, Other Inflammatory Diseases and Tumor Growth Recruitment of cells involved in angiogenesis and inflammatory are associated with tumor growth and development. The following references describe these relationships and that animal models for identifying therapies for tumors, angiogenesis and inflammatory response inhibitors are known to those of skill in the art. The conjugates used and the cells targeted in some of these studies are distinct from the conjugates and targeted cells herein. These references evidence the availability of animal models for the study therapeutics for inhibition of tumor growth and cells associated therewith.

Tumor Growth

Phillips et al. (1994) Transforming growth factor-alpha-*Pseudomonas* exotoxin fusion protein (TGF-alpha-PE38) treatment of subcutaneous and intracranial human glioma and medulloblastoma xenografts in athymic mice, *Cancer Res* 54:1008–15, exploits the differential expression of epidermal growth factor receptor (EGFR), which is amplified or overexpressed in many malignant gliomas and other primary brain tumors, but is low or undetectable in normal brain, for targeted brain tumor therapy using a TGF-alpha-*Pseudomonas* exotoxin recombinant toxin, TGF-alpha-PE38 using nude mice bearing glioblastoma or medulloblastoma s.c. xenografts. The xenograft model should be useful for studying chemokine receptor-targeting conjugates for treatment of inflammatory responses and targeting of cells involved in tumor development.

Debinski et al. (1994) Interleukin-4 receptors expressed on tumor cells may serve as a target for anticancer therapy using chimeric *Pseudomonas* exotoxin, *Int J Cancer* 58:744–748, reports the use of chimeric proteins composed of human IL4 (hIL4) and 2 different mutant forms of a powerful bacterial toxin, *Pseudomonas* exotoxin A (PE) in a human solid tumor xenograft model. The 2 chimeric toxins, termed hIL4-PE4E and hIL4-PE38QQR, showed specific, hIL4R-dependent and dose-dependent antitumor activities.

Husain, S. R.; Behari, N.; Kreitman, R. J.; Pastan, I.; Puri, R. K. 1998, Complete regression of established human glioblastoma tumor xenograft by interleukin-4 toxin therapy, *Cancer Res* 58:3649–53, shows use of an IL-4 toxin conjugate for targeted treatemtn of glioblastoma flank tumors in nude mice. Kreitman et al. (1998) Accumulation of a recombinant immunotoxin in a tumor in vivo: fewer than 1000 molecules per cell are sufficient for complete responses, *Cancer Res* 58:968–975, also demonstrate use of this model.

Angiogenesis

Folkman et al. (1987) Angiogenic factors *Science* 235:442–7, establishes the role of antiogenesis and factors, such as acidic and basic fibroblast growth factor, angiogenin, and transforming growth factors alpha and beta, and their significance in understanding growth regulation of the vascular system. When evaluated according to their putative targets, the factors fall into groups: those that act directly on vascular endothelial cells to stimulate locomotion or mitosis, and those that act indirectly by mobilizing host cells (for example, macrophages) to release endothelial growth factors. In addition to their presence in tumors undergoing neovascularization, the same angiogenic peptides are found in many normal tissues where neovascularization is not occurring. This suggests that physiological expression of angiogenic factors is tightly regulated. In addition to the persistent angiogenesis induced by tumors, it now appears that a variety of nonneoplastic diseases, previously thought to be unrelated, can be considered as "angiogenic diseases" because they are dominated by the pathologic growth of capillary blood vessels.

Leibovich et al. (1987) Macrophage-induced angiogenesis is mediated by tumour necrosis factor-alpha, *Nature* 329:630–632, describes that macrophages are important in the induction of new blood vessel growth during wound repair, inflammation and tumour growth and investigate this by studying capillary blood vessel formation in the rat cornea and the developing chick chorioallantoic membrane.

Koch et al. (1992) Interleukin-8 as a macrophage-derived mediator of angiogenesis, *Science* 258:1798–1801, describes that angiogenic factors produced by monocytes-macrophages are involved in the pathogenesis of chronic inflammatory disorders characterized by persistent angiogenesis. The role of interleukin-8 (IL-8), which is chemotactic for lymphocytes and neutrophils, was shown to be potently angiogenic when implanted in the rat cornea and induces proliferation and chemotaxis of human umbilical vein endothelial cells. The data indicate a role for macrophage-derived IL-8 in angiogenesis-dependent disorders, such as rheumatoid arthritis, tumor growth, and wound repair.

Human Immunodeficiency Virus (HIV)

Westmoreland et al. (1998) Chemokine receptor expression on resident and inflammatory cells in the brain of macaques with simian immunodeficiency virus encephalitis, *Am J Pathol* 152:659–665, describes that a correlation between monocyte/macrophage infiltrates in the brain and neurological disease exists, and that chemokines and chemokine receptors may play roles in HIV neuropathogenesis and describes their pattern of expression in the SIV-infected rhesus macaque model of HIV encephalitis. Elevated expression of the chemokines macrophage inflammatory protein (MIP)-1alpha, MIP-1beta, RANTES, and interferon-inducible protein (IP)-10 in brain of macaque monkeys with SIV encephalitis have been demonstrated and in this study the corresponding chemokine receptors CCR3, CCR5, CXCR3, and CXCR4 are shown to be expressed in perivascular infiltrates in these same tissues. In addition, CCR3, CCR5, and CXCR4 are detected on subpopulations of large hippocampal and neocortical pyramidal neurons and on glial cells in both normal and encephalitic brain. The data and results indicate that multiple chemokines and their receptors contribute to monocyte and lymphocyte recruitment to the brain in SIV encephalitis. Furthermore, the expression of known HIV/SIV co-receptors on neurons suggests a possible mechanism whereby HIV or SIV can directly interact with these cells, disrupting their normal physiological function and contributing to the pathogenesis of AIDS dementia complex.

Tyor et al. (1993) A model of human immunodeficiency virus encephalitis in scid mice, *Proc Natl Acad Sci USA* 90:8658–62, provides an animal model of HIV-associated dementia complex to aid in development of treatments therefor. Mice with severe combined immunodeficiency (scid mice), which accept xenografts without rejection, were intracerebrally inoculated with human peripheral blood mononuclear cells and HIV. One to 4 weeks after inoculation, the brains of these mice contained human macrophages (some of which were HIV p24 antigen positive), occasional multinucleated cells, and striking gliosis by immunocytochemical staining. Human macrophages also were frequently positive for tumor necrosis factor type alpha and occasionally for interleukin 1 and VLA-4. Cultures of these brains for HIV were positive. Generally, human macrophages were not present in the brains of control mice, nor was significant gliosis, and HIV was not recovered from mice that received HIV only intracerebrally. Pathologically, this model of HIV encephalitis in scid mice resembles HIV encephalitis in humans and the data suggest that the activation of macrophages by infection with HIV results in their accumulation and persistence in brain and in the development of gliosis. This model of HIV encephalitis provides insights into the pathogenesis and treatment of this disorder.

Toggas et al. (1994) Central nervous system damage produced by expression of the HIV-1 coat protein gp120 in transgenic mice, *Nature* 367:188–193, provides transgenic mice that express gp120 in their brains and used these mice to study the role of gp120 in the neuronal and glial observed in humans. The changes observed in brains of the transgenic mice resemble abnormalities in brains of HIV-1-infected humans. The severity of damage correlated positively with the brain level of gp120 expression. These results provide in vivo evidence that gp120 plays a key part in HIV-1-associated nervous system impairment. This facilitates the evaluation and development of therapeutic strategies aimed at HIV-brain interactions.

Wykrzykowska et al. (1998) Early regeneration of thymic progenitors in rhesus macaques infected with simian immunodeficiency virus, *J Exp Med* 187:1767–1778, using the SIV/macaque model of AIDS, examines the early effects of SIV on the thymus.

Krucker et al. (1998) Transgenic mice with cerebral expression of human immunodeficiency virus type-1 coat protein gp120 show divergent changes in short- and long-term potentiation in CA1 hippocampus, *Neuroscience* 83:691–700, study transgenic mice constitutively expressing glial fibrillary acidic protein-driven gp120 from brain astrocytes display neuronal and glial changes resembling abnormalities in human immunodeficiency virus type-1-infected human brains.

Power et al. (1998) Neurovirulence in feline immunodeficiency virus-infected neonatal cats is viral strain specific and dependent on systemic immune suppression, *J Virol* 72:9109–15, provide an animal model of HIV and its role in immune suppression. Feline immunodeficiency virus (FIV) is a lentivirus that causes immune suppression and neurological disease in cats. To determine the extent to which different FIV strains caused neurological disease, FIV V1CSF and Petaluma were compared in ex vivo assays and in vivo. Both viruses infected and replicated in macrophage and mixed glial cell cultures at similar levels, but V1CSF induced significantly greater neuronal death than Petaluma in a neurotoxicity assay. V1CSF-infected animals showed significant neurodevelopmental delay compared to the Petaluma-infected and uninfected animals. Magnetic resonance spectroscopy studies of frontal cortex revealed significantly reduced N-acetyl aspartate/creatine ratios in the V1CSF group compared to the other groups. Cyclosporin A treatment of Petaluma-infected animals caused neurodevelopmental delay and reduced N-acetyl aspartate/creatine ratios in the brain. Reduced CD4(+) and CD8(+) cell counts were observed in the V1CSF-infected group compared to the uninfected and Petaluma-infected groups. These findings indicate that neurodevelopmental delay and neuronal injury is FIV strain specific but that systemic immune suppression is also an important determinant of FIV-induced neurovirulence.

F. Formulation and Administration of Compositions Containing the Conjugates

Compositions for use in treatment of disoroders associated with pathophysiological inflammatory responses, including secondary tissue damage and associated disease states are provided herein. Such compositions contain a therapeutically effective amount of a chimeric ligand-toxin comprising a chemokine, or a biologically functional fragment thereof, and a cell toxin, as described above.

Effective concentrations of one or more of chemokine receptor targeting agents or pharmaceutically acceptable derivatives thereof are mixed with a suitable pharmaceutical carrier or vehicle for systemic, topical or local administration. Compounds are included in an amount effective for treating the selected disorder. The concentration of active compound in the composition will depend on absorption, inactivation, excretion rates of the active compound, the dosage schedule, and amount administered as well as other factors known to those of skill in the art.

Pharmaceutical carriers or vehicles suitable for administration of the conjugates and for the methods provided herein include any such carriers known to those skilled in the art to be suitable for the particular mode of administration. In addition, the compounds may be formulated as the sole pharmaceutically active ingredient in the composition or may be combined with other active ingredients.

The amount of the therapeutic agent administered is in the range from about 0.1 pg to about 1 ng per kg of body weight. It can be administered in a slow release delivery vehicle, such as, but are not limited to, microspheres, liposomes, microparticles, nanoparticles, and colloidal carbon. Typically a therapeutically effective dosage should produce a serum concentration of active ingredient of from about 0.1 ng/ml to about 50–100 µg/ml. The pharmaceutical compositions typically should provide a dosage of from about 0.01 mg to about 100–2000 mg of conjugate, depending upon the conjugate selected, per kilogram of body weight per day. Typically, for intravenous or systemic treatment a daily dosage of about between 0.05 and 0.5 mg/kg should be sufficient. Local application should provide about 1 ng up to 100 µg, preferably about 1 µg to about 10 µg, per single dosage administration. It is understood that the amount to administer will be a function of the conjugate selected, the indication treated, and possibly the side effects that will be tolerated. Dosages can be empirically determined using recognized models for each disorder.

The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the targeted condition and may be empirically determined. To formulate a composition, the weight fraction of compound is dissolved, suspended, dispersed, or otherwise mixed in a selected vehicle at an effective concentration such that the targeted condition is relieved or ameliorated.

For local internal administration, such as, intramuscular, parenteral or intra-articular administration, the compounds are preferably formulated as a solution suspension in an aqueous-based medium, such as isotonically buffered saline or are combined with a biocompatible support or bioadhesive intended for internal administration.

The resulting mixtures may be solutions, suspensions, emulsions or the like and can be formulated as an aqueous mixtures, a creams, gels, ointments, emulsions, solutions, elixirs, lotions, suspensions, tinctures, pastes, foams, aerosols, irrigations, sprays, suppositories, bandages, or any other formulation suitable for systemic, topical or local administration.

Pharmaceutical and cosmetic carriers or vehicles suitable for administration of the compounds provided herein include any such carriers known to those skilled in the art to be suitable for the particular mode of administration. In addition, the compounds may be formulated as the sole pharmaceutically active ingredient in the composition or may be combined with other active ingredients. The active compound is included in the carrier in an amount sufficient to exert a therapeutically useful effect in the absence of serious toxic effects on the treated individual. The effective concentration may be determined empirically by testing the compounds using in vitro and in vivo systems, including the animal models described herein.

Solutions or suspensions used for local application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid [EDTA]; buffers, such as acetates, citrates and phosphates; and agents for the adjustment of tonicity such as sodium chloride or dextrose. Liquid preparations can be enclosed in ampules, disposable syringes or multiple dose vials made of glass, plastic or other suitable material. Suitable carriers may include physiological saline or phosphate buffered saline [PBS], and the suspensions and solutions may contain thickening and solubilizing agents, such as glucose, polyethylene glycol, and polypropylene glycol and mixtures thereof. Liposomal suspensions, may also be suitable as pharmaceutically acceptable carriers. These may be prepared according to methods known to those skilled in the art.

The therapeutic agents for use in the methods can be administered by any route known to those of skill in the art, such as, but are not limited to, topically, intraarticularly, intracisternally, intraocularly, intraventricularly, intrathecally, intravenously, intramuscularly, intraperitoneally, intradermally, intratracheally, as well as by any combination of any two or more thereof.

The most suitable route for administration will vary depending upon the disease state to be treated, for example the location of the inflammatory condition. Modes of administration include, but are not limited to, topically, locally, intraarticularly, intracisternally, intraocularly, intraventricularly, intrathecally, intravenously, intramuscularly, intratracheally, intraperitoneally, intradermally, and by a combination of any two or more thereof. For example, for treatment of SCI and other CNS inflammatory conditions, local administration, including administration to the CNS fluid or into the brain (e.g., intrathecally, intraventricularly, or intracisternally) provides the advantage that the therapeutic agent can be administered in a high concentration without risk of the complications that may accompany systemic administration of a therapeutic agent. Similarly, for treatment of inflammatory joint diseases, local administration by injection of the therapeutic agent into the inflamed joint (i.e., intraarticularly) may be preferred. As another example, a disease state associated with an inflammatory skin condition may advantageously be treated by topical administration of the therapeutic agent, for example formulated as a cream, gel, or ointment. For treatment of a disease state associated with an inflammatory lung condition, the preferred route for administration of the therapeutic agent may be by inhalation in an aerosol, or intratracheally.

The therapeutic agent is administered in an effective amount. Amounts effective for therapeutic use will, of course, depend on the severity of the disease and the weight and general state of the subject as well as the route of administration. Local administration of the therapeutic agent will typically require a smaller dosage than any mode of systemic administration, although the local concentration of the therapeutic agent may, in some cases, be higher following local administration than can be achieved with safety upon systemic administration.

Since individual subjects may present a wide variation in severity of symptoms and each therapeutic agent has its unique therapeutic characteristics, it is up to the practitioner to determine a subject's response to treatment and vary the dosages accordingly. Dosages used in vitro may provide useful guidance in the amounts useful for in situ administration of the pharmaceutical composition, and animal models may in some cases be used to determine effective dosages for treatment of particular disorders. In general, however, for local administration, it is contemplated that an effective amount of the therapeutic agent will be an amount within the range from about 0.1 picograms (pg) up to about 1 ng per kg body weight. Various considerations in arriving at an effective amount are described, e.g., in, et al., eds., *Goodman And Gilman's: The Pharmacological Bases of Therapeutics*, 8th ed., Pergamon Press, 1990; and *Remington's Pharmaceutical Sciences*, 17th ed., Mack Publishing Co., Easton, Pa., 1990, and the studies of Mantyh et al., (*Science*, 278: 275–79, 1997) involving the intrathecal injection of a neuronal specific ligand-toxin, each of which is herein incorporated by reference in its entirety.

The conjugates can be administered by any appropriate route, for example, orally, parenterally, intravenously, intradermally, subcutaneously, or topically, in liquid, semi-liquid or solid form and are formulated in a manner suitable for each route of administration. Preferred modes of administration depend upon the indication treated. Dermatological and ophthalmologic indications will typically be treated locally; whereas, tumors and SCI and other such disorders, will typically be treated by systemic, intradermal or intramuscular, modes of administration.

In one embodiment of the compositions and methods provided herein, the therapeutic agent is administered locally in a slow release delivery vehicle, for example, encapsulated in a colloidal dispersion system or in polymer stabilized crystals. Useful colloidal dispersion systems include nanocapsules, microspheres, beads, and lipid-based systems, including oil-in-water emulsions, micelles, mixed micelles, and liposomes. The colloidal system presently preferred is a liposome or microsphere. Liposomes are artificial membrane vesicles which are useful as slow release delivery vehicles when injected or implanted. Some examples of lipid-polymer conjugates and liposomes are disclosed in U.S. Pat. No., 5,631,018, which is incorporated herein by reference in its entirety. Other examples of slow release delivery vehicles are biodegradable hydrogel matrices (U.S. Pat. No. 5,041,292), dendritic polymer conjugates (U.S. Pat. No. 5,714,166), and multivesicular liposomes (Depofoam®, Depotech, San Diego, Calif.) (U.S. Pat. Nos. 5,723,147 and 5,766,627). One type of microspheres suitable for encapsulating therapeutic agents for local injection (e.g., into subdermal tissue) is poly(D,L)lactide microspheres, as described in D. Fletcher, *Anesth. Analg.* 84:90–94, 1997.

Besides delivering an effective therapeutic dose to the site of trauma and decreasing the chance of systemic toxicity, local administration also decreases the exposure of the therapeutic to degradative processes, such as proteolytic degradation and immunological intervention via antigenic and immunogenic responses. Drug derivatization with, for example, monomethoxypoly(ethyleneglycol) can also decrease the likelihood of the above mentioned drawbacks. Pegylation of therapeutics has been reported to increase resistance to proteolysis; increase plasma half-life, and decrease antigenicity and immunogencity. One method of attaching PEG polymers (ranging in size from about 2,000 to 8,000 Da) is illustrated in Example 5 herein. Other examples of pegylation methodologies are given by Lu and Felix, *Int. J. Peptide Protein Res.*, 43: 127–138, 1994; Lu and Felix, *Peptide Res.*, 6: 142–6, 1993; Felix et al., *Int. J. Peptide Res.*, 46: 253–64, 1995; Benhar et al., *J. Biol. Chem.*, 269: 13398–404, 1994; Brumeanu et al., *J. Immunol.*, 154: 3088–95, 1995).

The composition provided herein further contain one or more adjuvants that facilitate delivery, such as, but are not limited to, inert carriers, or colloidal dispersion systems. Representative and non-limiting examples of such inert carriers can be selected from water, isopropyl alcohol, gaseous fluorocarbons, ethyl alcohol, polyvinyl pyrrolidone, propylene glycol, a gel-producing material, stearyl alcohol, stearic acid, spermaceti, sorbitan monooleate, methylcellulose, as well as suitable combinations of two or more thereof.

A composition provided herein can also be formulated as a sterile injectable suspension according to known methods using suitable dispersing or wetting agents and suspending agents. The sterile injectable preparation may also be a sterile injectable solution or suspension in a non-toxic parenterally-acceptable diluent or solvent, for example, as a solution in 1–4, butanediol. Sterile, fixed oils are conventionally employed as a solvent or suspending medium. For this purpose any bland fixed oil may be employed, including, but are not limited to, synthetic mono- or diglycerides, fatty acids (including oleic acid), naturally occurring vegetable oils like sesame oil, coconut oil, peanut oil, cottonseed oil, etc., or synthetic fatty vehicles like ethyl oleate. Buffers, preservatives, antioxidants, and the suitable ingredients, can be incorporated as required, or, alternatively, can comprise the formulation.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules or troches. Pharmaceutically compatible binding agents and adjuvant materials can be included as part of the composition.

The tablets, pills, capsules, troches and the like can contain any of the following ingredients, or compounds of a similar nature: a binder, such as microcrystalline cellulose, gum tragacanth and gelatin; an excipient such as starch and lactose, a disintegrating agent such as, but not limited to, alginic acid and corn starch; a lubricant such as, but not limited to, magnesium stearate; a glidant, such as, but not limited to, colloidal silicon dioxide; a sweetening agent such as sucrose or saccharin; and a flavoring agent such as peppermint, methyl salicylate, and fruit flavoring.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The conjugates can also be administered as a component of an elixir, suspension, syrup, wafer, chewing gum or the like. A syrup may contain, in addition to the active compounds, sucrose as a sweetening agent and certain preservatives, dyes and colorings and flavors.

The active materials can also be mixed with other active materials that do not impair the desired action, or with materials that supplement the desired action, such as cisplatin for treatment of tumors.

Finally, the compounds may be packaged as articles of manufacture containing packaging material, one or more conjugates or compositions as provided herein within the packaging material, and a label that indicates the indication for which the conjugate is provided.

G. Disease States Associated with the Inflammatory Response and Secondary Tissue Damage SCI and a number of other disease states are associated with the proliferation, activation, and migration of various types of leukocytes. These events combine to produce a very aggressive and inhospitable environment at the site of injury or disease. Current approaches to treatment, regardless of their success, tend to center around single components of the pro-inflammatory process. For example, many investigators have concentrated on the transplantation of neurons or CNS tissue into the injured nervous system in the hope of promoting the survival and regeneration of either transplanted cells, or existing cells which produce growth and neurotrophic factors. Other approaches have attempted to address secondary damage through ionotropic channel antagonism, by inhibiting the cytotoxic actions of excitatory amino acids using NMDA antagonists, and inhibiting lipid peroxidation using antioxidants, for example, with the steroid, methylprednisolone. All of these approaches have shown little or no long-term benefit. In short, the focus on single biochemical mechanisms fails to appreciate the capacity of the trauma response (or disease process) as a whole to make compensatory changes that either nullify the effect of the therapeutic intervention, or in some cases, may actually make things worse.

It is found herein that treatment is more effective if the normal inflammatory response is not initiated, and, the likelihood for improvement and recovery are significantly compromised the longer this process is allowed to continue. The methods and compositions provided herein are designed to transiently inhibit or suppress the activity of key leukocyte subtypes (and/or astrocytes) and remove the key sources that fuel inflammatory mechanisms and secondary damage.

The compositions and methods provided herein permit the selective, deliberate, and surreptitious delivery of therapeutic agent to cells that orchestrate the response to injury or disease. In order to initiate and sustain a disease process (e.g., cancer) or an inflammatory response, the cells involved are activated and upregulate their expression of cell surface receptors for a variety of ligands. Because receptors involved in trauma and disease are often upregulated, the likelihood of the therapeutic agent being internalized by the correct cells, is increased.

It has been found herein that the cell biology of more than seventy diseases and conditions, involving most organ systems, involved pathophysiological inflammatory responses in a manner similar to the cell biology of acute SCI. The following, non-exhaustive list, and the more detailed treatment of four clinical areas, are designed to illustrate some of the more important similarities. Exemplary disorders and conditions, in addition to spinal cord injury, include stroke, acute lung injury and acute respiratory distress syndrome (ARDS), Alzheimer's disease, Down's syndrome, inflammatory joint disease, HIV encephalitis, growth, neovascularization (angiogenesis) and metastases of several forms of cancer including, brain, breast, and lung cancers, multiple sclerosis, spongiform encephalopathies, sepsis, ulcerative colitis and Crohn's disease, proliferative vitreoretinopathy and uveitis.

HIV Infection and AIDS and Infections with other Pathogens

Activation and infection of CNS microglia and infiltrating macrophages is one hallmark of the pathogenesis of HIV induced diseases Human immunodeficiency viruses (HIV) can only enter a cell if the CD4 receptor is associated with a specific chemokine co-receptor. The CXCR4, CCR2b, CCR3, CCR5, CCR6, CCR8 and CX3CR1 can all act in a co-receptor capacity. For example, macrophage-tropic HIV-1 strains generally use CCR5 co-receptors, while T-cell-tropic strains generally use CXCR4. In addition, dual-tropic viruses can use CXCR4 and CCR5 co-receptors for entry, while other subsets of the HIV viral strains use a variety of other chemokine co-receptors.

In patients with HIV encephalitis, (HIVE) CXCR-4 is expressed on MNPs, astrocytes, and a sub-population of cholinergic neurons, whereas CCR5 is mainly expressed on MNPs. It should be noted that the majority of infected cells in HIVE patients (children and adults) appear to be MNPs and increased expression of CCR5 appears to correlate with the severity of the disease. This suggests that MNP-mediated events may be more important, at least in the late and severe stages of HIVE. The CCR5 receptor is also upregulated following bacterial infection of the CNS and in a rat model of ischemic brain injury.

Increased production of cytokines (e.g., TNF-$\alpha$) and chemokines (e.g., RANTES, MCP-1, MIP-1$\alpha$, and MIP-1$\beta$) is associated with HIV infection. Increased CNS chemokines in HIV would account for peripheral leukocyte recruitment and cytokine release with direct cytotoxic effects (at least in the case of TNF-$\alpha$) on neurons and oligodendrocytes, and precisely mirrors the experience in CNS trauma. Several cytokines including, GM-CSF, macrophage-CSF, IL-1$\beta$, IL2, IL-3, IL-6, TNF-$\alpha$, and TNF-$\beta$ may also contribute to the pathogenesis of HIV disease by activating and/or augmenting HIV replication.

Secondary damage occurs in HIV-1 positive, asymptomatic, pre-AIDS patients (An et al. (1997) *Arch Anat Cytol Pathol* 45, 94–105). These investigators were able to detect HIV-1 DNA in 50% of the brains of asymptomatic patients and nearly 90% displayed astrogliosis. These patients also have elevated levels of immunomolecules, and cytokines including, TNF-$\alpha$, IL-1, IL-4, and IL-6. Neuronal damage was confirmed by the detection of apoptotic neurons.

Direct neurotoxicity and upregulation of the CCR5 co-receptor by MNP-derived excitatory amino acids has also been implicated in the pathology of HIV infection. An increase in inducible nitric oxide synthase activity has been detected in HIV infected microglia from AIDS patients. This suggests that the production of nitric oxide could contribute to lesion formation in HIV infected areas of the nervous system. Once again, the pathology of HIV encephalopathies, and pre- and full blown AIDS affecting the CNS, appear to mimic the secondary tissue damage observed in SCI and other inflammatory diseases.

It has also been found that some chemokines and chemokine receptors are also promicrobial factors and facilitate infectious disease (see, Pease et al. (1998) *Seminar in Immunol* 10: 169–178). Pathogens exploit the chemokine system. For example, cellular chemokine receptors are used for cell entry by intracellular pathogens, including HIV. In addition viruses use virally-encoded chemokine receptors to promote host cell proliferation. Pathogens also subvert the chemokine system. Virally-encoded chemokine antagonists and virally-encoded chemokine scavengers are known. Hence conjugates provided herein may be used to interfere with viral and bacterial infection by a variety of mechanisms.

Inflammatory Joint Disease and Autoimmune Disease

Rheumatoid arthritis (RA) is an inflammatory autoimmune disease characterized by chronic connective tissue damage and bone erosion. The pathogenesis of the disease includes the infiltration of leukocytes into the synovial space, their activation, and the release of inflammatory mediators that ultimately deform and destroy the affected joint. The actual arthritic response appears to be initiated when MNPs release pro-inflammatory cytokines and chemokines. TNFα, IL-1, IL-6, GM-CSF, and the chemokine IL-8, are found in abundance in joint tissue from RA patients and their most likely source includes synovial fibroblasts, in addition to MNPs. The combination of MNPs, neutrophils, and T-cells, with the participation of synovial fibroblasts and synoviocytes, sets up a cascade of inflammation.

IL-1 and TNFα are believed to be responsible for the production of chemokines in the arthritic joint. In one study, increased concentrations of these two cytokines induced the expression of IL-8 (a potent T-cell chemoattractant) and RANTES (a potent neutrophil chemoattractant), in human synovial fibroblasts isolated from RA patients (Rathanaswami et al. (1993) *J Biol Chem* 268, 5834–9). Other investigators have shown that inflamed synovial tissue from RA and osteoarthritic patients contains high concentrations of MCP-1, and TNFα and IL-1 markedly increased the mRNA expression of this chemokine in cultured synoviocytes derived from these specimens. It appears that chemokines from MNPs and cytokine stimulated synovial fibroblasts and synoviocytes play a role in the pathology of RA by facilitating the recruitment and extravasation of peripheral monocytes, neutrophils and T-cells. In common with other diseases and conditions, activated leukocytes release a range of other tissue damaging mediators. More specifically, leukocyte-derived reactive oxygen species and proteolytic enzymes (e.g. matrix metalloproteinases, cathepsin and neutrophil-derived elastase) have been implicated in the initiation and maintenance of tissue damage in inflammatory joint diseases.

Pulmonary Disease

Lung injury covers a wide array of clinical conditions. For purposes herein they are collectively referred to as Inflammatory Diseases of the Lung (ILDs). An ILD is typically the result of specific insult, for example, systemic bacterial infections (e.g., sepsis), trauma (e.g., ischemia-reperfusion injury), and inhalation of antigens (e.g., toxins like cigarette smoke). ILDs also include allergic alveolitis, ARDS (acute or adult respiratory distress syndrome), various forms of asthma, bronchitis, collagen-vascular disease, pulmonary sarcoidosis, eosinophilic lung diseases, pneumonia, and pulmonary fibrosis. In brief, the pathology of these diseases and conditions, involves the activation of macrophages, particularly those located in the alveoli. Neutrophils, eosinophils and T-cells, are activated and recruited to the site of injury subsequent to the release of macrophage, and neighboring endothelial and epithelial cell derived cytokines and chemokines. The specific cytokines and chemokines involved include; GM-CSF, TNF-α, IL-1, 1L-3, IL-5, IL-8, MCP-1, MCP-3, MIP-1α, RANTES and Eotaxin.

Leukocytes respond to the pro-inflammatory cytokines and chemokines by releasing the many mediators of secondary tissue damage including; proteases, reactive oxygen species, and biologically active lipids, and by expressing cell surface antigens and cell adhesion molecules. In addition, it appears that specific leukocyte populations play a more prominent role in some ILDs than they do in others. Neutrophils and MNPs are more prominent contributors to secondary damage in acute lung injuries like ARDS and various lung fibroses; whereas T-cells and eosinophils are the chief culprits in eosinophilic lung diseases, which include allergic asthma, fibrosing alveolitis, and sarcoidosis.

Cancer

Tumor cell and MNP-generated growth factors, cytokines, and chemokines have been shown to regulate tumor angiogenesis and leukocyte recruitment to the tumor microenvironment. Although leukocytes have a tumoricidal function, leukocyte infiltration and an over-production of angiogenic factors result in neovascularization which nourishes the tumor cells and facilitates tumor progression. Quantitative examination of leukocyte infiltrates have revealed, for example, that MNPs make up to 50% of the cell mass in breast carcinomas. A recent study concluded that MCP-1 over-expression was responsible for leukocyte infiltration and the high numbers of macrophages and T-cells that are associated with ovarian tumors. Indeed, over-expression of other chemokines, and cytokines has been observed in other cancers, including lymphomas and gliomas. An elevated neutrophil count has been associated with bronchioloalveolar carcinoma and correlates with the increased concentration of IL-8, a powerful neutrophil chemoattractant, in lung biopsies and bronchoalveolar lavage samples.

Upregulation of cellular adhesion molecules and proteinases in response to cytokine and chemokine activation are an integral part of tumor metastasis. Leukocyte and epithelial cell proteases break down the extracellular matrices and are involved in the dispersal of cells from primary tumors. For example, neutrophil elastase is linked to the direct invasion of cells from non-small cell lung cancer (NSCLC) into the aorta. Furthermore, tumor cells contribute to the metastatic process by producing their own proteases. Cell adhesion molecule (CAM) expression on all types of cells (e.g., tumor, endothelial and leukocyte cells) is essential for metastasis. Integrin CAMs not only play a role in metastasis but are involved in the growth and survival of the tumor cells, and cooperate with various proteinases to promote metastasis and angiogenesis.

Secondary Tissue Damage

Disease states associated with secondary tissue damage can be treated according to the methods provided herein and using the conjugates provided herein as well as certain non-chemokine cytokines known to those of skill in the art for treatment of other conditions. These disease states, include, but are not limited to, CNS injury, CNS inflammatory diseases, neurodegenerative disorders, heart disease, inflammatory eye diseases, inflammatory bowel diseases, inflammatory joint diseases, inflammatory kidney or renal diseases, inflammatory lung diseases, inflammatory nasal diseases, inflammatory thyroid diseases, cytokine regulated cancers, and other disease states that involve or are associated with secondary tissue damage.

Examples of CNS inflammatory diseases and/or neurodegenerative disorders that can be treated using the methods herein and conjugates provided herein, include, but are not limited to, stroke, closed head injury, leukoencephalopathy, choriomeningitis, meningitis, adrenoleukodystrophy, AIDS dementia complex, Alzheimer's disease, Down's Syndrome, chronic fatigue syndrome, encephalitis, encephalomyelitis, spongiform encephalopathies, multiple sclerosis, Parkinson's disease, spinal cord injury/trauma (SCI), and traumatic brain injury; heart diseases that can be treated using the methods provided herein, include, but are not limited to, atherosclerosis, neointimal hyperplasia and restenosis; inflammatory eye diseases that can be treated using the methods and conjugates provided herein, include, but are not limited to, proliferative diabetes retinopathy, proliferative vitreoretinaopathy, retinitis, scleritis, sclerouritis, choroiditis and uevitis. Examples of inflammatory bowel diseases that can be treated using the methods and conjugates provided herein, include, but are not limited to, chronic colitis, Crohn's disease and ulcerative colitis. Examples of inflammatory joint diseases that can be treated using the methods and conjugates provided herein include, but are not limited to, juvenile rheumatoid arthritis, osteoarthritis, rheumatoid arthritis, spondylarthropathies, such as ankylosing spondylitis, Reiter's syndrome, reactive arthritis, psoriatic arthritis, spondylitis, undifferentiated spondylarthopathies and Behcet's syndrome; examples of inflammatory kidney or renal diseases that can be treated using the methods and conjugates provided herein include, but are not limited to, glomerulonephritis, lupus nephritis and IgA nephropathy. Examples of inflammatory lung diseases that can be treated using the methods and conjugates provided herein, include, but are not limited to, eosinophilic lung disease, chronic eosinophilic pneumonia, fibrotic lung diseases, acute eosinophilic pneumonia, bronchoconstriction, including asthma, bronchopulmonary dysplasia, bronchoalveolar eosinophilia, allergic bronchopulmonary aspergillosis, pneumonia, acute respiratory distress syndrome, and chronic obstructive pulmonary disease (COPD); examples of inflammatory nasal diseases that can be treated using the methods and conjugates provided herein, include, but are not limited to, polyposis, rhinitis, sinusitus; examples of inflammatory thyroid diseases that can be treated using the methods and conjugates provided herein, include, but are not limited to, thyroiditis; and examples of cytokine-regulated cancers that can be treated using the methods provided herein, include, but are not limited to, gliomas, atheromas carcinomas, adenocarcinomas, granulomas, glioblastomas, granulamatosis, lymphomas, leukemias, melanomas, lung cancers, myelomas, sarcomas, sarcoidosis, microgliomas, meningiomas, astrocytomas, oligodendrogliomas, Hodgkins disease, and breast and prostate cancers. Other inflammatory diseases susceptible to treatment using the methods and conjugates provided herein, include, but are not limited to, vasculitis, autoimmune diabetes, insulin dependent diabetes mellitus, graft versus host disease (GVHD), psoriasis, systemic lupus erythematosus, sepsis, systemic inflammatory response syndrome (SIRS), and injurious inflammation due to burns.

As noted above, these disorders, although diverse, share the common features related to the inflammatory response. Spinal cord injury or trauma, which can be treated by administering to a subject in need thereof an effective amount of a therapeutic agent as described herein, is exemplary of the disorders contemplated. The treatments herein are designed to attack the adverse results of this responses involving proliferation and migration of leukocytes. The treatments will eliminate or reduce the leukocyte proliferation and migration and by virtue of this lead to an amelioration of symptoms, a reduction in adverse events or other beneficial results that may enhance the effectiveness of other treatments.

The following examples are included for illustrative purposes only and are not intended to limit the scope of the invention.

EXAMPLE 1

Construction of Genes

To expedite the development process, a genetic construct, a cassette construct, that facilitates the interchange of fusion protein ligand, toxin, and linker sequences was designed. This "cassette construct" was chemically synthesized with the complete coding sequence of OPL98101 (see Table 6; and see SEQ ID No. 55) in place. The gene was designed such that the fusion protein starts with a methionine (Met) residue followed by the published sequence of mature MCP-3 and an alanine (Ala) residue. This sequence was followed by a Met residue (thereby forming the Ala-Met linker) and residues 23–268 of the Shiga-A1 toxin subunit.

Figure 3:
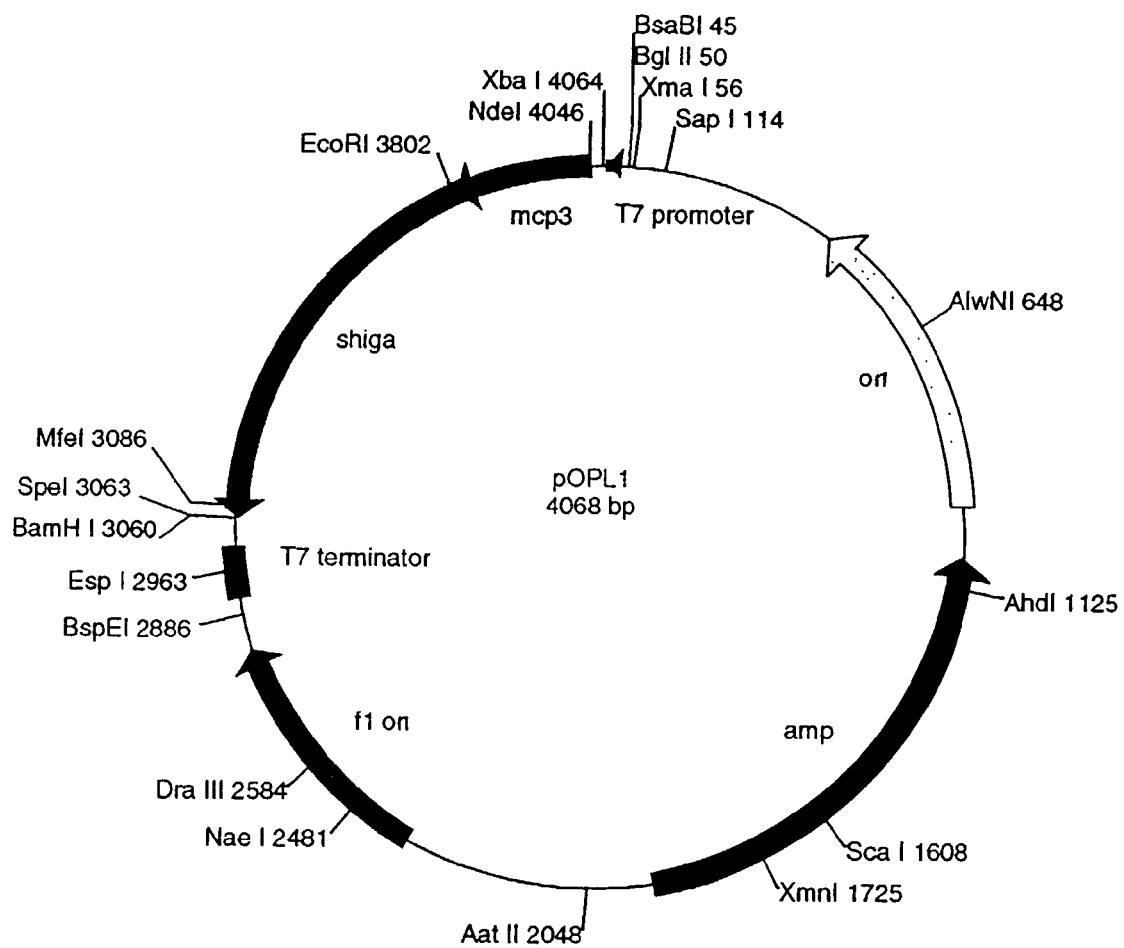
FIG. 3 is a schematic map of a conjugate MCP-3-AM-Shiga-A1 cloned into a pGEMEX vector as described in the Examples.
Figure 4:
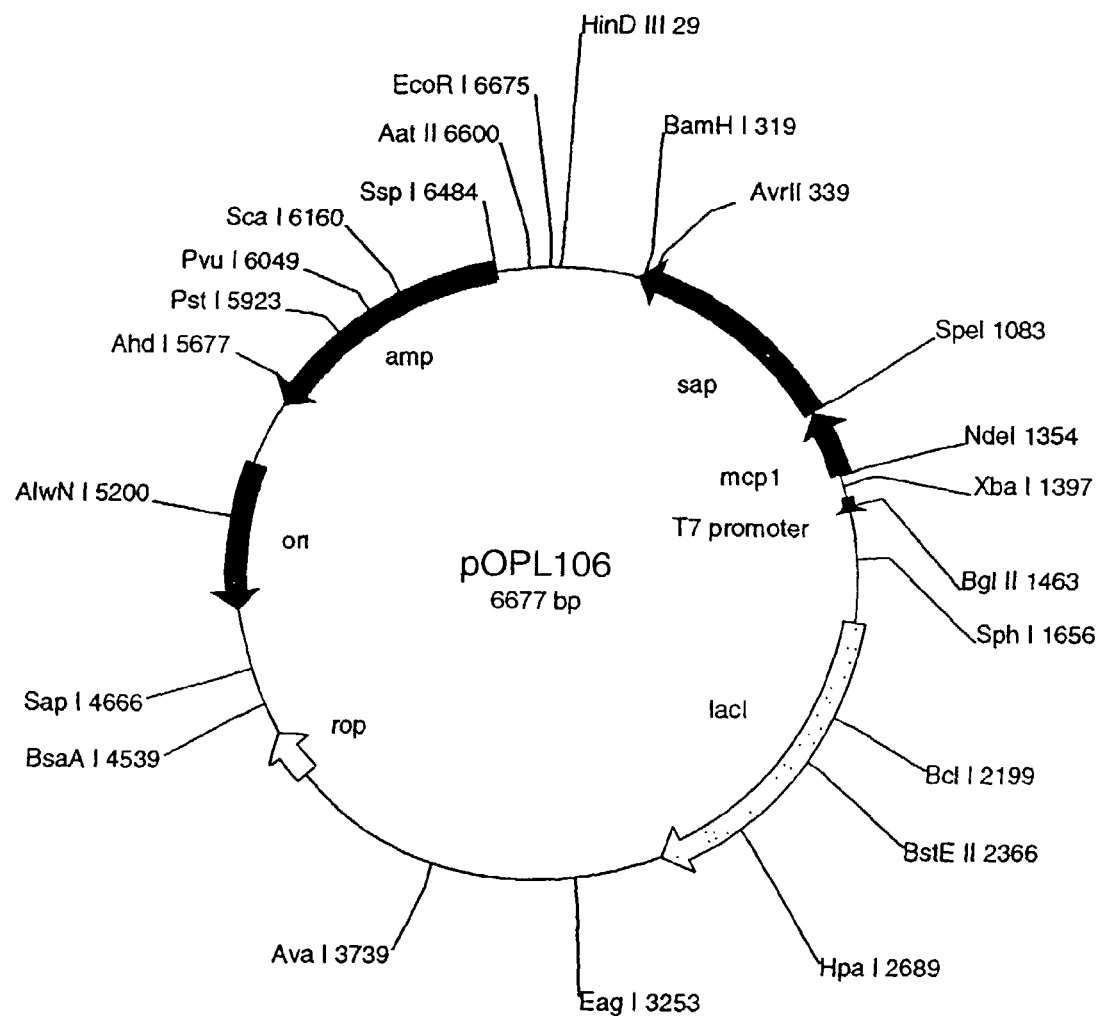
FIG. 4 is a schematic map of a conjugate MCP-1-AM-SAP cloned into a pET11c vector (see Examples and Table 6).
Figure 5:
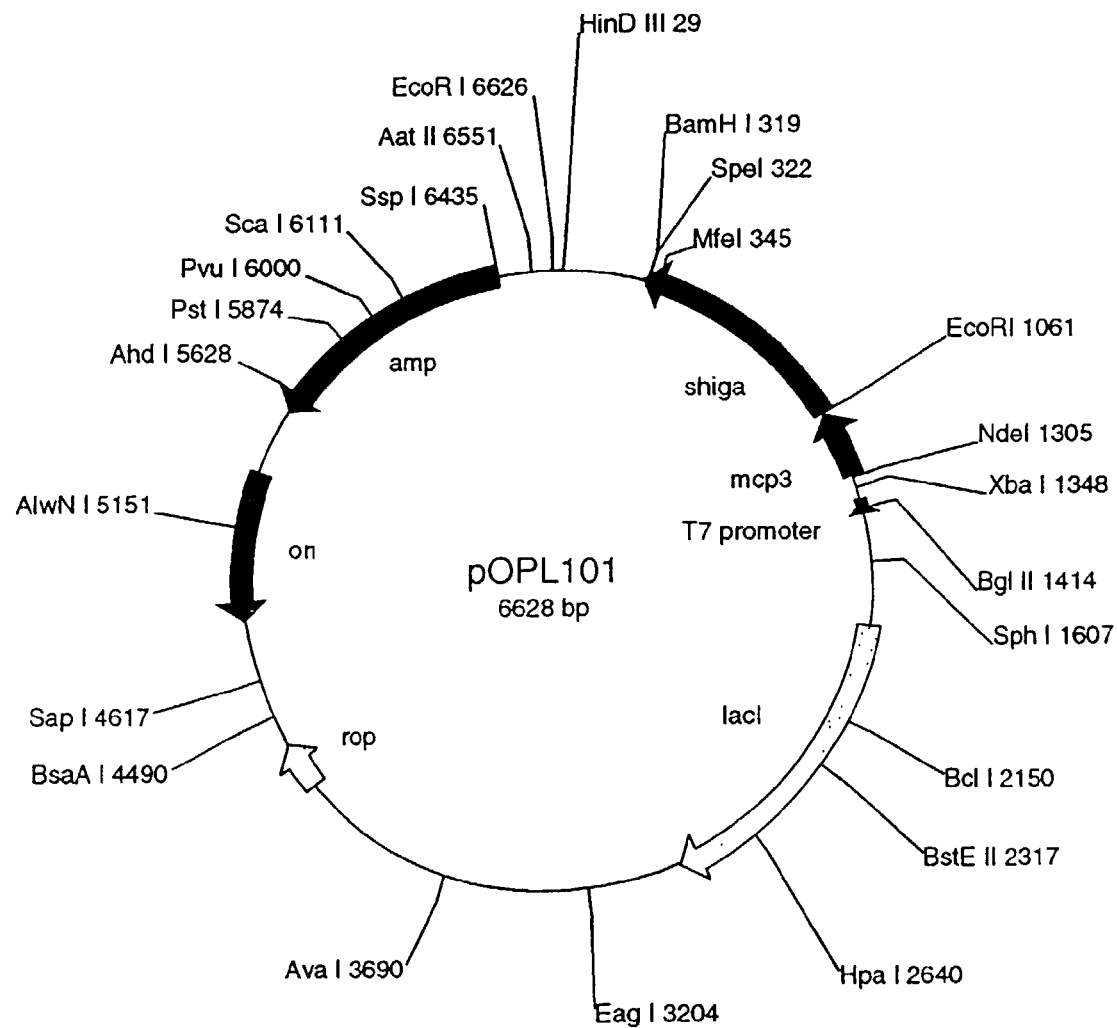
FIG. 5 is a schematic map of a conjugate MCP3-AM-Shiga-A1 cloned into a pET11c vector (see Examples and Table 6).

To facilitate removal and replacement with different ligand and toxin genes, restriction endonuclease sites were incorporated into each gene sequence close to their 3' and 5' ends (see, SEQ ID NOs. 52–67). In addition, a second toxin gene, with appropriate internal restriction sites, that codes for the mature form of Saporin-6 (OPL982) protein was synthesized. The shiga toxin was similarly subcloned. The chemokine-toxin fusions and free toxin genes contain flanking XbaI (5') and BamHI (3') restrictions sites. They were individually cloned into a pGemex-1 vector (Promega Inc). The resulting plasmid containing the free Saporin toxin was pOPL2 (free saporin toxin). The plasmid maps of the free Saporin toxin (pOPL2) is shown in FIG. 2. A plasmid map of a ligand-toxin fusion (MCP3-AM-SHIGA, designated OPL98101 in Table 6, is shown in FIG. 3, where the plasmid is designated pOPL1.

The ATG initiation codon of both genes included an NdeI site for sub-cloning into the pET11c expression system (T7 promoter, Novagen Inc.). Codon selection in both DNA constructs was optimized for expression in *E. coli* during the design phase. The genes from the pGemex-1 vectors were subcloned into the pET11c expression system using appropriate restriction enzymes. Plasmid maps of exemplary chemokine-toxin-containing plasmids in pET11c plasmids are set forth in FIGS. 4 (MCP1-AM-SAP) and 5 (MCP3-AM-SHIGA). Expression of constructs such as these gave rise to proteins, such as OPL98101 and OPL983 (see Table 6).

Cloning of Ligand and Toxin Genes

All remaining genes, and variants on the original sequences, were cloned using appropriate oligonucleotide primers (see Table 7) and polymerase chain reaction (PCR) techniques. Forward strand primers were designed with a restriction site for subcloning of the gene into pET11c. The reverse strand primers overlapped the linker and part of the required toxin sequence and coded for appropriate restriction sites for subsequent ligand and toxin removal and replacement, and subcloning into the expression vector. MCP-1 was cloned from the ATCC 65933 plasmid DNA (Rockville, Md.), while human Eotaxin and SDF-1β came from a Quick-Clone human lung cDNA library (Clonetech, Palo Alto, Calif.). The truncated Shiga-A1 genes (with and without a C-terminal six residue histidine tag sequence in the mature fusion protein) were cloned from pOPL98101. The PCR products were isolated from agarose gels using a Qiagen gel extraction kit and cloned into the vector pCR2.1 using a TOPO cloning kit (Invitrogen, Carlsbad, Calif.). To confirm their identity, finished genes were sequenced using M13 forward and reverse primers and an ABI Prism 310 Genetic Analyzer.

TABLE 7

| Primer Name orientation (gene) | Sequence (5' to 3') and Translation |
|---|---|
| 1 Eot forward (Eotaxin) | GGG TAA TAG CAT ATG GGG CCA GCT TCT GTC CCA ACC A<br>                NdeI  G   P   A   S   V   P   T<br>SEQ ID NO.41 |
| 2 Eot reverse (Eotaxin) | CCC GAA TTC TTT CAT CGC TGG CTT TGG AGT TGG AGA TTT TTG GT<br>     ECoRI  K   M   A   P   K   P   T   P   S   K   Q   D<br>SEQ ID NO.42 |
| 1 MCP-1 forward (MCP-1) | GGC TAA TAG CAT ATG CAG CCA GAT GCA ATC AAT GCC CCA<br>                NdeI  Q   P   D   A   I   N   A   P<br>SEQ ID NO.43 |
| 2 MCP-1 reverse (MCP-1) | CCC GAA TTC TTT CAT CGC ACT CTT CGG AGT TTC CCT TTC TT<br>     EcoRI  K   M   A   T   K   P   T   Q   T   Q   K<br>SEQ ID NO. 44 |
| 1 MCP-3 forward (MCP-3) | CAT ATG CAA CCG GTA GGC ATC AAC ACG<br>  NdeI   Q   P   V   G   I   N   T<br>SEQ ID NO.45 |
| 2 MCP-3 reverse (MCP-3) | C ACT AGT AAC CAT CGC AAG CTT CGG CGT CTG AG<br>    SpeI   V   M   A   L   K   P   T   Q   T<br>SEQ ID NO.46 |
| 1 SDF forward (SDF-1β) | GGG TAA TAG CAT ATG AAG CCC GTC AGC CTG AGC TAC AG<br>                NdeI  K   P   V   S   L   S   Y   R<br>SEQ ID NO.47 |
| 2 SDF reverse (SDF-1β) | CCC GAA TTC TTT CAT CGC CAT CTT GAA CCT CTT CTT TAA AGC TTT C<br>     ECoRI  K   M   A   M   K   F   R   K   N   L   A   K   E<br>SEQ ID NO.48 |
| 1 SHIGA forward (Shiga) | GGG TAA TAG CAT ATG AAA GAA TTC ACC CTG CAC TTT TCC<br>                NdeI  K   E   F   T   L   D   F   S<br>SEQ ID NO.49 |
| 2 SHIGA reverse | CCC GGA TCC ACT AGT A TTA ACC GTG GTG<br>    BamHI  SpeI    stop A   H   H<br>SEQ ID NO.50 |
| 3 SHIGA reverse (Shiga-His6) | CCC GGA TCC ACT AGT TTA ATG ATG ATG GTG GTG GTG GCA ATT GAG<br>    BamHI  SpeI    stop H   H   H   H   H   C   N   L<br>AAT CAG<br>  I    L<br>SEQ ID NO. 51 |

Screening for Expression of Chemokine-Toxin Conjugates

The chemokine-toxin-bearing pET11C constructs (Table 6) were transformed into E. coli BL21DE3 pLysS (Stratagene) and plated on Luria broth containing 1% glucose and 100 ug/ml carbenicillen (LB-car). Following an overnight incubation a single colony was used to inoculate 10 ml of LB-car grown to an $OD_{600}$ of 1.0, and induced with 1 mM IPTG. Samples were taken after one and two hours post induction, and the cells were concentrated by centrifugation and resuspended in SDS-sample buffer at OD 13. Expressed proteins were subjected to SDS-PAGE and visualized by Coomassie staining, while a parallel set of gels were Western and immunoblotted using appropriate antibodies (R&D systems, Minneapolis, Minn.). All of these chemokine-toxins (see Table 6) have been positively expressed. Aliquots of transformed cells (1 ml of LB containing 15% glycerol with $OD_{600}$~0.85) were frozen at −70° C. for future use.

Purification of Selected Fusion Proteins

Purification of OPL98110 by Nickel Affinity Chromatography

HIS-tagged chemokine-toxin genes were constructed so that small amounts of research material could be quickly expressed and purified to expedite in vitro bioassay, and to introduce an additional route for large scale purification, should one be required. A small amount of partially purified OPL98110 (~65% purity on SDS gels) was obtained using nickel-affinity chromatography. A two-step process of cation-exchange and nickel-affinity chromatography yields essentially pure chemokine-toxin.

Cells transformed with pOPL98110 were grown to an $OD_{600}$ of 1.28 (7 h incubation period at 37° C.) in a shake flask containing 500 ml of LB, induced with 1 mM IPTG for 1.5 h ($OD_{600}$=2.53) and harvested by centrifugation. Half the pellet (i.e., the equivalent of 250 ml of original culture) was sonicated on ice in 6 ml of 10 mM sodium phosphate (pH 7.4) containing 300 mM NaCl and 8 M urea. The lysate was centrifuged at 13,000 rpm in microcentrifuge tubes and the resultant supernatant was centrifuged at 100,000 g at 4° C. for 1 h. The final supernatant was mixed with a 1 ml slurry (50% v/v) of Nickel-NTA resin (Qiagen) previously equilibrated in lysis buffer containing 5 mM imidazole but no urea. The mixture was gently rotated for 5 h at 4° C., poured into a small column, and washed with 4 ml of 10 mM sodium phosphate (pH 7.4) containing 300 mM NaCl and 60 mM imidazole. The column was eluted with 4×1 ml of buffer containing 10 mM sodium phosphate (pH 7.4) and 0.5 M imidazole. OPL98110 positive fractions were identified by SDS-PAGE with Western and Immunoblotting. Once pooled, the yield and purity of the fusion protein were estimated at 200 ug and 65%, respectively.

Purification of a Non-His-Tagged Fusion Proteins (OPL98101)

OPL98101 was purified using a slightly modified version of a published method (McDonald et al. (1996) *Protein Expr Purif* 8, 97–108) as follows. OPL98101 plasmid-containing bacterial cells (strain BL21 (DE3)pLysS) from an overnight culture (1:100 dilution) were grown at 30° C. in an incubator shaker to an $OD_{600}$ of 0.7. IPTG (Sigma Chemical, St. Louis, Mo.) was added to a final concentration of 0.2 mM and growth was continued for 1.5 hours at which time cells were centrifuged. Growing the BL21 (DE3)pLysS cells at 30° C. instead of 37° C. improves yields. When the cells are grown at 30° C. they are grown to an $OD_{600}$ of 1.5 prior to induction. Following induction, growth is continued for about 2 to 2.5 hours at which time the cells are harvested by centrifugation.

Following fermentation the bacteria were sonicated in 5 volumes of 10 mM sodium phosphate (pH 7.4) containing 10 mM EGTA, 10 mM EDTA and 50 mM NaCl and centrifuged at 100,000 g. The supernatant was applied to a Q-Sepharose-FF column (equilibrated in the same buffer) connected to the inlet of an S-Sepharose-FF column. Under these conditions OPL98101 flows through the anion-exchange resin and sticks to the cation-exchange resin. The Q column was disconnected and the S-Sepharose column was eluted with a linear gradient of NaCl (0.05–1.0 M, 10 column volumes) in 10 mM sodium phosphate (1 mM EGTA, and 1 mM EDTA, pH 7.4). The chemokine-toxin was detected by immunoblotting and appropriately pooled fractions were applied to a Sephacryl S100 column.

Protein-containing fractions were analyzed by gel electrophoresis and Coomassie blue staining of the gels. The highly enriched chemokine-toxin co-purified with a ~28 kDa acidic (pI 6.3) protein at a ratio of ~1:1 (fusion protein: contaminant). No other protein bands were detected on Coomassie Blue-stained gels. N-terminal sequencing confirmed the presence of OPL98101 and the contaminant to be an *E. coli* "housekeeping protein". Further attempts to separate them, including hydrophobic interaction chromatography (HIC), were unsuccessful. It appears likely that the acidic contaminant was tightly bound to the basic fusion protein throughout purification. Lysing the cells at low pH (~5.0–5.8) in the presence of a denaturant, such as 8 M urea, the two proteins eliminates such tight associations. Subsequent experience with OPL98110 (stable in the presence of urea) supports this conclusion.

EXAMPLE 2

In Vitro Bioactivity of Selected Chemokine-Toxin Fusion Proteins

In Vitro Protein Synthesis Inhibition (RIP) Assays

Fusion protein and free ribosome-inactivating toxin-mediated inhibition of protein synthesis can be measured using a commercially available rabbit reticulocyte lysate system that assays the translation of luciferase RNA (Promega, Madison, Wis.). Briefly, samples were serially diluted in 20 mM Tricine, pH7.8, and 5 ul of diluted protein was combined with 5 ul of reaction mix (50 ug/ml of luciferase RNA, 0.1 mM amino acid mixture minus methionine) and 15 ul of rabbit reticulocyte lysate. In addition to several negative controls (buffer and a reagent blank), free Saporin (0.03–1 nM) was used as a positive control. Samples were incubated at 30° C. for 1 hour before 2.5 ul of reaction mixture was transferred to a Dynex 96-well plate (Dynex Technologies Inc. Chentilly, Va.), and analysed using a preheated (30° C.) LUMIstar* luminometer (BMG Lab Technologies, Durham, N.C.).

Inhibition Of Protein Synthesis—The RIP Assay

The toxic activity of OPL98101 was measured using a commercially available in vitro protein synthesis inhibition assay. At a concentration of 30 pM, Saporin was 90% inhibitory while a sample containing the same estimated concentration of the chemokine-toxin had to be diluted 500 fold to give a similar result. Assuming the concentration estimate was correct, this result is consistent with the published data that Shiga-A subunit is more potent than Saporin in this assay [see, Zollman, et al. (1994) Protein Expr Purif 5, 291–5; McDonald et al. (1996) *Protein Expr Purif* 8, 97–108; and Chandler et al. (1998) *Int J Cancer* 78, 106–11].

Tissue Culture Protocols

Primary Cultures

Protocols for adult human brain cell culture are known (see, e.g., Yong et al. (1997) Culture of glial cells from human brain biopsies. In *Protocols for Neural cell Culture* (A. Richardson and S. Fedoroff, eds), Humana Press, St. Louis 157–172). In brief, surgically resected brain tissue is cut into 1 mm cubes and incubated in 0.25% trypsin for one-hour at 37° C. The suspension is passed through a 130 um nylon filter which dissociates the tissue into single cells. Following centrifugation (15,000 rpm, 25 min.) in 30% Percoll, the supernatant contains viable neurons while the pellet is comprised of tissue debris, myelin, and red blood cells. The neural cells are collected and plated onto uncoated tissue culture plastic. The cultures are incubated for 24 hours at 37° C. by which time the microglia adhere to the plastic while the oligodendrocytes remain in solution. Oligodendrocytes are decanted, centrifuged, and plated onto poly-L-lysine, to which they adhere. Neurons and astrocytes do not survive this isolation process, however, the resulting populations of oligodendroglia and microglia are greater than 95% pure.

Neurons and astrocytes are derived from fetal brain specimens. Brain tissue is cut into small cubes and incubated with 0.25% trypsin and 100 ug/mg DNAase at 37° C., (see, Oh et al. (1996) *Glia* 17, 237–53). The suspension is passed through a 130 um nylon filter and the filtrate is collected, washed, and seeded onto poly-L-lysine-coated tissue culture plastic to allow the cells to adhere. A Percoll centrifugation step is not required since most fetal axonal tracts are not myelinated. To purify the neuronal population the mixed culture is treated with 25 uM cytosine arabinoside (Sigma, St. Louis) which destroys the mitotically active astrocytes. To purify the astrocytic population the mixed culture is passaged in the presence of 0.25% trypsin, which kills neurons. Adult astrocytes are isolated in a similar manner. Primary cultured adult and fetal astrocytes, and fetal neurons were prepared.

In general, neural cell cultures are fed twice weekly with minimum essential medium (MEM) supplemented with 10% fetal bovine serum, 20 ug/ml gentamicin, and 0.1% dextrose (Gibco, Grand Island, N.Y.).

Human peripheral blood leukocytes are harvested according to published methods (see, e.g., Chabot et al. (1997) *J Clin Invest* 100, 604–12). In brief, venous blood is layered on to Ficoll-Hypaque (Pharmacia) and centrifuged for 30 min at 2500 rpm. The mononuclear cell fraction is collected, washed twice, and seeded onto uncoated tissue culture substrates. Two hours later, floating cells (mostly T lymphocytes) are removed to leave behind an adherent population that consists primarily of monocytes. These cells are used immediately in cytotoxicity experiments, or they are activated prior to experimentation (three days, 1 mg/ml anti-CD3 receptor ligation for T-cells or 1 mg/ml lipopolysaccharide for monocytes).

In general, all hemapoietic cells (primary cells, or the cell lines described below) are maintained in RPMI medium supplemented with 10% fetal bovine serum, 20 mg/ml Gentamicin and 0.1% dextrose (Gibco).

Cell Lines

Cell lines derived from human mononuclear phagocytes are routinely cultured. For example, monocyte-derived U937 and THP-1 cells, and the microglia-like CHME line from fetal brain (obtained from Dr. Tardieu, France, see, also, Janabi et al. (1995) *Neurosci Lett* 195, 105–8), have been used to test the compounds. Numerous cell lines, including those of astrocytic and neuronal lineage, can be readily obtained from the ATCC (Rockville, Md.) and successfully cultured using the instructions that accompany the shipment.

Immunohistochemistry

Indirect immunohistochemistry is routinely performed to confirm the purity of enriched cultures, and by extension, to distinguish between different cell types in a mixed culture. There are a variety of academic and commercially available cell type-specific antibodies that can be used to facilitate this process. Examples include, an anti-galactocerebroside (GalC) antibody to identify oligodendrocytes, an anti—glial fibrillary acidic protein (GFAP) antibody for astrocytes, an anti-Mac-1 antibody for microglia, and an anti-neurofilament antibody for neurons (anti-NFL).

In brief, live cells on cover slips are treated with an appropriate fixative (e.g., 4% paraformaldehyde for galactocerebroside, and 95% ethanol/5% glacial acetic acid, v/v). A predetermined concentration of the primary antibody is applied followed by an appropriate secondary antibody (typically, rhodamine or fluorescein-conjugated goat anti-rabbit or anti-mouse IgG). The stained cells are examined using a microscope equipped to detect immunofluorescence. Analysis of adherent cell cultures primarily relies upon indirect immunohistochemical staining and labeling, and double labeling methods. Each cell type is counted in a sufficiently large number of randomly chosen microscope fields and the data are subjected to appropriate statistical analysis. Depending upon the mode and/or level of toxicity, i.e., apoptosis versus necrosis and/or subtle versus gross toxicity, the degree of cell death is recorded either qualitatively (toxicity grade of 0 to 4, see, e.g., Noble et al. (1994) *Brain Res* 633, 83–90) or quantitatively (the number of dead cells as a percentage of the total population; see, e.g., Oh et al. (1997) *Brain Res* 757, 236–44). In most instances data are analyzed using a one-way analysis of variance (ANOVA) with Tukey-Kramer multiple comparisons. Suspended cells are analyzed using a flow cytometer,) which typically automates data collection and appropriate statistical analysis (e.g., equipment from Becton Dickinson).

Cytotoxicity Assays

Briefly, test cells are supplied with fresh media containing control and test substances (at different concentrations) and incubated for a specified period (24–36 h). Cytotoxicity is then measured as the ability of adherent cells to reduce the vital dye MTT, as described in detail elsewhere (Mosmann, T. (1983) *J Immunol Methods* 65, 55–63; Gieni et al. (1995) *J Immunol Methods* 187, 85–93). Cytotoxicity in suspended cell cultures is measured using a Coulter counter, where the absolute number of cells is taken as an index of the number of surviving cells per test condition. Finally, general cell survival and morphology are monitored throughout the experiments using phase inverted microscopy and exclusion of the dye trypan blue (Yong et al. (1997) Culture of glial cells from human brain biopsies, In *Protocols for Neural cell Culture* (A. Richardson and S. Fedoroff, eds), Humana Press, St. Louis 157–172).

Chemotactic Assays

The chemotactic effect of each recombinant chemokine-toxin is of interest, principally as a test of the biological activity of the ligand component. Numerous chemotactic assays are known to those of skill in the art (see e.g., Stuve et al. (1996) *Ann Neurol* 40, 853–63; and Stuve et al. (1997) *J Neuroimmunol* 80, 38–46). In brief, the top and bottom compartments of a modified Boyden chamber are separated by a 3 μm membrane coated with fibronectin. Hematopoietic responder cells, appropriate to the chemokine being tested, are placed into the top compartment of the chamber while test materials are placed in the bottom. After an appropriate period of time, the number of cells that have migrated in response to a chemotactic stimulus is recorded. Migrating T-lymphocytes fall off the membrane into the lower chamber and the can be counted using a Coulter counter. In contrast migrating MNPs are retained on the underside of the membrane, and consequently, the upper surface must be washed and the lower surface fixed, prior to staining with Coomassie Blue and analysis by light microscopy.

OPL98110 Activity On Stationary Target Cells

Note: Control A is tissue culture medium. Control B is a wash fraction obtained prior to the elution of the chemokine-toxin from the nickel-affinity resin. This fraction was heavily enriched in *E. coli* proteins. Unless otherwise indicated all procedures were carried out in triplicate.

Human peripheral blood monocytes (from healthy donors) and THP-1 cells (a human monocytic cell line) were treated with 1:10 and 1:50 dilutions of Control B and OPL98101. Twenty-four hours later the cells were examined by phase contrast microscopy and representative fields were photographed and counted. OPL98110 caused marked membrane disruption and vacuolization in both cell types. Most of the treated cells appeared abnormal, and an increased amount of cellular debris indicated that some were already dead. At the lower concentration of the chemokine-toxin (1:50) 20–25% of both cell types were affected.

In another experiment THP-cells were grown for 48 in the presence and absence of OPL98110 (1:10 dilution) and cell viability examined by either microscopy or the ability to exclude trypan blue. Cells that exclude the stain are alive while stained cells are dead. Since THP-1 cells are naturally non adherent, and in order to produce a more accurate count, control and treated cells were dissociated from cellular debris by gentle pipetting prior to counting. After 48 hours, 7.4±3% of the control cells were dead (i.e. stained) in comparison to 58.8±13% of the OPL98110 treated group. This is a 51.4% difference. Sister wells examined after 96 hours revealed that control cells had proliferated and continued to appear quite normal and healthy while the chemokine-toxin treated cultures contained a lot of cellular debris, but few if any live cells.

These cultures were split and allowed to incubate for a further seven days. Control THP-1 cells continued to thrive and proliferate. There were no surviving cells in wells split from OPL98110 treated cultures). These studies demonstrate that treated cells become sick, and eventually die, over an extended period of time, suggesting an apoptotic mechanism.

OPL98110 Activity On Non Target Cells

OPL98110 was tested on non-target, primary human fetal neurons and a human U251 glioma (astrocytic tumor) cell line. Neurons were activated with TNF-α to simulate inflammation. The glioma cells were aggressively proliferating, and hence, activated. Following a 24 hour exposure to OPL98110 (1:50 dilution) there was no detectable effect on either cell type. Immunohistochemical staining of the neurons for b-tubulin and the detection of apoptosis (TUNEL) revealed healthy, intact cells.

OPL98110 Activity on Migrating Target Cells

In the first series of experiments target cells of leukocyte lineage (human peripheral monocytes and THP-1 cells) were tested in their quiescent, stationary state. As discussed above, upon focal injury or inflammation in vivo, immune cells are activated by a variety of stimuli (e.g., cytokines and chemokines) and respond by, amongst other things, upregulating the expression of chemokine receptors and migrating to the site of inflammation. It is well established that these characteristically in vivo responses can be mimicked in vitro by exposing target cells to various exogenous agents such as cytokines, chemokines, phorbol esters, and bacterial lipopolysaccharide. More specifically, the in vitro migration of leukocytes can be induced by chemokines, and measured by counting cells that migrate through a 3 μm filter separating the top and bottom chambers of a modified Boyden, tissue culture dish. Short term (e.g., 2–3 hours) incubations of the test chemokine and cells are typically employed in order to observe the temporal chemoattractant effect. Not every chemokine is an effective chemoattractant on every cell type, even though a given cell may have the appropriate receptor.

In the case of THP-1 cells, MCP-3 is chemoattractant but MCP-1 (and thus, OPL98110) is not. MCP-3 attracted THP-1 cells into the bottom chamber to 185±8% of control A. In addition, the very nature of OPL98110 makes it difficult to quantitate any chemoattractant activity given that any MCP-1 responsive cells would be killed. Normal THP-1 cells, however, naturally migrate without any specific exogenous stimulus (access to a region of low cell density is all that seems to be required), although at a much slower rate than that induced by chemokines.

Armed with this knowledge, experiments with longer term incubations to test the cytotoxic effects of OPL98110 on naturally migrating and migrated THP-1 cells (i.e., cells that reach the bottom chamber of the modified Boyden tissue culture dishes) were designed. THP-1 cells were plated into the top chambers of modified Boyden chambers. Lower chambers contained culture medium with and without serial dilutions of OPL98110. After 24 hours the cells in the top and bottom chambers were counted using a Coulter counter. There was no difference in cell numbers in the top chambers between control and tests, suggesting that equal numbers of cells had migrated under all conditions. In comparison to control, cell numbers in the bottom chambers of treated cells decreased as the concentration of OPL98110 increased. Migrated THP-1 cells were killed by OPL98110 in a dose dependent manner.

The "active" cells in the modified Boyden chamber experiments appear to be more susceptible to OPL98110 than cells tested in the "stationary" (quiescent) tissue culture model. For example after 24 hours, approximately 75–80% of stationary THP-1 cells treated with OPL98110 (1:50 dilution) appeared healthy when viewed under the microscope. The mean cell survival rate in migration assays using the same dilution of the chemokine-toxin was 50±15% (mean of 3 experiments in triplicate).

A similar experiment was performed using activated (with anti-CD3+) human T-lymphocytes isolated from healthy volunteers. OPL98110 (1:50 dilution) killed 32+/−7% ($p<0.05$) of the these cells, in comparison to 49+/−2% ($p<0.001$) of THP-1 cells tested at the same time.

EXAMPLE 3

Preparation of a Chemically Linked Chemokine-Toxin Conjuates

Attaching a Bifunctional Crosslinker via Primary Amine Groups

A bifunctional crosslinker is used to link a monoclonal antibody (IgG) to a compound having a primary amine as follows: The crosslinker used is N-succinimidyl 3-(2-pyridyidithio)propionate (SPDP), sulfosuccinimidyl 6-exanoate (Sulfo-LC-SPDP), or sulfosuccinimidyl 6-[3'(2-pyridyldithio)-propionamindo]hexanoate (Pierce Chemicals, Rockford, Ill.). The toxin and the IgG are initially derivatized with the crosslinker.

To 10 mg of toxin in 1.0 ml BBS is added a 20 nM stock solution of the crosslinker prepared according to the manufacturer's instruction, and the mixture is stirred for 30 minutes at room temperature. To remove the unconjugated cross-linker, the sample is applied to a 5 or 10 ml desalting column equilibrated with PBS, and 1 ml fractions are collected, the absorbance is monitored at 280 nm, and the peak fractions are determined and pooled. The collected peak fractions are concentrated to a final volume of 1.0 ml, using, for example, microdialysis.

Next, 25 mg of the antibody is added to 30 μl of the stock solution of the crosslinker and the mixture is stirred for 30 minutes at room temperature. The peak fractions are collected and concentrated from a desalting column equilibrated with acetate buffer as above. To the concentrate is added 12 mg dithiothreitol in 500 μl of the acetate buffer, and the mixture is stirred at room temperature for 30 min.

The mixture is applied to a 10 ml desalting column equilibrated with phosphate buffered saline (PBS) to remove excess reducing agent. Fractions of 1 ml are collected and absorbance of each is monitored at 280 nm. The first fraction having a 280 nm absorbance peak is added to the derivatized toxin, and the reaction mixture is incubated at room temperature for 18 hours, then applied to a Sephadex® G-200 column (1.5×45 cm) (Pharmacia) and equilibrated with PBS while 1 ml fractions are collected and monitored for absorbance at 280 nm. The fractions containing the conjugate are pooled.

EXAMPLE 4

Preparation of a Chemically Linked Chemokine-Toxin Conjuates

Attaching a Bifunctional Crosslinker via Sulfhydryl Groups

Conjugation of a monoclonal antibody ligand to a toxin with a sulfhydryl group is accomplished as follows using the crosslinkers described above. To 5 mg of the ligand in 1.0 ml of PBS is added 25 µl of a 20 mM stock solution of the crosslinker, and the mixture is incubated at room temperature for 30 minutes. To remove the excess crosslinker, the sample is applied to a 5 ml desalting column equilibrated with PBS/ethylene diamine tetraacetic acid (EDTA), and 1 ml fractions are collected and monitored for absorbance at 280 nm. The peak fractions containing the protein are pooled and concentrated to a final volume of 1.0 ml. To the protein concentrate is added 3 mg of β-galactosidase, and the reaction mixture is incubated overnight at room temperature. Then, the reaction mixture is applied to a Sephadex® G-200 column (1.5×45 cm) (Pharmacia) equilibrated with PBS, and 1 ml fractions are collected. The absorbance of the fraction is monitored at 280 nm, and the first absorbing peak to emerge from the column contains the protein conjugate.

EXAMPLE 5

Preparation of a Chemically Linked Chemokine-Toxin Conjuates

Pegylation of a Chemokine-Toxin Conjugate

Pegylation of a purified chemokine-toxin conjugate toxin is accomplished by mixing the toxin with methoxy-PEG-maleimide (MPEG-MAL) (MW 5000) (Sigma, St. Louis, Mo.) at a molar ratio of 1:10 in buffer A (20 mM sodium phosphate, 0.15 M NaCl, 5 mM EDTA, pH 7.0). After 30 min of incubation, the reaction is quenched by adding a 30-fold molar excess of Cys over MPEG-MAL. In order to concentrate the protein, the reaction mixture is applied to a suitable chromatography resin and eluted in a more concentrated form with salt-containing buffer (neutral pH). For example, the reaction mixture is applied to an S-Sepharose column (Pharmacia), equilibrated with 50 mM NaCl in buffer B (10 mM sodium phosphate, 1 mM EDTA, pH 6.0). Proteins are eluted batchwise with 1 M NaCl in buffer. The concentrated protein is loaded onto a gel filtration column and eluted with buffer C (50 mM sodium citrate, 80 mM NaCl, 0.1 mM EDTA, pH 6.0). Chemokine-toxin conjugate with attached PEG polymers is separated from non-derivatized chemokine-toxin conjugate by virtue of its molecular weight difference.

Since modifications will be apparent to those of skill in this art, it is intended that this invention be limited only by the scope of the appended claims.

What is claimed is:

1. A method for inhibiting proliferation or migration of activated immune effector cells, comprising administering a conjugate to an animal, whereby proliferation or migration of the immune effector cells is inhibited, wherein:
- the conjugate comprises a targeted agent or a portion thereof and a chemokine receptor targeting agent or a portion thereof sufficient to bind to a chemokine receptor on immune effector cells and facilitate internalization of the conjugate;
- the chemokine receptor targeting agent is a chemokine, an antibody that specifically binds to a chemokine receptor or a fragment of the chemokine or antibody, wherein the chemokine, antibody or fragment thereof binds to the receptor and internalizes the targeted agent in a cell;
- the targeted agent or portion thereof, when internalized in a cell, alters metabolism or gene expression in the cell, regulates or alters protein synthesis in the cell, inhibits proliferation of the cell or kills the cell; and the conjugate binds to a chemokine receptor resulting in internalization of the targeted agent in cells bearing the receptor.

2. The method of claim 1, wherein the immune effector cells are leukocytes that express chemokine receptors.

3. The method of claim 1, wherein the inflammatory response results in secondary tissue damage.

4. The method of claim 1, wherein the immune effector cells are selected from mononuclear phagocytes (MNP), leukocytes, natural killer cells, dendritic cells, T lymphocytes and B lymphocytes.

5. The method of claims 1, wherein the activated, proliferating or migrating immune cells occur in a disorder or disease state that is selected from the group consisting of CNS injury, CNS inflammatory diseases, neurodegenerative disorders, heart disease, inflammatory eye diseases, inflammatory bowel diseases, inflammatory joint diseases, inflammatory kidney or renal diseases, inflammatory lung diseases, inflammatory nasal diseases, inflammatory thyroid diseases, inflammatory responses associated with bacterial or viral infections and cytokine-regulated cancers.

6. The method of claim 5, wherein the CNS inflammatory diseases and neurodegenerative disorders are selected from the group consisting of stroke, closed head injury, leukoencephalopathy, choriomeningitis, meningitis, adrenoleukodystrophy, AIDS dementia complex, Alzheimer's disease, Down's Syndrome, chronic fatigue syndrome, encephalitis, encephalomyelitis, spongiform encephalopathies, multiple sclerosis, Parkison's disease, and spinal cord injury/trauma (SCI).

7. The method of claim 1, wherein the targeted agent is a toxin.

8. The method of claim 3, wherein the secondary tissue damage results from spinal cord injury or trauma.

9. A method for inhibiting the proliferation, migration or activity of secondary tissue damage-promoting inflammatory cells, comprising administering to a subject in need thereof an effective amount of a therapeutic agent that inhibits the proliferation, migration or physiological activity of secondary tissue damage-promoting inflammatory cells, wherein the therapeutic agent is a conjugate that comprises a chemokine receptor targeting agent and a targeted agent or portion thereof selected so that conjugate binds to a chemokine receptor and internalizes the targeted agent, which inhibits the proliferation, migration or physiological activity of the secondary tissue damage-promoting cells.

10. The method of claim 1, wherein the conjugate is selected from the group consisting of OPL98104, OPL98112, OPL98108, OPL98102, OPL98110, OPL98106, OPL98101, OPL98109, OPL98105, OPL98103, OPL98111 and OPL98107.

11. The method of claim 1, wherein the conjugate comprises the following components: (chemokine receptor targeting agent)n, (L)q and (targeted agent)m, wherein:

L is a linker for linking the chemokine receptor targeting agent to a targeted agent;

chemokine receptor targeting agent is any moiety that selectively binds to a chemokine receptor and effects internalization of the conjugate;

m and n, which are selected independently, are at least 1; and q is 0 or more as long as the resulting conjugate binds to the targeted receptor, is internalized and delivers the targeted agent;

the resulting conjugate binds to a receptor that interacts with and internalizes a chemokine, whereby the targeted agent(s) is internalized in a cell bearing the receptor; and when the conjugate contains a plurality of targeted agents, the targeted agents are the same or different, and when the conjugate contains a plurality of chemokine receptor targeting agents, the targeting agents are the same or different.

12. The method of claim 11, wherein m and n, which are selected independently, are 1–6.

13. The method of claim 11, wherein q is 1, n is 2 and m is 1.

14. The method of claim 11, wherein the chemokine receptor targeting agent specifically binds to chemokine receptors on activated leukocytes.

15. The method of claim 11, wherein the chemokine receptor targeting agent specifically binds to chemokine receptors on activated cells selected from mononuclear phagocytes (MNP), leukocytes, natural killer cells, dendritic cells, T lymphocytes and B lymphocytes.

16. The method of claim 15, wherein the activated leukocytes are selected from basophils, neutrophils, eosinophils or combinations of any two or more thereof.

17. The method of claim 11, wherein the targeted agent is a toxin, a nucleic acid or a therapeutic protein.

18. The method of claim 11, when the chemokine receptor targeting agent and targeted agent are linked directly via a covalent or ionic linkage.

19. The method of claim 11, wherein the chemokine receptor targeting agent and targeted agent are joined via a linker.

20. The method of claim 19, wherein the linker is a peptide linkage, a polypeptide or is chemical linker.

21. The method of claim 11, wherein the chemokine receptor targeting agent is a chemokine or a fragment thereof that binds to the receptor and internalizes the targeted agent.

22. The method of claim 1, wherein the chemokine receptor targeting agent is a chemokine or a sufficient portion thereof to specifically bind to a chemokine receptor and to facilitate internalization of the conjugate.

23. The method of claim 1, wherein the chemokine targeting agent is a chemokine that is a member of the superfamily of chemokines that interact with at least one of the chemokine receptors selected from the group consisting of the CC-, CXC-, CX3C- and XC-receptors.

24. The method of claim 1, wherein the chemokine targeting agent is a chemokine that is a member of the superfamily of chemokines that interact with at least one of the chemokine receptors selected from the group consisting of the CC- and CXC-receptors.

25. The method of claim 22, wherein the chemokine is selected from the group consisting of IL-8, GCP-2, GRO-α, GRO-β, GRP-γ, ENA-78, PBP, CTAP III, NAP-2, LAPF-4, MIG, IP-10, SDF-1α, SDF-1β, SDF-2, MCP-1, MCP-2, MCP-3, MCP4, MCP-5, MIP-1α, MIP-1β, MIP-1γ, MIP-2, MIP-2α, MIP-3α, MIP-3β, MIP-4, MIP-5, MDC, HCC-1, LD78μ, eotaxin-1, eotaxin-2, I-309, SCYA17, TARC, RANTES, DC-CK-1, lymphotactin and fractalkine.

26. The method of claim 22, wherein the chemokine is selected from the group consisting of lungkine, ALP, Tim-1, chemokine α-5, chemokine α-6 and chemokine β15.

27. The method of claim 1, wherein the chemokine receptor selected from the group-consisting of CXCR-1, CXCR-2, CXCR-3, CXCR4, CXCR-5, CCR-1, CCR-2A, CCR-2B, CCR-3, CCR4, CCR-5, CCR4, CCR-7, CCR-8, CCR-8, CX3CR-1, XCR1, Duffy antigen receptor for chemokines (DARC) and CD97.

28. The method of claim 22, wherein the chemokine receptor is selected from the group consisting of DARC, CXCR-1, CXCR-2, CXCR-3, CXCR4, CCR-1, CCR-2A, CCR-2B, CCR-3, CCR4, CCR-5, CCR6, CCR-7, CCR-8, CX3CR-1, and CD97.

29. A method of targeted delivery of an agent into cells that express chemokine receptors, comprising associating the agent with a chemokine receptor targeting agent, whereby:
the chemokine receptor targeting agent binds to a chemokine receptor expressed on the cells; and
the agent is internalized by the cells, wherein the cells are immune effector cells.

30. The method of claim 29, wherein the immune effector cells are activated leukocytes.

31. A method for inhibiting proliferation or migration of activated immune effector cells, comprising contacting immune effector cells with a conjugate that comprises a targeted agent or a portion thereof and a chemokine receptor targeting agent, whereby activation or proliferation of the immune effector cells is inhibited, wherein:
the targeted agent or portion thereof is a toxin;
the chemokine receptor targeting agent is a chemokine or a fragment of thereof that binds to a chemokine receptor and internalizes the targeted agent; and
the conjugate binds to a chemokine receptor resulting in internalization of the targeted agent in cells bearing the receptor.

32. The method of claim 31, wherein the conjugate comprises the following components: (chemokine receptor targeting agent)n, (L)q and (targeted agent)m, wherein:
L is a linker for linking the chemokine or fragment thereof to a targeted agent;
m and n, which are selected independently, are at least 1; and
q is 0 or more as long as the resulting conjugate binds to the targeted receptor, is internalized and delivers the targeted agent;
the resulting conjugate binds to a receptor that interacts with and internalizes a chemokine, whereby the targeted agent(s) is internalized in a cell bearing the receptor, and
when the conjugate contains a plurality of targeted agents, the targeted agents are the same or different, and when the conjugate contains a plurality of chemokine receptor targeting agents, the targeting agents are the same or different.

33. The method of claim 32, wherein m and n, which are selected independently, are 1–6.

34. The method of claim 32, wherein q is 1, n is 2 and m is 1.

35. The method of claim 32, wherein the chemokine specifically binds to chemokine receptors on activated leukocytes.

36. The method of claim 32, wherein the chemokine specifically binds to chemokine receptors on activated cells selected from mononuclear phagocytes (MNP), leukocytes, natural killer cells, dendritic cells, T lymphocytes and B lymphocytes.

37. The method of claim 35, wherein the activated leukocytes are selected from basophils, neutrophils, eosinophils or combinations of any two or more thereof.

38. The method of claim 32, wherein the chemokine is a member of the superfamily of chemokines that interact with at least one of the chemokine receptors selected from the group consisting of the CC-, CXC-, CX3C- and XC-receptors.

39. The method of claim 32, wherein the chemokine is a chemokine that is a member of the superfamily of chemokines that interact with at least one of the chemokine receptors selected from the group consisting of the CC- and CXC-receptors.

40. The method of claim 29, wherein the chemokine is selected from the group consisting of IL-8, GCP-2, GRO-α, GRO-β, GRP-γ, ENA-78, PBP, CTAP III, NAP-2, LAPF-4, MIG, IP-10, SDF-1α, SDF-1β, SDF-2, MCP-1, MCP-2, MCP-3, MCP4, MCP-5, MIP-1α, MIP-1β, MIP-1γ, MIP-2, MIP-2α, MIP-3α, MIP-3β, MIP-4, MIP-5, MDC, HCC-1, LD78μ, eotaxin-1, eotaxin-2, I-309, SCYA17, TARC, RANTES, DC-CK-1, lymphotactin, and fractalkine.

41. The method of claim 9, wherein the targeted agent, when internalized in a cell, alters metabolism or gene expression in the cell, regulates or alters protein synthesis in the cell, inhibits proliferation of the cell or kills the cell.

42. The method of claim 1, wherein the targeted agent is selected from among ribosome inactivating proteins (RIPs) and bacteriocins.

43. The method of claim 32, wherein the toxin is a ribosome inactivating protein or a toxic subunit thereof.

44. The method of claim 1, wherein the targeted agent is a toxin that is a ribosome inactivating protein or a toxic subunit thereof.

45. A method of preparing a candidate compound for treating a disease or disorder involving activated immune cells an inflammatory response, comprising:

identifying immune cells that are activated in the disease or disorder;

identifying chemokine receptors expressed on the cells;

preparing a conjugate or plurality thereof containing toxin linked to a chemokine or a plurality of chemokines that specifically bind to the identified chemokine receptors and effect or facilitate internalization of the toxin into the cells.

46. The method of claim 45, wherein a plurality of conjugates that bind to a plurality of chemokine receptors are prepared.

47. The method of claim 1, wherein the chemokine receptor targeting agent is selected from the group consisting of IL-8, GRO-α, GRO-β, IP-10, SDF-1β, MCP-1 MCP-3, eotaxin-1, eotaxin-2 and RANTES.

48. The method of claim 21, wherein the chemokine receptor targeting agent is selected from the group consisting of IL-8, GCP-2, GRO-α, GRO-β, GRP-γ, ENA-78, PBP, CTAP III, NAP-2, LAPF-4, MIG, IP-10, SDF-1α, SDF-1β, SDF-2, MCP-1, MCP-2, MCP-3, MCP4, MCP-5, MIP-1α, MIP-1β, MIP-1γ, MIP-2, MIP-2α, MIP-3α, MIP-3β, MIP-4, MIP-5, MDC, HCC-1, LD-78β, eotaxin-1, eotaxin-2, I-309, SCYA17, TARC, RANTES, DC-CK-1, lymphotactin, and fractalkine.

49. The method of claim 9, wherein the chemokine receptor targeting agent is selected from the group consisting of IL-8, GCP-2, GRO-α, GRO-β, GRP-γ, ENA-78, PBP, CTAP III, NAP-2, LAPF-4, MIG, IP-10, SDF-1α, SDF-1β, SDF-2, MCP-1, MCP-2, MCP-3, MCP-4, MCP-5, MIP-1α, MIP-1β, MIP-1γ, MIP-2, MIP-2α, MIP-3α, MIP-3β, MIP-4, MIP-5, MDC, HCC-1, LD78β, eotaxin-1, eotaxin-2, I-309, SCYA17, TARC, RANTES, DC-CK-1, lymphotactin, and fractalkine.

50. The method of claim 45, wherein the chemokine is selected from the group consisting of IL-8, GCP-2, GRO-α, GRO-β, GRP-γ, ENA-78, PBP, CTAP III, NAP-2, LAPF-4, MIG, IP-10, SDF-1α, SDF-1β, SDF-2, MCP-1, MCP-2, MCP-3, MCP4, MCP-5, MIP-1α, MIP-1β, MIP-1γ, MIP-2, MP-2α, MIP-3α, MIP-3β, MIP-4, MIP-5, MDC, HCC-1, LD78β, eotaxin-1, eotaxin-2, I-309, SCYA17, TARC, RANTES, DC-CK-1, lymphotactin, and fractalkine.

51. The method of claim 1, wherein the immune effector cells are selected from among monocytes, macrophages, leukocytes and microglia.

52. The method of claim 11, wherein the immune effector cells are selected from among monocytes, macrophages, leukocytes and microglia.

53. The method of claim 29, wherein the immune effector cells are selected from mononuclear phagocytes (MNP), leukocytes, natural killer cells, dendritic cells, T lymphocytes and B lymphocytes.

54. The method of claim 29, wherein the immune effector cells are selected from among monocytes, macrophages, leukocytes and microglia.

55. The method of claim 29, further comprising:

contacting the immune cells with the conjugate or plurality thereof, whereby the toxin is internalized.

56. The method of claim 55, wherein a plurality of conjugates that bind to a plurality of chemokine receptors are prepared, and the immune cells are contacted with each of the conjugates simultaneously or sequentially.

* * * * *

UNITED STATES PATENT AND TRADEMARK OFFICE
CERTIFICATE OF CORRECTION

| | | |
|---|---|---|
| PATENT NO. | : 7,157,418 B1 | |
| APPLICATION NO. | : 09/360242 | |
| DATED | : January 2, 2007 | |
| INVENTOR(S) | : John R. McDonald and Phillip J. Coggins | |

It is certified that error appears in the above-identified patent and that said Letters Patent is hereby corrected as shown below:

IN THE TITLE PAGES:

In Item [57] ABSTRACT, line 1 please delete the "a" between "ligand" and "chemokine"

in Item [57] ABSTRACT, please replace "neutrophiles" with --neutrophils-- in Item [56] *References Cited* please add to the list of OTHER PUBLICATIONS --Kreitman and Pastan, *Semin. Cancer Biol.* *6*(5):297-306 (1995).-- in Item [56] *References Cited* please add to the list of OTHER PUBLICATIONS --Kreitman, R.J., et al., Recombinant toxins, *Adv. Pharmacol.*, *28*:193-219 (1994).-- in Item [56] *References Cited* please add to the list of OTHER PUBLICATIONS --Medh, J.D., et al., *J. Biol. Chem.*, *270*:536-540 (1995).-- in Item [56] *References Cited* please add to the list of OTHER PUBLICATIONS --Puri, *Toxicol. Pathol.* *27*:53-57 (1999).-- in Item [56] *References Cited* please add to the list of OTHER PUBLICATIONS --Sawada, M., et al., *Neurosci. Lett.*, *160*:131-4 (1993).-- in Item [56] *References Cited* please add to the list of OTHER PUBLICATIONS --Stirpe, F., et al., *J. Biol. Chem.*, *255*:6947-6953 (1980).-- in Item [56] *References Cited* please add to the list of OTHER PUBLICATIONS --Ugoccioni, M., et al., *J. Exp. Med.*, *183*:2379-84 (1996).-- in Item [56] *References Cited* please add to the list of OTHER PUBLICATIONS --Zheng, G., et al., *J. Histochem. Cytochem.*, *42*: 531-42 (1994).-- in Item [56] *References Cited*, in OTHER PUBLICATIONS: in EMBL database ID HS1301003, please replace "(Lingkine)" with --(Lungkine)--

UNITED STATES PATENT AND TRADEMARK OFFICE
CERTIFICATE OF CORRECTION

| | | |
|---|---|---|
| PATENT NO. | : 7,157,418 B1 | Page 2 of 6 |
| APPLICATION NO. | : 09/360242 | |
| DATED | : January 2, 2007 | |
| INVENTOR(S) | : John R. McDonald and Phillip J. Coggins | |

It is certified that error appears in the above-identified patent and that said Letters Patent is hereby corrected as shown below:

in Hesselgesser et al., please replace "Chernokine" with --Chemokine--
      in Richmond et al., please replace "chernokine/chernokine receptor" with
           --chemokine/chemokine receptor--
      in Signoret et al., please replace "Chernokine" with --Chemokine--

IN THE SPECIFICATION:

At column 1, line 24, please insert --FIELD OF THE INVENTION The present invention relates to therapeutic compositions and their use in treatment of disease states. More particularly, compounds, compositions and methods for treating disease states associated with proliferation, migration and physiological activity of cells involved in inflammatory responses, including, but not limited to, secondary tissue damage, are provided.--
      at column 14, line 43, please replace "FIG. 1 is a schematic drawing" with --FIG. 1A-1C presents schematic drawings--
      at column 14, line 56, please insert --(also designated herein pOPL2)-- between "pGEMEX-SAP" and "encoding"
      at column 14, lines 59-60, please replace "map of a conjugate MCP-3-AM-Shiga-A1" with --map of a plasmid, designated pOPL1, encoding the conjugate MCP-3-AM Shiga-A1, which was--
      at column 14, lines 62-63, please replace "map of a conjugate MCP-1-AM-SAP" with --map of a plasmid, designated pOPL106, encoding the conjugate MCP-1-AM-SAP--
      at column 14, lines 65-66, please replace "map of a conjugate MCP3-AM-Shiga-A1" with --map of a plasmid, designated pOPL101, encoding the conjugate MCP-3-AM Shiga-A1--
      at column 16, line 56, please delete "ALP,"
      at column 32, line 25, please delete "of"
      at column 57, line 30, please insert --)-- between "1986" and "."
      at column 57, line 51, please replace "Ed." with --ed.--
      at column 68, line 56, please replace "MIP-1 alpha" with --MIP-1α--
      at column 69, line 13, please insert --which-- between "mice" and "predictably"

UNITED STATES PATENT AND TRADEMARK OFFICE
CERTIFICATE OF CORRECTION

| | |
|---|---|
| PATENT NO. | : 7,157,418 B1 |
| APPLICATION NO. | : 09/360242 |
| DATED | : January 2, 2007 |
| INVENTOR(S) | : John R. McDonald and Phillip J. Coggins |

It is certified that error appears in the above-identified patent and that said Letters Patent is hereby corrected as shown below:

IN THE CLAIMS:

Please replace Claims 5, 11, 18, 20, 25, 27, 28, 31, 32, 40, 45, 48, 50 and 55 with the following Claims:

5. The method of claim 1, wherein the activated, proliferating or migrating immune cells occur in a disorder or disease state that is selected from the group consisting of CNS injury, CNS inflammatory diseases, neurodegenerative disorders, heart disease, inflammatory eye diseases, inflammatory bowel diseases, inflammatory joint diseases, inflammatory kidney or renal diseases, inflammatory lung diseases, inflammatory nasal diseases, inflammatory thyroid diseases, inflammatory responses associated with bacterial or viral infections and cytokine-regulated cancers.

11. The method of claim 1, wherein the conjugate comprises the following components: (chemokine receptor targeting agent)$_n$, (L)$_q$ and (targeted agent)$_m$,
wherein: L is a linker for linking the chemokine receptor targeting agent to a targeted agent; chemokine receptor targeting agent is any moiety that selectively binds to a chemokine receptor and effects internalization of the conjugate;
m and n, which are selected independently, are at least 1; and
q is 0 or more as long as the resulting conjugate binds to the targeted receptor, is internalized and delivers the targeted agent;
the resulting conjugate binds to a receptor that interacts with and internalizes a chemokine, whereby the targeted agent(s) is internalized in a cell bearing the receptor; and
when the conjugate contains a plurality of targeted agents, the targeted agents are the same or different, and when the conjugate contains a plurality of chemokine receptor targeting agents, the targeting agents are the same or different.

18. The method of claim 11, wherein the chemokine receptor targeting agent and targeted agent are linked directly via a covalent or ionic linkage.

20. The method of claim 19, wherein the linker is a peptide linkage, a polypeptide or a chemical linker.

UNITED STATES PATENT AND TRADEMARK OFFICE
CERTIFICATE OF CORRECTION

| | | |
|---|---|---|
| PATENT NO. | : 7,157,418 B1 | |
| APPLICATION NO. | : 09/360242 | |
| DATED | : January 2, 2007 | |
| INVENTOR(S) | : John R. McDonald and Phillip J. Coggins | |

It is certified that error appears in the above-identified patent and that said Letters Patent is hereby corrected as shown below:

25. The method of claim 22, wherein the chemokine is selected from the group consisting of IL-8, GCP-2, GRO-$\alpha$, GRO-$\beta$, GRP-$\gamma$, ENA-78, PBP, CTAP III, NAP-2, LAPF-4, MIG, IP-10, SDF-1$\alpha$, SDF-1$\beta$, SDF-2, MCP-1, MCP-2, MCP-3, MCP-4, MCP-5, MIP-1$\alpha$, MIP-1$\beta$, MIP-1$\gamma$, MIP-2, MIP-2$\alpha$, MIP-3$\alpha$, MIP-3$\beta$, MIP-4, MIP-5, MDC, HCC-1, LD78$\beta$, eotaxin-1, eotaxin-2, I-309, SCYA17, TARC, RANTES, DC-CK-1, lymphotactin and fractalkine.

27. The method of claim 1, wherein the chemokine receptor is selected from the group consisting of CXCR-1, CXCR-2, CXCR-3, CXCR-4, CXCR-5, CCR-1, CCR-2A, CCR-2B, CCR-3, CCR-4, CCR-5, CCR-6, CCR-7, CCR-8, CX3CR-1, XCR1, Duffy antigen receptor for chemokines (DARC) and CD97.

28. The method of claim 22, wherein the chemokine receptor is selected from the group consisting of DARC, CXCR-1, CXCR-2, CXCR-3, CXCR-4, CCR-1, CCR-2A, CCR-2B, CCR-3, CCR-4, CCR-5, CCR-6, CCR-7, CCR-8, CX3CR-1, and CD97.

31. A method for inhibiting proliferation or migration of activated immune effector cells, comprising contacting immune effector cells with a conjugate that comprises a targeted agent or a portion thereof and a chemokine receptor targeting agent, whereby activation or proliferation of the immune effector cells is nhibited, wherein:
    the targeted agent or portion thereof is a toxin;
    the chemokine receptor targeting agent is a chemokine or a fragment thereof that binds to a chemokine receptor and internalizes the targeted agent; and
    the conjugate binds to a chemokine receptor resulting in internalization of the targeted agent in cells bearing the receptor.

UNITED STATES PATENT AND TRADEMARK OFFICE
CERTIFICATE OF CORRECTION

| | |
|---|---|
| PATENT NO. | : 7,157,418 B1 |
| APPLICATION NO. | : 09/360242 |
| DATED | : January 2, 2007 |
| INVENTOR(S) | : John R. McDonald and Phillip J. Coggins |

It is certified that error appears in the above-identified patent and that said Letters Patent is hereby corrected as shown below:

32. The method of claim 31, wherein the conjugate comprises the following components: (chemokine receptor targeting agent)$_n$, (L)$_q$ and (targeted agent)$_m$,
  wherein: L is a linker for linking the chemokine or fragment thereof to a targeted agent;
  m and n, which are selected independently, are at least 1; and
  q is 0 or more as long as the resulting conjugate binds to the targeted receptor, is internalized and delivers the targeted agent;
  the resulting conjugate binds to a receptor that interacts with and internalizes a chemokine, whereby the targeted agent(s) is internalized in a cell bearing the receptor; and
  when the conjugate contains a plurality of targeted agents, the targeted agents are the same or different, and when the conjugate contains a plurality of chemokine receptor targeting agents, the targeting agents are the same or different.

40. The method of claim 29, wherein the chemokine is selected from the group consisting of IL-8, GCP-2, GRO-α, GRO-β, GRP-γ, ENA-78, PBP, CTAP III, NAP-2, LAPF-4, MIG, IP-10, SDF-1α, SDF-1β, SDF-2, MCP-1, MCP-2, MCP-3, MCP-4, MCP-5, MIP-1α, MIP-1β, MIP-1γ, MIP-2, MIP-2α, MIP-3α, MIP-3β, MIP-4, MIP-5, MDC, HCC-1, LD78β, eotaxin-1, eotaxin-2, I-309, SCYA17, TARC, RANTES, DC-CK-1, lymphotactin, and fractalkine.

45. A method of preparing a candidate compound for treating a disease or disorder involving activated immune cells, comprising:
  identifying immune cells that are activated in the disease or disorder;
  identifying chemokine receptors expressed on the cells; and
  preparing a conjugate or plurality thereof containing a toxin linked to a chemokine or a plurality of chemokines that specifically bind to the identified chemokine receptors and effect or facilitate internalization of the toxin into the cells.

48. The method of claim 21, wherein the chemokine receptor targeting agent is selected from the group consisting of IL-8, GCP-2, GRO-α, GRO-β, GRP-γ, ENA-78, PBP, CTAP III, NAP-2, LAPF-4, MIG, IP-10, SDF-1α, SDF-1β, SDF-2, MCP-1, MCP-2, MCP-3, MCP-4, MCP-5, MIP-1α, MIP-1β, MIP-1γ, MIP-2, MIP-2α, MIP-3α, MIP-3β, MIP-4, MIP-5, MDC, HCC-1, LD78β, eotaxin-1, eotaxin-2, I-309, SCYA17, TARC, RANTES, DC-CK-1, lymphotactin, and fractalkine.

UNITED STATES PATENT AND TRADEMARK OFFICE
CERTIFICATE OF CORRECTION

PATENT NO. : 7,157,418 B1
APPLICATION NO. : 09/360242
DATED : January 2, 2007
INVENTOR(S) : John R. McDonald and Phillip J. Coggins It is certified that error appears in the above-identified patent and that said Letters Patent is hereby corrected as shown below:

50. The method of claim 45, wherein the chemokine is selected from the group consisting of IL-8, GCP-2, GRO-$\alpha$, GRO-$\beta$, GRP-$\gamma$, ENA-78, PBP, CTAP III, NAP-2, LAPF-4, MIG, IP-10, SDF-1$\alpha$, SDF-1$\beta$, SDF-2, MCP-1, MCP-2, MCP-3, MCP-4, MCP-5, MIP-1$\alpha$, MIP-1$\beta$, MIP-1$\gamma$, MIP-2, MIP-2$\alpha$, MIP-3$\alpha$, MIP-3$\beta$, MIP-4, MIP-5, MDC, HCC-1, LD78$\beta$, eotaxin-1, eotaxin-2, I-309, SCYA17, TARC, RANTES, DC-CK-1, lymphotactin, and fractalkine.

55. The method of claim 45, further comprising:
    contacting the immune cells with the conjugate or plurality thereof, whereby the toxin is internalized.

Signed and Sealed this

Eighteenth Day of March, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,157,418 B1 | |
| APPLICATION NO. | : 09/360242 | |
| DATED | : January 2, 2007 | |
| INVENTOR(S) | : John R. McDonald and Phillip J. Coggins | |

It is certified that error appears in the above-identified patent and that said Letters Patent is hereby corrected as shown below:

IN THE TITLE PAGES:

In Item [57] ABSTRACT, line 1 please delete the "a" between "ligand" and "chemokine"

in Item [57] ABSTRACT, please replace "neutrophiles" with --neutrophils-- in Item [56] *References Cited* please add to the list of OTHER PUBLICATIONS --Kreitman and Pastan, *Semin. Cancer Biol.* *6*(5):297-306 (1995).-- in Item [56] *References Cited* please add to the list of OTHER PUBLICATIONS --Kreitman, R.J., et al., Recombinant toxins, *Adv. Pharmacol.*, *28*:193-219 (1994).-- in Item [56] *References Cited* please add to the list of OTHER PUBLICATIONS --Medh, J.D., et al., *J. Biol. Chem.*, *270*:536-540 (1995).-- in Item [56] *References Cited* please add to the list of OTHER PUBLICATIONS --Puri, *Toxicol. Pathol.* *27*:53-57 (1999).-- in Item [56] *References Cited* please add to the list of OTHER PUBLICATIONS --Sawada, M., et al., *Neurosci. Lett.*, *160*:131-4 (1993).-- in Item [56] *References Cited* please add to the list of OTHER PUBLICATIONS --Stirpe, F., et al., *J. Biol. Chem.*, *255*:6947-6953 (1980).-- in Item [56] *References Cited* please add to the list of OTHER PUBLICATIONS --Ugoccioni, M., et al., *J. Exp. Med.*, *183*:2379-84 (1996).-- in Item [56] *References Cited* please add to the list of OTHER PUBLICATIONS --Zheng, G., et al., *J. Histochem. Cytochem.*, *42*: 531-42 (1994).-- in Item [56] *References Cited*, in OTHER PUBLICATIONS: in EMBL database ID HS1301003, please replace "(Lingkine)" with --(Lungkine)--

UNITED STATES PATENT AND TRADEMARK OFFICE
CERTIFICATE OF CORRECTION

| | | |
|---|---|---|
| PATENT NO. | : 7,157,418 B1 | Page 2 of 6 |
| APPLICATION NO. | : 09/360242 | |
| DATED | : January 2, 2007 | |
| INVENTOR(S) | : John R. McDonald and Phillip J. Coggins | |

It is certified that error appears in the above-identified patent and that said Letters Patent is hereby corrected as shown below:

in Hesselgesser et al., please replace "Chernokine" with --Chemokine--
in Richmond et al., please replace "chernokine/chernokine receptor" with
--chemokine/chemokine receptor--
in Signoret et al., please replace "Chernokine" with --Chemokine--

IN THE SPECIFICATION:

At column 1, line 24, please insert --FIELD OF THE INVENTION The present invention relates to therapeutic compositions and their use in treatment of disease states. More particularly, compounds, compositions and methods for treating disease states associated with proliferation, migration and physiological activity of cells involved in inflammatory responses, including, but not limited to, secondary tissue damage, are provided.--
at column 14, line 43, please replace "FIG. 1 is a schematic drawing" with --FIG. 1A-1C presents schematic drawings--
at column 14, line 56, please insert --(also designated herein pOPL2)-- between "pGEMEX-SAP" and "encoding"
at column 14, lines 59-60, please replace "map of a conjugate MCP-3-AM-Shiga-A1" with --map of a plasmid, designated pOPL1, encoding the conjugate MCP-3-AM Shiga-A1, which was--
at column 14, lines 62-63, please replace "map of a conjugate MCP-1-AM-SAP" with --map of a plasmid, designated pOPL106, encoding the conjugate MCP-1-AM-SAP--
at column 14, lines 65-66, please replace "map of a conjugate MCP3-AM-Shiga-A1" with --map of a plasmid, designated pOPL101, encoding the conjugate MCP-3-AM Shiga-A1--
at column 16, line 56, please delete "ALP,"
at column 32, line 25, please delete "of"
at column 57, line 30, please insert --)-- between "1986" and "."
at column 57, line 51, please replace "Ed." with --ed.--
at column 68, line 56, please replace "MIP-1 alpha" with --MIP-1α--
at column 69, line 13, please insert --which-- between "mice" and "predictably"

UNITED STATES PATENT AND TRADEMARK OFFICE
CERTIFICATE OF CORRECTION

| | |
|---|---|
| PATENT NO. | : 7,157,418 B1 |
| APPLICATION NO. | : 09/360242 |
| DATED | : January 2, 2007 |
| INVENTOR(S) | : John R. McDonald and Phillip J. Coggins |

It is certified that error appears in the above-identified patent and that said Letters Patent is hereby corrected as shown below:

IN THE CLAIMS:

Please replace Claims 5, 11, 18, 20, 25, 27, 28, 31, 32, 40, 45, 48, 50 and 55 with the following Claims:

Column 201, delete lines 41-50 and insert:
--5. The method of claim 1, wherein the activated, proliferating or migrating immune cells occur in a disorder or disease state that is selected from the group consisting of CNS injury, CNS inflammatory diseases, neurodegenerative disorders, heart disease, inflammatory eye diseases, inflammatory bowel diseases, inflammatory joint diseases, inflammatory kidney or renal diseases, inflammatory lung diseases, inflammatory nasal diseases, inflammatory thyroid diseases, inflammatory responses associated with bacterial or viral infections and cytokine-regulated cancers.--

Column 202, delete lines 24-46 and insert:
--11. The method of claim 1, wherein the conjugate comprises the following components: (chemokine receptor targeting agent)$_n$, (L)$_q$ and (targeted agent)$_m$,
    wherein: L is a linker for linking the chemokine receptor targeting agent
    to a targeted agent; chemokine receptor targeting agent is any moiety
    that selectively binds to a chemokine receptor and effects
internalization of the conjugate;
    m and n, which are selected independently, are at least 1; and
    q is 0 or more as long as the resulting conjugate binds to the targeted
receptor, is internalized and delivers the targeted agent;
    the resulting conjugate binds to a receptor that interacts with and
internalizes a chemokine, whereby the targeted agent(s) is internalized in a cell bearing the receptor; and
    when the conjugate contains a plurality of targeted agents, the targeted agents are the same or different, and when the conjugate contains a plurality of chemokine receptor targeting agents, the targeting agents are the same or different.--

Column 202, delete lines 65-67 and insert:
--18. The method of claim 11, wherein the chemokine receptor targeting agent and targeted agent are linked directly via a covalent or ionic linkage.--

Column 203, delete lines 4 and 5 and insert:
--20. The method of claim 19, wherein the linker is a peptide linkage, a polypeptide or a chemical linker.--

UNITED STATES PATENT AND TRADEMARK OFFICE
CERTIFICATE OF CORRECTION

PATENT NO. : 7,157,418 B1
APPLICATION NO. : 09/360242
DATED : January 2, 2007
INVENTOR(S) : John R. McDonald and Phillip J. Coggins It is certified that error appears in the above-identified patent and that said Letters Patent is hereby corrected as shown below:

Column 203, delete lines 23-30 and insert:
--25. The method of claim 22, wherein the chemokine is selected from the group consisting of IL-8, GCP-2, GRO-α, GRO-β, GRP-γ, ENA-78, PBP, CTAP III, NAP-2, LAPF-4, MIG, IP-10, SDF-1α, SDF-1β, SDF-2, MCP-1, MCP-2, MCP-3, MCP-4, MCP-5, MIP-1α, MIP-1β, MIP-1γ, MIP-2, MIP-2α, MIP-3α, MIP-3β, MIP-4, MIP-5, MDC, HCC-1, LD78β, eotaxin-1, eotaxin-2, I-309, SCYA17, TARC, RANTES, DC-CK-1, lymphotactin and fractalkine.--

Column 203, delete lines 34-39 and insert:
--27. The method of claim 1, wherein the chemokine receptor is selected from the group consisting of CXCR-1, CXCR-2, CXCR-3, CXCR-4, CXCR-5, CCR-1, CCR-2A, CCR-2B, CCR-3, CCR-4, CCR-5, CCR-6, CCR-7, CCR-8, CX3CR-1, XCR1, Duffy antigen receptor for chemokines (DARC) and CD97.--

Column 203, delete lines 40-44 and insert:
--28. The method of claim 22, wherein the chemokine receptor is selected from the group consisting of DARC, CXCR-1, CXCR-2, CXCR-3, CXCR-4, CCR-1, CCR-2A, CCR-2B, CCR-3, CCR-4, CCR-5, CCR-6, CCR-7, CCR-8, CX3CR-1, and CD97.--

Column 203, delete lines 55-67 and insert:
--31. A method for inhibiting proliferation or migration of activated immune effector cells, comprising contacting immune effector cells with a conjugate that comprises a targeted agent or a portion thereof and a chemokine receptor targeting agent, whereby activation or proliferation of the immune effector cells is nhibited, wherein:
    the targeted agent or portion thereof is a toxin;
    the chemokine receptor targeting agent is a chemokine or a fragment thereof that binds to a chemokine receptor and internalizes the targeted agent; and
    the conjugate binds to a chemokine receptor resulting in internalization of the targeted agent in cells bearing the receptor.--

UNITED STATES PATENT AND TRADEMARK OFFICE
CERTIFICATE OF CORRECTION

| | | |
|---|---|---|
| PATENT NO. | : 7,157,418 B1 | |
| APPLICATION NO. | : 09/360242 | |
| DATED | : January 2, 2007 | |
| INVENTOR(S) | : John R. McDonald and Phillip J. Coggins | |

It is certified that error appears in the above-identified patent and that said Letters Patent is hereby corrected as shown below:

Column 204, delete lines 1-19 and insert:
--32. The method of claim 31, wherein the conjugate comprises the following components: (chemokine receptor targeting agent)$_n$, (L)$_q$ and (targeted agent)$_m$,
 wherein: L is a linker for linking the chemokine or fragment thereof to a targeted agent;
 m and n, which are selected independently, are at least 1; and
 q is 0 or more as long as the resulting conjugate binds to the targeted receptor, is internalized and delivers the targeted agent;
 the resulting conjugate binds to a receptor that interacts with and internalizes a chemokine, whereby the targeted agent(s) is internalized in a cell bearing the receptor; and
 when the conjugate contains a plurality of targeted agents, the targeted agents are the same or different, and when the conjugate contains a plurality of chemokine receptor targeting agents, the targeting agents are the same or different.--

Column 204, delete lines 45-52 and insert:
--40. The method of claim 29, wherein the chemokine is selected from the group consisting of IL-8, GCP-2, GRO-α, GRO-β, GRP-γ, ENA-78, PBP, CTAP III, NAP-2, LAPF-4, MIG, IP-10, SDF-1α, SDF-1β, SDF-2, MCP-1, MCP-2, MCP-3, MCP-4, MCP-5, MIP-1α, MIP-1β, MIP-1γ, MIP-2, MIP-2α, MIP-3α, MIP-3β, MIP-4, MIP-5, MDC, HCC-1, LD78β, eotaxin-1, eotaxin-2, I-309, SCYA17, TARC, RANTES, DC-CK-1, lymphotactin, and fractalkine.--

Column 204, delete lines 65-67 and insert:
--45. A method of preparing a candidate compound for treating a disease or disorder involving activated immune cells, comprising:
 identifying immune cells that are activated in the disease or disorder;
 identifying chemokine receptors expressed on the cells; and
 preparing a conjugate or plurality thereof containing a toxin linked to a chemokine or a plurality of chemokines that specifically bind to the identified chemokine receptors and effect or facilitate internalization of the toxin into the cells.--

UNITED STATES PATENT AND TRADEMARK OFFICE
CERTIFICATE OF CORRECTION

PATENT NO. : 7,157,418 B1
APPLICATION NO. : 09/360242
DATED : January 2, 2007
INVENTOR(S) : John R. McDonald and Phillip J. Coggins It is certified that error appears in the above-identified patent and that said Letters Patent is hereby corrected as shown below:

Column 205, delete lines 16-24 and insert:
--48. The method of claim 21, wherein the chemokine receptor targeting agent is selected from the group consisting of IL-8, GCP-2, GRO-α, GRO-β, GRP-γ, ENA-78, PBP, CTAP III, NAP-2, LAPF-4, MIG, IP-10, SDF-1α, SDF-1β, SDF-2, MCP-1, MCP-2, MCP-3, MCP-4, MCP-5, MIP-1α, MIP-1β, MIP-1γ, MIP-2, MIP-2α, MIP-3α, MIP-3β, MIP-4, MIP-5, MDC, HCC-1, LD78β, eotaxin-1, eotaxin-2, I-309, SCYA17, TARC, RANTES, DC-CK-1, lymphotactin, and fractalkine.--

Column 206, delete lines 1-8 and insert:
--50. The method of claim 45, wherein the chemokine is selected from the group consisting of IL-8, GCP-2, GRO-α, GRO-β, GRP-γ, ENA-78, PBP, CTAP III, NAP-2, LAPF-4, MIG, IP-10, SDF-1α, SDF-1β, SDF-2, MCP-1, MCP-2, MCP-3, MCP-4, MCP-5, MIP-1α, MIP-1β, MIP-1γ, MIP-2, MIP-2α, MIP-3α, MIP-3β, MIP-4, MIP-5, MDC, HCC-1, LD78β, eotaxin-1, eotaxin-2, I-309, SCYA17, TARC, RANTES, DC-CK-1, lymphotactin, and fractalkine.--

Column 206, delete lines 24-26 and insert:
--55. The method of claim 45, further comprising:
    contacting the immune cells with the conjugate or plurality thereof, whereby the toxin is internalized.--

This certificate supersedes the Certificate of Correction issued March 18, 2008.

Signed and Sealed this

Fifteenth Day of April, 2008

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,157,418 B1 |
| APPLICATION NO. | : 09/360242 |
| DATED | : January 2, 2007 |
| INVENTOR(S) | : John R. McDonald and Phillip J. Coggins |

It is certified that error appears in the above-identified patent and that said Letters Patent is hereby corrected as shown below:

IN THE TITLE PAGES:

In Item [57] ABSTRACT, line 1 please delete the "a" between "ligand" and "chemokine"

in Item [57] ABSTRACT, please replace "neutrophiles" with --neutrophils-- in Item [56] *References Cited* please add to the list of OTHER PUBLICATIONS --Kreitman and Pastan, *Semin. Cancer Biol.* *6*(5):297-306 (1995).-- in Item [56] *References Cited* please add to the list of OTHER PUBLICATIONS --Kreitman, R.J., et al., Recombinant toxins, *Adv. Pharmacol.*, *28*:193-219 (1994).-- in Item [56] *References Cited* please add to the list of OTHER PUBLICATIONS --Medh, J.D., et al., *J. Biol. Chem.*, *270*:536-540 (1995).-- in Item [56] *References Cited* please add to the list of OTHER PUBLICATIONS --Puri, *Toxicol. Pathol.* 27:53-57 (1999).-- in Item [56] *References Cited* please add to the list of OTHER PUBLICATIONS --Sawada, M., et al., *Neurosci. Lett.*, *160*:131-4 (1993).-- in Item [56] *References Cited* please add to the list of OTHER PUBLICATIONS --Stirpe, F., et al., *J. Biol. Chem.*, *255*:6947-6953 (1980).-- in Item [56] *References Cited* please add to the list of OTHER PUBLICATIONS --Ugoccioni, M., et al., *J. Exp. Med.*, *183*:2379-84 (1996).-- in Item [56] *References Cited* please add to the list of OTHER PUBLICATIONS --Zheng, G., et al., *J. Histochem. Cytochem.*, *42*: 531-42 (1994).-- in Item [56] *References Cited*, in OTHER PUBLICATIONS: in EMBL database ID HS1301003, please replace "(Lingkine)" with --(Lungkine)--

UNITED STATES PATENT AND TRADEMARK OFFICE
CERTIFICATE OF CORRECTION

| | |
|---|---|
| PATENT NO. | : 7,157,418 B1 |
| APPLICATION NO. | : 09/360242 |
| DATED | : January 2, 2007 |
| INVENTOR(S) | : John R. McDonald and Phillip J. Coggins |

It is certified that error appears in the above-identified patent and that said Letters Patent is hereby corrected as shown below:

in Hesselgesser et al., please replace "Chernokine" with --Chemokine--
in Richmond et al., please replace "chernokine/chernokine receptor" with --chemokine/chemokine receptor--
in Signoret et al., please replace "Chernokine" with --Chemokine--

IN THE SPECIFICATION:

At column 1, line 24, please insert --FIELD OF THE INVENTION The present invention relates to therapeutic compositions and their use in treatment of disease states. More particularly, compounds, compositions and methods for treating disease states associated with proliferation, migration and physiological activity of cells involved in inflammatory responses, including, but not limited to, secondary tissue damage, are provided.--
at column 14, line 43, please replace "FIG. 1 is a schematic drawing" with --FIG. 1A-1C presents schematic drawings--
at column 14, line 56, please insert --(also designated herein pOPL2)-- between "pGEMEX-SAP" and "encoding"
at column 14, lines 59-60, please replace "map of a conjugate MCP-3-AM-Shiga-A1" with --map of a plasmid, designated pOPL1, encoding the conjugate MCP-3-AM Shiga-A1, which was--
at column 14, lines 62-63, please replace "map of a conjugate MCP-1-AM-SAP" with --map of a plasmid, designated pOPL106, encoding the conjugate MCP-1-AM-SAP--
at column 14, lines 65-66, please replace "map of a conjugate MCP3-AM-Shiga-A1" with --map of a plasmid, designated pOPL101, encoding the conjugate MCP-3-AM Shiga-A1--
at column 16, line 56, please delete "ALP,"
at column 32, line 25, please delete "of"
at column 57, line 30, please insert --)-- between "1986" and "."
at column 57, line 51, please replace "Ed." with --ed.--
at column 68, line 56, please replace "MIP-1 alpha" with --MIP-1á--
at column 69, line 13, please insert --which-- between "mice" and "predictably"

UNITED STATES PATENT AND TRADEMARK OFFICE
CERTIFICATE OF CORRECTION

| | |
|---|---|
| PATENT NO. | : 7,157,418 B1 |
| APPLICATION NO. | : 09/360242 |
| DATED | : January 2, 2007 |
| INVENTOR(S) | : John R. McDonald and Phillip J. Coggins |

It is certified that error appears in the above-identified patent and that said Letters Patent is hereby corrected as shown below:

IN THE CLAIMS:

Please replace Claims 5, 11, 18, 20, 25, 27, 28, 31, 32, 40, 45, 48, 50 and 55 with the following Claims:

Column 201, delete lines 41-50 and insert:
--5. The method of claim 1, wherein the activated, proliferating or migrating immune cells occur in a disorder or disease state that is selected from the group consisting of CNS injury, CNS inflammatory diseases, neurodegenerative disorders, heart disease, inflammatory eye diseases, inflammatory bowel diseases, inflammatory joint diseases, inflammatory kidney or renal diseases, inflammatory lung diseases, inflammatory nasal diseases, inflammatory thyroid diseases, inflammatory responses associated with bacterial or viral infections and cytokine-regulated cancers.--

Column 202, delete lines 24-46 and insert:
--11. The method of claim 1, wherein the conjugate comprises the following components: (chemokine receptor targeting agent)$_n$, (L)$_q$ and (targeted agent)$_m$,
    wherein: L is a linker for linking the chemokine receptor targeting agent
    to a targeted agent; chemokine receptor targeting agent is any moiety
    that selectively binds to a chemokine receptor and effects
internalization of the conjugate;
    m and n, which are selected independently, are at least 1; and
    q is 0 or more as long as the resulting conjugate binds to the targeted
receptor, is internalized and delivers the targeted agent;
    the resulting conjugate binds to a receptor that interacts with and
internalizes a chemokine, whereby the targeted agent(s) is internalized in a cell bearing the receptor; and
    when the conjugate contains a plurality of targeted agents, the targeted agents are the same or different, and when the conjugate contains a plurality of chemokine receptor targeting agents, the targeting agents are the same or different.--

Column 202, delete lines 65-67 and insert:
--18. The method of claim 11, wherein the chemokine receptor targeting agent and targeted agent are linked directly via a covalent or ionic linkage.--

Column 203, delete lines 4 and 5 and insert:
--20. The method of claim 19, wherein the linker is a peptide linkage, a polypeptide or a chemical linker.--

UNITED STATES PATENT AND TRADEMARK OFFICE
CERTIFICATE OF CORRECTION

PATENT NO. : 7,157,418 B1
APPLICATION NO. : 09/360242
DATED : January 2, 2007
INVENTOR(S) : John R. McDonald and Phillip J. Coggins It is certified that error appears in the above-identified patent and that said Letters Patent is hereby corrected as shown below:

Column 203, delete lines 23-30 and insert:
--25. The method of claim 22, wherein the chemokine is selected from the group consisting of IL-8, GCP-2, GRO-á, GRO-â, GRP-ã, ENA-78, PBP, CTAP III, NAP-2, LAPF-4, MIG, IP-10, SDF-1á, SDF-1â, SDF-2, MCP-1, MCP-2, MCP-3, MCP-4, MCP-5, MIP-1á, MIP-1â, MIP-1ã, MIP-2, MIP-2á, MIP-3á, MIP-3â, MIP-4, MIP-5, MDC, HCC-1, LD78â, eotaxin-1, eotaxin-2, I-309, SCYA17, TARC, RANTES, DC-CK-1, lymphotactin and fractalkine.--

Column 203, delete lines 34-39 and insert:
--27. The method of claim 1, wherein the chemokine receptor is selected from the group consisting of CXCR-1, CXCR-2, CXCR-3, CXCR-4, CXCR-5, CCR-1, CCR-2A, CCR-2B, CCR-3, CCR-4, CCR-5, CCR-6, CCR-7, CCR-8, CX3CR-1, XCR1, Duffy antigen receptor for chemokines (DARC) and CD97.--

Column 203, delete lines 40-44 and insert:
--28. The method of claim 22, wherein the chemokine receptor is selected from the group consisting of DARC, CXCR-1, CXCR-2, CXCR-3, CXCR-4, CCR-1, CCR-2A, CCR-2B, CCR-3, CCR-4, CCR-5, CCR-6, CCR-7, CCR-8, CX3CR-1, and CD97.--

Column 203, delete lines 55-67 and insert:
--31. A method for inhibiting proliferation or migration of activated immune effector cells, comprising contacting immune effector cells with a conjugate that comprises a targeted agent or a portion thereof and a chemokine receptor targeting agent, whereby activation or proliferation of the immune effector cells is inhibited,wherein:
    the targeted agent or portion thereof is a toxin;
    the chemokine receptor targeting agent is a chemokine or a fragment thereof that binds to a chemokine receptor and internalizes the targeted agent; and
    the conjugate binds to a chemokine receptor resulting in internalization of the targeted agent in cells bearing the receptor.--

UNITED STATES PATENT AND TRADEMARK OFFICE
CERTIFICATE OF CORRECTION

| | | |
|---|---|---|
| PATENT NO. | : 7,157,418 B1 | Page 5 of 6 |
| APPLICATION NO. | : 09/360242 | |
| DATED | : January 2, 2007 | |
| INVENTOR(S) | : John R. McDonald and Phillip J. Coggins | |

It is certified that error appears in the above-identified patent and that said Letters Patent is hereby corrected as shown below:

Column 204, delete lines 1-19 and insert:
--32. The method of claim 31, wherein the conjugate comprises the following components: (chemokine receptor targeting agent)$_n$, (L)$_q$ and (targeted agent)$_m$,
    wherein: L is a linker for linking the chemokine or fragment thereof to a targeted agent;
    m and n, which are selected independently, are at least 1; and
    q is 0 or more as long as the resulting conjugate binds to the targeted receptor, is internalized and delivers the targeted agent;
    the resulting conjugate binds to a receptor that interacts with and internalizes a chemokine, whereby the targeted agent(s) is internalized in a cell bearing the receptor; and
    when the conjugate contains a plurality of targeted agents, the targeted agents are the same or different, and when the conjugate contains a plurality of chemokine receptor targeting agents, the targeting agents are the same or different.--

Column 204, delete lines 45-52 and insert:
--40. The method of claim 29, wherein the chemokine is selected from the group consisting of IL-8, GCP-2, GRO-á, GRO-â, GRP-ã, ENA-78, PBP, CTAP III, NAP-2, LAPF-4, MIG, IP-10, SDF-1á, SDF-1â, SDF-2, MCP-1, MCP-2, MCP-3, MCP-4, MCP-5, MIP-1á, MIP-1â, MIP-1ã, MIP-2, MIP-2á, MIP-3á, MIP-3â, MIP-4, MIP-5, MDC, HCC-1, LD78â, eotaxin-1, eotaxin-2, I-309, SCYA17, TARC, RANTES, DC-CK-1, lymphotactin, and fractalkine.--

Column 204, delete lines 65-67 and insert:
--45. A method of preparing a candidate compound for treating a disease or disorder involving activated immune cells, comprising:
    identifying immune cells that are activated in the disease or disorder;
    identifying chemokine receptors expressed on the cells; and
    preparing a conjugate or plurality thereof containing a toxin linked to a chemokine or a plurality of chemokines that specifically bind to the identified chemokine receptors and effect or facilitate internalization of the toxin into the cells.--

UNITED STATES PATENT AND TRADEMARK OFFICE
CERTIFICATE OF CORRECTION

PATENT NO. : 7,157,418 B1
APPLICATION NO. : 09/360242
DATED : January 2, 2007
INVENTOR(S) : John R. McDonald and Phillip J. Coggins It is certified that error appears in the above-identified patent and that said Letters Patent is hereby corrected as shown below:

Column 205, delete lines 16-24 and insert:
--48. The method of claim 21, wherein the chemokine receptor targeting agent is selected from the group consisting of IL-8, GCP-2, GRO-á, GRO-â, GRP-ã, ENA-78, PBP, CTAP III, NAP-2, LAPF-4, MIG, IP-10, SDF-1á, SDF-1â, SDF-2, MCP-1, MCP-2, MCP-3, MCP-4, MCP-5, MIP-1á, MIP-1â, MIP-1ã, MIP-2, MIP-2á, MIP-3á, MIP-3â, MIP-4, MIP-5, MDC, HCC-1, LD78â, eotaxin-1, eotaxin-2, I-309, SCYA17, TARC, RANTES, DC-CK-1, lymphotactin, and fractalkine.--

Column 206, delete lines 1-8 and insert:
--50. The method of claim 45, wherein the chemokine is selected from the group consisting of IL-8, GCP-2, GRO-á, GRO-â, GRP-ã, ENA-78, PBP, CTAP III, NAP-2, LAPF-4, MIG, IP-10, SDF-1á, SDF-1â, SDF-2, MCP-1, MCP-2, MCP-3, MCP-4, MCP-5, MIP-1á, MIP-1â, MIP-1ã, MIP-2, MIP-2á, MIP-3á, MIP-3â, MIP-4, MIP-5, MDC, HCC-1, LD78â, eotaxin-1, eotaxin-2, I-309, SCYA17, TARC, RANTES, DC-CK-1, lymphotactin, and fractalkine.--

Column 206, delete lines 24-26 and insert:
--55. The method of claim 45, further comprising:
    contacting the immune cells with the conjugate or plurality thereof, whereby the toxin is internalized.--

This certificate supersedes all previously issued Certificate of Corrections.

Signed and Sealed this

Twenty-fourth Day of June, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,157,418 B1 | |
| APPLICATION NO. | : 09/360242 | |
| DATED | : January 2, 2007 | |
| INVENTOR(S) | : John R. McDonald and Phillip J. Coggins | |

It is certified that error appears in the above-identified patent and that said Letters Patent is hereby corrected as shown below:

IN THE TITLE PAGES:

In Item [57] ABSTRACT, line 1 please delete the "a" between "ligand" and "chemokine"

in Item [57] ABSTRACT, please replace "neutrophiles" with --neutrophils-- in Item [56] *References Cited* please add to the list of OTHER PUBLICATIONS --Kreitman and Pastan, *Semin. Cancer Biol.* *6*(5):297-306 (1995).-- in Item [56] *References Cited* please add to the list of OTHER PUBLICATIONS --Kreitman, R.J., et al., Recombinant toxins, *Adv. Pharmacol., 28*:193-219 (1994).-- in Item [56] *References Cited* please add to the list of OTHER PUBLICATIONS --Medh, J.D., et al., *J. Biol. Chem., 270*:536-540 (1995).-- in Item [56] *References Cited* please add to the list of OTHER PUBLICATIONS --Puri, *Toxicol. Pathol. 27*:53-57 (1999).-- in Item [56] *References Cited* please add to the list of OTHER PUBLICATIONS --Sawada, M., et al., *Neurosci. Lett., 160*:131-4 (1993).-- in Item [56] *References Cited* please add to the list of OTHER PUBLICATIONS --Stirpe, F., et al., *J. Biol. Chem., 255*:6947-6953 (1980).-- in Item [56] *References Cited* please add to the list of OTHER PUBLICATIONS --Ugoccioni, M., et al., *J. Exp. Med., 183*:2379-84 (1996).-- in Item [56] *References Cited* please add to the list of OTHER PUBLICATIONS --Zheng, G., et al., *J. Histochem. Cytochem., 42*:531-42 (1994).-- in Item [56] *References Cited*, in OTHER PUBLICATIONS: in EMBL database ID HS1301003, please replace "(Lingkine)" with --(Lungkine)--

UNITED STATES PATENT AND TRADEMARK OFFICE
CERTIFICATE OF CORRECTION

PATENT NO. : 7,157,418 B1
APPLICATION NO. : 09/360242
DATED : January 2, 2007
INVENTOR(S) : John R. McDonald and Phillip J. Coggins It is certified that error appears in the above-identified patent and that said Letters Patent is hereby corrected as shown below:

in Hesselgesser et al., please replace "Chernokine" with --Chemokine--
in Richmond et al., please replace "chernokine/chernokine receptor" with --chemokine/chemokine receptor--
in Signoret et al., please replace "Chernokine" with --Chemokine--

IN THE SPECIFICATION:

At column 1, line 24, please insert --FIELD OF THE INVENTION The present invention relates to therapeutic compositions and their use in treatment of disease states. More particularly, compounds, compositions and methods for treating disease states associated with proliferation, migration and physiological activity of cells involved in inflammatory responses, including, but not limited to, secondary tissue damage, are provided.--
at column 14, line 43, please replace "FIG. 1 is a schematic drawing" with --FIG. 1A-1C presents schematic drawings--
at column 14, line 56, please insert --(also designated herein pOPL2)-- between "pGEMEX-SAP" and "encoding"
at column 14, lines 59-60, please replace "map of a conjugate MCP-3-AM-Shiga-A1" with --map of a plasmid, designated pOPL1, encoding the conjugate MCP-3-AM Shiga-A1, which was--
at column 14, lines 62-63, please replace "map of a conjugate MCP-1-AM-SAP" with --map of a plasmid, designated pOPL106, encoding the conjugate MCP-1-AM-SAP--
at column 14, lines 65-66, please replace "map of a conjugate MCP3-AM-Shiga-A1" with --map of a plasmid, designated pOPL101, encoding the conjugate MCP-3-AM Shiga-A1--
at column 16, line 56, please delete "ALP,"
at column 32, line 25, please delete "of"
at column 57, line 30, please insert --)-- between "1986" and "."
at column 57, line 51, please replace "Ed." with --ed.--
at column 68, line 56, please replace "MIP-1 alpha" with --MIP-1á--
at column 69, line 13, please insert --which-- between "mice" and "predictably"

UNITED STATES PATENT AND TRADEMARK OFFICE
CERTIFICATE OF CORRECTION

| | | |
|---|---|---|
| PATENT NO. | : 7,157,418 B1 | Page 3 of 6 |
| APPLICATION NO. | : 09/360242 | |
| DATED | : January 2, 2007 | |
| INVENTOR(S) | : John R. McDonald and Phillip J. Coggins | |

It is certified that error appears in the above-identified patent and that said Letters Patent is hereby corrected as shown below:

IN THE CLAIMS:

Please replace Claims 5, 11, 18, 20, 25, 27, 28, 31, 32, 40, 45, 48, 50 and 55 with the following Claims:

Column 201, delete lines 41-50 and insert:
--5. The method of claim 1, wherein the activated, proliferating or migrating immune cells occur in a disorder or disease state that is selected from the group consisting of CNS injury, CNS inflammatory diseases, neurodegenerative disorders, heart disease, inflammatory eye diseases, inflammatory bowel diseases, inflammatory joint diseases, inflammatory kidney or renal diseases, inflammatory lung diseases, inflammatory nasal diseases, inflammatory thyroid diseases, inflammatory responses associated with bacterial or viral infections and cytokine-regulated cancers.--

Column 202, delete lines 24-46 and insert:
--11. The method of claim 1, wherein the conjugate comprises the following components: (chemokine receptor targeting agent)$_n$, (L)$_q$ and (targeted agent)$_m$,
    wherein: L is a linker for linking the chemokine receptor targeting agent
    to a targeted agent; chemokine receptor targeting agent is any moiety
    that selectively binds to a chemokine receptor and effects
internalization of the conjugate;
    m and n, which are selected independently, are at least 1; and
    q is 0 or more as long as the resulting conjugate binds to the targeted
receptor, is internalized and delivers the targeted agent;
    the resulting conjugate binds to a receptor that interacts with and
internalizes a chemokine, whereby the targeted agent(s) is internalized in a cell bearing the receptor; and
    when the conjugate contains a plurality of targeted agents, the targeted agents are the same or different, and when the conjugate contains a plurality of chemokine receptor targeting agents, the targeting agents are the same or different.--

Column 202, delete lines 65-67 and insert:
--18. The method of claim 11, wherein the chemokine receptor targeting agent and targeted agent are linked directly via a covalent or ionic linkage.--

Column 203, delete lines 4 and 5 and insert:
--20. The method of claim 19, wherein the linker is a peptide linkage, a polypeptide or a chemical linker.--

UNITED STATES PATENT AND TRADEMARK OFFICE
CERTIFICATE OF CORRECTION

PATENT NO. : 7,157,418 B1
APPLICATION NO. : 09/360242
DATED : January 2, 2007
INVENTOR(S) : John R. McDonald and Phillip J. Coggins It is certified that error appears in the above-identified patent and that said Letters Patent is hereby corrected as shown below:

Column 203, delete lines 23-30 and insert:
--25. The method of claim 22, wherein the chemokine is selected from the group consisting of IL-8, GCP-2, GRO-α, GRO-β, GRP-γ, ENA-78, PBP, CTAP III, NAP-2, LAPF-4, MIG, IP-10, SDF-1α, SDF-1β, SDF-2, MCP-1, MCP-2, MCP-3, MCP-4, MCP-5, MIP-1α, MIP-1β, MIP-1γ, MIP-2, MIP-2α, MIP-3α, MIP-3β, MIP-4, MIP-5, MDC, HCC-1, LD78β, eotaxin-1, eotaxin-2, I-309, SCYA17, TARC, RANTES, DC-CK-1, lymphotactin and fractalkine.--

Column 203, delete lines 34-39 and insert:
--27. The method of claim 1, wherein the chemokine receptor is selected from the group consisting of CXCR-1, CXCR-2, CXCR-3, CXCR-4, CXCR-5, CCR-1, CCR-2A, CCR-2B, CCR-3, CCR-4, CCR-5, CCR-6, CCR-7, CCR-8, CX3CR-1, XCR1, Duffy antigen receptor for chemokines (DARC) and CD97.--

Column 203, delete lines 40-44 and insert:
--28. The method of claim 22, wherein the chemokine receptor is selected from the group consisting of DARC, CXCR-1, CXCR-2, CXCR-3, CXCR-4, CCR-1, CCR-2A, CCR-2B, CCR-3, CCR-4, CCR-5, CCR-6, CCR-7, CCR-8, CX3CR-1, and CD97.--

Column 203, delete lines 55-67 and insert:
--31. A method for inhibiting proliferation or migration of activated immune effector cells, comprising contacting immune effector cells with a conjugate that comprises a targeted agent or a portion thereof and a chemokine receptor targeting agent, whereby activation or proliferation of the immune effector cells is inhibited, wherein:
    the targeted agent or portion thereof is a toxin;
    the chemokine receptor targeting agent is a chemokine or a fragment thereof that binds to a chemokine receptor and internalizes the targeted agent; and
    the conjugate binds to a chemokine receptor resulting in internalization of the targeted agent in cells bearing the receptor.--

UNITED STATES PATENT AND TRADEMARK OFFICE
CERTIFICATE OF CORRECTION

| | | |
|---|---|---|
| PATENT NO. | : 7,157,418 B1 | |
| APPLICATION NO. | : 09/360242 | |
| DATED | : January 2, 2007 | |
| INVENTOR(S) | : John R. McDonald and Phillip J. Coggins | |

It is certified that error appears in the above-identified patent and that said Letters Patent is hereby corrected as shown below:

Column 204, delete lines 1-19 and insert:
--32. The method of claim 31, wherein the conjugate comprises the following components: (chemokine receptor targeting agent)$_n$, (L)$_q$ and (targeted agent)$_m$,
    wherein: L is a linker for linking the chemokine or fragment thereof to a targeted agent;
    m and n, which are selected independently, are at least 1; and
    q is 0 or more as long as the resulting conjugate binds to the
targeted receptor, is internalized and delivers the targeted agent;
    the resulting conjugate binds to a receptor that interacts with and internalizes a chemokine, whereby the targeted agent(s) is internalized in a cell bearing the receptor; and
    when the conjugate contains a plurality of targeted agents, the targeted agents are the same or different, and when the conjugate contains a plurality of chemokine receptor targeting agents, the targeting agents are the same or different.--

Column 204, delete lines 45-52 and insert:
--40. The method of claim 29, wherein the chemokine is selected from the group consisting of IL-8, GCP-2, GRO-α, GRO-β, GRP-γ, ENA-78, PBP, CTAP III, NAP-2, LAPF-4, MIG, IP-10, SDF-1α, SDF-1β, SDF-2, MCP-1, MCP-2, MCP-3, MCP-4, MCP-5, MIP-1α, MIP-1β, MIP-1γ, MIP-2, MIP-2α, MIP-3α, MIP-3β, MIP-4, MIP-5, MDC, HCC-1, LD78β, eotaxin-1, eotaxin-2, I-309, SCYA17, TARC, RANTES, DC-CK-1, lymphotactin, and fractalkine.--

Column 204, delete lines 65-67 and insert:
--45. A method of preparing a candidate compound for treating a disease or disorder involving activated immune cells, comprising:
    identifying immune cells that are activated in the disease or disorder;
    identifying chemokine receptors expressed on the cells; and
    preparing a conjugate or plurality thereof containing a toxin linked to a chemokine or a plurality of chemokines that specifically bind to the identified chemokine receptors and effect or facilitate internalization of the toxin into the cells.--

UNITED STATES PATENT AND TRADEMARK OFFICE
CERTIFICATE OF CORRECTION

PATENT NO. : 7,157,418 B1
APPLICATION NO. : 09/360242
DATED : January 2, 2007
INVENTOR(S) : John R. McDonald and Phillip J. Coggins It is certified that error appears in the above-identified patent and that said Letters Patent is hereby corrected as shown below:

Column 205, delete lines 16-24 and insert:
--48. The method of claim 21, wherein the chemokine receptor targeting agent is selected from the group consisting of IL-8, GCP-2, GRO-α, GRO-β, GRP-γ, ENA-78, PBP, CTAP III, NAP-2, LAPF-4, MIG, IP-10, SDF-1α, SDF-1β, SDF-2, MCP-1, MCP-2, MCP-3, MCP-4, MCP-5, MIP-1α, MIP-1β, MIP-1γ, MIP-2, MIP-2α, MIP-3α, MIP-3β, MIP-4, MIP-5, MDC, HCC-1, LD78β, eotaxin-1, eotaxin-2, I-309, SCYA17, TARC, RANTES, DC-CK-1, lymphotactin, and fractalkine.--

Column 206, delete lines 1-8 and insert:
--50. The method of claim 45, wherein the chemokine is selected from the group consisting of IL-8, GCP-2, GRO-α, GRO-β, GRP-γ, ENA-78, PBP, CTAP III, NAP-2, LAPF-4, MIG, IP-10, SDF-1α, SDF-1β, SDF-2, MCP-1, MCP-2, MCP-3, MCP-4, MCP-5, MIP-1α, MIP-1β, MIP-1γ, MIP-2, MIP-2α, MIP-3α, MIP-3β, MIP-4, MIP-5, MDC, HCC-1, LD78β, eotaxin-1, eotaxin-2, I-309, SCYA17, TARC, RANTES, DC-CK-1, lymphotactin, and fractalkine.--

Column 206, delete lines 24-26 and insert:
--55. The method of claim 45, further comprising:
    contacting the immune cells with the conjugate or plurality thereof, whereby the toxin is internalized.--

This certificate supersedes all previously issued Certificate of Corrections.

Signed and Sealed this

Twenty-fourth Day of February, 2009

JOHN DOLL
*Acting Director of the United States Patent and Trademark Office*